US009725497B2

(12) United States Patent
Anderson et al.

(10) Patent No.: US 9,725,497 B2
(45) Date of Patent: *Aug. 8, 2017

(54) EGFR AND C-MET FIBRONECTIN TYPE III DOMAIN BINDING MOLECULES

(71) Applicant: Janssen Biotech, Inc., Horsham, PA (US)

(72) Inventors: Mark Anderson, Spring House, PA (US); Ricardo Attar, Spring House, PA (US); Michael Diem, Spring House, PA (US); Linus Hyun, Spring House, PA (US); Steven Jacobs, Spring House, PA (US); Alastair King, Norristown, PA (US); Donna Klein, Spring House, PA (US); Sheri Moores, Spring House, PA (US); Karyn O'Neil, Spring House, PA (US); Kristen Picha, Spring House, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/086,250

(22) Filed: Nov. 21, 2013

(65) Prior Publication Data

US 2014/0155326 A1 Jun. 5, 2014

Related U.S. Application Data

(60) Provisional application No. 61/728,906, filed on Nov. 21, 2012, provisional application No. 61/728,914, filed on Nov. 21, 2012, provisional application No. 61/728,912, filed on Nov. 21, 2012, provisional application No. 61/782,550, filed on Mar. 14, 2013, provisional application No. 61/809,541, filed on Apr. 8, 2013.

(51) Int. Cl.
| | |
|---|---|
| *C07K 19/00* | (2006.01) |
| *C07K 14/78* | (2006.01) |
| *A61K 45/06* | (2006.01) |
| *C07K 16/28* | (2006.01) |
| *C07K 14/705* | (2006.01) |
| *C07K 14/71* | (2006.01) |
| *C07K 14/47* | (2006.01) |
| *A61K 38/00* | (2006.01) |
| *A61K 39/00* | (2006.01) |

(52) U.S. Cl.
CPC .............. *C07K 14/78* (2013.01); *A61K 45/06* (2013.01); *C07K 14/47* (2013.01); *C07K 14/705* (2013.01); *C07K 14/71* (2013.01); *C07K 16/28* (2013.01); *C07K 16/2863* (2013.01); *A61K 38/00* (2013.01); *A61K 2039/505* (2013.01); *C07K 2317/31* (2013.01); *C07K 2317/73* (2013.01); *C07K 2317/76* (2013.01); *C07K 2317/92* (2013.01); *C07K 2318/20* (2013.01); *C07K 2319/70* (2013.01)

(58) Field of Classification Search
None
See application file for complete search history.

(56) References Cited

U.S. PATENT DOCUMENTS

| | | |
|---|---|---|
| 5,223,409 A | 6/1993 | Ladner et al. |
| 5,643,768 A | 7/1997 | Kawasaki |
| 5,856,456 A | 1/1999 | Whitlow et al. |
| 6,172,197 B1 | 1/2001 | McCafferty et al. |
| 6,472,147 B1 | 10/2002 | Janda et al. |
| 6,582,915 B1 | 6/2003 | Griffiths et al. |
| 6,673,901 B2 | 1/2004 | Koide |
| 6,969,108 B2 | 11/2005 | Fukumoto et al. |
| 7,842,476 B2 | 11/2010 | McGregor et al. |
| 2004/0197332 A1 | 10/2004 | Ullrich et al. |
| 2005/0004029 A1 | 1/2005 | Garcia |
| 2005/0272083 A1 | 12/2005 | Seshagiri |
| 2008/0241159 A1 | 10/2008 | Gerritsen et al. |
| 2009/0042906 A1 | 2/2009 | Huang et al. |
| 2010/0179094 A1 | 7/2010 | Emanuel et al. |
| 2010/0216708 A1 | 8/2010 | Jacobs et al. |
| 2010/0254989 A1 | 10/2010 | Bossenmaier et al. |
| 2011/0053842 A1 | 3/2011 | Camphausen et al. |
| 2011/0118144 A1 | 5/2011 | Hyun et al. |
| 2011/0274623 A1 | 11/2011 | Jacobs |
| 2011/0287009 A1 | 11/2011 | Scheer et al. |
| 2012/0225870 A1 | 9/2012 | Janne et al. |
| 2012/0244164 A1 | 9/2012 | Beste et al. |
| 2013/0226834 A1 | 8/2013 | Gannalo, II |

FOREIGN PATENT DOCUMENTS

| | | |
|---|---|---|
| WO | WO 2008/127710 A2 | 10/2008 |
| WO | WO 2009/085462 A1 | 7/2009 |
| WO | WO 2009/102421 A2 | 8/2009 |

(Continued)

OTHER PUBLICATIONS

Jacobs et al. (2012) Protein Engineering ed. By Pravin Kaumaya. pp. 145-162.*
PCT International Search Report dated May 19, 2014.
Supplemental Partial European Search Report dated May 20, 2016.
Adjei, et al., "Early Clinical Development of ARQ 197, a Selective, Non-ATP-Competitive Inhibitor Targeting MET Tyrosine Kinase for the Treatment of Advanced Cancers," the Oncologist, 16: 788-799 (2011).
Alfthan, et al., "Properties of a single-chain antibody containing different linker peptides," Protein Engineering, 8(7): 725-731 (1995).
Baselga, et al., "Critical Update and Emerging Trends in Epidermal Growth Factor Receptor Targeting in Cancer," Journal of Clinical Oncology, 23(11): 2445-2459 (2005).

(Continued)

*Primary Examiner* — Michael Pak
(74) *Attorney, Agent, or Firm* — Eric Dichter

(57) ABSTRACT

Monospecific and bispecific EGFR and/or c-Met FN3 domain containing molecules, isolated nucleotides encoding the molecules, vectors, host cells, and methods of making thereof are useful in the generation of therapeutic molecules and treatment and diagnosis of diseases and disorders.

13 Claims, 11 Drawing Sheets

(56) References Cited

FOREIGN PATENT DOCUMENTS

| WO | WO 2009/111691 A2 | 9/2009 |
|---|---|---|
| WO | WO 2009/126834 A2 | 10/2009 |
| WO | 2010/115551 A1 | 10/2010 |
| WO | WO 2010/039248 A1 | 10/2010 |
| WO | WO 2011/110642 A2 | 9/2011 |
| WO | WO 2011/131746 A2 | 10/2011 |
| WO | WO 2014/081954 A1 | 5/2014 |

OTHER PUBLICATIONS

Batley, et al., "Inhibition of FGF-1 Receptor Tyrosine Kinase Activity by PD 161570, a New Protein-Tyrosine Kinase Inhibitor," Life Sciences, 62(2): 143-150 (1998).
Bean, et al., "MET amplification occurs with or without T790M mutations in EGFR mutant lung tumors with acquired resistance to gefitinib or erlotinib," Proceedings of the National Academy of Science, 104(52): 20932-20937 (2007).
Berzofsky, et al., "Antigen-Antibody Interaction," Fundamental Immunology, Chapter 23, edited by W.E. Paul, 595-644 (1984).
Birtalan, et al., "The Intrinsic Contributions of Tyrosine, Serine, Glycine and Arginine to the Affinity and Specificity and Antibodies," Journal of Molecular Biology, 377: 1518-1528 (2008).
Bork, et al., Proposed acquisition of an animal protein domain by bacteria, Proceedings of the National Academy of Science, 89: 8990-8994 (1992).
Cappuzzo, et al., "Epidermal Growth Factor Receptor Gene and Protein and Gefitinib Sensitivity in Non-small-Cell Lung Cancer," Journal of the National Cancer Institute, 97: 643-655 (2005).
Christensen, et al., "c-Met as a target for human cancer and characterization of inhibitors for therapeutic intervention," Cancer Letters, 225: 1-26 (2005).
Cooper, et al., "Molecular cloning of a new transforming gene from a chemically transformed human cell line," Nature, 311: 29-33 (1984).
DeRoock, et al., "Effects of KRAS, BRAF, NRAS, and PIK3CA mutations on the efficacy of cetuximab plus chemotherapy in chemotherapy-refractory metastatic colorectal cancer: a retrospective consortium analysis," Lancet Oncology, 11: 753-762 (2010).
Downward, et al., "Autophosphorylation sites on the epidermal growth factor receptor," Nature, 311: 483-485 (1984).
Engelman, et al., "MET Amplification Leads to Gefitinib Resistance in Lung Cancer by Activating ERBB3 Signaling," Science, 316: 1039-1043 (2007).
Kathryn M. Ferguson, "Structure-Based View of Epidermal Growth Factor Receptor Regulation," Annual Review of Biophysics, 37: 535-373 (2008).
GenBank Accession No. NP_005219.
GenBank Accession No. NP_001120972.
Gill, et al., "Monoclonal Anti-epidermal Growth Factor Receptor Antibodies Which Are Inhibitors of Epidermal Growth Factor Binding and Antagonists of Epidermal Growth Factor-stimulated tyrosine Protein Kinase Activity," The Journal of Biological Chemistry, 259(12): 7755-7760 (1984).
Goldstein, et al., "Biological efficacy of a chimeric antibody to the epidermal growth factor receptor in a human tumor xenograft model," Clinical Cancer Research, 1: 1311-1318 (1995).
Viktor Grünwald, et al., "Developing Inhibitors of the Epidermal Growth Factor Receptor for Cancer Treatment," Journal of the National Cancer Institute, 95(12): 851-867 (2003).
Hallewell, et al., "Genetically Engineered Polymers of Human CuZN Superoxide Dismutase," The Journal of Biological Chemistry, 264(9): 5260-5268 (1989).
Hanes, et al., "*In vitro* selection and evaluation of functional proteins by using ribosome display," Proceedings of the National Academy of Science USA, 94: 4937-4942 (1997).
Hirsch, et al., "Combination of EGFR gene copy number and protein expression predicts outcome for advanced non-small-cell lung cancer patients treated with gefitinib," annals of Oncology, 18: 752-760 (2007).

Hynes, et al., "ERBB Receptors and Cancer: the Complexity of Targeted Inhibitors," Nature Reviews, 5: 341-356 (2005).
Ichimura, et al., "Expression of c-met/HGF Receptor in Human Non-small Cell Lung Carcinomas in vitro and in vivo and Its Prognostic Significance," Japan Journal of Cancer Research, 87: 1063-1069 (1996).
Jacobs, et al., "Design of novel FN3 domains with high stability by a consensus sequence approach," Protein Engineering, Design & Selection, 25(3): 107-117 (2012).
Jänne, et al., "Effect of Epidermal Growth Factor Receptor Tyrosine Kinase Domain Mutations on the Outcome of Patients with Non-small Cell Lung Cancer Treated with Epidermal Growth Factor Receptor Tyrosine Kinase Inhibitors," Clinical Cancer Research, 12(14 Suppl): 4416s-4420s (2006).
Lehmann, et al., "Engineering proteins for thermostability: the use of sequence alignments versus rational design and directed evolution," Current Opinion in Biotechnology, 12: 371-375 (2001).
Linardou, et al., "Somatic EGFR mutations and efficacy of tyrosine kinase inhibitors in NSCLC," National Review of Clinical Oncology, 6: 352-366 (2009).
Li, et al., "Skin toxicities associated with epidermal growth factor receptor inhibitors," Target Oncology, 4: 107-119 (2009).
Määttä, et al., "Proteolytic Cleavage and Phosphorylation of a Tumor-associated ErbB4 Isoform Promote Ligand-independent Survival and cancer Cell Growth," Molecular Biology, 17: 67-79 (2006).
Ma, et al., "c-Met: Structure, functions and potential for therapeutic inhibition," Cancer and Metastasis Reviews, 22: 309-325 (2003).
Meinke, et al., "Cellulose-Binding Polypeptides from Cellulomonas fimi: Endoglucanase D (CenD), a Family A β-1,4-Glucanase, " Journal of Bacteriology, 175(7): 1910-1918 (1993).
Mendelsohn, et al., "Epidermal Growth Factor Receptor Targeting in Cancer," Seminars in Oncology, 33: 369-385 (2006).
Mendelsohn, et al., "The EGF receptor family as targets for cancer therapy," Oncogene, 19: 6550-6565 (2000).
Nakata, et al., "Recent understanding of the molecular mechanisms for the efficacy and resistance of EGF receptor-specific tyrosine kinase inhibitors in non-small cell lung cancer," Expert Opinions in Therapeutic Targets, 16(8): 771-781 (2012).
Odegrip, et al., "CIS display: In vitro selection of peptides from libraries or protein-DNA complexes," Proceedings of the National Academy of Science USA, 101(9): 2806-2810 (2004).
Olson, et al., "Design, expression, and stability of a diverse protein library based on the human fibronectin type III domain," Protein Science, 16: 476-484 (2007).
Panek, et al.,"In Vitro Pharmacological Characterization of PD 166285, a New Nanomolar Potent and Broadly Active Protein Tyrosine Kinase Inhibitor," The Journal of Pharmacology and Experimental Therapeutics, 283(3): 1433-1444 (1997).
Peters, et al., "MET: a promising anticancer therapeutic target," National Review of Clinical Oncology, 9: 314-326 (2012).
Prewett, et al., "Mouse-Human chimeric Anti-Epidermal Growth Factor Receptor Antibody C225 Inhibits the Growth of Human Renal Cell Carcinoma Xenografts in Nude Mice," Clinical Cancer Research, 4: 2957-2966 (1998).
Riely, et al., "Clinical Course of Patients with Non-Small Cell Lung Cancer and Epidermal Growth Factor Receptor Exon 19 and Exon 21 Mutations Treated with Gefitinib or Erlotinib," Clinical Cancer Research, 12(3): 839-844 (2006).
Roberts, et al., "RNA-peptide fusions for the in vitro selection of peptides and proteins," Proceedings of the National Academy of Science USA, 94: 12297-12302 (1997).
Robinson, et al., "Covalent Attachment of Arc Repressor Subunits by a Peptide Linker Enhances Affinity for Operator DNA," Biochemistry, 35: 109-116 (1996).
Sakakura, et al., "Gains, Losses, and amplifications of Genomic Materials in Primary Gastric Cancers Analyzed by Comparative Genomic Hybridization," Genes, Chromosomes & Cancer, 24: 299-305 (1999).

(56) References Cited

OTHER PUBLICATIONS

Schmidt, et al., "Novel mutations of the MET proto-oncogene in papillary renal carcinomas," Oncogene, 18: 2343-2350 (1999).

Siegfried, et al., "The Clinical Significance of Hepatocyte Growth Factor for Non-Small Cell Lung Cancer," Annals of Thoracic Surgeons, 66: 1915-1918 (1998).

Sierra, et al., "c-MET as a potential therapeutic target and biomarker in cancer," Therapeutic Advances in Medical Oncology, 3(S1): S21-S25 (2011).

Stamos, et al., "Crystal structure of the HGF β-chain in complex with the Sema domain of the Met receptor," The EMBO Journal, 23: 2325-2335 (2004).

SwissProt Accession No. P00533.

William R Strobl, "Optimization of Fc-mediated effector functions of monoclonal antibodies," Current Opinion in Biotechnology, 20: 685-691 (2009).

Turke, et al., "Preexistence and Clonal Selection of MET Amplification in EGFR Mutant NSCLC," Cancer Cell, 17: 77-88 (2010).

Ullrich, et al., "Human epidermal growth factor receptor cDNA sequence and aberrant expression of the amplified gene in A431 epidermoid carcinoma cells," Nature, 309: 418-425 (1984).

Watanabe, et al., "Gene cloning of chitinase A1 from Bacillus circulans WL-12 revealed its evolutionary relationship to Serratia chitinase and to the type III homology units of fibronectin," Journal of Biological Chemistry, 265: 15659-15665 (1990).

Zucali, et al., "Role of cMET expression in non-small-cell lung cancer patients treated with Egfr tyrosine kinase inhibitors," Annals of Oncology, 19(0): 1605-1612 (2008).

\* cited by examiner

Figure 1A.

| SEQ ID NO: | | |
|---|---|---|
| 18 | LPAPKNLVVSEVTEDSLRLRLSWADP-HGFYDSFLIQYQESEKVGEAINLTVPGSERSYDLTG | (60) |
| 19 | LPAPKNLVVSEVTEDSLRLRLSWTYD-RDGYDSFLIQYQESEKVGEAINLTVPGSERSYDLTG | |
| 20 | LPAPKNLVVSEVTEDSLRLSWGYN-GDHFDSFLIQYQESEKVGEAINLTVPGSERSYDLTG | |
| 21 | LPAPKNLVVSEVTEDSLRLSWDDP-RGFYESFLIQYQESEKVGEAINLTVPGSERSYDLTG | |
| 22 | LPAPKNLVVSEVTEDSLRLSWTWP-YADLDSFLIQYQESEKVGEAINLTVPGSERSYDLTG | |
| 23 | LPAPKNLVVSEVTEDSLRLSWGYN-GDHFDSFLIQYQESEKVGEAINLTVPGSERSYDLTG | |
| 24 | LPAPKNLVVSEVTEDSLRLSWDYDLGDHFDSFLIQYQESEKVGEAINLTVPGSERSYDLTG | |
| 25 | LPAPKNLVVSEVTEDSLRLSWDDP-WAFYESFLIQYQESEKVGEAINLTVPGSERSYDLTG | |
| 27 | LPAPKNLVVSEVTEDSARLSWDDP-WAFYESFLIQYQESEKVGEAIVLTVPGSERSYDLTG | |
| 29 | LPAPKNLVVSEVTEDSLRLSWTWP-YADLDSFLIQYQESEKVGEAIVLTVPGSERSYDLTG | |
| 107 | LPAPKNLVVSEVTEDSARLSWADP-HGFYDSFLIQYQESEKVGEAIVLTVPGSERSYDLTG | |
| 108 | LPAPKNLVVSEVTEDSARLSWDDP-WAFYESFLIQYQESEKVGEAIVLTVPGSERSYDLTG | |
| 109 | LPAPKNLVVSEVTEDSARLSWDDP-HAFYESFLIQYQESEKVGEAIVLTVPGSERSYDLTG | |
| 110 | LPAPKNLVVSEVTEDSARLSWADP-HGFYDSFLIQYQESEKVGEAIVLTVPGSERSYDLTG | |
| | ******************: * ******:******** | |

| 18 | LKPGTEYTVSIYGVHNVYKDTNMRGLPLSAEFTT | (94) |
|---|---|---|
| 19 | LKPGTEYTVSIYGVHNVYKDTNMRGLPLSAEFTT | |
| 20 | LKPGTEYTVSIYGVHNVYKDTNMRGLPLSAEFTT | |
| 21 | LKPGTEYTVSIYGVHNVYKDTNMRGLPLSAEFTT | |
| 22 | LKPGTEYTVSIYGVHNVYKDTNMRGLPLSAEFTT | |
| 23 | LKPGTEYTVSIYGVHNVYKDTNMRGLPLSAEFTT | |
| 24 | LKPGTEYTVSIYGVHNVYKDTNMRGLPLSAEFTT | |
| 25 | LKPGTEYTVSIYGVHNVYKDTNMRGLPLSAEFTT | |
| 27 | LKPGTEYTVSIYGVHNVYKDTNMRGLPLSAEFTT | |
| 29 | LKPGTEYTVSIYGVHNVYKDTNMRGLPLSAIFTT | |
| 107 | LKPGTEYTVSIYGVHNVYKDTNMRGLPLSAIFTT | |
| 108 | LKPGTEYTVSIYGVHNVYKDTNMRGLPLSAIFTT | |
| 109 | LKPGTEYTVSIYGVHNVYKDTNIRGLPLSAIFTT | |
| 110 | LKPGTEYTVSIYGVHNVYKDTNIRGLPLSAIFTT | |
| | *************.*****:*:* | |

Figure 1B

| SEQ ID NO: | | |
|---|---|---|
| 26 | LPAPKNLVVSEVTEDSLRLSWTAP-DAAFDSFLIQYQESEKVGEAINLTVPGSERSYDLTG | (60) |
| 28 | LPAPKNLVVSEVTEDSARLSWTAP-DAAFDSFLIQYQESEKVGEAIVLTVPGSERSYDLTG | |
|    | ********************* ***************************** ****** | |
| 26 | LKPGTEYTVSIYGVLGSYVFEHDVMLPLSAEFTT | (94) |
| 28 | LKPGTEYTVSIYGVLGSYVFEHDVMLPLSAIFTT | |
|    | ****************************** *** | |

Figure 2.

```
               A          AB    B         BC
TENCON27 (1)  LPAPKNLVVSRV TEDS ARLSW TAPDAAFDS  (30)
TCL14    (1)  LPAPKNLVVSRVTEDSARLSWTAPDAAFDS     (30)

C          CD    D       DE  E
TENCON27 (31) FLIQYQE SEKVGE AIVLTVP GSER SYDLTG  (60)
TCL14    (31) FXIXYXEXXXXGEAIVLTVPGSERSYDLTG      (60)

EF         F     FG        G
TENCON27 (61) LKPG TEYTVSIYGV KGGHRSN PLSAIFTT    (89)
TCL14    (61) LKPGTEYXVXIXGVKGGXXSXPLSAIFTT       (89)
```

Figure 3.

| SEQ ID NO: | Sequence | |
|---|---|---|
| 32 | LPAPKNLVVSRVTEDSARLSWTAPDAAFDSFWIRYDEVVGGEAIVLTVPGSERSYDLTG | (60) |
| 33 | LPAPKNLVVSRVTEDSARLSWTAPDAAFDSFEIRYDEFLRSGEAIVLTVPGSERSYDLTG | |
| 34 | LPAPKNLVVSRVTEDSARLSWTAPDAAFDSFWIRYFEFLGSSGEAIVLTVPGSERSYDLTG | |
| 35 | LPAPKNLVVSRVTEDSARLSWTAPDAAFDSFWIRYFEFLGSSGEAIVLTVPGSERSYDLTG | |
| 36 | LPAPKNLVVSRVTEDSARLSWTAPDAAFDSFVIRYFEFLGSSGEAIVLTVPGSERSYDLTG | |
| 37 | LPAPKNLVVSRVTEDSARLSWTAPDAAFDSFWIRYLEFLLGGEAIVLTVPGSERSYDLTG | |
| 38 | LPAPKNLVVSRVTEDSARLSWTAPDAAFDSFWIRYFEFLGSSGEAIVLTVPGSERSYDLTG | |
| 39 | LPAPKNLVVSRVTEDSARLSWTAPDAAFDSFWIRYFEFLGSSGEAIVLTVPGSERSYDLTD | |
| 40 | LPAPKNLVVSRVTEDSARLSWTAPDAAFDSFWIRYFEFLGSSGEAIVLTVPGSERSYDLTG | |
| 41 | LPAPKNLVVSRVTEDSARLSWTAPDAAFDSFWIRYFEFLGSSGEAIVLTVPGSERSYDLTG | |
| 42 | LPAPKNLVVSRVTEDSARLSWTAPDAAFDSFWIRYFEFLGSSGEAIVLTVPGSERSYDLTG | |
| 43 | LPAPKNLVVSRVTEDSARLSWTAPDAAFDSFWIRYFEFLGSSGEAIVLTVPGSERSYDLTG | |
| 44 | LPAPKNLVVSRVTEDSARLSWTAPDAAFDSFWIRYFEFLGSSGEAIVLTVPGSERSYDLTG | |
| 45 | LPAPKNLVVSRVTEDSARLSWTAPDAAFDSFWIRYFEFLGSSGEAIVLTVPGSERSYDLTG | |
| 46 | LPAPKNLVVSRVTEDSARLSWTAPDAAFDSFWIRYFEFLGSSGEAIVLTVPGSERSYDLTG | |
| 47 | LPAPKNLVVSRVTEDSARLSWTAPDAAFDSFWIRYFEFTTAGEAIVLTVPGSERSYDLTG | |
| 48 | LPAPKNLVVSRVTEDSARLSWTAPDAAFDSFWIRYFELLSTGEAIVLTVPGSERSYDLTG | |
| 49 | LPAPKNLVVSRVTEDSARLSWTAPDAAFDSFWIRYFEFVSKGEAIVLTVPGSERSYDLTG | |
| 111 | LPAPKNLVVSRVTEDSARLSWTAPDAAFDSFWIRYFEFLGSSGEAIVLTVPGSERSYDLTG | |
| 112 | LPAPKNLVVSRVTEDSARLSWTAPDAAFDSFWIRYFEFVGSSGEAIVLTVPGSERSYDLTG | |
| 113 | LPAPKNLVVSRVTEDSARLSWTAPDAAFDSFWIRYFEFVSKGDAIVLTVPGSERSYDLTG | |
| 114 | LPAPKNLVVSRVTEDSARLSWTAPDAAFDSFWIRYFEFLGSSGEAIVLTVPGSERSYDLTG | |
|  | ************************************* *  *  **  ************ | |

Figure 3 (continued)

| SEQ ID NO: | Sequence | |
|---|---|---|
| 32 | LKPGTEYYVNILGVKGGSISVPLSAIFTT | |
| 33 | LKPGTEYWTILGVKGGLVSTPLSAIFTT | |
| 34 | LKPGTEYIVNIMGVKGGSISHPLSAIFTT | |
| 35 | LKPGTEYVVNILGVKGGGLSVPLSAIFTT | |
| 36 | LKPGTEYVVQILGVKGGYISIPLSAIFTT | |
| 37 | LKPGTEYVVQIMGVKGGTVSPPLSAIFTT | |
| 38 | LKPGTEYVVGINGVKGGYISYPLSAIFTT | |
| 39 | LKPGTEYGVTINGVKGGRVSTPLSAIFTT | |
| 40 | LKPGTEYVVQIIGVKGGHISLPLSAIFTT | |
| 41 | LKPGTEYVVNIMGVKGGKISPPLSAIFTT | |
| 42 | LKPGTEYAVNIMGVKGGRVSVPLSAIFTT | |
| 43 | LKPGTEYVVQILGVKGGSISVPLSAIFTT | |
| 44 | LKPGTEYVVNIMGVKGGSISYPLSAIFTT | |
| 45 | LKPGTEYVVQILGVKGGYISIPLSAIFTT | |
| 46 | LKPGTEYVVQIMGVKGGTVSPPLSAIFTT | |
| 47 | LKPGTEYVVNIMGVKGGSISPPLSAIFTT | |
| 48 | LKPGTEYVVNIMGVKGGKISPPLSAIFTT | |
| 49 | LKPGTEYVVNILGVKGGSISPPLSAIFTT | |
| 111 | LKPGTEYVVNIMGVKGGSISPPLSAIFTT | |
| 112 | LKPGTEYVVNILGVKGGSISPPLSAIFTT | |
| 113 | LKPGTEYVVNILGVKGGSISPPLSAIFTT | |
| 114 | LKPGTEYVVNILSVKGGSISPPLSAIFTT | (89) |
|  | ****.* * * ****.* ****** | |

EGFR AND C-MET FIBRONECTIN TYPE III DOMAIN BINDING MOLECULES

CROSS REFERENCE TO RELATED APPLICATIONS

This application claims the benefit of U.S. Provisional Application No. 61/728,906, filed 21 Nov. 2012, U.S. Provisional Application No. 61/728,914, filed 21 Nov. 2012, U.S. Provisional Application No. 61/728,912, filed 21 Nov. 2012, U.S. Provisional Application No. 61/782,550, filed 14 Mar. 2013 and U.S. Provisional Application No. 61/809,541, filed 8 Apr. 2013, the entire contents of which are incorporated herein by reference.

FIELD OF THE INVENTION

The present invention relates to monospecific or bispecific EGFR and/or c-Met binding molecules and methods of making and using the molecules.

BACKGROUND OF THE INVENTION

Epidermal growth factor receptor (EGFR, ErbB1 or HER1) is a transmembrane glycoprotein of 170 kDa that is encoded by the c-erbB1 proto-oncogene. EGFR is a member of the human epidermal growth factor receptor (HER) family of receptor tyrosine kinases (RTK) which includes HER2 (ErbB2), HER3 (ErbB3) and HER4 (ErbB4). EGFR signaling is initiated by ligand binding followed by induction of conformational change, homodimerization or heterodimerization of the receptor with other ErbB family members, and trans-autophosphorylation of the receptor (Ferguson et al., Annu Rev Biophys, 37: 353-73, 2008), which initiates a signal transduction cascades that ultimately affects a wide variety of cellular functions, including cell proliferation and survival. Increases in expression or kinase activity of EGFR have been linked with a range of human cancers, making EGFR an attractive target for therapeutic intervention (Mendelsohn et al., Oncogene 19: 6550-6565, 2000; Grünwald et al., J Natl Cancer Inst 95: 851-67, 2003; Mendelsohn et al., Semin Oncol 33: 369-85, 2006). Increases in both the EGFR gene copy number and protein expression have been associated with favorable responses to the EGFR tyrosine kinase inhibitor, IRESSA™ (gefitinib), in non-small cell lung cancer (Hirsch et al., Ann Oncol 18:752-60, 2007).

EGFR therapies include both small molecules and anti-EGFR antibodies, approved for treatment of colorectal cancer, pancreatic cancer, head and neck cancer, and non-small cell lung cancer (NSCLC) (Baselga and Arteaga, J Clin Oncol 23:2445-2459 (20005; Gill et al., J Biol Chem, 259:7755-7760, 1984; Goldstein et al., Clin Cancer Res, 1:1311-1318; 1995; Prewett et al., Clin Cancer Res, 4:2957-2966, 1998).

Efficacy of anti-EGFR therapies may depend on tumor type and EFGR mutation/amplification status in the tumor. Side effects of current therapeutics may include skin toxicity (De Roock et al., Lancet Oncol 11:753-762, 2010; Linardou et al., Nat Rev Clin Oncol, 6: 352-366, 2009; Li and Perez-Soler, Targ Oncol 4: 107-119, 2009). EGFR tyrosine kinase inhibitors (TKI) are commonly used as $2^{nd}$ line therapies for non small cell lung cancer (NSCLC), but often stop working within twelve months due to resistance pathways (Riely et al., Clin Cancer Res 12: 839-44, 2006).

c-Met encodes a tyrosine kinase receptor. It was first identified as a proto-oncogene in 1984 after it was found that treatment with a carcinogen resulted in a constitutively active fusion protein TPR-MET (Cooper et al., Nature 311:29-33, 1984). Activation of c-Met by its ligand hepatocyte growth factor (HGF) stimulates a plethora of cell processes including growth, motility, invasion, metastasis, epithelial-mesenchymal transition, angiogenesis/wound healing, and tissue regeneration (Christensen et al., Cancer Lett 225:1-26, 2005; Peters and Adjei, Nat Rev Clin Oncol 9:314-26, 2012). c-Met is synthesized as a single chain protein that is proteolytically cleaved into a 50 kDa alpha- and 140 kDa beta-subunit linked by a disulphide bond (Ma et al., Cancer and Metastasis Reviews, 22: 309-325, 2003). c-Met is structurally similar to other membrane receptors such as Ron and. The exact stoichiometry of HGF:c-Met binding is unclear, but it is generally believed that two HGF molecules bind to two c-Met molecules leading to receptor dimerization and autophosphorylation at tyrosines 1230, 1234, and 1235 (Stamos et al., The EMBO Journal 23: 2325-2335, 2004). Ligand-independent c-Met autophosphorylation can also occur due to gene amplification, mutation or receptor over-expression.

c-Met is frequently amplified, mutated or over-expressed in many types of cancer including gastric, lung, colon, breast, bladder, head and neck, ovarian, prostate, thyroid, pancreatic, and CNS cancers. Missense mutations typically localized to the kinase domain are commonly found in hereditary papillary renal carcinomas (PRCC) and in 13% of sporadic PRCCs (Schmidt et al., Oncogene 18: 2343-2350, 1999). c-Met mutations localized to the semaphorin or juxtamembrane domains of c-Met are frequently found in gastric, head and neck, liver, ovarian, NSCLC and thyroid cancers (Ma et al., Cancer and Metastasis Reviews, 22: 309-325, 2003; Sakakura et al., Chromosomes and Cancer, 1999. 24:299-305). c-Met amplification has been detected in brain, colorectal, gastric, and lung cancers, often correlating with disease progression (Ma et al., Cancer and Metastasis Reviews, 22: 309-325, 2003). Up to 4% and 20% of non-small cell lung cancer (NSCLC) and gastric cancers, respectively, exhibit c-Met amplification (Sakakura et al., Chromosomes and Cancer, 1999. 24:299-305: Sierra and Tsao, Therapeutic Advances in Medical Oncology, 3:S21-35, 2011). Even in the absence of gene amplification, c-Met overexpression is frequently observed in lung cancer (Ichimura et al., Jpn J Cancer Res, 87:1063-9, 1996). Moreover, in clinical samples, nearly half of lung adenocarcinomas exhibited high levels of c-Met and HGF, both of which correlated with enhanced tumor growth rate, metastasis and poor prognosis (Sierra and Tsao, Therapeutic Advances in Medical Oncology, 3:S21-35, 2011; Siegfried et al., Ann Thorac Surg 66: 1915-8, 1998).

Nearly 60% of all tumors that become resistant to EGFR tyrosine kinase inhibitors increase c-Met expression, amplify c-Met, or increase its only known ligand, HGF (Turke et al., Cancer Cell, 17:77-88, 2010), suggesting the existence of a compensatory pathway for EGFR through c-Met. c-Met amplification was first identified in cultured cells that became resistant to gefinitib, an EGFR kinase inhibitor, and exhibited enhanced survival through the Her3 pathway (Engelman et al., Science, 316:1039-43, 2007). This was further validated in clinical samples where nine of 43 patients with acquired resistance to either erlotinib or gefitinib exhibited c-Met amplification, compared to only two of 62 untreated patients. Four of the nine treated patients also acquired the EGFR activating mutation, T790M, demonstrating simultaneous resistance pathways (Beat et al., Proc Natl Acad Sci USA, 104:20932-7, 2007).

The individual roles of both EGFR and c-Met in cancer is well established, making these targets attractive for combination therapy. Both receptors signal through the same survival and anti-apoptotic pathways (ERK and AKT); thus, inhibiting the pair in combination may limit the potential for compensatory pathway activation thereby improving overall efficacy. Combination therapies targeting EGFR and c-Met are tested in clinical trials with Tarceva® (erlotinib) in combination with anti-c-Met monovalent antibody for NSCL (Spigel et al., 2011 ASCO Annual Meeting Proceedings 2011, Journal of Clinical Oncology: Chicago, Ill. p. 7505) and Tarceva (erlotinib) in combination with ARQ-197, a small molecule inhibitor of c-Met (Adjei et al., Oncologist, 16:788-99, 2011). Combination therapies or bispecific anti-EGFR/c-Met molecules have been disclosed for example in: Int. Pat. Publ. No. WO2008/127710, U.S. Pat. Publ. No. US2009/0042906, Int. Pat. Publ. No. WO2009/111691, Int. Pat. Publ. No. WO2009/126834, Int. Pat. Publ. No. WO2010/039248, Int. Pat. Publ. No. WO2010/115551.

Current small molecule and large molecule therapeutic approaches to antagonize EGFR and/or c-Met signaling pathways for therapy may be sub-optimal due to possible lack of specificity, potential off-target activity and dose-limiting toxicity that may be encountered with small molecule inhibitors. Typical bivalent antibodies may result in clustering of membrane bound receptors and unwanted activation of the downstream signaling pathways. Monovalent antibodies (half arms) pose significant complexity and cost to the manufacturing process.

Accordingly, the need exists for additional monospecific and bispecific EGFR and/or c-Met inhibitors for both therapeutic and diagnostic purpose.

SUMMARY OF THE INVENTION

One aspect of the invention is an isolated bispecific FN3 domain containing molecule comprising a first fibronectin type III (FN3) domain and a second FN3 domain, wherein the first FN3 domain specifically binds epidermal growth factor receptor (EGFR) and blocks binding of epidermal growth factor (EGF) to EGFR, and the second FN3 domain specifically binds hepatocyte growth factor receptor (c-Met), and blocks binding of hepatocyte growth factor (HGF) to c-Met.

Another aspect of the invention is an isolated bispecific FN3 domain containing molecule comprising a first fibronectin type III (FN3) domain and a second FN3 domain wherein the first FN3 domain comprises an amino acid sequence at least 87% identical to the amino acid sequence of SEQ ID NO: 27, and the second FN3 domain comprises an amino acid sequence at least 83% identical to the amino acid sequence of SEQ ID NO: 41.

In other embodiments, the invention provides for bispecific EGFR/c-Met binding and monospecific EGFR or c-Met binding FN3 domain containing molecules having certain sequences.

Another aspect of the invention is an isolated fibronectin type III (FN3) domain that specifically binds epidermal growth factor receptor (EGFR) and blocks binding of epidermal growth factor (EGF) to EGFR, wherein the FN3 domain is isolated from a library designed based on the Tencon amino acid sequence of SEQ ID NO: 1.

Another aspect of the invention is an isolated fibronectin type III (FN3) domain that specifically binds hepatocyte growth factor receptor (c-Met) and blocks binding of hepatocyte growth factor (HGF) to c-Met.

Another aspect of the invention is an isolated polynucleotide encoding the molecule of the invention. Another aspect of the invention is a vector comprising the polynucleotide of the invention.

Another aspect of the invention is a host cell comprising the vector of the invention Another aspect of the invention is a method of producing a bispecific molecule, comprising culturing the isolated host cell of the invention under conditions such that the bispecific molecule is expressed, and purifying the bispecific molecule.

Another aspect of the invention is a pharmaceutical composition comprising the molecule of the invention and a pharmaceutically acceptable carrier.

Another aspect of the invention is a method of treating a subject having cancer, comprising administering a therapeutically effective amount of the bispecific EGFR/c-Met FN3 domain containing molecule or the EGFR or c-Met binding FN3 domain to a patient in need thereof for a time sufficient to treat cancer.

BRIEF DESCRIPTION OF THE DRAWINGS

FIGS. 1A and 1B. Amino acid alignment of the EGFR-binding FN3 domains. The BC and FG loops are boxed at residues 22-28 and 75-86 of SEQ ID NO: 18. Some variants include thermal stability improving L17A, N46K and E86I substitutions (residue numbering according to Tencon SEQ ID NO: 1). P54AR4-83v2 (SEQ ID NO: 27) paratope residues are underlined (D23, F27, Y28, V77, G85 in SEQ ID NO: 27).

FIG. 2. Sequence alignment of the Tencon27 scaffold (SEQ ID NO: 99) and a TCL14 library (SEQ ID NO: 100) having randomized C-CD-F-FG alternative surface. The loop residues are boxed. Loops and strands are indicated above the sequences.

FIG. 3. Sequence alignment of the c-Met-binding FN3 domains. The C loop and the CD strand and the F loop and the FG strand are boxed and span residues 29-43 and 65-81. P114AR7P95-A3 (SEQ ID NO: 41) paratope residues are underlined (R34S, F38S, M72S and I79S).

DETAILED DESCRIPTION OF THE INVENTION

Figure 4:
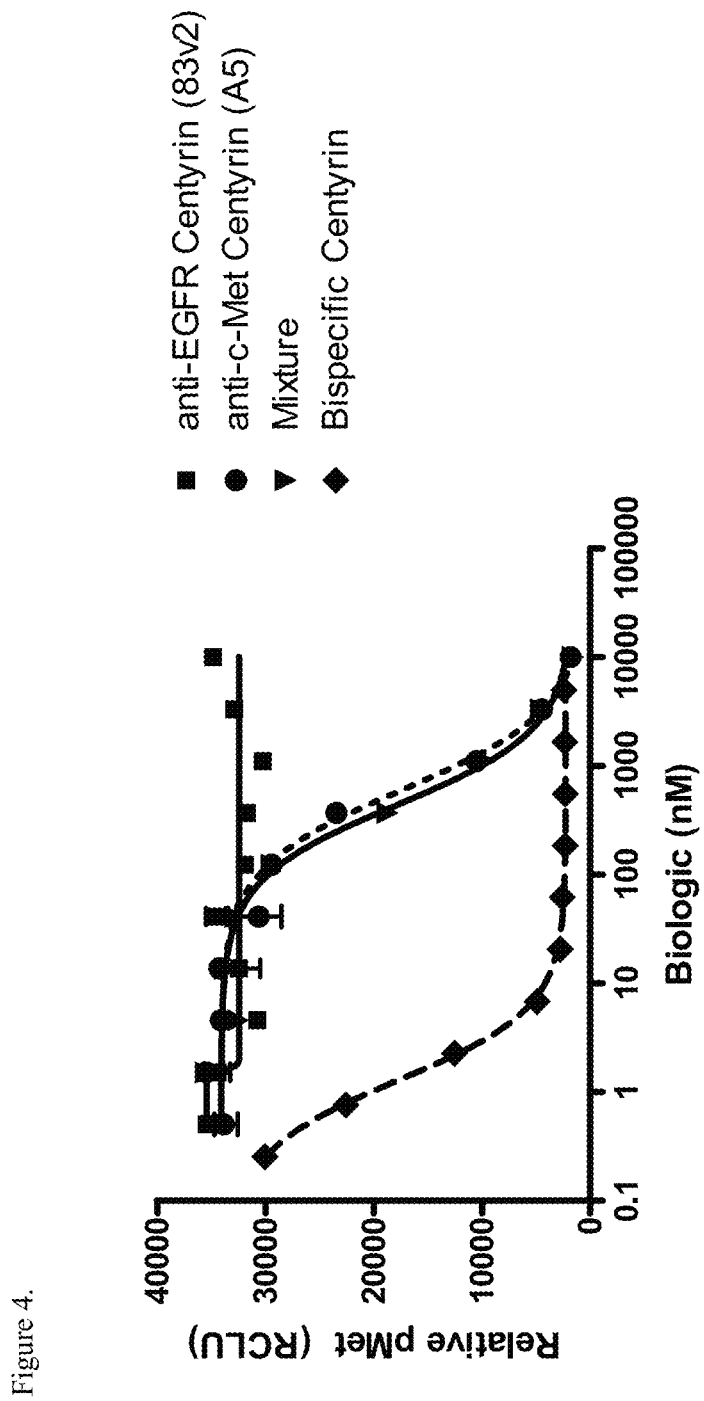
FIG. 4. Inhibition of c-Met phosphorylation in H292 cells pre-treated with monospecific or bispecific FN3 domain containing molecules and stimulated with HGF is shown. Substantial increase in the potency of the bispecific EGFR/c-Met molecule (ECB1) was observed when compared to a monospecific c-Met-binding FN3 domain (P114AR5P74-A5, shown as A5 in the Figure) on its own or in combination with an EGFR-binding FN3 domain (P54AR4-83v2, shown as 83v2 in the Figure).

The term "fibronectin type III (FN3) domain" (FN3 domain) as used herein refers to a domain occurring frequently in proteins including fibronectins, tenascin, intracellular cytoskeletal proteins, cytokine receptors and prokaryotic enzymes (Bork and Doolittle, Proc Nat Acad Sci USA 89:8990-8994, 1992; Meinke et al., J Bacteriol 175:1910-1918, 1993; Watanabe et al., J Biol Chem 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. Publ. No. 2010/0216708. Individual FN3 domains are referred to by domain number and protein name, e.g., the 3$^{rd}$ FN3 domain of tenascin (TN3), or the 10$^{th}$ FN3 domain of fibronectin (FN10).

The term "substituting" or "substituted" or 'mutating" or "mutated" as used herein refers to altering, deleting of inserting one or more amino acids or nucleotides in a polypeptide or polynucleotide sequence to generate a variant of that sequence.

The term "randomizing" or "randomized" or "diversified" or "diversifying" as used herein refers to making at least one substitution, insertion or deletion in a polynucleotide or polypeptide sequence.

"Variant" as used herein refers to a polypeptide or a polynucleotide that differs from a reference polypeptide or a reference polynucleotide by one or more modifications for example, substitutions, insertions or deletions.

The term "specifically binds" or "specific binding" as used herein refers to the ability of the FN3 domain of the invention to bind to a predetermined antigen with a dissociation constant ($K_D$) of about $1 \times 10^{-6}$ M or less, for example about $1 \times 10^{-7}$ M or less, about $1 \times 10^{-8}$ M or less, about $1 \times 10^{-9}$ M or less, about $1 \times 10^{-16}$ M or less, about $1 \times 10^{-11}$ M or less, about $1 \times 10^{-12}$ M or less, or about $1 \times 10^{-13}$ M or less. Typically the FN3 domain of the invention binds to a predetermined antigen (i.e. EGFR or c-Met) with a $K_D$ that is at least ten fold less than its $K_D$ for a nonspecific antigen (for example BSA or casein) as measured by surface plasmon resonance using for example a Proteon Instrument (BioRad). Thus, a bispecific EGFR/c-Met FN3 domain containing molecule of the invention specifically binds to each EGFR and c-Met with a binding affinity ($K_D$) of at least $1 \times 10^{-6}$ M or less for both EGFR and c-Met. The isolated FN3 domain of the invention that specifically binds to a predetermined antigen may, however, have cross-reactivity to other related antigens, for example to the same predetermined antigen from other species (homologs).

The term "library" refers to a collection of variants. The library may be composed of polypeptide or polynucleotide variants.

The term "stability" as used herein refers to the ability of a molecule to maintain a folded state under physiological conditions such that it retains at least one of its normal functional activities, for example, binding to a predetermined antigen such as EGFR or c-Met.

"Epidermal growth factor receptor" or "EGFR" as used here refers to the human EGFR (also known as HER-1 or Erb-B1 (Ullrich et al., Nature 309:418-425, 1984) having the sequence shown in SEQ ID NO: 73 and in GenBank accession number NP_005219, as well as naturally-occurring variants thereof. Such variants include the well known EGFRvIII and other alternatively spliced variants (e.g., as identified by SwissProt Accession numbers P00533-1 (wild type; identical to SEA ID NO: 73 and NP_005219), P00533-2 (F404L/L4055), P00533-3 (628-705: CTGPG-LEGCP . . . GEAPNQALLR→PGNESLKAML . . . SVII-TASSCH and 706-1210 deleted), P00533-4 (C628S and 629-1210 deleted), variants Q98, 8266, K521, I674, G962, and P988 (Livingston et al., NIEHS-SNPs, environmental genome project, NIEHS ES15478), T790M, L858R/T790M and del(E746, A750).

"EGFR ligand" as used herein encompasses all (e.g., physiological) ligands for EGFR, including EGF, TGF-α, heparin binding EGF (HB-EGF), amphiregulin (AR), and epiregulin (EPI).

"Epidermal growth factor" (EGF) as used herein refers to the well known 53 amino acid human EGF having an amino acid sequence shown in SEQ ID NO: 74.

"Hepatocyte growth factor receptor" or "c-Met" as used herein refers to the human c-Met having the amino acid sequence shown in SEQ ID NO: 101 or in GenBank Accession No: NP_001120972 and natural variants thereof.

"Hepatocyte growth factor" (HGF) as used herein refers to the well known human HGF having the amino acid sequence shown in SEQ ID NO: 102 which is cleaved to form a dimer of an alpha and beta chain linked by a disulfide bond.

"Blocks binding" or "inhibits binding", as used herein interchangeably refers to the ability of the FN3 domains of the invention of the bispecific EGFR/c-Met FN3 domain containing molecule to block or inhibit binding of the EGFR ligand such as EGF to EGFR and/or HGF to c-Met, and encompass both partial and complete blocking/inhibition. The blocking/inhibition of EGFR ligand such as EGF to EGFR and/or HGF to c-Met by the FN3 domain or the bispecific EGFR/c-Met FN3 domain containing molecule of the invention reduces partially or completely the normal level of EGFR signaling and/or c-Met signaling when compared to the EGFR ligand binding to EGFR and/or HGF binding to c-Met without blocking or inhibition. The FN3 domain or the bispecific EGFR/c-Met FN3 domain containing molecule of the invention "blocks binding" of the EGFR ligand such as EGF to EGFR and/or HGF to c-Met when the inhibition is at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% Inhibition of binding can be measured using well known methods, for example by measuring inhibition of binding of biotinylated EGF on EGFR expressing A431 cells exposed to the FN3 domain or the bispecific EGFR/c-Met FN3 domain containing molecule of the invention using FACS, and using methods described herein, or measuring inhibition of binding of biotinylated HGF on c-Met extracellular domain using well known methods and methods described herein.

The term "EGFR signaling" refers to signal transduction induced by EGFR ligand binding to EGFR resulting in autophosphorylation of at least one tyrosine residue in the EGFR. An exemplary EGFR ligand is EGF.

"Neutralizes EGFR signaling" as used herein refers to the ability of the FN3 domain of the invention to inhibit EGFR signaling induced by EGFR ligand such as EGF by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100%.

The term "c-Met signaling" refers to signal transduction induced by HGF binding to c-Met resulting in autophosphorylation of at least one tyrosine residue in the c-Met. Typically at least one tyrosine residue at positions 1230, 1234, 1235 or 1349 is autophosphorylated upon HGF binding.

"Neutralizes c-Met signaling" as used herein refers to the ability of the FN3 domain of the invention to inhibit c-Met signaling induced by HGF by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100%.

"Overexpress", "overexpressed" and "overexpressing" as used herein interchangeably refer to a cancer or malignant cell that has measurably higher levels of EGFR and/or c-Met on the surface compared to a normal cell of the same tissue type. Such overexpression may be caused by gene amplification or by increased transcription or translation. EGFR and/or c-Met expression and overexpression can be measured using well know assays using for example ELISA, immunofluorescence, flow cytometry or radioimmunoassay on live or lysed cells. Alternatively, or additionally, levels of EGFR and/or c-Met-encoding nucleic acid molecules may be measured in the cell for example using fluorescent in situ hybridization, Southern blotting, or PCR techniques. EGFR and/or c-Met is overexpressed when the level of EGFR and/or c-Met on the surface of the cell is at least 1.5-fold higher when compared to the normal cell.

"Tencon" as used herein refers to the synthetic fibronectin type III (FN3) domain having the sequence shown in SEQ ID NO: 1 and described in U.S. Pat. Publ. No. US2010/0216708.

A "cancer cell" or a "tumor cell" as used herein refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is exemplified by, e.g., morphological changes, immortalization of cells, aberrant growth control, foci formation, proliferation, malignancy, tumor specific markers levels, invasiveness, tumor growth or suppression in suitable animal hosts such as nude mice, and the like, in vitro, in vivo, and ex vivo (Freshney, Culture of Animal Cells: A Manual of Basic Technique (3rd ed. 1994)).

The term "vector" means a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or in a reconstituted biological system to direct the translation of a polypeptide encoded by a polynucleotide sequence present in the expression vector.

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "polypeptide" or "protein" means a molecule that comprises at least two amino acid residues linked by a peptide bond to form a polypeptide. Small polypeptides of less than about 50 amino acids may be referred to as "peptides".

The term "bispecific EGFR/c-Met molecule" or "bispecific EGFR/c-Met FN3 domain containing molecule" as used herein refers to a molecule comprising an EGFR binding FN3 domain and a distinct c-Met binding FN3 domain that are covalently linked together either directly or via a linker. An exemplary bispecific EGFR/c-Met binding molecule comprises a first FN3 domain specifically binding EGFR and a second FN3 domain specifically binding c-Met.

"Valent" as used herein refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule.

"Mixture" as used herein refers to a sample or preparation of two or more FN3 domains not covalently linked together. A mixture may consist of two or more identical FN3 domains or distinct FN3 domains.

Compositions of Matter

The present invention provides monospecific and bispecific EGFR and/or c-Met binding FN3 domain containing molecules. The present invention provides polynucleotides encoding the FN3 domains of the invention or complementary nucleic acids thereof, vectors, host cells, and methods of making and using them.

Monospecific EGFR Binding Molecules

The present invention provides fibronectin type III (FN3) domains that bind specifically to epidermal growth factor receptor (EGFR) and block binding of epidermal growth factor (EGF) to EGFR, and thus can be widely used in therapeutic and diagnostic applications. The present invention provides polynucleotides encoding the FN3 domains of the invention or complementary nucleic acids thereof, vectors, host cells, and methods of making and using them.

The FN3 domains of the invention bind EGFR with high affinity and inhibit EGFR signaling, and may provide a benefit in terms of specificity and reduced off-target toxicity when compared to small molecule EGFR inhibitors, and improved tissue penetration when compared to conventional antibody therapeutics.

One embodiment of the invention an isolated fibronectin type III (FN3) domain that specifically binds epidermal growth factor receptor (EGFR) and blocks binding of epidermal growth factor (EGF) to EGFR.

The FN3 domains of the invention may block EGF binding to the EGFR with an $IC_{50}$ value of less than about $1\times10^{-7}$ M, less than about $1\times10^{-8}$ M, less than about $1\times10^{-9}$ M, less than about $1\times10^{-10}$ M, less than about $1\times10^{-11}$ M, or less than about $1\times10^{-12}$ M in a competition assay employing A431 cells and detecting amount of fluorescence from bound biotinylated EGF using streptavidin-phycoerythrin conjugate at 600 nM on A431 cells incubated with or without the FN3 domains of the invention. Exemplary FN3 domains may block EGF binding to the EGFR with an $IC_{50}$ value between about $1\times10^{-9}$ M to about $1\times10^{-7}$ M, such as EGFR binding FN3 domains having the amino acid sequence of SEQ ID NOs: 18-29, 107-110, or 122-137. The FN3 domains of the invention may block EGF binding to the EGFR by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to binding of EGF to the EGFR in the absence of the FN3 domains of the invention using the same assay conditions.

The FN3 domain of the invention may inhibit EGFR signaling by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to the level of signaling in the absence of the FN3 domains of the invention using the same assay conditions.

Binding of a ligand such as EGF to EGFR stimulates receptor dimerization, autophosphorylation, activation of the receptor's internal, cytoplasmic tyrosine kinase domain, and initiation of multiple signal transduction and transactivation pathways involved in regulation of DNA synthesis (gene activation) and cell cycle progression or division. Inhibition of EGFR signaling may result in inhibition in one or more EGFR downstream signaling pathways and therefore neutralizing EGFR may have various effects, including inhibition of cell proliferation and differentiation, angiogenesis, cell motility and metastasis.

EGFR signaling may be measured using various well known methods, for example measuring the autophosphorylation of the receptor at any of the tyrosines Y1068, Y1148, and Y1173 (Downward et al., Nature 311:483-5, 1984) and/or phosphorylation of natural or synthetic substrates. Phosphorylation can be detected using well known methods such as an ELISA assay or a western plot using a phosphotyrosine specific antibody. Exemplary assays can be found in Panek et al., J Pharmacol Exp Thera 283:1433-44, 1997 and Batley et al., Life Sci 62:143-50, 1998, and assays described herein.

In one embodiment, the FN3 domain of the invention inhibits EGF-induced EGFR phosphorylation at EGFR residue position Tyrosine 1173 with an $IC_{50}$ value of less than about $2.5\times10^{-6}$ M, for example less than about $1\times10^{-6}$ M, less than about $1\times10^{-7}$ M, less than about $1\times10^{-8}$ M, less than about $1\times10^{-9}$ M, less than about $1\times10^{-10}$ M, less than about $1\times10^{-11}$ M, or less than about $1\times10^{-12}$ M when measured in A431 cells using 50 ng/mL human EGF.

In one embodiment, the FN3 domain of the invention inhibits EGF-induced EGFR phosphorylation at EGFR residue position Tyrosine 1173 with an $IC_{50}$ value between about $1.8\times10^{-8}$ M to about $2.5\times10^{-6}$ M when measured in A431 cells using 50 ng/mL human EGF. Such exemplary FN3 domains are those having the amino acid sequence of SEQ ID NOs: 18-29, 107-110, or 122-137.

In one embodiment, the FN3 domain of the invention binds human EGFR with a dissociation constant ($K_D$) of less than about $1\times10^{-8}$ M, for example less than about $1\times10^{-9}$ M, less than about $1\times10^{-10}$ M, less than about $1\times10^{-11}$ M, less than about $1\times10^{-12}$ M, or less than about $1\times10^{-13}$ M as determined by surface plasmon resonance or the Kinexa method, as practiced by those of skill in the art. In some embodiments, the FN3 domain of the invention binds human EGFR with a $K_D$ of between about $2\times10^{-10}$ to about $1\times10^{-8}$ M. The affinity of a FN3 domain for EGFR can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W.H. Freeman and Company: New York, N.Y. (1992); and methods described herein). The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are preferably made with standardized solutions of protein scaffold and antigen, and a standardized buffer, such as the buffer described herein.

Exemplary FN3 domains of the invention that bind EGFR include FN3 domains of SEQ ID NOs: 18-29, 107-110, or 122-137.

In one embodiment, the FN3 domain that specifically binds EGFR comprises an amino acid sequence at least 87% identical to the amino acid sequence of SEQ ID NO: 27.

In one embodiment, the FN3 domain that specifically binds EGFR comprises an FG loop comprising the sequence HNVYKDTNX$_9$RGL (SEQ ID NO: 179) or the sequence LGSYVFEHDVML (SEQ ID NO: 180), wherein X$_9$ is M or I; and a BC loop comprising the sequence X$_1$X$_2$X$_3$X$_4$X$_5$X$_6$X$_7$X$_8$ (SEQ ID NO: 181);

wherein

X$_1$ is A, T, G or D;

X$_2$ is A, D, Y or W;

$X_3$ is P, D or N;
$X_4$ is L or absent;
$X_5$ is D, H, R, G, Y or W;
$X_6$ is G, D or A;
$X_7$ is A, F, G, H or D; and
$X_8$ is Y, F or L.

The FN3 domains of the invention that specifically bind EGFR and inhibit autophosphorylation of EGFR may comprise as a structural feature an FG loop comprising the sequence HNVYKDTNX$_9$RGL (SEQ ID NO: 179) or the sequence LGSYVFEHDVML (SEQ ID NO: 180), wherein $X_9$ is M or I. Such FN3 domains may further comprise a BC loop of 8 or 9 amino acids in length and defined by the sequence $X_1X_2X_3X_4X_5X_6X_7X_8$ (SEQ ID NO: 181), and inhibit EGFR autophosphorylation with an IC$_{50}$ value of less than about $2.5\times10^{-6}$ M, or with an IC$_{50}$ value of between about $1.8\times10^{-8}$ M to about $2.5\times10^{-6}$ M when measured in A431 cells using 50 ng/mL human EGF.

The FN3 domains of the invention that specifically bind EGFR and inhibit autophosphorylation of EGFR further comprise the sequence of
LPAPKNLVVSEVTEDSLRLSWX$_1$X$_2$X$_3$X$_4$X$_5$X$_6$X$_7$X$_8$DS FLIQYQESEKVGEAINLTVPGSERSYDLTGLKPG TEYTVSIYGVHNVYKDTNX$_9$RGLPLSAEFTT (SEQ ID NO: 182), or the sequence
LPAPKNLVVSEVTEDSLRLSWX$_1$X$_2$X$_3$X$_4$X$_5$X$_6$X$_7$X$_8$DS FLIQYQESEKVGEAINLTVPGSERSYDLTGLK-PGTEYTVSIYGVLGSYVFEHDVMLPLSAEFTT
(SEQ ID NO: 183),
wherein
$X_1$ is A, T, G or D;
$X_2$ is A, D, Y or W;
$X_3$ is P, D or N;
$X_4$ is L or absent;
$X_5$ is D, H, R, G, Y or W;
$X_6$ is G, D or A;
$X_7$ is A, F, G, H or D;
$X_8$ is Y, F or L; and
$X_9$ is M or I The EGFR binding FN3 domains can be generated and tested for their ability to inhibit EGFR autophosphorylation using well known methods and methods described herein.

Another embodiment of the invention is an isolated FN3 domain that specifically binds EGFR, wherein the FN3 domain comprises the sequence shown in SEQ ID NOs: 18-29, 107-110, 122-137 or 194-211.

In some embodiments, the EGFR binding FN3 domains comprise an initiator methionine (Met) linked to the N-terminus or a cysteine (Cys) linked to a C-terminus of a particular FN3 domain, for example to facilitate expression and/or conjugation of half-life extending molecules.

Another embodiment of the invention is an isolated fibronectin type III (FN3) domain that specifically binds EGFR and blocks binding of EGF to the EGFR, wherein the FN3 domain is isolated from a library designed based on Tencon sequence of SEQ ID NO: 1.

Another embodiment of the invention is an isolated fibronectin type III (FN3) domain that specifically binds EGFR and blocks binding of EGF to the EGFR, wherein the FN3 domain binds EGFR with one or more amino acid residues corresponding to residues D23, F27, Y28, V77 and G85 of P54AR4-83v2 (SEQ ID NO: 27).

Amino acid residues contributing to FN3 domain binding to EGFR can be identified using methods such as mutagenesis and evaluating of binding residues/surface by crystal structure. Substitutions at residues D23, F27, Y28, V77, G85 in EGFR binding FN3 domain P54AR4-83v2 (SEQ ID NO: 27) reduced EGFR binding to the FN3 domain by greater than 100-fold. EGFR-binding FN3 domains P54AR4-48, P54AR4-81, P53A1R5-17v2, P54AR4-83v22 and P54AR4-83v23 share these residues and can be expected to bind to EGFR with the same paratope residues as P54AR4-83v2. Other EGFR binding FN3 domains can be created by holding positions D23, F27, Y28, V77, G85 constant while changing the amino acids located at the other positions of the BC and FG loops (positions 24, 25, 75, 76, 78, 79, 80, 81, 82, 83, 84, and 86). These changes can be done by design of specific amino acids at specific positions or by incorporation of these positions into a library that replaces these sites with random amino acids. New FN3 domains designed in such a way can be used to screen for or select for optimized properties such as EGFR binding, solubility, stability, immunogenicity or serum half-life.

Monospecific c-Met Binding Molecules

The present invention provides fibronectin type III (FN3) domains that bind specifically to hepatocyte growth factor receptor (c-Met) and block binding of hepatocyte growth factor (HGF) to c-Met, and thus can be widely used in therapeutic and diagnostic applications. The present invention provides polynucleotides encoding the FN3 domains of the invention or complementary nucleic acids thereof, vectors, host cells, and methods of making and using them.

The FN3 domains of the invention bind c-Met with high affinity and inhibit c-Met signaling, and may provide a benefit in terms of specificity and reduced off-target toxicity when compared to small molecule c-Met inhibitors, and improved tissue penetration when compared to conventional antibody therapeutics. The FN3 domains of the invention are monovalent, therefore preventing unwanted receptor clustering and activation that may occur with other bivalent molecules.

One embodiment of the invention an isolated fibronectin type III (FN3) domain that specifically binds hepatocyte growth factor receptor (c-Met) and blocks binding of hepatocyte growth factor (HGF) to c-Met.

The FN3 domains of the invention may block HGF binding to c-Met with an IC$_{50}$ value of less than about $1\times10^{-7}$ M, less than about $1\times10^{-8}$ M, less than about $1\times10^{-9}$ M, less than about $1\times10^{-10}$ M, less than about $1\times10^{-11}$ M, or less than about $1\times10^{-12}$ M in an assay detecting inhibition of binding of biotinylated HGF to c-Met-Fc fusion protein in the presence of the FN3 domains of the invention. Exemplary FN3 domains my block HGF binding to the c-Met with an IC$_{50}$ value between about $2\times10^{-10}$ M to about $6\times10^{-8}$M. The FN3 domains of the invention may block HGF binding to c-Met by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to binding of HGF to c-Met in the absence of the FN3 domains of the invention using the same assay conditions.

The FN3 domain of the invention may inhibit c-Met signaling by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to the level of signaling in the absence of FN3 domains of the invention using the same assay conditions.

Binding of HGF to c-Met stimulates receptor dimerization, autophosphorylation, activation of the receptor's internal, cytoplasmic tyrosine kinase domain, and initiation of multiple signal transduction and transactivation pathways involved in regulation of DNA synthesis (gene activation) and cell cycle progression or division. Inhibition of c-Met signaling may result in inhibition of one or more c-Met downstream signaling pathways and therefore neutralizing c-Met may have various effects, including inhibition of cell proliferation and differentiation, angiogenesis, cell motility and metastasis.

c-Met signaling may be measured using various well know methods, for example measuring the autophosphorylation of the receptor on at least one tyrosine residues Y1230, Y1234, Y1235 or Y1349, and/or phosphorylation of natural or synthetic substrates. Phosphorylation can be detected, for example, using an antibody specific for phosphotyrosine in an ELISA assay or on a western blot. Assays for tyrosine kinase activity (Panek et al., J Pharmacol Exp Thera 283:1433-44, 1997; Batley et al., Life Sci 62:143-50, 1998), and assays described herein.

In one embodiment, the FN3 domain of the invention inhibits HGF-induced c-Met phosphorylation at c-Met residue position 1349 with an $IC_{50}$ value of less than about $1\times10^{-6}$ M, less than about $1\times10^{-7}$ M, less than about $1\times10^{-8}$ M, less than about $1\times10^{-9}$ M, less than about $1\times10^{-10}$ M, less than about $1\times10^{-11}$ M, or less than about $1\times10^{-12}$ M when measured in NCI-H441 cells using 100 ng/mL recombinant human HGF.

In one embodiment, the FN3 domain of the invention inhibits HGF-induced c-Met phosphorylation at c-Met tyrosine Y1349 with an $IC_{50}$ value between about $4\times10^{-9}$ M to about $1\times10^{-6}$ M when measured in NCI-H441 cells using 100 ng/mL recombinant human HGF.

In one embodiment, the FN3 domain of the invention binds human c-Met with an dissociation constant ($K_D$) of equal to or less than about $1\times10^{-7}$ M, $1\times10^{-8}$ M, $1\times10^{-9}$ M, $1\times10^{-10}$ M, $1\times10^{-11}$ M, $1\times10^{-12}$ M, $1\times10^{-13}$ M, $1\times10^{-14}$ M, or $1\times10^{-15}$ M as determined by surface plasmon resonance or the Kinexa method, as practiced by those of skill in the art. I some embodiments, the FN3 domain of the invention binds human c-Met with a $K_D$ of between about $3\times10^{-10}$ M to about $5\times10^{-8}$ M. The affinity of a FN3 domain for c-Met can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, *Janis Immunology*, W.H. Freeman and Company: New York, N.Y. (1992); and methods described herein). The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are preferably made with standardized solutions of protein scaffold and antigen, and a standardized buffer, such as the buffer described herein.

Exemplary FN3 domains of the invention that bind c-Met include FN3 domains having the amino acid sequence of SEQ ID NOs: 32-49, 111-114 or 212-223.

In one embodiment, the FN3 domain that specifically binds c-Met comprises an amino acid sequence at least 83% identical to the amino acid sequence of SEQ ID NO: 41.

In one embodiment, the FN3 domain that specifically binds c-Met comprises a C strand and a CD loop comprising the sequence DSFX$_{10}$IRYX$_{11}$E X$_{12}$X$_{13}$X$_{14}$X$_{15}$GX$_{16}$ (SEQ ID NO: 184), wherein
X$_{10}$ is W, F or V;
X$_{11}$ is D, F or L;
X$_{12}$ is V, F or L;
X$_{13}$ is V, L or T;
X$_{14}$ is V, R, G, L, T or S;
X$_{15}$ is G, S, A, T or K; and
X$_{16}$ is E or D; and a F strand and a FG loop comprising the sequence TEYX$_{17}$VX$_{18}$IX$_{19}$X$_{20}$V KGGX$_{21}$X$_{22}$SX$_{23}$ (SEQ ID NO: 185), wherein
X$_{17}$ is Y, W, I, V, G or A;
X$_{18}$ is N, T, Q or G;
X$_{19}$ is L, M, N or I;
X$_{20}$ is G or S;
X$_{21}$ is S, L, G, Y, T, R, H or K;
X$_{22}$ is I, V or L; and
X$_{23}$ is V, T, H, I, P, Y or L.

The FN3 domains of the invention that specifically bind c-Met and inhibit autophosphorylation of c-Met further comprises the sequence:
LPAPKNLVVSRVTEDSARLSWTAPDAAF DSFX$_{10}$IRYX$_{11}$EX$_{12}$X$_{13}$X$_{14}$X$_{15}$GX$_{16}$ AIVLTVPGSERSYDLTGLKPGTEYX$_{17}$VX$_{18}$IX$_{19}$X$_{20}$ VKGGX$_{21}$X$_{22}$SX$_{23}$PLSAEFTT (SEQ ID NO: 186),
wherein
X$_{10}$ is W, F or V; and
X$_{11}$ is D, F or L;
X$_{12}$ is V, F or L;
X$_{13}$ is V, L or T;
X$_{14}$ is V, R, G, L, T or S;
X$_{15}$ is G, S, A, T or K;
X$_{16}$ is E or D;
X$_{17}$ is Y, W, I, V, G or A;
X$_{18}$ is N, T, Q or G;
X$_{19}$ is L, M, N or I;
X$_{20}$ is G or S;
X$_{21}$ is S, L, G, Y, T, R, H or K;
X$_{22}$ is I, V or L; and
X$_{23}$ is V, T, H, I, P, Y or L.

Another embodiment of the invention is an isolated FN3 domain that specifically binds c-Met, wherein the FN3 domain comprises the sequence shown in SEQ ID NOs: 32-49 or 111-114.

Another embodiment of the invention is an isolated fibronectin type III (FN3) domain that specifically binds c-Met and blocks binding of HGF to the c-Met, wherein the FN3 domain is isolated from a library designed based on Tencon sequence of SEQ ID NO: 1.

Another embodiment of the invention is an isolated fibronectin type III (FN3) domain that specifically binds c-Met and blocks binding of HGF to c-Met, wherein the FN3 domain binds c-Met with one or more amino acid residues corresponding to residues R34, F38, M72 and I79 in P114AR7P95-A3 (SEQ ID NO: 41).

Amino acid residues contributing to FN3 domain binding to c-Met can be identified using methods such as mutagenesis and evaluating of binding residues/surface by crystal structure. Substitutions at residues R34S, F38S, M72S and I79S in the c-Met-binding FN3 domain P114AR7P95-A3 (SEQ ID NO: 27) reduced c-Met binding to the FN3 domain by greater than 100-fold. c-Met-binding FN3 domains molecules P114AR7P92-F3, P114AR7P95-D3, P114AR7P95-F10 and P114AR7P95-H8 share these residues and can be expected to bind to c-Met with the same paratope residues as P114AR7P95-A3. Other c-Met binding FN3 domains can be created by holding positions R34S, F38S, M72S and I79S constant while changing the amino acids located at the other positions of the C-strand, F-strand, CD-Loop and/or FG-loops (positions 32, 36, 39, 40, 68, 70, 78, and 81). These changes can be done by design of specific amino acids at specific positions or by incorporation of these positions into a library that replaces these sites with random amino acids. New FN3 domains designed in such a way can be used to screen for or select for optimized properties such as c-Met binding, solubility, stability, immunogenicity, or serum half-life.

Isolation of EGFR or c-Met Binding FN3 Domains from a Library Based on Tencon Sequence Tencon (SEQ ID NO: 1) is a non-naturally occurring fibronectin type III (FN3) domain designed from a consensus sequence of fifteen FN3 domains from human tenascin-C (Jacobs et al., Protein Engineering, Design, and Selection, 25:107-117, 2012; U.S. Pat. Publ. No. 2010/0216708). The crystal structure of Tencon shows six surface-exposed loops that connect seven beta-strands as is characteristic to the FN3 domains, the beta-strands referred to as A, B, C, D, E, F, and G, and the loops referred to as AB, BC, CD, DE, EF, and FG loops (Bork and Doolittle, Proc Natl Acad Sci USA 89:8990-8992, 1992; U.S. Pat. No. 6,673,901). These loops, or selected residues within each loop, can be randomized in order to construct libraries of fibronectin type III (FN3) domains that can be used to select novel molecules that bind EGFR or c-Met. Table 1 shows positions and sequences of each loop and beta-strand in Tencon (SEQ ID NO: 1).

Library designed based on Tencon sequence may thus have randomized FG loop, or randomized BC and FG loops, such as libraries TCL1 or TCL2 as described below. The Tencon BC loop is 7 amino acids long, thus 1, 2, 3, 4, 5, 6 or 7 amino acids may be randomized in the library diversified at the BC loop and designed based on Tencon sequence. The Tencon FG loop is 7 amino acids long, thus 1, 2, 3, 4, 5, 6 or 7 amino acids may be randomized in the library diversified at the FG loop and designed based on Tencon sequence. Further diversity at loops in the Tencon libraries may be achieved by insertion and/or deletions of residues at loops. For example, the FG and/or BC loops may be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop may be diversified in sequence as well as in length to correspond to the antibody CDR3 length range of 4-28 residues. For example, the FG loop can further be diversified in length by extending the loop by additional 1, 2, 3, 4 or 5 amino acids.

Library designed based on Tencon sequence may also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface and is shown in FIG. 1 and detailed generation of such libraries is described in U.S. Pat. Publ. No. US2013/0226834. Library designed based on Tencon sequence also includes libraries designed based on Tencon variants, such as Tencon variants having substitutions at residues positions 11, 14, 17, 37, 46, 73, or 86 (residue numbering corresponding to SEQ ID NO: 1), and which variants display improve thermal stability. Exemplary Tencon variants are described in US Pat. Publ. No. 2011/0274623, and include Tencon27 (SEQ ID NO: 99) having substitutions E11R, L17A, N46V and E86I when compared to Tencon of SEQ ID NO: 1.

TABLE 1

| FN3 domain | Tencon (SEQ ID NO: 1) |
|---|---|
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Tencon and other FN3 sequence based libraries can be randomized at chosen residue positions using a random or defined set of amino acids. For example, variants in the library having random substitutions can be generated using NNK codons, which encode all 20 naturally occurring amino acids. In other diversification schemes, DVK codons can be used to encode amino acids Ala, Trp, Tyr, Lys, Thr, Asn, Lys, Ser, Arg, Asp, Glu, Gly, and Cys. Alternatively, NNS codons can be used to give rise to all 20 amino acid residues and simultaneously reducing the frequency of stop codons. Libraries of FN3 domains with biased amino acid distribution at positions to be diversified can be synthesized for example using Slonomics® technology (http:_//www_s-loning_com). This technology uses a library of pre-made double stranded triplets that act as universal building blocks sufficient for thousands of gene synthesis processes. The triplet library represents all possible sequence combinations necessary to build any desired DNA molecule. The codon designations are according to the well known IUB code.

The FN3 domains specifically binding EGFR or c-Met of the invention can be isolated by producing the FN3 library such as the Tencon library using cis display to ligate DNA fragments encoding the scaffold proteins to a DNA fragment encoding RepA to generate a pool of protein-DNA complexes formed after in vitro translation wherein each protein is stably associated with the DNA that encodes it (U.S. Pat. No. 7,842,476; Odegrip et al., Proc Natl Acad Sci USA 101, 2806-2810, 2004), and assaying the library for specific binding to EGFR and/or c-Met by any method known in the art and described in the Example. Exemplary well known methods which can be used are ELISA, sandwich immunoassays, and competitive and non-competitive assays (see, e.g., Ausubel et al., eds, 1994, Current Protocols in Molecular Biology, Vol. 1, John Wiley & Sons, Inc., New York). The identified FN3 domains specifically binding EGFR or c-Met are further characterized for their ability to block EGFR ligand such as EGF binding to EGFR, or HGF binding to c-Met, and for their ability to inhibit EGFR and/or c-Met signaling using methods described herein.

The FN3 domains specifically binding to EGFR or c-Met of the invention can be generated using any FN3 domain as a template to generate a library and screening the library for molecules specifically binding EGFR or c-Met using methods provided within. Exemplar FN3 domains that can be used are the 3rd FN3 domain of tenascin C (TN3) (SEQ ID NO: 75), Fibcon (SEQ ID NO: 76), and the 10$^{th}$ FN3 domain of fibronectin (FN10) (SEQ ID NO: 77). Standard cloning and expression techniques are used to clone the libraries into a vector or synthesize double stranded cDNA cassettes of the library, to express, or to translate the libraries in vitro. For example ribosome display (Hanes and Pluckthun, Proc Natl Acad Sci USA, 94, 4937-4942, 1997), mRNA display (Roberts and Szostak, *Proc Natl Acad Sci USA*, 94, 12297-12302, 1997), or other cell-free systems (U.S. Pat. No. 5,643,768) can be used. The libraries of the FN3 domain variants may be expressed as fusion proteins displayed on the surface for example of any suitable bacteriophage. Methods for displaying fusion polypeptides on the surface of a bacteriophage are well known (U.S. Pat. Publ. No. 2011/0118144; Int. Pat. Publ. No. WO2009/085462; U.S. Pat. No. 6,969,108; U.S. Pat. No. 6,172,197; U.S. Pat. No. 5,223,409; U.S. Pat. No. 6,582,915; U.S. Pat. No. 6,472,147).

The FN3 domains specifically binding EGFR or c-Met of the invention can be modified to improve their properties such as improve thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, Curr Opin Biotechnol, 12, 371-375, 2001). High thermal stability may increase the yield of the expressed protein, improve solubility or activity, decrease immunogenicity, and minimize the need of a cold chain in manufacturing. Residues that can be substituted to improve thermal stability of Tencon (SEQ ID NO: 1) are residue positions 11, 14, 17, 37, 46, 73, or 86, and are described in US Pat. Publ. No. 2011/0274623. Substitutions corresponding to these residues can be incorporated to the FN3 domains or the bispecific FN3 domain containing molecules of the invention.

Another embodiment of the invention is an isolated FN3 domain that specifically binds EGFR and blocks binding of EGF to EGFR, comprising the sequence shown in SEQ ID NOs: 18-29, 107-110, 122-137, further comprising substitutions at one or more residue positions corresponding to positions 11, 14, 17, 37, 46, 73, and 86 in Tencon (SEQ ID NO: 1).

Another embodiment of the invention is an isolated FN3 domain that specifically binds c-Met and blocks binding of HGF to c-Met, comprising the sequence shown in SEQ ID NOs: 32-49 or 111-114, further comprising substitutions at one or more residue positions corresponding to positions 11, 14, 17, 37, 46, 73, and 86 in Tencon (SEQ ID NO: 1).

Exemplary substitutions are substitutions E11N, E14P, L17A, E37P, N46V, G73Y and E86I (numbering according to SEQ ID NO: 1).

In some embodiments, the FN3 domains of the invention comprise substitutions corresponding to substitutions L17A, N46V, and E86I in Tencon (SEQ ID NO: 1).

The FN3 domains specifically binding EGFR (FIG. 1) have an extended FG loop when compared to Tencon (SEQ ID NO: 1). Therefore, the residues corresponding to residues 11, 14, 17, 37, 46, 73, and 86 in Tencon (SEQ ID NO: 1) are residues 11, 14, 17, 37, 46, 73 and 91 in EGFR FN3 domains shown in FIGS. 1A and 1B except for the FN3 domain of SEQ ID NO: 24, wherein the corresponding residues are residues 11, 14, 17, 38, 74, and 92 due to an insertion of one amino acid in the BC loop.

Another embodiment of the invention is an isolated FN3 domain that specifically binds EGFR and blocks binding of EGF to EGFR comprising the amino acid sequence shown in SEQ ID NOs: 18-29, 107-110, 122-137 or 194-211, optionally having one, two or three substitutions corresponding to substitutions L17A, N46V and E86I in Tencon (SEQ ID NO: 1).

Another embodiment of the invention is an isolated FN3 domain that specifically binds c-Met and blocks binding of HGF to c-Met comprising the amino acid sequence shown in SEQ ID NOs: 32-49, 111-114 or 212-223, optionally having one, two or three substitutions corresponding to substitutions L17A, N46V, and E86I in Tencon (SEQ ID NO: 1).

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ("TM") temperature, the temperature in ° Celsius (° C.) at which half of the molecules become unfolded, using standard methods. Typically, the higher the TM, the more stable the molecule. In addition to heat, the chemical environment also changes the ability of the protein to maintain a particular three dimensional structure.

In one embodiment, the FN3 domains binding EGFR or c-Met of the invention exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same domain prior to engineering measured by the increase in the TM.

Chemical denaturation can likewise be measured by a variety of methods. Chemical denaturants include guanidinium hydrochloride, guanidinium thiocyanate, urea, acetone, organic solvents (DMF, benzene, acetonitrile), salts (ammonium sulfate, lithium bromide, lithium chloride, sodium bromide, calcium chloride, sodium chloride); reducing agents (e.g. dithiothreitol, beta-mercaptoethanol, dinitrothiobenzene, and hydrides, such as sodium borohydride), non-ionic and ionic detergents, acids (e.g. hydrochloric acid (HCl), acetic acid ($CH_3COOH$), halogenated acetic acids), hydrophobic molecules (e.g. phosopholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

In one embodiment, the FN3 domain of the invention binding EGFR or c-Met exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same scaffold prior to engineering, measured by using guanidinium hydrochloride as a chemical denaturant. Increased stability can be measured as a function of decreased tryptophan fluorescence upon treatment with increasing concentrations of guanidine hydrochloride using well known methods.

The FN3 domains of the invention may be generated as monomers, dimers, or multimers, for example, as a means to increase the valency and thus the avidity of target molecule binding, or to generate bi- or multispecific scaffolds simultaneously binding two or more different target molecules. The dimers and multimers may be generated by linking monospecific, bi- or multispecific protein scaffolds, for example, by the inclusion of an amino acid linker, for example a linker containing poly-glycine, glycine and serine, or alanine and proline. Exemplary linker include (GS)$_2$, (SEQ ID NO: 78), (GGGS)$_2$ (SEQ ID NO: 224), (GGGGS)$_5$ (SEQ ID NO: 79), (AP)$_2$ (SEQ ID NO: 80), (AP)$_5$ (SEQ ID NO: 81), (AP)$_{10}$ (SEQ ID NO: 82), (AP)$_{20}$ (SEQ ID NO: 83) and A(EAAAK)$_5$AAA (SEQ ID NO: 84). The dimers and multimers may be linked to each other in a N-to C-direction. The use of naturally occurring as well as artificial peptide linkers to connect polypeptides into novel linked fusion polypeptides is well known in the literature (Hallewell et al., *J Biol Chem* 264, 5260-5268, 1989; Alfthan et al., *Protein Eng.* 8, 725-731, 1995; Robinson & Sauer, *Biochemistry* 35, 109-116, 1996; U.S. Pat. No. 5,856,456).

Bispecific EGFR/c/Met Binding Molecules

The bispecific EGFR/c-Met FN3 domain containing molecules of the invention may provide a benefit in terms of specificity and reduced off-target toxicity when compared to small molecule EGFR inhibitors, and improved tissue penetration when compared to conventional antibody therapeutics. The present invention is based at least in part on the surprising finding that the bispecific EGFR/c-Met FN3 domain containing molecules of the invention provide a significantly improved synergistic inhibitory effect when compared to a mixture of EGFR-binding and c-Met-binding FN3 domains. The molecules may be tailored to specific affinity towards both EGFR and c-Met to maximize tumor penetration and retention. The bispecific EGFR/c-Met FN3 domain containing molecules of the invention provide more efficient inhibition of EGFR and/or c-Met signaling pathways and inhibit tumor growth more efficiently than cetuximab (Eribtux®)

One embodiment of the invention is an isolated bispecific FN3 domain containing molecule comprising a first fibronectin type III (FN3) domain and a second FN3 domain, wherein the first FN3 domain specifically binds epidermal growth factor receptor (EGFR) and blocks binding of epidermal growth factor (EGF) to EGFR, and the second FN3 domain specifically binds hepatocyte growth factor receptor (c-Met) and blocks binding of hepatocyte growth factor (HGF) to c-Met.

The bispecific EGFR/c-Met FN3 domain containing molecules of the invention can be generated by covalently linking any EGFR-binding FN3 domain and any c-Met-binding FN3 domain of the invention directly or via a linker. Therefore, the first FN3 domain of the bispecific molecule may have characteristics as described above for the EGFR-binding FN3 domains, and the second FN3 domain of the bispecific molecule may have characteristics as described above for the c-Met-binding FN3 domains.

In one embodiment, the first FN3 domain of the bispecific EGFR/c-Met FN3 domain containing molecule inhibits EGF-induced EGFR phosphorylation at EGFR residue Tyrosine 1173 with an IC$_{50}$ value of less than about $2.5 \times 10^{-6}$ M when measured in A431 cells using 50 ng/mL human EGF, and the second FN3 domain of the bispecific EGFR/c-Met FN3 domain containing molecule inhibits HGF-induced c-Met phosphorylation at c-Met residue Tyrosine 1349 with an IC$_{50}$ value of less than about $1.5 \times 10^{-6}$ M when measured in NCI-H441 cells using 100 ng/mL human HGF.

In another embodiment, the first FN3 domain of the bispecific EGFR/c-Met FN3 domain containing molecule inhibits EGF-induced EGFR phosphorylation at EGFR residue Tyrosine 1173 with an IC$_{50}$ value of between about $1.8 \times 10^{-8}$ M to about $2.5 \times 10^{-6}$ M when measured in NCI-H292 cells using 50 ng/mL human EGF, and the second FN3 domain of the bispecific EGFR/c-Met FN3 domain containing molecule inhibits HGF-induced c-Met phosphorylation at c-Met residue Tyrosine 1349 with an IC$_{50}$ value between about $4 \times 10^{-9}$ M to about $1.5 \times 10^{-6}$ M when measured in NCI-H441 cells using 100 ng/mL human HGF.

In another embodiment, the first FN3 domain of the bispecific EGFR/c-Met FN3 domain containing molecule binds human EGFR with a dissociation constant (K$_D$) of less than about $1 \times 10^{-8}$ M, and the second FN3 domain of the bispecific EGFR/c-Met FN3 domain containing molecule binds human c-Met with a K$_D$ of less than about $5 \times 10^{-8}$ M.

In the bispecific molecule binding both EGFR and c-Met, the first FN3 domain binds human EGFR with a K$_D$ of between about $2 \times 10^{-10}$ to about $1 \times 10^{-8}$ M, and the second FN3 domain binds human c-Met with a K$_D$ of between about $3 \times 10^{-10}$ to about $5 \times 10^{-8}$ M.

The affinity of the bispecific EGFR/c-Met molecule for EGFR and c-Met can be determined as described in Example 3 and Example 5 for the monospecific molecules.

The first FN3 domain in the bispecific EGFR/c-Met molecule of the invention may block EGF binding to EGFR with an IC$_{50}$ value of between about $1 \times 10^{-9}$ M to about $1.5 \times 10^{-7}$ M in an assay employing A431 cells and detecting the amount of fluorescence from bound biotinylated EGF using streptavidin-phycoerythrin conjugate at 600 nM on A431 cells incubated with or without the first FN3 domain. The first FN3 domain in the bispecific EGFR/c-Met molecule of the invention may block EGF binding to the EGFR by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to binding of EGF to EGFR in the absence of the first FN3 domains using the same assay conditions.

The second FN3 domain in the bispecific EGFR/c-Met molecule of the invention may block HGF binding to c-Met with an IC$_{50}$ value of between about $2 \times 10^{-10}$ M to about $6 \times 10^{-8}$ M in an assay detecting inhibition of binding of biotinylated HGF to c-Met-Fc fusion protein in the presence of the second FN3 domain. The second FN3 domain in the bispecific EGFR/c-Met molecule may block HGF binding to c-Met by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to binding of HGF to c-Met in the absence of the second FN3 domain using the same assay conditions.

The bispecific EGFR/c-Met molecule of the invention may inhibit EGFR and/or c-Met signaling by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to the level of signaling in the absence of the bispecific EGFR/c-Met molecule of the invention using the same assay conditions.

EGFR and c-Met signaling may be measured using various well know methods as described above for the monospecific molecules.

The bispecific EGFR/c-Met molecules of the invention comprising the first FN3 domain specifically binding EGFR and the second FN3 domain specifically binding c-Met provide a significantly increased synergistic inhibition of EGFR and c/Met signaling and tumor cell proliferation when compared to the synergistic inhibition observed by a mixture of the first and the second FN3 domain. Synergistic inhibition can be assessed for example by measuring inhibition of ERK phosphorylation by the bispecific EGFR/c-Met FN3 domain containing molecules and by a mixture of two monospecific molecules, one binding EGFR and the other c-Met. The bispecific EGFR/c-Met molecules of the invention may inhibit ERK phosphorylation with an at least about 100 fold smaller, for example at least 500, 1000, 5000 or 10,000 fold smaller $IC_{50}$ value when compared to the $IC_{50}$ value for a mixture of two monospecific FN3 domains, indicating at least 100 fold increased potency for the bispecific EGFR/c-Met FN3 domain containing molecules when compared to the mixture of two monospecific FN3 domains. Exemplary bispecific EGFR-c-Met FN3 domain containing molecules may inhibit ERK phosphorylation with and $IC_{50}$ value of about $5\times10^{-9}$ M or less. ERK phosphorylation can be measured using standard methods and methods described herein.

The bispecific EGFR/c-Met FN3 domain containing molecule of the invention may inhibit H292 cell proliferation with an $IC_{50}$ value that is at least 30-fold less when compared to the $IC_{50}$ value of inhibition of H292 cell growth with a mixture of the first FN3 domain and the second FN3, wherein the cell proliferation is induced with medium containing 10% FBS supplemented with 7.5 ng/mL HGF. The bispecific molecule of the invention may inhibit tumor cell proliferation with an $IC_{50}$ value that is about 30, 40, 50, 60, 70, 80, 90, 100, 150, 200, 300, 400, 500, 600, 700, 800, or about 1000 fold less when compared to the $IC_{50}$ value of inhibition of tumor cell proliferation with a mixture of the first FN3 domain and the second FN3 domain Inhibition of tumor cell proliferation can be measured using standard methods and methods described herein.

In some embodiments, the bispecific EGFR/c-Met FN3 domain containing molecule binds EGFR with one or more amino acid residues corresponding to residues D23, F27, Y28, V77 and G85 of P54AR4-83v2 (SEQ ID NO: 27).

In other embodiments, the bispecific EGFR/c-Met FN3 domain containing molecule binds c-Met with one or more amino acid residues corresponding to residues R34, F38, M72 and I79 in P114AR7P95-A3 (SEQ ID NO: 41).

Paratope residues in the bispecific molecules can be identified by mutagenesis studies or from co-crystal structures of the FN3 domain and EGFR or c-Met. Mutagenesis studies may be employed by for example using alanine scanning, and the resulting variants may be tested for their binding to EGFR or c-Met using standard methods. Typically paratope residues are those residues that when mutagenized, result in variants with reduced or abolished binding to EGFR or c-Met. EGFR-binding FN3 domains with substitutions at amino acid residue positions corresponding to residues D23, F27, Y28, V77 and G85 of P54AR4-83v2 (SEQ ID NO: 27), when substituted, reduce EGFR binding at least 100-fold when compared to the wild type P54AR4-83v2. Bispecific molecules ECB1, ECB2, ECB3, ECB4, ECB5, ECB6, ECB7, ECB15, ECB17, ECB60, ECB37, ECB94, ECB95, ECB96, ECB97, ECB91, ECB18, ECB28, ECB38, ECB39, ECB168 and ECB176 have D, F, Y, V and G at residue positions corresponding to residues D23, F27, Y28, V77 and G85 of P54AR4-83v2 and expected to bind to EGFR with these residues. c-Met binding FN3 domains with substitutions at amino acid residue positions corresponding to residues R34, F38, M72 and I79 of P114AR7P95-A3 (SEQ ID NO: 41), when substituted, abolish or reduce c-Met binding at least 100-fold when compared to the wild type P114AR7P95-A3. Bispecific molecules ECB2, ECB5, ECB15, ECB60, ECB38 and ECB39 have R, F, M and I at residue positions corresponding to residues R34, F38, M72 and I79 of P114AR7P95-A3 (SEQ ID NO: 41) and expected to bind to c-Met with these residues.

Another embodiment of the invention is a bispecific FN3 domain containing molecule comprising a first fibronectin type III (FN3) domain and a second FN3 domain, wherein the first FN3 domain specifically binds epidermal growth factor receptor (EGFR) and blocks binding of epidermal growth factor (EGF) to EGFR, and the second FN3 domain specifically binds hepatocyte growth factor receptor (c-Met), and blocks binding of hepatocyte growth factor (HGF) to c-Met, wherein the first FN3 domain comprises
an FG loop comprising the sequence HNVYKDTNX$_9$RGL (SEQ ID NO: 179) or the sequence LGSYVFEHDVML (SEQ ID NO: 180), wherein X$_9$ is M or I; and
a BC loop comprising the sequence X$_1$X$_2$X$_3$X$_4$X$_5$X$_6$X$_7$X$_8$ (SEQ ID NO: 181), wherein
X$_1$ is A, T, G or D;
X$_2$ is A, D, Y or W;
X$_3$ is P, D or N;
X$_4$ is L or absent;
X$_5$ is D, H, R, G, Y or W;
X$_6$ is G, D or A;
X$_7$ is A, F, G, H or D; and
X$_8$ is Y, F or L; and
the second FN3 domain comprises
a C strand and a CD loop comprising the sequence DSFX$_{10}$IRYX$_{11}$E X$_{12}$X$_{13}$X$_{14}$X$_{15}$GX$_{16}$ (SEQ ID NO: 184), wherein
X$_{10}$ is W, F or V;
X$_{11}$ is D, F or L;
X$_{12}$ is V, F or L;
X$_{13}$ is V, L or T;
X$_{14}$ is V, R, G, L, T or S;
X$_{15}$ is G, S, A, T or K; and
X$_{16}$ is E or D; and
a F strand and a FG loop comprising the sequence TEYX$_{17}$VX$_{18}$IX$_{19}$X$_{20}$V KGGX$_{21}$X$_{22}$SX$_{23}$ (SEQ ID NO: 185), wherein
X$_{17}$ is Y, W, I, V, G or A;
X$_{18}$ is N, T, Q or G;
X$_{19}$ is L, M, N or I;
X$_{20}$ is G or S;
X$_{21}$ is S, L, G, Y, T, R, H or K;
X$_{22}$ is I, V or L; and
X$_{23}$ is V, T, H, I, P, Y or L.

In another embodiment, the bispecific molecule comprises the first FN3 domain that binds EGFR comprising the sequence:
LPAPKNLVVSEVTEDSLRLSWX$_1$X$_2$X$_3$X$_4$X$_5$X$_6$X$_7$X$_8$DS FLIQYQESEKVGEAINLTVPGSERSYDLTGLKP GTE YTVSIYGVHNVYKDTNX$_9$RGLPLSAEFTT (SEQ ID NO: 182), or the sequence
LPAPKNLVVSEVTEDSLRLSWX$_1$X$_2$X$_3$X$_4$X$_5$X$_6$X$_7$X$_8$ DSFLIQYQESEKVGEAINLTVP GSERSYDLTGLK-PGTEYTVSIYGV LGSYVFEHDVMLPLSAEFTT (SEQ ID NO: 183),
wherein in the SEQ ID NOs: 182 and 183;
X$_1$ is A, T, G or D;
X$_2$ is A, D, Y or W;
X$_3$ is P, D or N;
X$_4$ is L or absent;
X$_5$ is D, H, R, G, Y or W;
X$_6$ is G, D or A;
X$_7$ is A, F, G, H or D;
X$_8$ is Y, F or L; and
X$_9$ is M or I.

In another embodiment, the bispecific molecule comprises the second FN3 domain that binds c-Met comprising the sequence
LPAPKNLVVSRVTEDSARLSWTAPDAAF DSFX$_{10}$IRYX$_{11}$E X$_{12}$X$_{13}$X$_{14}$X$_{15}$GX$_{16}$ AIVLTVPGSER- SYDLTGLKPGTEYX$_{17}$VX$_{18}$IX$_{19}$X$_{20}$VKGGX$_{21}$X$_{22}$SX$_{23}$ PLSAEFTT (SEQ ID NO: 186), wherein X$_{10}$ is W, F or V; and
X$_{11}$ is D, F or L;
X$_{12}$ is V, F or L;
X$_{13}$ is V, L or T;
X$_{14}$ is V, R, G, L, T or S;
X$_{15}$ is G, S, A, T or K;
X$_{16}$ is E or D;
X$_{17}$ is Y, W, I, V, G or A;
X$_{18}$ is N, T, Q or G;
X$_{19}$ is L, M, N or I;
X$_{20}$ is G or S;
X$_{21}$ is S, L, G, Y, T, R, H or K;
X$_{22}$ is I, V or L; and
X$_{23}$ is V, T, H, I, P, Y or L.

Exemplary bispecific EGFR/c-Met FN3 domain containing molecules comprise the amino acid sequences shown in SEQ ID NOs: 50-72, 106, 118-121, 138-165, 170-178 or 190-193.

The bispecific EGFR/c-Met molecules of the invention comprise certain structural characteristics associated with their functional characteristics, such as inhibition of EGFR autophosphorylation, such as the FG loop of the first FN3 domain that binds EGFR comprising the sequence HNVYKDTNX$_9$RGL (SEQ ID NO: 179) or the sequence LGSYVFEHDVML (SEQ ID NO: 180), wherein X$_9$ is M or I.

In one embodiment, the bispecific EGFR/c-Met FN3 domain containing molecules of the invention inhibit EGF-induced EGFR phosphorylation at EGFR residues Tyrosine 1173 with an IC$_{50}$ value of less than about $8 \times 10^{-7}$ M when measured in H292 cells using 50 ng/mL human EGF;

inhibit HGF-induced c-Met phosphorylation at c-Met residue Tyrosine 1349 with and IC$_{50}$ value of less than about $8.4 \times 10^{-7}$ M when measured in NCI-H441 cells using 100 ng/mL human HGF;

inhibit HGF-induced NCI-H292 cell proliferation with an IC$_{50}$ value of less than about $9.5 \times 10^{-6}$M wherein the cell proliferation is induced with 10% FBS containing 7.5 ng HGF;

bind EGFR with a K$_D$ of less than about $2.0 \times 10^{-8}$ M; or bind c-Met with a K$_D$ of less than about $2.0 \times 10^{-8}$ M; wherein the K$_D$ is measured using surface plasmon resonance as described in Example 3 or Example 5.

In another embodiment, the bispecific EGFR/c-Met FN3 domain containing molecules of the invention inhibit EGF-induced EGFR phosphorylation at EGFR residues Tyrosine 1173 with and IC$_{50}$ of between about $4.2 \times 10^{-9}$ M and $8 \times 10^{-7}$ M when measured in H292 cells using 50 ng/mL human EGF;

inhibit HGF-induced c-Met phosphorylation at c-Met residues Tyrosine 1349 with and IC$_{50}$ value of between about $2.4 \times 10^{-8}$ M to about $8.4 \times 10^{-7}$ M when measured in NCI-H441 cells using 100 ng/mL human HGF;

inhibit HGF-induced NCI-H292 cell proliferation with an IC$_{50}$ value between about $2.3 \times 10^{-8}$ M to about $9.5 \times 10^{-6}$M wherein the cell proliferation is induced with 10% FBS containing 7.5 ng HGF;

bind EGFR with a K$_D$ of between about $2 \times 10^{-10}$ M to about $2.0 \times 10^{-8}$ M; or bind c-Met with a K$_D$ of between about $1 \times 10^{-9}$ M to about $2.0 \times 10^{-8}$ M, wherein the K$_D$ is measured using surface plasmon resonance as described in Example 3 or Example 5.

In one embodiment, bispecific EGFR/c-Met molecules comprise the EGFR-binding FN3 domain comprising the sequence
LPAPKNLVVSEVTEDSLRLSWX$_1$X$_2$X$_3$X$_4$X$_5$X$_6$X$_7$X$_8$DS FLIQYQESEKVGEAINLTVP GSERSYDLTGLK-PGTEYTVSIYGV HNVYKDTNX$_9$RGL PLSAEFTT (SEQ ID NO: 182), wherein X$_1$ is D;
X$_2$ is D;
X$_3$ is P;
X$_4$ is absent;
X$_5$ is H or W;
X$_6$ is A;
X$_7$ is F
X$_8$ is Y; and
X$_9$ is M or I; and the c-Met-binding FN3 domain comprising the sequence LPAPKNLVVSRVTEDSARLSWTAPDAAF DSFX$_{10}$IRYX$_{11}$E X$_{12}$X$_{13}$X$_{14}$X$_{15}$GX$_{16}$ AIVLTVPGSER-SYDLTGLKPG
TEYX$_{17}$VX$_{18}$IX$_{19}$X$_{20}$VKGGX$_{21}$X$_{22}$SX$_{23}$ PLSAEFTT (SEQ ID NO: 186), wherein X$_{10}$ is W;
X$_{11}$ is F;
X$_{12}$ is F;
X$_{13}$ is V or L;
X$_{14}$ is G or S;
X$_{15}$ is S or K;
X$_{16}$ is E or D;
X$_{17}$ is V;
X$_{18}$ is N;
X$_{19}$ is L or M;
X$_{20}$ is G or S;
X$_{21}$ is S or K;
X$_{22}$ is I; and
X$_{23}$ is P.

Exemplary bispecific EGFR/c-Met molecules are those having the sequence shown in SEQ ID NOs: 57, 61, 62, 63, 64, 65, 66, 67, 68 or 190-193.

The bispecific molecules of the invention may further comprise substitutions at one or more residue positions in the first FN3 domain and/or the second FN3 domain corresponding to positions 11, 14, 17, 37, 46, 73 and 86 in Tencon (SEQ ID NO: 1) as described above, and a substitution at position 29. Exemplary substitutions are substitutions E11N, E14P, L17A, E37P, N46V, G73Y, E86I and D29E (numbering according to SEQ ID NO: 1). Skilled in the art will appreciate that other amino acids can be used for substitutions, such as amino acids within a family of amino acids that are related in their side chains as described infra. The generated variants can be tested for their stability and binding to EGFR and/or c-Met using methods herein.

In one embodiment, the bispecific EGFR/c-Met FN3 domain containing molecule comprises the first FN3 domain that binds specifically EGFR and the second FN3 domain that binds specifically c-Met, wherein the first FN3 domain comprises the sequence:
LPAPKNLVVSX$_{24}$VTX$_{25}$DSX$_{26}$RLSWDDPX$_{27}$AFYX$_{28}$ SFLIQYQX$_{29}$SEKVGEAIX$_{30}$LT VPGSERSYDLTGL KPGTEYTVSIYX$_{31}$VHNVYKDTNX$_{32}$RGLPLSAX$_{33}$ FTT (SEQ ID NO: 187), wherein X$_{24}$ is E, N or R;
X$_{25}$ is E or P;

$X_{26}$ is L or A;
$X_{27}$ is H or W;
$X_{28}$ is E or D;
$X_{29}$ is E or P;
$X_{30}$ is N or V;
$X_{31}$ is G or Y;
$X_{32}$ is M or I; and
$X_{33}$ is E or I;

and the second FN3 domain comprises the sequence:
LPAPKNLVVSX$_{34}$VTX$_{35}$DSX$_{36}$RLSWTAPDAAFDSFWI
RYFX$_{37}$FX$_{38}$X$_{39}$X$_{40}$GX$_{41}$AIX$_{42}$LTVPGSERSYDLT
GLKPGTEYVVNIX$_{43}$X$_{44}$VKGGX$_{45}$ISPPLSAX$_{46}$FTT
(SEQ ID NO: 188); wherein $X_{34}$ is E, N or R;
$X_{35}$ is E or P;
$X_{36}$ is L or A;
$X_{37}$ is E or P;
$X_{38}$ is V or L;
$X_{39}$ is G or S;
$X_{40}$ is S or K;
$X_{41}$ is E or D;
$X_{42}$ is N or V;
$X_{43}$ is L or M;
$X_{44}$ is G or S;
$X_{45}$ is S or K; and
$X_{46}$ is E or I.

In other embodiments, the bispecific EGFR/c-Met FN3 domain containing molecule comprises the first FN3 domain comprising an amino acid sequence at least 87%, 88%, 89%, 90%, 91%, 92%, 93%, 94%, 95%, 96%, 97%, 98% or 99% identical to the amino acid sequence of SEQ ID NO: 27, and the second FN3 domain comprising an amino acid sequence at least 83%, 84%, 85%, 86%, 87%, 88%, 89%, 90%, 91%, 92%, 93%, 94%, 95%, 96%, 97%, 98% or 99% identical to the amino acid sequence of SEQ ID NO: 41.

The bispecific EGFR/c-Met FN3 domain containing molecules of the invention may be tailored to a specific affinity towards EGFR and c-Met to maximize tumor accumulation.

Another embodiment of the invention is an isolated bispecific FN3 domain containing molecule comprising a first fibronectin type III (FN3) domain and a second FN3 domain, wherein the first FN3 domain specifically binds epidermal growth factor receptor (EGFR) and blocks binding of epidermal growth factor (EGF) to EGFR, and the second FN3 domain specifically binds hepatocyte growth factor receptor (c-Met), and blocks binding of hepatocyte growth factor (HGF) to c-Met, wherein the first FN3 domain and the second FN3 domain is isolated from a library designed based on Tencon sequence of SEQ ID NO: 1.

The bispecific EGFR/c-Met FN3 domain containing molecule of the invention can be generated by covalently coupling the EGFR-binding FN3 domain and the c-Met binding FN3 domain of the invention using well known methods. The FN3 domains may be linked via a linker, for example a linker containing poly-glycine, glycine and serine, or alanine and proline. Exemplary linker include (GS)$_2$, (SEQ ID NO: 78), (GGGS)$_2$ (SEQ ID NO: 224), (GGGGS)$_5$ (SEQ ID NO: 79), (AP)$_2$ (SEQ ID NO: 80), (AP)$_5$ (SEQ ID NO: 81), (AP)$_{10}$ (SEQ ID NO: 82), (AP)$_{20}$ (SEQ ID NO: 83), A(EAAAK)$_5$AAA (SEQ ID NO: 84). The use of naturally occurring as well as artificial peptide linkers to connect polypeptides into novel linked fusion polypeptides is well known in the literature (Hallewell et al., *J Biol Chem* 264, 5260-5268, 1989; Alfthan et al., *Protein Eng.* 8, 725-731, 1995; Robinson & Sauer, *Biochemistry* 35, 109-116, 1996; U.S. Pat. No. 5,856,456). The bispecific EGFR/c-Met molecules of the invention may be linked together from a C-terminus of the first FN3 domain to the N-terminus of the second FN3 domain, or from the C-terminus of the second FN3 domain to the N-terminus of the first FN3 domain. Any EGFR-binding FN3 domain may be covalently linked to a c-Met-binding FN3 domain. Exemplary EGFR-binding FN3 domains are domains having the amino acid sequence shown in SEQ ID NOs: 18-29, 107-110, 122-137 or 194-211, and exemplary c-Met binding FN3 domains are domains having the amino acid sequence shown in SEQ ID NOs: 32-49, 111-114 or 212-223. The EGFR-binding FN3 domains to be coupled to a bispecific molecule may additionally comprise an initiator methionine (Met) at their N-terminus Variants of the bispecific EGFR/c-Met FN3 domain containing molecules are within the scope of the invention. For example, substitutions can be made in the bispecific EGFR/c-Met FN3 domain containing molecule as long as the resulting variant retains similar selectivity and potency towards EGFR and c-Met when compared to the parent molecule. Exemplary modifications are for example conservative substitutions that will result in variants with similar characteristics to those of the parent molecules. Conservative substitutions are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981). Non-conservative substitutions can be made to the bispecific EGFR/c-Met FN3 domain containing molecule that involves substitutions of amino acid residues between different classes of amino acids to improve properties of the bispecific molecules. Whether a change in the amino acid sequence of a polypeptide or fragment thereof results in a functional homolog can be readily determined by assessing the ability of the modified polypeptide or fragment to produce a response in a fashion similar to the unmodified polypeptide or fragment using the assays described herein. Peptides, polypeptides or proteins in which more than one replacement has taken place can readily be tested in the same manner.

The bispecific EGFR/c-Met FN3 domain containing molecules of the invention may be generated as dimers or multimers, for example, as a means to increase the valency and thus the avidity of target molecule binding. The multimers may be generated by linking one or more EGFR-binding FN3 domain and one or more c-Met-binding FN3 domain to form molecules comprising at least three individual FN3 domains that are at least bispecific for either EGFR or c-Met, for example by the inclusion of an amino acid linker using well known methods.

Another embodiment of the invention is a bispecific FN3 domain containing molecule comprising a first fibronectin type III (FN3) domain and a second FN3 domain, wherein the first FN3 domain specifically binds epidermal growth factor receptor (EGFR) and blocks binding of epidermal growth factor (EGF) to EGFR, and the second FN3 domain specifically binds hepatocyte growth factor receptor (c-Met), and blocks binding of hepatocyte growth factor (HGF) to c-Met comprising the amino acid sequence shown in SEQ ID NOs: 50-72, 106, 118-121, 138-165, 170-179 or 190-193.

Half-Life Extending Moieties

The bispecific EGFR/c-Met FN3 domain containing molecules or the monospecific EGFR or c-Met binding FN3 domains of the invention may incorporate other subunits for example via covalent interaction. In one aspect of the invention, the bispecific EGFR/c-Met FN3 domain containing molecules of the invention further comprise a half-life extending moiety. Exemplary half-life extending moieties are albumin, albumin variants, albumin-binding proteins and/or domains, transferrin and fragments and analogues thereof, and Fc regions. An exemplary albumin-binding domain is shown in SEQ ID NO: 117 and an exemplary albumin variant is shown in SEQ ID NO: 189.

All or a portion of an antibody constant region may be attached to the molecules of the invention to impart antibody-like properties, especially those properties associated with the Fc region, such as Fc effector functions such as C1q binding, complement dependent cytotoxicity (CDC), Fc receptor binding, antibody-dependent cell-mediated cytotoxicity (ADCC), phagocytosis, down regulation of cell surface receptors (e.g., B cell receptor; BCR), and can be further modified by modifying residues in the Fc responsible for these activities (for review; see Strohl, *Curr Opin Biotechnol.* 20, 685-691, 2009).

Additional moieties may be incorporated into the bispecific molecules of the invention such as polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the protein scaffold coding sequences and may be generated by standard cloning and expression techniques. Alternatively, well known chemical coupling methods may be used to attach the moieties to recombinantly produced molecules of the invention.

A pegyl moiety may for example be added to the bispecific or monospecific molecules of the invention by incorporating a cysteine residue to the C-terminus of the molecule and attaching a pegyl group to the cysteine using well known methods. Exemplary bispecific molecules with the C-terminal cysteine are those having the amino acid sequence shown in SEQ IN NO: 170-178.

Monospecific and bispecific molecules of the invention incorporating additional moieties may be compared for functionality by several well known assays. For example, altered properties of monospecific and/or bispecific molecules due to incorporation of Fc domains and/or Fc domain variants may be assayed in Fc receptor binding assays using soluble forms of the receptors, such as the FcγRI, FcγRII, FcγRIII or FcRn receptors, or using well known cell-based assays measuring for example ADCC or CDC, or evaluating pharmacokinetic properties of the molecules of the invention in in vivo models.

Polynucleotides, Vectors, Host Cells

The invention provides for nucleic acids encoding the EGFR-binding or c-Met binding FN3 domains or the bispecific EGFR/c-Met FN3 domain containing molecules of the invention as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions or directed mutagens thereof. Certain exemplary polynucleotides are disclosed herein, however, other polynucleotides which, given the degeneracy of the genetic code or codon preferences in a given expression system, encode the EGFR-binding or c-Met binding FN3 domains or the bispecific EGFR/c-Met FN3 domain containing molecules of the invention are also within the scope of the invention.

One embodiment of the invention is an isolated polynucleotide encoding the FN3 domain specifically binding EGFR having the amino acid sequence of SEQ ID NOs: 18-29, 107-110, 122-137 or 194-211.

One embodiment of the invention is an isolated polynucleotide encoding the FN3 domain specifically binding c-Met having the amino acid sequence of the sequence shown in SEQ ID NOs: 32-49, 111-114 or 212-223.

One embodiment of the invention is an isolated polynucleotide encoding the bispecific EGFR/-c-Met FN3 domain containing molecule having the amino acid sequence of SEQ ID NOs: 50-72, 106, 118-121, 138-165, 170-179 or 190-193.

One embodiment of the invention is an isolated polynucleotide comprising the polynucleotide sequence of SEQ ID NOs: 97, 98, 103, 104, 115, 116 or 166-169.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

Another embodiment of the invention is a vector comprising at least one polynucleotide of the invention. Such vectors may be plasmid vectors, viral vectors, vectors for baculovirus expression, transposon based vectors or any other vector suitable for introduction of the polynucleotides of the invention into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

Another embodiment of the invention is a host cell comprising the vector of the invention. A monospecific EGFR-binding or c-Met binding FN3 domain or the bispecific EGFR/c-Met FN3 domain containing molecule of the invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2$^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

The host cell chosen for expression may be of mammalian origin or may be selected from COS-1, COS-7, HEK293, BHK21, CHO, BSC-1, He G2, SP2/0, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as BL21, BL21(DE3), BL21-GOLD (DE3), XL1-Blue, JM109, HMS174, HMS174(DE3), and any of the natural or engineered *E. coli spp, Klebsiella* spp., or *Pseudomonas* spp strains.

Another embodiment of the invention is a method of producing the isolated FN3 domain specifically binding EGFR or c-Met of the invention or the isolated bispecific EGFR/c-Met FN3 domain containing molecule of the invention, comprising culturing the isolated host cell of the invention under conditions such that the isolated FN3 domain specifically binding EGFR or c-Met or the isolated bispecific EGFR/c-Met FN3 domain containing molecule is expressed, and purifying the domain or molecule.

The FN3 domain specifically binding EGFR or c-Met or the isolated bispecific EGFR/c-Met FN3 domain containing molecule of the invention can be purified from recombinant cell cultures by well-known methods, for example by protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography, or high performance liquid chromatography (HPLC).

Uses of Bispecific EGFR/c-Met FN3 Domain Containing Molecules and EGFR-Binding or c-Met Binding FN3 Domains of the Invention The bispecific EGFR/c-Met FN3 domain containing molecules, the EGFR binding FN3 domains or the c-Met binding FN3 domains of the invention may be used to diagnose, monitor, modulate, treat, alleviate, help prevent the incidence of, or reduce the symptoms of human disease or specific pathologies in cells, tissues, organs, fluid, or, generally, a host. The methods of the invention may be used to treat an animal patient belonging to any classification. Examples of such animals include mammals such as humans, rodents, dogs, cats and farm animals.

One aspect of the invention is a method for inhibiting growth or proliferation of cells that express EGFR and/or c-Met, comprising contacting the cells with the isolated bispecific EGFR/c-Met FN3 domain containing molecule, the EGFR binding FN3 domain or the c-Met binding FN3 domain of the invention.

Another aspect of the invention is a method for inhibiting growth or metastasis of EGFR and/or c-Met-expressing tumor or cancer cells in a subject comprising administering to the subject an effective amount of the isolated bispecific EGFR/c-Met FN3 domain containing molecule, the EGFR binding FN3 domain or the c-Met binding FN3 domain of the invention so that the growth or metastasis of EGFR- and/or c-Met-expressing tumor or cancer cell is inhibited.

Another aspect of the invention is a method of treating a subject having cancer, comprising administering a therapeutically effective amount of the isolated bispecific EGFR/c-Met FN3 domain containing molecule, the EGFR binding FN3 domain, or the c-Met binding FN3 domain of the invention to a patient in need thereof for a time sufficient to treat the cancer.

The bispecific EGFR/c-Met FN3 domain containing molecule, the EGFR binding FN3 domain or the c-Met binding FN3 domain of the invention may be used for treatment of any disease or disorder characterized by abnormal activation or production of EGFR, c-Met, EGF or other EGFR ligand or HGF, or disorder related to EGFR or c-Met expression, which may or may not involve malignancy or cancer, where abnormal activation and/or production of EGFR, c-Met, EGF or other EGFR ligand, or HGF is occurring in cells or tissues of a subject having, or predisposed to, the disease or disorder. The bispecific EGFR/c-Met FN3 domain containing molecule, the EGFR binding FN3 domain or the c-Met binding FN3 domain of the invention may be used for treatment of tumors, including cancers and benign tumors. Cancers that are amenable to treatment by the bispecific molecules of the invention include those that overexpress EGFR and/or c-Met, cancers associated with elevated EGFR activity and/or expression levels (such as, for example, an EGFR activating mutation, an EGFR gene amplification, or ligand mediated EGFR activation) and elevated c-Met activity and/or expression levels (such as, for example, a c-Met activating mutation, a c-Met gene amplification, or HGF mediated c-Met activation.

Exemplary EGFR activating mutations that may be associated with cancer include point mutations, deletion mutations, insertion mutations, inversions or gene amplifications that lead to an increase in at least one biological activity of EGFR, such as elevated tyrosine kinase activity, formation of receptor homodimers and heterodimers, enhanced ligand binding etc. Mutations can be located in any portion of an EGFR gene or regulatory region associated with an EGFR gene and include mutations in exon 18, 19, 20 or 21 or mutations in the kinase domain. Exemplary activating EGFR mutations are G719A, L861X (X being any amino acid), L858R, E746K, L747S, E749Q, A750P, A755V, V765M, L858P or T790M substitutions, deletion of E746-A750, deletion of R748-P753, insertion of Ala between M766 and A767, insertion of SVA (Ser, Val, Ala) between 5768 and V769, and insertion of NS (Asn, Ser) between P772 and H773. Other examples of EGFR activating mutations are known in the art (see e.g., U.S. Pat. Publ. No. US2005/0272083). Information about EGFR and other ErbB receptors including receptor homo- and hetero-dimers, receptor ligands, autophosphorylation sites, and signaling molecules involved in ErbB mediated signaling is known in the art (see e.g., Hynes and Lane, Nature Reviews Cancer 5: 341-354, 2005).

Exemplary c-Met activating mutations include point mutations, deletion mutations, insertion mutations, inversions or gene amplifications that lead to an increase in at least one biological activity of a c-Met protein, such as elevated tyrosine kinase activity, formation of receptor homodimers and heterodimers, enhanced ligand binding etc. Mutations can be located in any portion of the c-Met gene or regulatory regions associated with the gene, such as mutations in the kinase domain of c-Met. Exemplary c-Met activating mutations are mutations at residue positions N375, V13, V923, R175, V136, L229, S323, R988, S1058/T1010 and E168. Methods for detecting EGFR and c-Met mutations or gene amplifications are well known.

Exemplary cancers that are amenable to treatment by the bispecific EGFR/c-Met FN3 domain containing molecule, the EGFR binding FN3 domain or the c-Met binding FN3 domain of the invention include epithelial cell cancers, breast cancer, ovarian cancer, lung cancer, non-small cell lung cancer (NSCLC), lung adenocarcinoma, colorectal cancer, anal cancer, prostate cancer, kidney cancer, bladder cancer, head and neck cancer, ovarian cancer, pancreatic cancer, skin cancer, oral cancer, esophageal cancer, vaginal cancer, cervical cancer, cancer of the spleen, testicular cancer, gastric cancer, cancer of the thymus, colon cancer, thyroid cancer, liver cancer, or sporadic or hereditary papillary renal carcinoma (PRCC).

The FN3 domains that specifically bind c-Met and block binding of HGF to c-Met of the invention may be for treatment of tumors, including cancers and benign tumors. Cancers that are amenable to treatment by the c-Met binding FN3 domains of the invention include those that overexpress c-Met. Exemplary cancers that are amenable to treatment by the FN3 domains of the invention include epithelial cell cancers, breast cancer, ovarian cancer, lung cancer, colorectal cancer, anal cancer, prostate cancer, kidney cancer, bladder cancer, head and neck cancer, ovarian cancer, pancreatic cancer, skin cancer, oral cancer, esophageal cancer, vaginal cancer, cervical cancer, cancer of the spleen, testicular cancer, and cancer of the thymus.

The FN3 domains that specifically bind EGFR and blocks binding of EGF to the EGFR of the invention may be used for treatment of tumors, including cancers and benign tumors. Cancers that are amenable to treatment by the FN3 domains of the invention include those that overexpress EGFR or variants. Exemplary cancers that are amenable to treatment by the FN3 domains of the invention include epithelial cell cancers, breast cancer, ovarian cancer, lung cancer, colorectal cancer, anal cancer, prostate cancer, kidney cancer, bladder cancer, head and neck cancer, ovarian cancer, pancreatic cancer, skin cancer, oral cancer, esophageal cancer, vaginal cancer, cervical cancer, cancer of the spleen, testicular cancer, and cancer of the thymus.

In some methods described herein, the bispecific EGFR/c-Met FN3 domain containing molecule, the EGFR binding FN3 domain or the c-Met binding FN3 domain of the invention may be used to treat a subject with a cancer that is resistant or has acquired resistance to treatment with one or more EGFR inhibitors. Exemplary EGFR inhibitors for which cancer may acquire resistance are anti-EGFR antibodies cetuximab (Erbitux®), pantinumumab (Vectibix®), matuzumab, nimotuzumab, small molecule EGFR inhibitors Tarceva® (erlotinib), IRESSA (gefitinib), EKB-569 (pelitinib, irreversible EGFR TKI), pan-ErbB and other receptor tyrosine kinase inhibitors lapatinib (EGFR and HER2 inhibitor), pelitinib (EGFR and HER2 inhibitor), vandetanib (ZD6474, ZACTIMA™, EGFR, VEGFR2 and RET TKI), PF00299804 (dacomitinib, irreversible pan-ErbB TKI), CI-1033 (irreversible pan-erbB TKI), afatinib (BIBW2992, irreversible pan-ErbB TKI), AV-412 (dual EGFR and ErbB2 inhibitor)EXEL-7647 (EGFR, ErbB2, GEVGR and EphB4 inhibitor), CO-1686 (irreversible mutant-selective EGFR TKI), AZD9291 (irreversible mutant-selective EGFR TKI), and HKI-272 (neratinib, irreversible EGFR/ErbB2 inhibitor). The methods described herein may be used to treat cancer that is resistant or has acquired resistance to treatment with gefitinib, erlotinib, afatinib, CO-1686, AZD9291 and/or cetuximab. Exemplary bispecific EGFR/c-Met FN3 domain containing molecules, the EGFR binding FN3 domains or the c-Met binding FN3 domains that can be used are those described herein having amino acid sequences shown in SEQ ID NOs: 18-29, 107-110, 122-137, 194-211, 32-49, 111-114, 212-223, 50-72, 106, 118-121, 138-165, 170-178 or 190-193.

Another aspect of the invention is a method of treating a subject having cancer, comprising administering a therapeutically effective amount of the bispecific EGFR/c-Met FN3 domain containing molecule, the FN3 domain that specifically bind c-Met or the FN3 domain that specifically bind EGFR to a patient in need thereof for a time sufficient to treat the cancer, wherein the subject is resistant or has acquired resistant to treatment with erlotinib, gefitinib, afatinib, CO-1686 (CAS number: 1374640-70-6), AZD9291 or cetuximab.

Various qualitative and/or quantitative methods may be used to determine if a subject is resistant, has developed or is susceptible to developing a resistance to treatment with an EGFR inhibitor. Symptoms that may be associated with resistance to an EGFR inhibitor include, for example, a decline or plateau of the well-being of the patient, an increase in the size of a tumor, arrested or slowed decline in growth of a tumor, and/or the spread of cancerous cells in the body from one location to other organs, tissues or cells. Re-establishment or worsening of various symptoms associated with cancer may also be an indication that a subject has developed or is susceptible to developing resistance to EGFR inhibitors, such as anorexia, cognitive dysfunction, depression, dyspnea, fatigue, hormonal disturbances, neutropenia, pain, peripheral neuropathy, and sexual dysfunction. The symptoms associated with cancer may vary according to the type of cancer. For example, symptoms associated with cervical cancer may include abnormal bleeding, unusual heavy vaginal discharge, pelvic pain that is not related to the normal menstrual cycle, bladder pain or pain during urination, and bleeding between regular menstrual periods, after sexual intercourse, douching, or pelvic exam. Symptoms associated with lung cancer may include persistent cough, coughing up blood, shortness of breath, wheezing chest pain, loss of appetite, losing weight without trying and fatigue. Symptoms for liver cancer may include loss of appetite and weight, abdominal pain, especially in the upper right part of abdomen that may extend into the back and shoulder, nausea and vomiting, general weakness and fatigue, an enlarged liver, abdominal swelling (ascites), and a yellow discoloration of the skin and the whites of eyes (jaundice). One skilled in oncology may readily identify symptoms associated with a particular cancer type.

Others means to determine if a subject has developed a resistance to an EGFR inhibitor include examining EGFR phosphorylation, ERK1/2 phosphorylation and/or AKT phosphorylation in cancer cells, where increased phosphorylation may be indicative that the subject has developed or is susceptible to developing resistance to an EGFR inhibitor. Methods of determining EGFR, ERK1/2 and/or AKT phosphorylation are well known and described herein. Identification of a subject who has developed a resistance to an EGFR inhibitor may involve detection of elevated c-Met expression levels or elevated c-Met activity, for example, arising from increased levels of circulating HGF, an activating mutation of the c-Met gene or a c-Met gene amplification.

Another embodiment of the invention is a method of treating NSCLC in a patient having an NSCLC tumor or tumor metastasis having an activating EGFR mutation or EGFR gene amplification, comprising administering to the patient a therapeutically effective amount of the bispecific EGFR/c-Met FN3 domain containing molecule, the EGFR binding FN3 domain or the c-Met binding FN3 domain of the invention.

The bispecific EGFR/c-Met FN3 domain containing molecule, the EGFR binding FN3 domain or the c-Met binding FN3 domain of the invention can be used to treat non-small cell lung cancer (NSCLC), which includes squamous cell carcinoma, adenocarcinoma, and large cell carcinoma. In some embodiments, cells of the NSCLC have an epithelial phenotype. In some embodiments, the NSCLC has acquired resistance to treatment with one or more EGFR inhibitors.

In NSCLC, specific mutations in the EGFR gene are associated with high response rates (70-80%) to EGFR tyrosine kinase inhibitors (EGFR-TKIs). A 5 amino acid deletion in exon 19 or the point mutation L858R in EGFR are associated with EGFR-TKI sensitivity (Nakata and Gotoh, Expert Opin Ther Targets 16:771-781, 2012). These mutations result in a ligand-independent activation of the EGFR kinase activity. Activating EGFR mutations occur in 10-30% of NSCLC patients and are significantly more common in East Asians, women, never smokers, and patients with adenocarcinoma histology (Janne and Johnson Clin Cancer Res 12(14 Suppl): 4416s-4420s, 2006). EGFR gene amplification is also strongly correlated with response after EGFR-TKI treatment (Cappuzzo et al., J Natl Cancer Inst 97:643-55, 2005).

Although the majority of NSCLC patients with EGFR mutations initially respond to EGFR TKI therapy, virtually all acquire resistance that prevents a durable response. 50-60% of patients acquire resistance due to a second-site point mutation in the kinase domain of EGFR (T790M). Nearly 60% of all tumors that become resistant to EGFR tyrosine kinase inhibitors increase c-Met expression, amplify the c-Met gene, or increase its only known ligand, HGF (Turke et al., Cancer Cell, 17:77-88, 2010).

Another embodiments of the invention is a method of treating patient having cancer, comprising administering a therapeutically effective amount of the bispecific EGFR/c-Met FN3 domain containing molecule, the EGFR binding FN3 domain or the c-Met binding FN3 domain of the invention to a patient in need thereof for a time sufficient to treat the cancer, wherein the cancer is associated with an EGFR activating mutation, an EGFR gene amplification, a c-Met activating mutation or a c-Met gene amplification.

In some embodiments the EGFR activating mutation is G719A, G719X (X being any amino acid), L861X (X being any amino acid), L858R, E746K, L747S, E749Q, A750P, A755V, V765M, L858P or T790M substitution, deletion of E746-A750, deletion of R748-P753, insertion of Ala (A) between M766 and A767, insertion of Ser, Val and Ala (SVA) between S768 and V769, and insertion of Asn and Ser (NS) between P772 and H773.

Another embodiments of the invention is a method of treating patient having cancer, comprising administering a therapeutically effective amount of the bispecific EGFR/c-Met FN3 domain containing molecule, the EGFR binding FN3 domain or the c-Met binding FN3 domain of the invention to a patient in need thereof for a time sufficient to treat the cancer, wherein the cancer is associated with an EGFR mutation L858R, T790M or deletion of residues E746-A750 (del(E746, A750)), EGFR amplification or c-Met amplification.

In some embodiments, the cancer is associated with wild type EGFR and wild type c-Met.

In some embodiments, the cancer is associated with wild type EGFR and c-Met amplification.

In some embodiments, the cancer is associated with EGFR L858R and T790M mutations and wild type c-Met.

In some embodiments, the cancer is associated with EGFR deletion del (E764, A750) and wild type c-Met.

In some embodiments, the cancer is associated with EGFR deletion del(E764, A750) and c-Met amplification.

In some embodiments, the cancer is associated with EGFR deletion del(E764, A750), EGFR amplification and c-Met amplification.

In some embodiments, the patient has a NSCLC associated with EGFR L858R and T790M mutations and wild type c-Met.

In some embodiments, the patient has a NSCLC associated with EGFR amplification and wild type c-Met.

In some embodiments, the patient has a NSCLC associated with EGFR amplification and c-Met amplification.

In some embodiments, the patient has a NSCLC associated with EGFR deletion del(E764, A750) and wild type c-Met.

In some embodiments, the patient has a NSCLC associated with EGFR deletion del(E764, A750) and c-Met amplification. Amplification of EGFR or c-Met may be evaluated by standard methods, for example by determining the copy number of the EGFR or c-Met gene by southern blotting, FISH, or comparative genomic hybridization (CGH)

The terms "treat" or "treatment" refers to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "therapeutically effective amount" refers to an amount effective, at dosages and for periods of time necessary, to achieve a desired therapeutic result. A therapeutically effective amount of the bispecific EGFR/c-Met FN3 domain containing molecule, the EGFR binding FN3 domain or the c-Met binding FN3 domain of the invention may vary according to factors such as the disease state, age, sex, and weight of the individual, and the ability of the bispecific EGFR/c-Met FN3 domain containing molecule, the EGFR binding FN3 domain or the c-Met binding FN3 domain of the invention to elicit a desired response in the individual. Exemplary indicators of an effective EGFR/c-Met therapeutic that may decline or abate in association with resistance include, for example, improved well-being of the patient, decrease or shrinkage of the size of a tumor, arrested or slowed growth of a tumor, and/or absence of metastasis of cancer cells to other locations in the body.

Administration/Pharmaceutical Compositions

The invention provides for pharmaceutical compositions the bispecific EGFR/c-Met FN3 domain containing molecule, the EGFR binding FN3 domain or the c-Met binding FN3 domain of the invention and a pharmaceutically acceptable carrier. For therapeutic use, the bispecific EGFR/c-Met FN3 domain containing molecules, the EGFR-binding FN3 domains or the c-Met-binding FN3 domains of the invention may be prepared as pharmaceutical compositions containing an effective amount of the domain or molecule as an active ingredient in a pharmaceutically acceptable carrier. The term "carrier" refers to a diluent, adjuvant, excipient, or vehicle with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules of the invention in such pharmaceutical formulation can vary widely, i.e., from less than about 0.5%, usually at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration for therapeutic use of the bispecific EGFR/c-Met FN3 domain containing molecules, the EGFR binding FN3 domains or the c-Met binding FN3 domains of the invention may be any suitable route that delivers the agent to the host, such as parenteral administration, e.g., intradermal, intramuscular, intraperitoneal, intravenous or subcutaneous, pulmonary; transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Thus, a pharmaceutical composition of the invention for intramuscular injection could be prepared to contain 1 ml sterile buffered water, and between about 1 ng to about 100 mg, e.g. about 50 ng to about 30 mg or more preferably, about 5 mg to about 25 mg, of the FN3 domain of the invention.

The bispecific EGFR/c-Met FN3 domain containing molecules, the EGFR binding FN3 domains or the c-Met binding FN3 domains of the invention may be administered to a patient by any suitable route, for example parentally by intravenous (IV) infusion or bolus injection, intramuscularly or subcutaneously or intraperitoneally. IV infusion can be given over as little as 15 minutes, but more often for 30 minutes, 60 minutes, 90 minutes or even 2 or 3 hours. The bispecific EGFR/c-Met FN3 domain containing molecules, the EGFR binding FN3 domains or the c-Met binding FN3 domains of the invention may also be injected directly into the site of disease (e.g., the tumor itself). The dose given to a patient having a cancer is sufficient to alleviate or at least partially arrest the disease being treated ("therapeutically effective amount") and may be sometimes 0.1 to 10 mg/kg body weight, for example 1, 2, 3, 4, 5, 6, 7, 8, 9 or 10 mg/kg, but may even higher, for example 15, 20, 30, 40, 50, 60, 70, 80, 90 or 100 mg/kg. A fixed unit dose may also be given, for example, 50, 100, 200, 500 or 1000 mg, or the dose may be based on the patient's surface area, e.g., 400, 300, 250, 200, or 100 mg/m$^2$. Usually between 1 and 8 doses, (e.g., 1, 2, 3, 4, 5, 6, 7 or 8) may be administered to treat cancer, but 10, 12, 20 or more doses may be given. Administration of the bispecific EGFR/c-Met FN3 domain containing molecules, the EGFR binding FN3 domains or the c-Met binding FN3 domains of the invention may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose.

For example, a pharmaceutical composition of the bispecific EGFR/c-Met FN3 domain containing molecules, the EGFR binding FN3 domains or the c-Met binding FN3 domains of the invention for intravenous infusion may be made up to contain about 200 ml of sterile Ringer's solution, and about 8 mg to about 2400 mg, about 400 mg to about 1600 mg, or about 400 mg to about 800 mg of the bispecific EGFR/c-Met antibody for administration to a 80 kg patient. Methods for preparing parenterally administrable compositions are well known and are described in more detail in, for example, "Remington's Pharmaceutical Science", 15th ed., Mack Publishing Company, Easton, Pa.

The bispecific EGFR/c-Met FN3 domain containing molecules, the EGFR-binding FN3 domains or the c-Met-binding FN3 domains of the invention can be lyophilized for storage and reconstituted in a suitable carrier prior to use. This technique has been shown to be effective with conventional protein preparations and art-known lyophilization and reconstitution techniques can be employed.

The bispecific EGFR/c-Met FN3 domain containing molecules, the EGFR-binding FN3 domains or the c-Met-binding FN3 domains of the invention may be administered to a subject in a single dose or the administration may be repeated, e.g. after one day, two days, three days, five days, six days, one week, two weeks, three weeks, one month, five weeks, six weeks, seven weeks, two months or three months. The repeated administration can be at the same dose or at a different dose. The administration can be repeated once, twice, three times, four times, five times, six times, seven times, eight times, nine times, ten times, or more.

The bispecific EGFR/c-Met FN3 domain containing molecules, the EGFR-binding FN3 domains or the c-Met-binding FN3 domains of the invention may be administered in combination with a second therapeutic agent simultaneously, sequentially or separately. The second therapeutic agent may be a chemotherapeutic agent, an anti-angiogenic agent, or a cytotoxic drug. When used for treating cancer, the bispecific EGFR/c-Met FN3 domain containing molecules, the EGFR-binding FN3 domains or the c-Met-binding FN3 domains may be used in combination with conventional cancer therapies, such as surgery, radiotherapy, chemotherapy or combinations thereof. Exemplary agents that can be used in combination with the FN3 domains of the invention are antagonists of HER2, HER3, HER4, VEGF, and protein tyrosine kinase inhibitors such as Iressa® (gefitinib) and Tarceva (erlotinib).

The bispecific EGFR/c-Met FN3 domain containing molecules, the EGFR-binding FN3 domains or the c-Met-binding FN3 domainmay be administered together with any one or more of the chemotherapeutic drugs or other anti-cancer therapeutics known to those of skill in the art. Chemotherapeutic agents are chemical compounds useful in the treatment of cancer and include growth inhibitory agents or other cytotoxic agents and include alkylating agents, anti-metabolites, anti-microtubule inhibitors, topoisomerase inhibitors, receptor tyrosine kinase inhibitors, angiogenesis inhibitors and the like. Examples of chemotherapeutic agents include alkylating agents such as thiotepa and cyclosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-FU; folic acid analogues such as denopterin, methotrexate, pteropterin, trimetrexate; purine analogues such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; members of taxoid or taxane family, such as paclitaxel (TAXOL®docetaxel (TAXOTERE®) and analogues thereof; chlorambucil; gemcitabine; 6-thioguanine; mercaptopurine; methotrexate; platinum analogues such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; inhibitors of receptor tyrosine kinases and/or angiogenesis, including sorafenib (NEXAVAR®), sunitinib (SUTENT®), pazopanib (VOTRIENT™), toceranib (PALLADIA™), vandetanib (ZACTIMA™), cediranib (RECENTIN®), regorafenib (BAY 73-4506), axitinib (AG013736), lestaurtinib (CEP-701), erlotinib (TARCEVA®), gefitinib (IRESSA™), BIBW 2992 (TOVOK™), lapatinib (TYKERB®), neratinib (HKI-272), and the like, and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (FARESTON®); and anti-androgens such as flutamide, nilutamide, bicalutamide, leuprolide, and goserelin; and pharmaceutically acceptable salts, acids or derivatives of any of the above. Other conventional cytotoxic chemical compounds as those disclosed in Wiemann et al., 1985, in *Medical Oncology* (Calabresi et al., eds.), Chapter 10, McMillan Publishing, are also applicable to the methods of the present invention.

Exemplary agents that may be used in combination with the bispecific EGFR/c-Met FN3 domain containing molecules, the EGFR-binding FN3 domains or the c-Met-binding FN3 domaininclude tyrosine kinase inhibitors and targeted anti-cancer therapies such as Iressa® (gefitinib) and Tarceva (erlotinib) and other antagonists of HER2, HER3, HER4 or VEGF. Exemplary HER2 antagonists include CP-724-714, HERCEPTIN™ (trastuzumab), OMNITARG™ (pertuzumab), TAK-165, lapatinib (EGFR and HER2 inhibitor), and GW-282974. Exemplary HER3 antagonists include anti-Her3 antibodies (see e.g., U.S. Pat. Publ. No. US2004/0197332). Exemplary HER4 antagonists include anti-HER4 siRNAs (see e.g., Maatta et al., Mol Biol Cell 17: 67-79, 2006. An exemplary VEGF antagonist is Bevacizumab (Avastin™)

When a small molecule is used in combination with the bispecific EGFR/c-Met FN3 domain containing molecules, the EGFR-binding FN3 domains or the c-Met-binding FN3 domains of the invention, it is typically administered more often, preferably once a day, but 2, 3, 4 or more times per day is also possible, as is every two days, weekly or at some other interval. Small molecule drugs are often taken orally but parenteral administration is also possible, e.g., by IV infusion or bolus injection or subcutaneously or intramuscularly. Doses of small molecule drugs may typically be from 10 to 1000 mg, or about 100, 150, 200 or 250 mg.

When the bispecific EGFR/c-Met FN3 domain containing molecules, the EGFR-binding FN3 domains or the c-Met-binding FN3 domains of the invention is administered in combination with a second therapeutic agent, the combination may take place over any convenient timeframe. For example, the bispecific EGFR/c-Met FN3 domain containing molecule, the EGFR-binding FN3 domain or the c-Met-binding FN3 domain of the invention and the second therapeutic agent may be administered to a patient on the same day, and even in the same intravenous infusion. However, the bispecific EGFR/c-Met FN3 domain containing molecule, the EGFR-binding FN3 domain or the c-Met-binding FN3 domain of the invention and the second therapeutic agent may also be administered on alternating days or alternating weeks, fortnights or months, and so on. In some methods, the bispecific EGFR/c-Met FN3 domain containing molecule, the EGFR-binding FN3 domain or the c-Met-binding FN3 domain of the invention and the second therapeutic agent are administered with sufficient proximity in time that they are simultaneously present (e.g., in the serum) at detectable levels in the patient being treated. In some methods, an entire course of treatment of the bispecific EGFR/c-Met FN3 domain containing molecule, the EGFR-binding FN3 domain or the c-Met-binding FN3 domain of the invention consisting of a number of doses over a time period is followed or preceded by a course of treatment of the second therapeutic agent also consisting of a number of doses. In some methods, treatment with the bispecific EGFR/c-Met FN3 domain containing molecule, the EGFR-binding FN3 domain or the c-Met-binding FN3 domain of the invention administered second is begun if the patient has resistance or develops resistance to the second therapeutic agent administered initially. The patient may receive only a single course or multiple courses of treatment with one or both the bispecific EGFR/c-Met FN3 domain containing molecule, the EGFR-binding FN3 domain or the c-Met-binding FN3 domain of the invention and the second therapeutic agent. A recovery period of 1, 2 or several days or weeks may be used between administration of the bispecific EGFR/c-Met FN3 domain containing molecule, the EGFR-binding FN3 domain or the c-Met-binding FN3 domain of the invention and the second therapeutic agent. When a suitable treatment regiment has already been established for the second therapeutic agent, that regimen may be used in combination with the bispecific EGFR/c-Met FN3 domain containing molecule, the EGFR-binding FN3 domain or the c-Met-binding FN3 domain of the invention. For example, Tarceva® (erlotinib) is taken as a 100 mg or 150 mg pill once a day, and Iressa® (gefitinib) is taken as 250 mg tablet daily.

The bispecific EGFR/c-Met FN3 domain containing molecule, the EGFR-binding FN3 domain or the c-Met-binding FN3 domain of the invention, optionally in combination with the second therapeutic agent may be administered together with any form of radiation therapy including external beam radiation, intensity modulated radiation therapy (IMRT) and any form of radiosurgery including Gamma Knife, Cyberknife, Linac, and interstitial radiation (e.g. implanted radioactive seeds, GliaSite balloon), and/or with surgery. Combination with radiation therapy can be especially appropriate for head and neck cancer and brain tumors.

While having described the invention in general terms, the embodiments of the invention will be further disclosed in the following examples that should not be construed as limiting the scope of the claims.

EXAMPLE 1

Construction of Tencon libraries

Tencon (SEQ ID NO: 1) is an immunoglobulin-like scaffold, fibronectin type III (FN3) domain, designed from a consensus sequence of fifteen FN3 domains from human tenascin-C (Jacobs et al., Protein Engineering, Design, and Selection, 25:107-117, 2012; U.S. Pat. Publ. No. 2010/0216708). The crystal structure of Tencon shows six surface-exposed loops that connect seven beta-strands. These loops, or selected residues within each loop, can be randomized in order to construct libraries of fibronectin type III (FN3) domains that can be used to select novel molecules that bind to specific targets.

Tencon:
LPAPKNLVVSEVTEDSLRLSWTAPDAAFDSFLIQY-
QESEKVGEAINLTVPGSERSYDLTGLK PGTEYT-
VSIYGVKGGHRSNPLSAEFTT (SEQ ID NO 1):
Construction of TCL1 Library A library designed to randomize only the FG loop of Tencon (SEQ ID NO: 1), TCL1, was constructed for use with the cis-display system (Jacobs et al., Protein Engineering, Design, and Selection, 25:107-117, 2012). In this system, a single-strand DNA incorporating sequences for a Tac promoter, Tencon library coding sequence, RepA coding sequence, cis-element, and on element is produced. Upon expression in an in vitro transcription/translation system, a complex is produced of the Tencon-RepA fusion protein bound in cis to the DNA from which it is encoded. Complexes that bind to a target molecule are then isolated and amplified by polymerase chain reaction (PCR), as described below.

Construction of the TCL1 library for use with cis-display was achieved by successive rounds of PCR to produce the final linear, double-stranded DNA molecules in two halves; the 5' fragment contains the promoter and Tencon sequences, while the 3' fragment contains the repA gene and the cis- and on elements. These two halves are combined by restriction digest in order to produce the entire construct. The TCL1 library was designed to incorporate random amino acids only in the FG loop of Tencon, KGGHRSN (SEQ ID NO: 86). NNS codons were used in the construction of this library, resulting in the possible incorporation of all 20 amino acids and one stop codon into the FG loop. The TCL1 library contains six separate sub-libraries, each having a different randomized FG loop length, from 7 to 12 residues, in order to further increase diversity. Design of tencon-based libraries are shown in Table 2.

TABLE 2

| Library | BC Loop Design | FG Loop Design |
|---------|----------------|----------------|
| WT Tencon | TAPDAAFD* | KGGHRSN** |
| TCL1 | TAPDAAFD* | XXXXXXX |
|  |  | XXXXXXXX |
|  |  | XXXXXXXXX |
|  |  | XXXXXXXXXX |
|  |  | XXXXXXXXXXX |
|  |  | XXXXXXXXXXXX |
| TCL2 | ######## | #####S## |

*TAPDAAFD: residues 22-28 of SEQ ID NO: 1;
**KGGHRSN: SEQ ID NO: 86
X refers to degenerate amino acids encoded by NNS codons.
# refers to the "designed distribution of amino acids" described in the text.

To construct the TCL1 library, successive rounds of PCR were performed to append the Tac promoter, build degeneracy into the FG loop, and add necessary restriction sites for final assembly. First, a DNA sequence containing the promoter sequence and Tencon sequence 5' of the FG loop was generated by PCR in two steps. DNA corresponding to the full Tencon gene sequence was used as a PCR template with primers POP2220 (SEQ ID NO: 2) and TC5' toFG (SEQ ID NO: 3). The resulting PCR product from this reaction was used as a template for the next round of PCR amplification with primers 130mer (SEQ ID NO: 4) and Tc5' toFG to complete the appending of the 5' and promoter sequences to Tencon. Next, diversity was introduced into the FG loop by amplifying the DNA product produced in the first step with forward primer POP2222 (SEQ ID NO: 5), and reverse primers TCF7 (SEQ ID NO: 6), TCF8 (SEQ ID NO: 7), TCF9 (SEQ ID NO: 8), TCF10 (SEQ ID NO: 9), TCF11 (SEQ ID N NO: 10), or TCF12 (SEQ ID NO: 11), which contain degenerate nucleotides. At least eight 100 µL PCR reactions were performed for each sub-library to minimize PCR cycles and maximize the diversity of the library. At least 5 µg of this PCR product were gel-purified and used in a subsequent PCR step, with primers POP2222 (SEQ ID NO: 5) and POP2234 (SEQ ID NO: 12), resulting in the attachment of a 6×His tag and NotI restriction site to the 3' end of the Tencon sequence. This PCR reaction was carried out using only fifteen PCR cycles and at least 500 ng of template DNA. The resulting PCR product was gel-purified, digested with NotI restriction enzyme, and purified by Qiagen column.

The 3' fragment of the library is a constant DNA sequence containing elements for display, including a PspOMI restriction site, the coding region of the repA gene, and the cis- and ori elements. PCR reactions were performed using a plasmid (pCR4Blunt) (Invitrogen) containing this DNA fragment with M13 Forward and M13 Reverse primers. The resulting PCR products were digested by PspOMI overnight and gel-purified. To ligate the 5' portion of library DNA to the 3' DNA containing the repA gene, 2 pmol of 5' DNA were ligated to an equal molar amount of 3' repA DNA in the presence of NotI and PspOMI enzymes and T4 ligase. After overnight ligation at 37° C., a small portion of the ligated DNA was run on a gel to check ligation efficiency. The ligated library product was split into twelve PCR amplifications and a 12-cycle PCR reaction was run with primer pair POP2250 (SEQ ID NO: 13) and DidLigRev (SEQ ID NO: 14). The DNA yield for each sub-library of TCL1 library ranged from 32-34 μg.

To assess the quality of the library, a small portion of the working library was amplified with primers Tcon5new2 (SEQ ID NO: 15) and Tcon6 (SEQ ID NO: 16), and was cloned into a modified pET vector via ligase-independent cloning. The plasmid DNA was transformed into BL21-GOLD (DE3) competent cells (Stratagene) and 96 randomly picked colonies were sequenced using a T7 promoter primer. No duplicate sequences were found. Overall, approximately 70-85% of clones had a complete promoter and Tencon coding sequence without frame-shift mutation. The functional sequence rate, which excludes clones with STOP codons, was between 59% and 80%.

Construction of TCL2 Library

TCL2 library was constructed in which both the BC and the FG loops of Tencon were randomized and the distribution of amino acids at each position was strictly controlled. Table 3 shows the amino acid distribution at desired loop positions in the TCL2 library. The designed amino acid distribution had two aims. First, the library was biased toward residues that were predicted to be structurally important for Tencon folding and stability based on analysis of the Tencon crystal structure and/or from homology modeling. For example, position 29 was fixed to be only a subset of hydrophobic amino acids, as this residue was buried in the hydrophobic core of the Tencon fold. A second layer of design included biasing the amino acid distribution toward that of residues preferentially found in the heavy chain HCDR3 of antibodies, to efficiently produce high-affinity binders (Birtalan et al., J Mol Biol 377:1518-28, 2008; Olson et al., Protein Sci 16:476-84, 2007). Towards this goal, the "designed distribution" of Table 3 refers to the distribution as follows: 6% alanine, 6% arginine, 3.9% asparagine, 7.5% aspartic acid, 2.5% glutamic acid, 1.5% glutamine, 15% glycine, 2.3% histidine, 2.5% isoleucine, 5% leucine, 1.5% lysine, 2.5% phenylalanine, 4% proline, 10% serine, 4.5% threonine, 4% tryptophan, 17.3% tyrosine, and 4% valine. This distribution is devoid of methionine, cysteine, and STOP codons.

TABLE 3

| Residue Position* | WT residues | Distribution in the TCL2 library |
| --- | --- | --- |
| 22 | T | designed distribution |
| 23 | A | designed distribution |
| 24 | P | 50% P + designed distribution |
| 25 | D | designed distribution |
| 26 | A | 20% A + 20% G + designed distribution |
| 27 | A | designed distribution |
| 28 | F | 20% F, 20% I, 20% L, 20% V, 20% Y |
| 29 | D | 33% D, 33% E, 33% T |
| 75 | K | designed distribution |
| 76 | G | designed distribution |
| 77 | G | designed distribution |
| 78 | H | designed distribution |
| 79 | R | designed distribution |
| 80 | S | 100% S |
| 81 | N | designed distribution |
| 82 | P | 50% P + designed distribution |

*residue numbering is based on Tencon sequence of SEQ ID NO: 1

The 5' fragment of the TCL2 library contained the promoter and the coding region of Tencon (SEQ ID NO: 1), which was chemically synthesized as a library pool (Sloning Biotechnology). This pool of DNA contained at least $1 \times 10^{11}$ different members. At the end of the fragment, a BsaI restriction site was included in the design for ligation to RepA.

The 3' fragment of the library was a constant DNA sequence containing elements for display including a 6×His tag, the coding region of the repA gene, and the cis-element. The DNA was prepared by PCR reaction using an existing DNA template (above), and primers LS1008 (SEQ ID NO: 17) and DidLigRev (SEQ ID NO: 14). To assemble the complete TCL2 library, a total of 1 μg of BsaI-digested 5' Tencon library DNA was ligated to 3.5 μg of the 3' fragment that was prepared by restriction digestion with the same enzyme. After overnight ligation, the DNA was purified by Qiagen column and the DNA was quantified by measuring absorbance at 260 nm. The ligated library product was amplified by a 12-cycle PCR reaction with primer pair POP2250 (SEQ ID NO: 13) and DidLigRev (SEQ ID NO: 14). A total of 72 reactions were performed, each containing 50 ng of ligated DNA products as a template. The total yield of TCL2 working library DNA was about 100 μg. A small portion of the working library was sub-cloned and sequenced, as described above for library TCL1. No duplicate sequences were found. About 80% of the sequences contained complete promoter and Tencon coding sequences with no frame-shift mutations.

Construction of TCL14 Library

The top (BC, DE, and FG) and the bottom (AB, CD, and EF) loops, e.g., the reported binding surfaces in the FN3 domains are separated by the beta-strands that form the center of the FN3 structure. Alternative surfaces residing on the two "sides" of the FN3 domains having different shapes than the surfaces formed by loops only are formed at one side of the FN3 domain by two anti-parallel beta-strands, the C and the F beta-strands, and the CD and FG loops, and is herein called the C-CD-F-FG surface.

A library randomizing an alternative surface of Tencon was generated by randomizing select surface exposed residues of the C and F strands, as well as portions of the CD and FG loops as shown in FIG. 1. A Tencon variant, Tencon27 (SEQ ID NO: 99) having following substitutions when compared to Tencon (SEQ ID NO: 1) was used to generate the library; E11R L17A, N46V, E86I. A full description of the methods used to construct this library is described in US. Pat. Publ. No. US2013/0226834.

EXAMPLE 2

Selection of Fibronectin Type III (FN3) Domains that Bind EGFR and Inhibit EGF Binding Library Screening Cis-display was used to select EGFR binding domains from the TCL1 and TCL2 libraries. A recombinant human extracellular domain of EGFR fused to an IgG1 Fc (R&D Systems) was biotinylated using standard methods and used for panning (residues 25-645 of full length EGFR of SEQ ID NO: 73). For in vitro transcription and translation (ITT), 2-6 µg of library DNA were incubated with 0.1 mM complete amino acids, 1× S30 premix components, and 30 µL of S30 extract (Promega) in a total volume of 100 µL and incubated at 30° C. After 1 hour, 450 µL of blocking solution (PBS pH 7.4, supplemented with 2% bovine serum albumin, 100 µg/mL herring sperm DNA, and 1 mg/mL heparin) were added and the reaction was incubated on ice for 15 minutes. EGFR-Fc:EGF complexes were assembled at molar ratios of 1:1 and 10:1 EGFR to EGF by mixing recombinant human EGF (R&D Systems) with biotinylated recombinant EGFR-Fc in blocking solution for 1 hour at room temperature. For binding, 500 µL of blocked ITT reactions were mixed with 100 µL of EGFR-Fc:EGF complexes and incubated for 1 hour at room temperature, after which bound complexes were pulled down with magnetic neutravidin or streptavidin beads (Seradyne). Unbound library members were removed by successive washes with PBST and PBS. After washing, DNA was eluted from the bound complexes by heating to 65° C. for 10 minutes, amplified by PCR, and attached to a DNA fragment encoding RepA by restriction digestion and ligation for further rounds of panning. High affinity binders were isolated by successively lowering the concentration of target EGFR-Fc during each round from 200 nM to 50 nM and increasing the washing stringency. In rounds 4 and 5, unbound and weakly bound FN3 domains were removed by washing in the presence of a 10-fold molar excess of non-biotinylated EGFR-Fc overnight in PBS.

Following panning, selected FN3 domains were amplified by PCR using oligos Tcon5new2 (SEQ ID NO: 15) and Tcon6 (SEQ ID NO: 16), subcloned into a pET vector modified to include a ligase independent cloning site, and transformed into BL21-GOLD (DE3) (Stratagene) cells for soluble expression in *E. coli* using standard molecular biology techniques. A gene sequence encoding a C-terminal poly-histidine tag was added to each FN3 domain to enable purification and detection. Cultures were grown to an optical density of 0.6-0.8 in 2YT medium supplemented with 100 µg/mL carbenicillin in 1-mL 96-well blocks at 37° C. before the addition of IPTG to 1 mM, at which point the temperature was reduced to 30° C. Cells were harvested approximately 16 hours later by centrifugation and frozen at −20° C. Cell lysis was achieved by incubating each pellet in 0.6 mL of BugBuster® HT lysis buffer (Novagen EMD Biosciences) with shaking at room temperature for 45 minutes.

Selection of FN3 Domains that Bind EGFR on Cells

To assess the ability of different FN3 domains to bind EGFR in a more physiological context, their ability to bind A431 cells was measured. A431 cells (American Type Culture Collection, cat. #CRL-1555) over-express EGFR with ~2×10$^6$ receptors per cell. Cells were plated at 5,000/well in opaque black 96-well plates and allowed to attach overnight at 37° C., in a humidified 5% $CO_2$ atmosphere. FN3 domain-expressing bacterial lysates were diluted 1,000-fold into FACS stain buffer (Becton Dickinson) and incubated for 1 hour at room temperature in triplicate plates. Lysates were removed and cells were washed 3 times with 150 µL/well of FACS stain buffer. Cells were incubated with 50 µL/well of anti-penta His-Alexa488 antibody conjugate (Qiagen) diluted 1:100 in FACS stain buffer for 20 minutes at room temperature. Cells were washed 3 times with 150 µL/well of FACS stain buffer, after which wells were filled with 100 µL of FACS stain buffer and read for fluorescence at 488 nm using an Acumen eX3 reader. Bacterial lysates containing FN3 domains were screened for their ability to bind A431 cells (1320 crude bacterial lysates for TCL1 and TCL2 libraries) and 516 positive clones were identified, where binding was ≥10-fold over the background signal. 300 lysates from the TCL14 library were screened for binding, resulting in 58 unique FN3 domain sequences that bind to EGFR.

Selection of FN3 Domains that Inhibit EGF Binding to EGFR on Cells

To better characterize the mechanism of EGFR binding, the ability of various identified FN3 domain clones to bind EGFR in an EGF-competitive manner was measured using A431 cells and run in parallel with the A431 binding assay screen. A431 cells were plated at 5,000/well in opaque black 96-well plates and allowed to attach overnight at 37° C. in a humidified 5% $CO_2$ atmosphere. Cells were incubated with 50 µL/well of 1:1,000 diluted bacterial lysate for 1 hour at room temperature in triplicate plates. Biotinylated EGF (Invitrogen, cat. #E-3477) was added to each well for a final concentration of 30 ng/mL and incubated for 10 minutes at room temperature. Cells were washed 3 times with 150 µL/well of FACS stain buffer. Cells were incubated with 50 µL/well of streptavidin-phycoerythrin conjugate (Invitrogen) diluted 1:100 in FACS stain buffer for 20 minutes at room temperature. Cells were washed 3 times with 150 µL/well of FACS stain buffer, after which wells were filled with 100 µL of FACS stain buffer and read for fluorescence at 600 nm using an Acumen eX3 reader.

Bacterial lysates containing the FN3 domains were screened in the EGF competition assay described above. 1320 crude bacterial lysates from TCL1 and TCL2 libraries were screened resulting in 451 positive clones that inhibited EGF binding by >50%.

Expression and Purification of Identified FN3 Domains Binding EGFR

His-tagged FN3 domains were purified from clarified *E. coli* lysates with His MultiTrap™ HP plates (GE Healthcare) and eluted in buffer containing 20 mM sodium phosphate, 500 mM sodium chloride, and 250 mM imidazole at pH 7.4. Purified samples were exchanged into PBS pH 7.4 for analysis using PD MultiTrap™ G-25 plates (GE Healthcare).

Size Exclusion Chromatography Analysis

Size exclusion chromatography was used to determine the aggregation state of the FN3 domains binding EGFR. Aliquots (10 µL) of each purified FN3 domain were injected onto a Superdex 75 5/150 column (GE Healthcare) at a flow rate of 0.3 mL/min in a mobile phase of PBS pH 7.4. Elution from the column was monitored by absorbance at 280 nm. FN3 domains that exhibited high levels of aggregation by SEC were excluded from further analysis.

Off-Rate of Selected EGFR-Binding FN3 Domains from EGFR-Fc

Select EGFR-binding FN3 domains were screened to identify those with slow off-rates ($k_{off}$) in binding to EGFR-Fc on a ProteOn XPR-36 instrument (Bio-Rad) to facilitate selection of high affinity binders. Goat anti-human Fc IgG (R&D systems), at a concentration of 5 μg/mL, was directly immobilized via amine coupling (at pH 5.0) on all 6 ligand channels in horizontal orientation on the chip with a flow rate of 30 μL/min in PBS containing 0.005% Tween-20. The immobilization densities averaged about 1500 Response Units (RU) with less than 5% variation among different channels. EGFR-Fc was captured on the anti-human Fc IgG surface to a density around 600 RU in vertical ligand orientation. All tested FN3 domains were normalized to a concentration of 1 μM and tested for their binding in horizontal orientation. All 6 analyte channels were used for the FN3 domains to maximize screening throughput. The dissociation phase was monitored for 10 minutes at a flow rate of 100 μL/min. The inter-spot binding signals were used as references to monitor non-specific binding between analytes and the immobilized IgG surface, and were subtracted from all binding responses. The processed binding data were locally fit to a 1:1 simple Langmuir binding model to extract the $k_{off}$ for each FN3 domain binding to captured EGFR-Fc.

Inhibition of EGF-Stimulated EGFR Phosphorylation

Purified EGFR-binding FN3 domains were tested for their ability to inhibit EGF-stimulated phosphorylation of EGFR in A431 cells at a single concentration. EGFR phosphorylation was monitored using the EGFR phospho(Tyr1173) kit (Meso Scale Discovery). Cells were plated at 20,000/well in clear 96-well tissue culture-treated plates (Nunc) in 100 μL/well of RPMI medium (Gibco) containing GlutaMAX™ with 10% fetal bovine serum (FBS) (Gibco) and allowed to attach overnight at 37° C. in a humidified 5% $CO_2$ atmosphere. Culture medium was removed completely and cells were starved overnight in 100 μL/well of medium containing no FBS at 37° C. in a humidified 5% $CO_2$ atmosphere. Cells were then treated with 100 μL/well of pre-warmed (37° C.) starvation medium containing EGFR-binding FN3 domains at a concentration of 2 μM for 1 hour at 37° C. in a humidified 5% $CO_2$ atmosphere. Controls were treated with starvation medium only. Cells were stimulated by the addition and gentle mixing of 100 μL/well of pre-warmed (37° C.) starvation medium containing 100 ng/mL recombinant human EGF (R&D Systems, cat. #236-EG), for final concentrations of 50 ng/mL EGF and 1 μM EGFR-binding FN3 domain, and incubation at 37° C., 5% $CO_2$ for 15 minutes. One set of control wells was left un-stimulated as negative controls. Medium was completely removed and cells were lysed with 100 μL/well of Complete Lysis Buffer (Meso Scale Discovery) for 10 minutes at room temperature with shaking, as per the manufacturer's instructions. Assay plates configured for measuring EGFR phosphorylated on tyrosine 1173 (Meso Scale Discovery) were blocked with the provided blocking solution as per the manufacturer's instructions at room temperature for 1.5-2 hours. Plates were then washed 4 times with 200 μL/well of 1× Tris Wash Buffer (Meso Scale Discovery). Aliquots of cell lysate (30 μL/well) were transferred to assay plates, which were covered with plate sealing film (VWR) and incubated at room temperature with shaking for 1 hour. Assay plates were washed 4 times with 200 μL/well of Tris Wash Buffer, after which 25 μL of ice-cold Detection Antibody Solution (Meso Scale Discovery) were added to each well, being careful not to introduce bubbles. Plates were incubated at room temperature with shaking for 1 hour, followed by 4 washes with 200 μL/well of Tris Wash Buffer. Signals were detected by addition of 150 μL/well of Read Buffer (Meso Scale Discovery) and reading on a SECTOR® Imager 6000 instrument (Meso Scale Discovery) using manufacturer-installed assay-specific default settings. Percent inhibition of the EGF-stimulated positive control signal was calculated for each EGFR-binding FN3 domain.

Inhibition of EGF-stimulated EGFR phosphorylation was measured for 232 identified clones from the TCL1 and TCL2 libraries. 22 of these clones inhibited EGFR phosphorylation by ≥50% at 1 μM concentration. After removal of clones that either expressed poorly or were judged to be multimeric by size exclusion chromatography, nine clones were carried forward for further biological characterization. The BC and FG loop sequences of these clones are shown in Table 4. Eight of the nine selected clones had a common FG loop sequence (HNVYKDTNMRGL; SEQ ID NO: 95) and areas of significant similarity were seen between several clones in their BC loop sequences.

TABLE 4

| FN3 Domain | BC Loop | | FG Loop | |
|---|---|---|---|---|
| Clone ID | SEQ ID NO: | Sequence | SEQ ID NO: | Sequence | SEQ ID NO: |
| P53A1R5-17 | 18 | ADPHGFYD | 87 | HNVYKDTNMRGL | 95 |
| P54AR4-17 | 19 | TYDRDGYD | 88 | HNVYKDTNMRGL | 95 |
| P54AR4-47 | 20 | WDPFSFYD | 89 | HNVYKDTNMRGL | 95 |
| P54AR4-48 | 21 | DDPRGFYE | 90 | HNVYKDTNMRGL | 95 |
| P54AR4-73 | 22 | TWPYADLD | 91 | HNVYKDTNMRGL | 95 |
| P54AR4-74 | 23 | GYNGDHFD | 92 | HNVYKDTNMRGL | 95 |
| P54AR4-81 | 24 | DYDLGVYD | 93 | HNVYKDTNMRGL | 95 |
| P54AR4-83 | 25 | DDPWDFYE | 94 | HNVYKDTNMRGL | 95 |
| P54CR4-31 | 26 | TAPDAAFD | 85 | LGSYVFEHDVM | 96 |

EXAMPLE 3

Characterization of EGFR-Binding FN3 Domains that Inhibit EGF Binding

Large-Scale Expression, Purification, and Endotoxin Removal

The FN3 domains shown in Table 4 were scaled up to provide more material for detailed characterization. An overnight culture containing each EGFR-binding FN3 domain variant was used to inoculate 0.8 L of Terrific broth medium supplemented with 100 μg/mL ampicillin at a 1/80 dilution of overnight culture into fresh medium, and incubated with shaking at 37° C. The culture was induced when the optical density at 600 nm reached ~1.2-1.5 by addition of IPTG to a final concentration of 1 mM and the temperature was reduced to 30° C. After 4 hours, cells were collected by centrifugation and the cell pellet was stored at −80° C. until needed.

For cell lysis, the thawed pellet was resuspended in 1× BugBuster® supplemented with 25 U/mL Benzonase® (Sigma-Aldrich) and 1 kU/mL rLysozyme™ (Novagen EMD Biosciences) at a ratio of 5 mL of BugBuster® per gram of pellet. Lysis proceeded for 1 hour at room temperature with gentle agitation, followed by centrifugation at 56,000×g for 50 minutes at 4° C. The supernatant was collected and filtered through a 0.2 μm filter, then loaded on to a 5-mL HisTrap FF column pre-equilibrated with Buffer A (50 mM Tris-HCl pH 7.5, 500 mM NaCl, 10 mM imidazole) using a GE Healthcare ÄKTAexplorer 100s chromatography system. The column was washed with 20 column volumes of Buffer A and further washed with 16% Buffer B (50 mM Tris-HCl pH7.5, 500 mM NaCl, 250 mM imidazole) for 6 column volumes. The FN3 domains were eluted with 50% B for 10 column volumes, followed by a gradient from 50-100% B over 6 column volumes. Fractions containing the FN3 domain protein were pooled, concentrated using a Millipore 10K MWCO concentrator, and filtered before loading onto a HiLoad™ 16/60 Superdex™ 75 column (GE Healthcare) pre-equilibrated with PBS. The protein monomer peak eluting from the size exclusion column was retained.

Endotoxins were removed using a batch approach with ActiClean Etox resin (Sterogene Bioseparations). Prior to endotoxin removal, the resin was pre-treated with 1 N NaOH for 2 hours at 37° C. (or overnight at 4° C.) and washed extensively with PBS until the pH had stabilized to ~7 as measured with pH indicator paper. The purified protein was filtered through a 0.2 µm filter before adding to 1 mL of Etox resin at a ratio of 10 mL of protein to 1 mL of resin. The binding of endotoxin to resin was allowed to proceed at room temperature for at least 2 hours with gentle rotation. The resin was removed by centrifugation at 500×g for 2 minutes and the protein supernatant was retained. Endotoxin levels were measured using EndoSafe®-PTST™ cartridges and analyzed on an EndoSafe®-MCS reader (Charles River). If endotoxin levels were above 5 EU/mg after the first Etox treatment, the above procedure was repeated until endotoxin levels were decreased to ≤5 EU/mg. In cases where the endotoxin level was above 5 EU/mg and stabilized after two consecutive treatments with Etox, anion exchange or hydrophobic interaction chromatography conditions were established for the protein to remove the remaining endotoxins.

Affinity Determination of Selected EGFR-Binding FN3 Domains to EGFR-Fc (EGFR-Fc Affinity)

Binding affinity of selected EGFR-binding FN3 domains to recombinant EGFR extracellular domain was further characterized by surface Plasmon resonance methods using a Proteon Instrument (BioRad). The assay set-up (chip preparation, EGFR-Fc capture) was similar to that described above for off-rate analysis. Selected EGFR binding FN3 domains were tested at 1 µM concentration in 3-fold dilution series in the horizontal orientation. A buffer sample was also injected to monitor the baseline stability. The dissociation phase for all concentrations of each EGFR-binding FN3 domain was monitored at a flow rate of 100 µL/min for 30 minutes (for those with $k_{off}$~$10^{-2}$ s$^{-1}$ from off-rate screening), or 1 hour (for those with $k_{off}$~$10^{-3}$ s$^{-1}$ or slower). Two sets of reference data were subtracted from the response data: 1) the inter-spot signals to correct for the non-specific interactions between the EGFR-binding FN3 domain and the immobilized IgG surface; 2) the buffer channel signals to correct for baseline drifting due to the dissociation of captured EGFR-Fc surface over time. The processed binding data at all concentrations for each FN3 domain were globally fit to a 1:1 simple Langmuir binding model to extract estimates of the kinetic ($k_{on}$, $k_{off}$) and affinity ($K_D$) constants. Table 5 shows the kinetic constants for each of the constructs, with the affinity varying from 200 pM to 9.6 nM.

Binding of Selected EGFR-Binding FN3 Domains to EGFR on Cells ("A431 Cell Binding Assay")

A431 cells were plated at 5,000/well in opaque black 96-well plates and allowed to attach overnight at 37° C., in a humidified 5% $CO_2$ atmosphere. Purified EGFR-binding FN3 domains (1.5 nM to 30 µM) were added to the cells (in 50 uL) for 1 hour at room temperature in triplicate plates. Supernatant was removed and cells were washed 3 times with 150 µL/well of FACS stain buffer. Cells were incubated with 50 µL/well of anti-penta His-Alexa488 antibody conjugate (Qiagen) diluted 1:100 in FACS stain buffer for 20 minutes at room temperature. Cells were washed 3 times with 150 µL/well of FACS stain buffer, after which wells were filled with 100 µL of FACS stain buffer and read for fluorescence at 488 nm using an Acumen eX3 reader. Data were plotted as raw fluorescence signal against the logarithm of the FN3 domain molar concentration and fitted to a sigmoidal dose-response curve with variable slope using GraphPad Prism 4 (GraphPad Software) to calculate $EC_{50}$ values. Table 5 reports the $EC_{50}$ for each of the constructs ranging from 2.2 nM to >

Inhibition of EGF Binding to EGFR on Cells Using Selected EGFR-Binding FN3 Domains (A431 Cell EGF Competition Assay)

A431 cells were plated at 5,000/well in opaque black 96-well plates and allowed to attach overnight at 37° C., in a humidified 5% $CO_2$ atmosphere. Purified EGFR-binding FN3 domains (1.5 nM to 30 µM) were added to the cells (50 µL/well) for 1 hour at room temperature in triplicate plates. Biotinylated EGF (Invitrogen, Cat #: E-3477) was added to each well to give a final concentration of 30 ng/mL and incubated for 10 minutes at room temperature. Cells were washed 3 times with 150 µL/well of FACS stain buffer. Cells were incubated with 50 µL/well of streptavidin-phycoerythrin conjugate (Invitrogen) diluted 1:100 in FACS stain buffer for 20 minutes at room temperature. Cells were washed 3 times with 150 µL/well of FACS stain buffer, after which wells were filled with 100 µL of FACS stain buffer and read for fluorescence at 600 nm using an Acumen eX3 reader. Data were plotted as the raw fluorescence signal against the logarithm of FN3 domain molar concentration and fitted to a sigmoidal dose-response curve with variable slope using GraphPad Prism 4 (GraphPad Software) to calculate $IC_{50}$ values. Table 5 reports the $IC_{50}$ values ranging from 1.8 nM to 121 nM.

Inhibition of EGF-Stimulated EGFR Phosphorylation (Phoshpo-EGRF Assay)

Select FN3 domains that significantly inhibited EGF-stimulated EGFR phosphorylation were assessed more completely by measuring $IC_{50}$ values for inhibition. Inhibition of EGF-stimulated EGFR phosphorylation was assessed at varying FN3 domain concentrations (0.5 nM to 10 µM) as described above in "inhibition of EGF stimulated EGFR phosphorylation". Data were plotted as electrochemiluminescence signal against the logarithm of the FN3 domain molar concentration and $IC_{50}$ values were determined by fitting data to a sigmoidal dose response with variable slope using GraphPad Prism 4 (GraphPad Software). Table 5 shows the $IC_{50}$ values which ranged from 18 nM to >2.5 µM.

Inhibition of Human Tumor Cell Growth (NCI-H292 Growth and NCI-H322 Growth Assay)

Inhibition of EGFR-dependent cell growth was assessed by measuring viability of the EGFR over-expressing human tumor cell lines, NCI-H292 and NCI-H322 (American Type Culture Collection, cat. #CRL-1848 & #CRL-5806, respectively), following

TABLE 5

| FN3 Domain Clone ID | SEQ ID NO: | EGFR-Fc Affinity (nM) | A431 Cell Binding EC$_{50}$ (nM) | A431 Cell EGF Competition IC$_{50}$ (nM) | Phospho-EGFR IC$_{50}$ (nM) | NCI-H292 Growth IC$_{50}$ (nM) | NCI-H322 Growth IC$_{50}$ (nM) |
|---|---|---|---|---|---|---|---|
| P53A1R5-17 | 18 | 1.89 | 4.0 | 9.8 | >2500 | 86 | 65 |
| P54AR4-17 | 19 | 9.62 | 16 | 21 | 184 | ND | ND |
| P54AR4-47 | 20 | 2.51 | 8.6 | 7.1 | 295 | 44 | 39 |
| P54AR4-48 | 21 | 7.78 | 12 | 9.8 | 170 | ND | ND |
| P54AR4-73 | 22 | 0.197 | 9.4 | 4.6 | 141 | 83 | 73 |
| P54AR4-74 | 23 | ND | 77 | ND | ND | ND | ND |
| P54AR4-81 | 24 | ND | 84 | 121 | ND | ND | ND |
| P54AR4-83 | 25 | 0.255 | 2.2 | 1.8 | 18 | 5.9 | 9.2 |
| P54CR4-31 | 26 | 0.383 | >20000 | 55 | 179 | 1150 | >3073 | exposure to EGFR-binding FN3 domains. Cells were plated at 500 cells/well (NCI-H292) or 1,000 cells/well (NCI-H322) in opaque white 96-well tissue culture-treated plates (Nunc) in 100 µL/well of RPMI medium (Gibco) containing GlutaMAX™ and 10 mM HEPES, supplemented with 10% heat inactivated fetal bovine serum (Gibco) and 1% penicillin/streptomycin (Gibco), and allowed to attach overnight at 37° C. in a humidified 5% CO$_2$ atmosphere. Cells were treated by addition of 5 µL/well of phosphate-buffered saline (PBS) containing a concentration range of EGFR-binding FN3 domains. Controls were treated with 5 µL/well of PBS only or 25 mM ethylenediaminetetraacetic acid in PBS. Cells were incubated at 37° C., 5% CO$_2$ for 120 hours. Viable cells were detected by addition of 75 µL/well of CellTiter-Glo® reagent (Promega), followed by mixing on a plate shaker for 2 minutes, and incubation in the dark at room temperature for a further 10 minutes. Plates were read on a SpectraMax M5 plate reader (Molecular Devices) set to luminescence mode, with a read time of 0.5 seconds/well against a blank of medium only. Data were plotted as a percentage of PBS-treated cell growth against the logarithm of FN3 domain molar concentration. IC$_{50}$ values were determined by fitting data to the equation for a sigmoidal dose response with variable slope using GraphPad Prism 4 (GraphPad Software). Table 5 shows IC$_{50}$ values ranging from 5.9 nM to 1.15 µM and 9.2 nM to >3.1 µM, using the NCI-H292 and NCI-H322 cells respectively. Table 5 shows the summary of biological properties of EGFR-binding FN3 domains for each assay.

EXAMPLE 4

Engineering of EGFR-Binding FN3 Domains

A subset of the EGFR binding FN3 domains was engineered to increase the conformational stability of each molecule. The mutations L17A, N46V and E86I which have been shown to improve FN3 domain stability (described in US Pat. Publ. No. US2011/0274623) were incorporated into clones P54AR4-83, P54CR4-31, and P54AR4-37 by DNA synthesis. The new mutants, P54AR5-83v2, P54CR431-v2, and P54AR4-37v2 were expressed and purified as described above. Differential scanning calorimetry in PBS was used to assess the stability of each mutant in order to compare it to that of the corresponding parent molecule. Table 6 shows that each variant molecule was stabilized significantly, with an average increase in the T$_m$ of 18.5° C.

TABLE 6

| FN3 domain Clone | SEQ ID NO: | T$_m$ (° C.) |
|---|---|---|
| P54AR4-83 | 25 | 50.6 |
| P54AR4-83v2 | 27 | 69.8 |
| P54CR4-31 | 26 | 60.9 |
| P54CR4-31v2 | 28 | 78.9 |
| P54AR4-37 | 22 | 45.9 |
| P54AR4-37v2 | 29 | 64.2 |

EXAMPLE 5

Selection of Fibronectin Type III (FN3) Domains that Bind c-Met and Inhibit HGF Binding Panning on Human c-Met The TCL14 library was screened against biotinylated-human c-Met extracellular domain (bt-c-Met) to identify FN3 domains capable of specifically binding c-Met. For selections, 3 µg of TCL14 library was in vitro transcribed and translated (IVTT) in E. Coli S30 Linear Extract (Promega, Madison, Wis.) and the expressed library blocked with C is Block (2% BSA (Sigma-Aldrich, St. Louis, Mo.), 100 µg/ml Herring Sperm DNA (Promega), 1 mg/mL heparin (Sigma-Aldrich)). For selections, bt-c-Met was added at concentrations of 400 nM (Round 1), 200 nM (Rounds 2 and 3) and 100 nM (Rounds 4 and 5). Bound library members were recovered using neutravidin magnetic beads (Thermo Fisher, Rockford, Ill.) (Rounds 1, 3, and 5) or streptavidin magnetic beads (Promega) (Rounds 2 and 4) and unbound library members were removed by washing the beads 5-14 times with 500 uL PBS-T followed by 2 washes with 500 µL PBS.

Additional selection rounds were performed to identify FN3 domains molecules with improved affinities. Briefly, outputs from round 5 were prepared as described above and subjected to additional iterative rounds of selection with the following changes: incubation with bt-c-Met was decreased from 1 hour to 15 minutes and bead capture was decreased from 20 minutes to 15 minutes, bt-c-Met decreased to 25 nM (Rounds 6 and 7) or 2.5 nM (Rounds 8 and 9), and an additional 1 hour wash was performed in the presence of an excess of non-biotinylated c-Met. The goal of these changes was to simultaneously select for binders with a potentially faster on-rate and a slower off-rate yielding a substantially lower K$_D$.

Rounds 5, 7 and 9 outputs were PCR cloned into a modified pET 15 vector (EMD Biosciences, Gibbstown, N.J.) containing a ligase independent cloning site (pET15-LIC) using TCON6 (SEQ ID No. 30) and TCON5 E86I short (SEQ ID No. 31) primers, and the proteins were expressed as C-terminal His6-tagged proteins after transformations and IPTG induction (1 mM final, 30° C. for 16 hours) using standard protocols. The cells were harvested by centrifugation and subsequently lysed with Bugbuster HT (EMD Biosciences) supplemented with 0.2 mg/mL Chicken Egg White Lysozyme (Sigma-Aldrich). The bacterial lysates were clarified by centrifugation and the supernatants were transferred to new 96 deep-well plates.

Screening for FN3 Domains that Inhibit HGF Binding to c-Met

FN3 domains present in E. coli lysates were screened for their ability to inhibit HGF binding to purified c-Met extracellular domain in a biochemical format. Recombinant human c-Met Fc chimera (0.5 μg/mL in PBS, 100 μL/well) was coated on 96-well White Maxisorp Plates (Nunc) and incubated overnight at 4° C. The plates were washed two times with 300 μl/well of Tris-buffered saline with 0.05% Tween 20 (TBS-T, Sigma-Aldrich) on a Biotek plate washer. Assay plates were blocked with StartingBlock T20 (200 μL/well, Thermo Fisher Scientific, Rockland, Ill.) for 1 hour at room temperature (RT) with shaking and again washed twice with 300 μl of TBS-T. FN3 domain lysates were diluted in StartingBlock T20 (from 1:10 to 1:100,000) using the Hamilton STARplus robotics system. Lysates (50 μL/well) were incubated on assay plates for 1 hour at RT with shaking. Without washing the plates, bt-HGF (1 μg/mL in StartingBlock T20, 50 biotinylated) was added to the plate for 30 min at RT while shaking. Control wells containing Tencon27 lysates received either Starting Block T20 or diluted bt-HGF. Plates were then washed four times with 300 μA/well of TBS-T and incubated with 100 μL/well of Streptavidin-HRP (1:2000 in TBS-T, Jackson Immunoresearch, West Grove, Pa.) for 30-40 minutes at RT with shaking. Again the plates were washed four times with TBS-T. To develop signal, POD Chemiluminescence Substrate (50 μL/well, Roche Diagnostics, Indianapolis, Ind.), prepared according to manufacturer's instructions, was added to the plate and within approximately 3 minutes luminescence was read on the Molecular Devices M5 using SoftMax Pro. Percent inhibition was determined using the following calculation: 100−((RLU$_{sample}$−Mean RLU$_{NO\ bt\text{-}HGF\ control}$)/(Mean RLU$_{bt\text{-}HGF\ control}$−Mean RLU$_{NO\ bt\text{-}HGF\ control}$)*100). Percent inhibition values of 50% or greater were considered hits.

High-Throughput Expression and Purification of FN3 Domains

His-tagged FN3 domains were purified from clarified E. coli lysates with His MultiTrap™ HP plates (GE Healthcare) and eluted in buffer containing 20 mM sodium phosphate, 500 mM sodium chloride, and 250 mM imidazole at pH 7.4. Purified samples were exchanged into PBS pH 7.4 for analysis using PD MultiTrap™ G-25 plates (GE Healthcare).

$IC_{50}$ Determination of Inhibition of HGF Binding to c-Met

Select FN3 domains were further characterized in the HGF competition assay. Dose response curves for purified FN3 domains were generated utilizing the assay described above (starting concentrations of 5 μM). Percent inhibition values were calculated. The data were plotted as % inhibition against the logarithm of FN3 domain molar concentrations and $IC_{50}$ values were determined by fitting data to a sigmoidal dose response with variable slope using GraphPad Prism 4.

35 unique sequences were identified from Round 5 to exhibit activity at dilutions of 1:10, with $IC_{50}$ values ranging from 0.5 to 1500 nM. Round 7 yielded 39 unique sequences with activity at dilutions of 1:100 and $IC_{50}$ values ranging from 0.16 to 2.9 nM. 66 unique sequences were identified from Round 9, where hits were defined as being active at dilutions of 1:1000. $IC_{50}$ values as low as 0.2 nM were observed in Round 9 (Table 8).

Affinity Determination of Selected c-Met-Binding FN3 Domains to c-Met-Fc (c-Met-Fc Affinity)

Affinities were determined fro select c-Met binding FN3 domains according to the protocol described for determination of affinities to EGFR binding FN3 domains in Example 3 except that c-Met-Fc fusion protein was used in the experiments.

EXAMPLE 6

Characterization of FN3 Domains that Bind c-Met and Inhibit HGF Binding

FN3 domains were expressed and purified as described above in Example 2. Size exclusion chromatography and kinetic analysis was done as described above in Examples 1 and 2, respectively. Table 7 shows the sequences of the C-strand, CD loop, F-strand, and FG loop, and a SEQ ID NO: for the entire amino acid sequence for each domain.

TABLE 7

| Clone Name | SEQ ID NO: | C loop | CD strand | F loop | FG strand |
|---|---|---|---|---|---|
| P114AR5P74-A5 | 32 | FDSFWIRYDE | VVVGGE | TEYYVNILGV | KGGSISV |
| P114AR5P75-E9 | 33 | FDSFFIRYDE | FLRSGE | TEYWVTILGV | KGGLVST |
| P114AR7P92-F3 | 34 | FDSFWIRYFE | FLGSGE | TEYIVNIMGV | KGGSISH |
| P114AR7P92-F6 | 35 | FDSFWIRYFE | FLGSGE | TEYVVNILGV | KGGGLSV |
| P114AR7P92-G8 | 36 | FDSFVIRYFE | FLGSGE | TEYVVQILGV | KGGYISI |
| P114AR7P92-H5 | 37 | FDSFWIRYLE | FLLGGE | TEYVVQIMGV | KGGTVSP |
| P114AR7P93-D11 | 38 | FDSFWIRYFE | FLGSGE | TEYVVGINGV | KGGYISY |
| P114AR7P93-G8 | 39 | FDSFWIRYFE | FLGSGE | TEYGVTINGV | KGGRVST |
| P114AR7P93-H9 | 40 | FDSFWIRYFE | FLGSGE | TEYVVQIIGV | KGGHISL |

TABLE 7-continued

| Name | SEQ ID NO: | C loop | CD strand | F loop | FG strand |
|---|---|---|---|---|---|
| P114AR7P94-A3 | 41 | FDSFWIRYFE | FLGSGE | TEYVVNIMGV | KGGKISP |
| P114AR7P94-E5 | 42 | FDSFWIRYFE | FLGSGE | TEYAVNIMGV | KGGRVSV |
| P114AR7P95-B9 | 43 | FDSFWIRYFE | FLGSGE | TEYVVQILGV | KGGSISV |
| P114AR7P95-D3 | 44 | FDSFWIRYFE | FLGSGE | TEYVVNIMGV | KGGSISY |
| P114AR7P95-D4 | 45 | FDSFWIRYFE | FLGSGE | TEYVVQILGV | KGGYISI |
| P114AR7P95-E3 | 46 | FDSFWIRYFE | FLGSGE | TEYVVQIMGV | KGGTVSP |
| P114AR7P95-F10 | 47 | FDSFWIRYFE | FTTAGE | TEYVVNIMGV | KGGSISP |
| P114AR7P95-G7 | 48 | FDSFWIRYFE | LLSTGE | TEYVVNIMGV | KGGSISP |
| P114AR7P95-H8 | 49 | FDSFWIRYFE | FVSKGE | TEYVVNIMGV | KGGSISP |

C loop residues correspond to residues 28-37 of indicated SEQ ID NO:
CD strand residues correspond to residues 38-43 of indicated SEQ ID NO:
F loop residues correspond to residues 65-74 of indicated SEQ ID NO:
FG strand residues correspond to residues 75-81 of indicated SEQ ID NO:

Binding of Selected c-Met-Binding FN3 Domains to c-Met on Cells ("H441 Cell Binding Assay")

NCI-H441 cells (Cat # HTB-174, American Type Culture Collection, Manassas, Va.) were plated at 20,000 cells per well in Poly-D-lysine coated black clear bottom 96-well plates (BD Biosciences, San Jose, Calif.) and allowed to attach overnight at 37° C., 5% $CO_2$. Purified FN3 domains (50 µL/well; 0 to 1000 nM) were added to the cells for 1 hour at 4° C. in duplicate plates. Supernatant was removed and cells were washed three times with FACS stain buffer (150 µL/well, BD Biosciences, cat #554657). Cells were incubated with biotinylated-anti HIS antibody (diluted 1:160 in FACS stain buffer, 50 µL/well, R&D Systems, cat #BAM050) for 30 minutes at 4° C. Cells were washed three times with FACS stain buffer (150 µL/well), after which wells were incubated with anti mouse IgG1-Alexa 488 conjugated antibody (diluted 1:80 in FACS stain buffer, 50 µL/well, Life Technologies, cat #A21121) for 30 minutes at 4° C. Cells were washed three times with FACS stain buffer (150 µL/well) and left in FACS stain buffer (50 µL/well). Total fluorescence was determined using an Acumen eX3 reader. Data were plotted as raw fluorescence signal against the logarithm of the FN3 domain molar concentration and fitted to a sigmoidal dose-response curve with variable slope using GraphPad Prism 4 (GraphPad Software) to calculate $EC_{50}$ values. FN3 domains were found to exhibit a range of binding activities, with $EC_{50}$ values between 1.4 nM and 22.0 nM, as shown in Table 8.

Inhibition of HGF-Stimulated c-Met Phosphorylation

Purified FN3 domains were tested for their ability to inhibit HGF-stimulated phosphorylation of c-Met in NCI-H441, using the c-Met phospho(Tyr1349) kit from Meso Scale Discovery (Gaithersburg, Md.). Cells were plated at 20,000/well in clear 96-well tissue culture-treated plates in 100 µL/well of RPMI medium (containing Glutamax and HEPES, Life Technologies) with 10% fetal bovine serum (FBS; Life Technologies) and allowed to attach overnight at 37° C., 5% $CO_2$. Culture medium was removed completely and cells were starved overnight in serum-free RPMI medium (100 µL/well) at 37° C., 5% $CO_2$. Cells were then replenished with fresh serum-free RPMI medium (100 µL/well) containing FN3 domains at a concentration of 20 µM and below for 1 hour at 37° C., 5% $CO_2$. Controls were treated with medium only. Cells were stimulated with 100 ng/mL recombinant human HGF (100 µL/well, R&D Systems cat #294-HGN) and incubated at 37° C., 5% $CO_2$ for 15 minutes. One set of control wells was left un-stimulated as negative controls. Medium was then completely removed and cells were lysed with Complete Lysis Buffer (50 µL/well, Meso Scale Discovery) for 10 minutes at RT with shaking, as per manufacturer's instructions. Assay plates configured for measuring phosphorylated c-Met were blocked with the provided blocking solution as per the manufacturer's instructions at room temperature for 1 hour. Plates were then washed three times with Tris Wash Buffer (200 µL/well, Meso Scale Discovery). Cell lysates (30 µL/well) were transferred to assay plates, and incubated at RT with shaking for 1 hour. Assay plates were then washed four times with Tris Wash Buffer, after which ice-cold Detection Antibody Solution (25 µL/well, Meso Scale Discovery) was added to each well for 1 hr at RT with shaking. Plates were again rinsed four times with Tris Wash Buffer. Signals were detected by addition of 150 Read Buffer (150 µL/well, Meso Scale Discovery) and reading on a SECTOR® Imager 6000 instrument (Meso Scale Discovery) using manufacturer-installed assay-specific default settings. Data were plotted as electrochemiluminescence signal against the logarithm of FN3 domain molar concentration and $IC_{50}$ values were determined by fitting data to a sigmoidal dose response with variable slope using GraphPad Prism 4. FN3 domains were found to inhibit phosphorylated c-Met with IC50 values ranging from 4.6 nM to 1415 nM as shown in Table 8.

Inhibition of Human Tumor Cell Growth

Inhibition of c-Met-dependent cell growth was assessed by measuring viability of U87-MG cells (American Type Culture Collection, cat #HTB-14), following exposure to c-Met-binding FN3 domains. Cells were plated at 8000 cells per well in opaque white 96-well tissue culture-treated plates (Nunc) in 100 µL/well of RPMI medium, supplemented with 10% FBS and allowed to attach overnight at 37° C., 5% $CO_2$. Twenty-four hours after plating, medium was aspirated and cells were replenished with serum-free RPMI medium.

TABLE 8

| Clone Name | SEQ ID NO: | Affinity (Kd, nM) | HGF competition IC50 (nM) | H441 Cell binding (EC50, nM) | pMet inhibition in H441 cells (IC50, nM) | Inhibition of Proliferation of U87-MG cells (IC50, nM) |
|---|---|---|---|---|---|---|
| P114AR5P74-A5 | 32 | 10.1 | 5.2 | 18.7 | 1078 | 464.4 |
| P114AR5P75-E9 | 33 | 45.8 | 51.9 | ND | 1415 | 1193.9 |
| P114AR7P92-F3 | 34 | 0.4 | 0.2 | 1.5 | 8.3 | 2.7 |
| P114AR7P92-F6 | 35 | 3.1 | 2.2 | 4.9 | 165.3 | 350.5 |
| P114AR7P92-G8 | 36 | 1.0 | 1.6 | 5.9 | 155.3 | 123.9 |
| P114AR7P92-H5 | 37 | 11.6 | ND | 22.0 | 766.4 | 672.3 |
| P114AR7P93-D11 | 38 | ND | ND | 2.3 | 16 | 14.4 |
| P114AR7P93-G8 | 39 | 6.9 | 1 | 3.8 | 459.5 | 103.5 |
| P114AR7P93-H9 | 40 | 3.3 | 2.9 | 12.9 | 288.2 | 269.9 |
| P114AR7P94-A3 | 41 | 0.4 | 0.2 | 1.4 | 5 | 9.3 |
| P114AR7P94-E5 | 42 | 4.2 | 0.7 | 3.4 | 124.3 | 195.6 |
| P114AR7P95-B9 | 43 | 0.5 | 0.3 | ND | 9.8 | 17.4 |
| P114AR7P95-D3 | 44 | 0.3 | 0.2 | 1.5 | 4.6 | 1.7 |
| P114AR7P95-D4 | 45 | 0.4 | ND | 1.4 | 19.5 | 19.4 |
| P114AR7P95-E3 | 46 | 1.5 | ND | 3.2 | 204.6 | 209.2 |
| P114AR7P95-F10 | 47 | 4.2 | 1.4 | 4.4 | 187.6 | 129.7 |
| P114AR7P95-G7 | 48 | 20.0 | ND | 11.3 | 659.3 | 692 |
| P114AR7P95-H8 | 49 | 3.7 | ND | 4.1 | 209.8 | 280.7 |

Twenty-four hours after serum starvation, cells were treated by addition of serum-free medium containing c-Met-binding FN3 domains (30 μL/well). Cells were incubated at 37° C., 5% $CO_2$ for 72 hours. Viable cells were detected by addition of 100 μL/well of CellTiter-Glo® reagent (Promega), followed by mixing on a plate shaker for 10 minutes. Plates were read on a SpectraMax M5 plate reader (Molecular Devices) set to luminescence mode, with a read time of 0.5 seconds/well. Data were plotted as raw luminescence units (RLU) against the logarithm of FN3 domain molar concentration. $IC_{50}$ values were determined by fitting data to an equation for a sigmoidal dose response with variable slope using GraphPad Prism 4. Table 8 reports $IC_{50}$ values ranging from 1 nM to >1000 nM.

Characteristics of the c-Met binding FN3 domains are summarized in Table 8.

Thermal Stability of c-Met-Binding FN3 Domains

Differential scanning calorimetry in PBS was used to assess the stability of each FN3 domain. Results of the experiment are shown in Table 9.

TABLE 9

| Clone Name | SEQ ID NO: | Thermal Stability (Tm, C.) |
|---|---|---|
| P114AR5P74-A5 | 32 | 74.1 |
| P114AR5P75-E9 | 33 | ND |
| P114AR7P92-F3 | 34 | 81.5 |
| P114AR7P92-F6 | 35 | 76.8 |
| P114AR7P92-G8 | 36 | 90.9 |
| P114AR7P92-H5 | 37 | 87 |
| P114AR7P93-D11 | 38 | ND |
| P114AR7P93-G8 | 39 | 76.8 |
| P114AR7P93-H9 | 40 | 88.2 |
| P114AR7P94-A3 | 41 | 86.2 |
| P114AR7P94-E5 | 42 | 80 |
| P114AR7P95-B9 | 43 | 86.3 |
| P114AR7P95-D3 | 44 | 82 |
| P114AR7P95-D4 | 45 | 85.3 |
| P114AR7P95-E3 | 46 | 94.2 |
| P114AR7P95-F10 | 47 | 85.2 |
| P114AR7P95-G7 | 48 | 87.2 |
| P114AR7P95-H8 | 49 | 83 |

EXAMPLE 7

Generation and Characterization of Bispecific Anti-EGFR/c-Met Molecules

Generation of Bispecific EGFR/c-Met Molecules

Numerous combinations of the EGFR and c-Met-binding FN3 domains described in Examples 1-6 were joined into bispecific molecules capable of binding to both EGFR and c-Met. Additionally, EGFR-binding FN3 domains having amino acid sequences shown in SEQ ID NOs: 107-110 and c-Met binding FN3 domains having amino acid sequences shown in SEQ ID NOs: 111-114 were made and joined into bispecific molecules. Synthetic genes were created to encode for the amino acid sequences described in SEQ ID NOs: 50-72, 106, 118-121 or 190-193 (Table 10) such that the following format was maintained: EGFR-binding FN3 domain followed by a peptide linker followed by a c-Met-binding FN3 domain. A poly-histidine tag was incorporated at the C-terminus to aid purification. In addition to those molecules described in Table 10, the linker between the two FN3 domains was varied according to length, sequence composition and structure according to those listed in Table 11. It is envisioned that a number of other linkers could be used to link such FN3 domains Bispecific EGFR/c-Met molecules were expressed and purified from *E. coli* as described for monospecific EGFR or c-Met FN3 domains using IMAC and gel filtration chromatography steps. It is evident to the skilled in art that the bispecific EGFR/c-Met molecules may or may not contain an initiator methionine. Exemplary molecules with the initiator methionine are molecules having the amino acid sequence shown in SEQ ID NOs: 106, 118-121, 138-165, 190 and 192, and exemplary molecules without the initiator methionine are shown in SEQ ID NOs: 50-72, 191 and 193. The presence of the initiator methionine for the EGFR binding FN3 domains ensures proper activity; the initiator methionine has less impact on the c-Met FN3 domains.

TABLE 10

| Bispecific EGFR/c-Met molecule | | EGFR-binding FN3 domain | | cMET-binding FN3 domain | | Linker | |
|---|---|---|---|---|---|---|---|
| Clone ID | SEQ ID NO: | Clone ID | SEQ ID NO: | Clone ID | SEQ ID NO: | Sequence | SEQ ID NO: |
| ECB1 | 50 | P54AR4-83v2 | 27 | P114AR5P74-A5 | 32 | (GGGGS)4 | 79 |
| ECB2 | 51 | P54AR4-83v2 | 27 | P114AR7P94-A3 | 41 | (GGGGS)4 | 79 |
| ECB3 | 52 | P54AR4-83v2 | 27 | P114AR7P93-H9 | 40 | (GGGGS)4 | 79 |
| ECB4 | 53 | P54AR4-83v2 | 27 | P114AR5P75-E9 | 33 | (GGGGS)4 | 79 |
| ECB5 | 54 | P53A1R5-17v2 | 107 | P114AR7P94-A3 | 41 | (GGGGS)4 | 79 |
| ECB6 | 55 | P53A1R5-17v2 | 107 | P114AR7P93-H9 | 40 | (GGGGS)4 | 79 |
| ECB7 | 56 | P53A1R5-17v2 | 107 | P114AR5P75-E9 | 33 | (GGGGS)4 | 79 |
| ECB15 | 57 | P54AR4-83v2 | 27 | P114AR7P94-A3 | 41 | (AP)5 | 81 |
| ECB27 | 58 | P54AR4-83v2 | 27 | P114AR5P74-A5 | 32 | (AP)5 | 81 |
| ECB60 | 59 | P53A1R5-17v2 | 107 | P114AR7P94-A3 | 41 | (AP)5 | 81 |
| ECB37 | 60 | P53A1R5-17v2 | 107 | P114AR5P74-A5 | 32 | (AP)5 | 81 |
| ECB94 | 61 | P54AR4-83v22 | 108 | P114AR7P94-A3v22 | 111 | (AP)5 | 81 |
| ECB95 | 62 | P54AR4-83v22 | 108 | P114AR9P121-A6v2 | 112 | (AP)5 | 81 |
| ECB96 | 63 | P54AR4-83v22 | 108 | P114AR9P122-A7v2 | 113 | (AP)5 | 81 |
| ECB97 | 64 | P54AR4-83v22 | 108 | P114AR7P95-O5v2 | 114 | (AP)5 | 81 |
| ECB106 | 65 | P54AR4-83v23 | 109 | P114AR7P94-A3v22 | 111 | (AP)5 | 81 |
| ECB107 | 66 | P54AR4-83v23 | 109 | P114AR9P121-A6v2 | 112 | (AP)5 | 81 |
| ECB108 | 67 | P54AR4-83v23 | 109 | P114AR9P122-A7v2 | 113 | (AP)5 | 81 |
| ECB109 | 68 | P54AR4-83v23 | 109 | P114AR7P95-O5v2 | 114 | (AP)5 | 81 |
| ECB118 | 69 | P53A1R5-17v22 | 110 | P114AR7P94-A3v22 | 111 | (AP)5 | 81 |
| ECB119 | 70 | P53A1R5-17v22 | 110 | P114AR9P121-A6v2 | 112 | (AP)5 | 81 |
| ECB120 | 71 | P53A1R5-17v22 | 110 | P114AR9P122-A7v2 | 113 | (AP)5 | 81 |
| ECB121 | 72 | P53A1R5-17v22 | 110 | P114AR7P95-O5v2 | 114 | (AP)5 | 81 |
| ECB91 | 106 | P54AR4-83v22 | 108 | P114AR7P95-O5v2 | 114 | (AP)5 | 81 |
| ECB18 | 118 | P54AR4-83v2 | 27 | P114AR5P74-A5 | 32 | (AP)5 | 81 |
| ECB28 | 119 | P53A1R5-17v2 | 107 | P114AR5P74-A5 | 32 | (AP)5 | 81 |
| ECB38 | 120 | P54AR4-83v2 | 27 | P114AR7P94-A3 | 41 | (AP)5 | 81 |
| ECB39 | 121 | P53A1R5-17v2 | 107 | P114AR7P94-A3 | 41 | (AP)5 | 81 |
| ECB168 | 190 | P54AR4-83v22 | 108 | P114AR7P95-O5v2 | 114 | (AP)5 | 81 |
| ECB176 | 192 | P53A1R5-17v2 | 107 | P114AR7P95-O5v2 | 114 | (AP)5 | 81 |

TABLE 11

| Linker | SEQ ID NO: | Linker ength in amino acids | Structure |
|---|---|---|---|
| GS | 78 | 2 | Disordered |
| GGGGS | 105 | 5 | Disordered |
| (GGGGS)2 | 224 | 10 | Disordered |
| (GGGGS)4 | 79 | 20 | Disordered |
| (AP)2 | 80 | 4 | Rigid |
| (AP)5 | 81 | 5 | Rigid |

TABLE 11-continued

| Linker | SEQ ID NO: | Linker ength in amino acids | Structure |
|---|---|---|---|
| (AP)10 | 82 | 20 | Rigid |
| (AP)20 | 83 | 40 | Rigid |
| A(EAAAK)5AAA | 84 | 29 | a-helical |

Bispecific EGFR/c-Met Molecules Enhance Potency Compared to Monospecific Molecules Alone, Suggesting Avidity NCI-H292 cells were plated in 96 well plates in RPMI medium containing 10% FBS. 24 hours later, medium was replaced with serum free RPMI. 24 hours after serum starvation, cells were treated with varying concentrations of FN3 domains: either a high affinity monospecific EGFR FN3 domain (P54AR4-83v2), a weak affinity monospecific c-Met FN3 domain (P114AR5P74-A5), the mixture of the two monospecific EGFR and c-Met FN3 domains, or a bispecific EGFR/c-Met molecules comprised of the low affinity c-Met FN3 domain linked to the high affinity EGFR FN3 domain (ECB1). Cells were treated for 1 h with the monospecific or bispecific molecules and then stimulated with EGF, HGF, or a combination of EGF and HGF for 15 minutes at 37° C., 5% $CO_2$. Cells were lysed with MSD Lysis Buffer and cell signaling was assessed using appropriate MSD Assay plates, according to manufacturer's instructions, as described above.

The low affinity c-Met FN3 domain inhibited phosphorylation of c-Met with an $IC_{50}$ of 610 nM (FIG. 4). As expected the EGFR FN3 domain was not able to inhibit c-Met phosphorylation and the mixture of the mono-specific molecules looked identical to the c-Met FN3 domain alone. However, the bi-specific EGFR/c-Met molecule inhibited phosphorylation of c-Met with an $IC_{50}$ of 1 nM (FIG. 4), providing more than a 2-log shift in improving potency relative to the c-Met monospecific alone.

Figure 5:
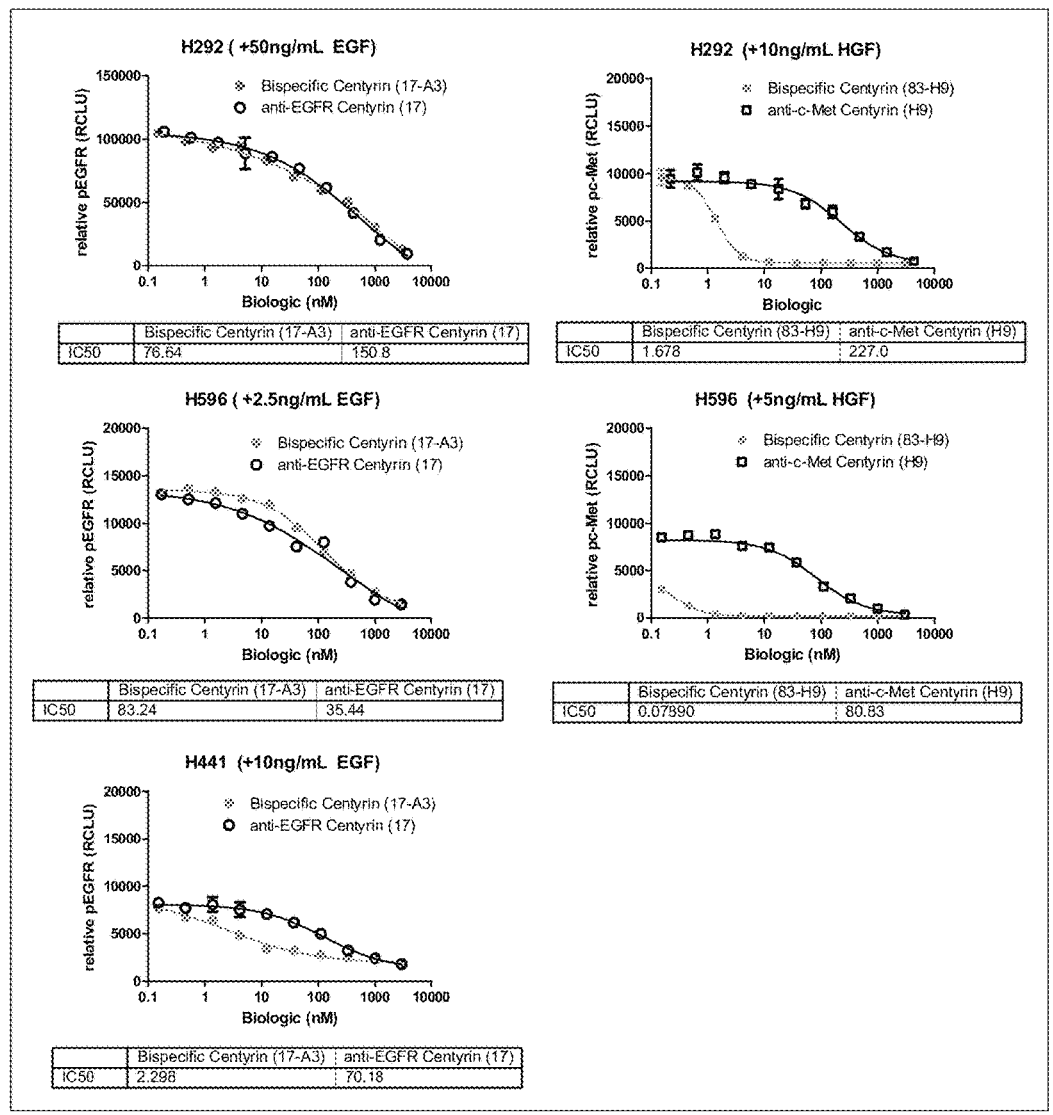
FIG. 5. Inhibition of EGFR and c-Met phosphorylation in cells pre-treated with monospecific or bispecific FN3 domain containing molecules. In cell lines expressing high levels of EGFR, NCI-H292 (FIG. 5A) and H596 FIG. 5(B), anti-EGFR monospecific and bispecific FN3 domain containing molecules are equally potent at decreasing EGFR phosphorylation. In cell lines expressing low levels of EGFR relative to c-Met, H441 (FIG. 5C), bispecific EGFR/c-Met molecules improve the potency for inhibition of EGFR phosphorylation compared to the monospecific EGFR-binding FN3 domain alone. In cell lines with low levels of c-Met, relative to EGFR, H292 (FIG. 5D) and H596 (FIG. 5E), inhibition of c-Met phosphorylation is significantly potentiated with bispecific EGFR/c-Met molecule, compared to monospecific c-Met-binding FN3 domain only. Molecules used in the study were: bispecific ECB5 (shown as 17-A3 in the Figure), monospecific EGFR-binding FN3 domain P53A1R5-17 (shown as "17" in the Figure), bispecific EGFR/c-Met molecule ECB3 (shown as 83-H9 in the Figure), and monospecific c-Met binding FN3 domain P114AR7P93-H9 (shown as H9 in the Figure).

The potential for the bispecific EGFR/c-Met molecule to enhance the inhibition of c-Met and/or EGFR phosphorylation through an avidity effect was evaluated in multiple cell types with variable c-Met and EGFR densities and ratios (FIG. 5). NCI-H292, NCI-H441, or NCI-H596 cells were plated in 96 well plates in RPMI medium containing 10% FBS. 24 hours later, medium was replaced with serum free RPMI. 24 hours after serum starvation, cells were treated with varying concentrations of either monospecific EGFR-binding FN3 domain, monospecific c-Met FN3 domain, or a bispecific EGFR/c-Met molecule (ECB5, comprised of P53A1R5-17v2 and P114AR7P94-A3). Cells were treated for 1 h with the monospecific or bispecific molecules and then stimulated with EGF, HGF, or a combination of EGF and HGF for 15 minutes at 37° C., 5% $CO_2$. Cells were lysed with MSD Lysis Buffer and cell signaling was assessed using appropriate MSD Assay plates, according to manufacturer's instructions, as described above.

FIG. 5 (A-C) shows the inhibition of EGFR using a monospecific EGFR-binding FN3 domain compared to a bispecific EGFR/cMet molecule in three different cell lines. To assess avidity in an EGFR phosphorylation assay, a medium affinity EGFR-binding FN3 domain (1.9 nM) (P53A1R5-17v2) was compared to a bispecific EGFR/c-Met molecule containing the same EGFR-binding FN3 domain linked to a high-affinity c-Met-binding FN3 domain (0.4 nM) (P114AR7P94-A3). In H292 and H596 cells, inhibition of phosphorylation of EGFR was comparable for the monospecific and bispecific molecules (FIGS. 5A and 5B), likely because these cell lines have a high ratio of EGFR to c-Met receptors. To test this theory, inhibition of EGFR phosphorylation was evaluated in NCI-H441 cells which exhibit more c-Met receptors than EGFR. Treatment of NCI-H441 cells with the bispecific EGFR/c-Met molecule decreased the $IC_{50}$ for inhibition of EGFR phosphorylation compared to the monospecific EGFR-binding FN3 domain by 30-fold (FIG. 5C).

The potential for enhanced potency with a bi-specific EGFR/c-Met molecule was evaluated in a c-Met phosphorylation assay using a molecule with a high affinity to EGFR (0.26 nM) and medium affinity to c-Met (10.1 nM). In both NCI-H292 and NCI-H596 cells, the inhibition of phosphorylation of c-Met was enhanced with the bispecific molecule compared to the monospecific c-Met-binding FN3 domain, by 134 and 1012 fold, respectively (FIGS. 3D and 3E).

It was verified that the enhanced potency for inhibition of EGFR and c-Met phosphorylation with the bispecific EGFR/c-Met molecules translated into an enhanced inhibition of signaling and proliferation. For these experiments, the mixture of FN3 EGFR-binding and c-Met-binding FN3 domains was compared to a bispecific EGFR/c-Met molecule. As described in Tables 12 and 13, the $IC_{50}$ values for ERK phosphorylation (Table 12) and proliferation of H292 cells (Table 13) were decreased when cells were treated with the bispecific EGFR/c-Met molecule compared to the mixture of the monospecific binders. The $IC_{50}$ for inhibition of ERK phosphorylation for the bi-specific EGFR/c-Met molecule was 143-fold lower relative to the mixture of the two monospecific EGFR and c-Met FN3 domains, showing the effect of avidity to the potency of the molecules in this assay. In Table 12, the monospecific EGFR- and c-Met binding FN3 domains do not fully inhibit activity and therefore the $IC_{50}$ values shown should be considered lower limits. The proliferation assay was completed using different combinations EGFR and c-Met binding FN3 domains either as a mixture or linked in a bispecific format. The $IC_{50}$ for inhibition of proliferation for the bispecific EGFR/c-Met molecule was 34-236-fold lower relative to the mixture of the monospecific parent EGFR or c-Met binding FN3 domains. This confirmed that the avidity effect observed at the level of the receptors (FIG. 4 and FIG. 5) translates into an improvement in inhibiting cell signaling (Table 12) and cell proliferation (Table 13).

TABLE 12

| Specificity of the FN3-domain molecule | Clone # | Type | IC50 (nM) (ERK phosphorylation) |
|---|---|---|---|
| EGFR | P54AR4-83v2 | monospecific | >10,000 |
| c-Met | P114AR5P74-A5 | monospecific | 2366 |
| EGFR or c-Met | P54AR4-83v2 + P114AR5P74-A5 | mixture of monospecific molecules | 798.4 |
| EGFR and c-Met | ECB1 | bispecific | 5.6 |

TABLE 13

| EGFR-binding FN3 domain (affinity) | c-Met binding FN3 domain (affinity) | IC50 for mixture of mono-specifics (nM) | IC50 for bispecific (nM) | Fold increase in IC50 for bispecific/ mixture of monospecifics |
|---|---|---|---|---|
| P54AR4-83v2 (0.26 nM) | P114ARP94-A3 (0.4 nM) | 36.5 | 1.04 | 35 |

TABLE 13-continued

| EGFR-binding FN3 domain (affinity) | c-Met binding FN3 domain (affinity) | IC50 for mixture of mono-specifics (nM) | IC50 for bispecific (nM) | Fold increase in IC50 for bispecific/ mixture of monospecifics |
|---|---|---|---|---|
| P54AR4-83v2 (0.26 nM) | P114AR7P93-H9 (3.3 nM) | 274.5 | 8.05 | 34 |
| P54AR4-83v2 (0.26 nM) | P114AR5P74-A5 (10.1 nM) | 1719 | 7.29 | 236 |

In Vivo Tumor Xenografts: PK/PD

In order to determine efficacy of the monospecific and bispecific FN3 domain molecules in vivo, tumor cells were engineered to secrete human HGF (murine HGF does not bind to humanc-Met). Human HGF was stably expressed in NCI-H292 cells using lentiviral infection (Lentiviral DNA vector expressing human HGF (Accession #X16322) and lentiviral packaging kit from Genecopoeia). After infection, HGF-expressing cells were selected with 4 μg/mL puromycin (Invitrogen). Human HGF protein was detected in the conditioned medium of pooled cells using assay plates from MesoScale Discovery.

SCID Beige mice were subcutaneously inoculated with NCI-H292 cells expressing human HGF ($2.0 \times 10^6$ cells in Cultrex (Trevigen) in a volume of 200 μL) on the dorsal flank of each animal. Tumor measurements were taken twice weekly until tumor volumes ranged between 150-250 mm$^3$ Mice were then given a single i.p. dose of bispecific EGFR/c-Met molecules (linked to an albumin binding domain to increase half-life) or PBS vehicle. At 6 h or 72 h after dosing, tumors were extracted and immediately frozen in liquid nitrogen. Blood samples were collected via cardiac puncture into 3.8% citrate containing protease inhibitors. Immediately after collection, the blood samples were centrifuged and the resulting plasma was transferred to sample tubes and stored at −80° C. Tumors were weighed, cut into small pieces, and lysed in Lysing Matrix A tubes (LMA) containing RIPA buffer with HALT protease/phosphatase inhibitors (Pierce), 50 mM sodium fluoride (Sigma), 2 mM activated sodium orthovanadate (Sigma), and 1 mM PMSF (MesoScale Discovery). Lysates were removed from LMA matrix and centrifuged to remove insoluble protein. The soluble tumor protein was quantified with a BCA protein assay and diluted to equivalent protein levels in tumor lysis buffer. Phosphorylated c-Met, EGFR and ERK were measured using assay plates from MesoScale Discovery (according to Manufacturer's protocol and as described above).

Figure 6:
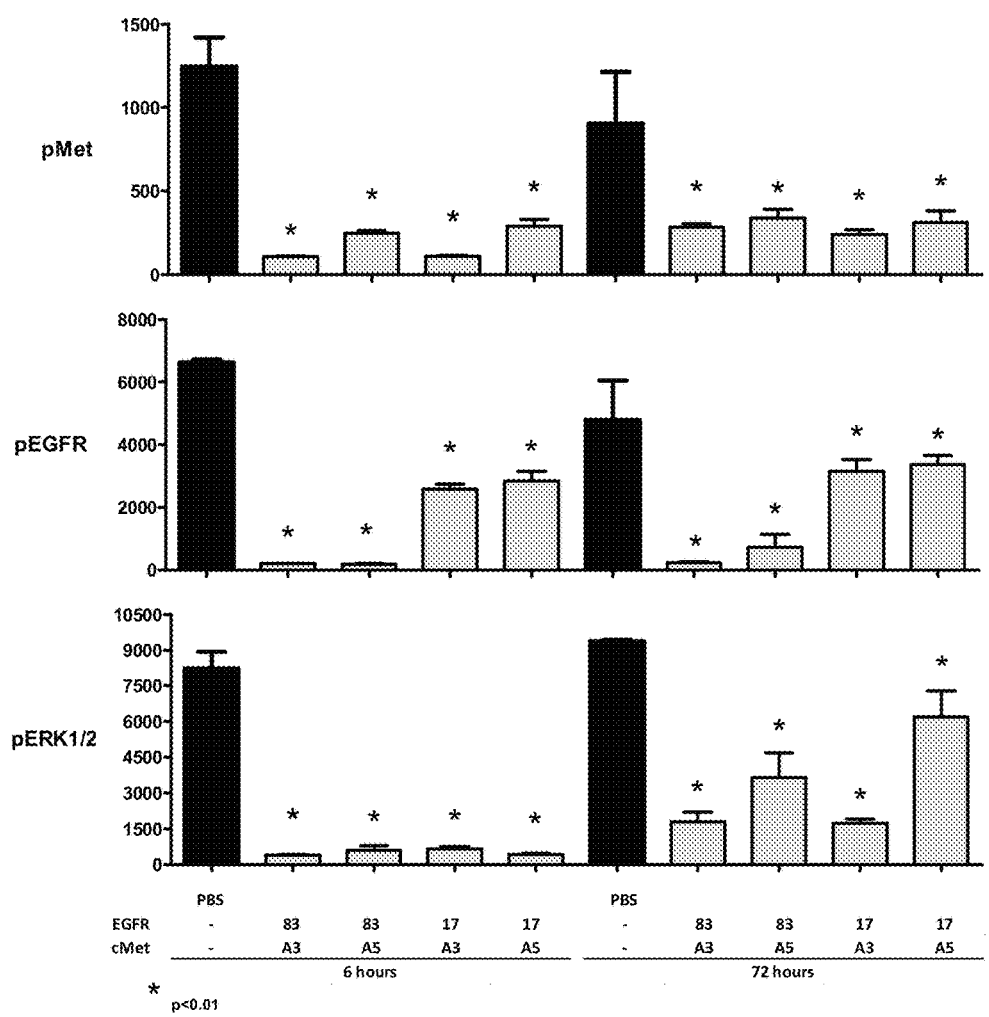
FIG. 6. Pharmacodynamic signaling in tumors isolated from mice dosed with bispecific EGFR/c-Met molecules for 6 h or 72 h. All molecules significantly reduced c-Met, EGFR and ERK phosphorylation at both 6 h and 72 h, the degree if inhibition was dependent on the affinity of the FN3 domains to EGFR and/or c-Met. Bispecific molecules were generated by joining EGFR-binding FN3 domain with a high ("83" in the Figure is p54AR4-83v2) or medium ("17v2" in the Figure is P53A1R5-17v2) affinity to a c-Met-binding FN3 domain with high ("A3" in the Figure is P114AR7P94-A3) or medium ("A5" in the Figure is P114AR5P74-A5) affinity.

FIG. 6 shows the results of the experiments. Each bispecific EGFR/c-Met molecule significantly reduced the levels of phosphorylated c-Met, EGFR, and ERK at both 6 h and 72 h. The data presented in FIG. 6 show the importance of inhibiting both c-Met and EGFR simultaneously and how the affinity of the bispecific EGFR/c-Met molecule for each receptor plays a role in inhibition of downstream ERK. The molecules containing the high affinity EGFR-binding FN3 domains (P54AR4-83v2; shown as "8" in the Figure, $K_D$=0.26 nM) inhibited phosphorylation of EGFR to a larger extent compared to those containing the medium affinity EGFR-binding FN3 domains (P53A1R5-17v2; shown as "17" in the figure $K_D$=1.9 nM) at both 6 h and 72 h. All four bispecific molecules tested completely inhibited phosphorylation of ERK at the 6 hour time point, regardless of affinity. At the 72 hour time point, the molecules containing the tight affinity c-Met-binding domain (P114AR7P94-A3; shown as "A3" in the figure $K_D$=0.4 nM) significantly inhibited phosphorylation of ERK compared to the medium affinity c-Met-binding FN3 domain (P114AR5P74-A5; shown as "A5" in the Figure; $K_D$=10.1 nM; FIG. 6).

Figure 7:
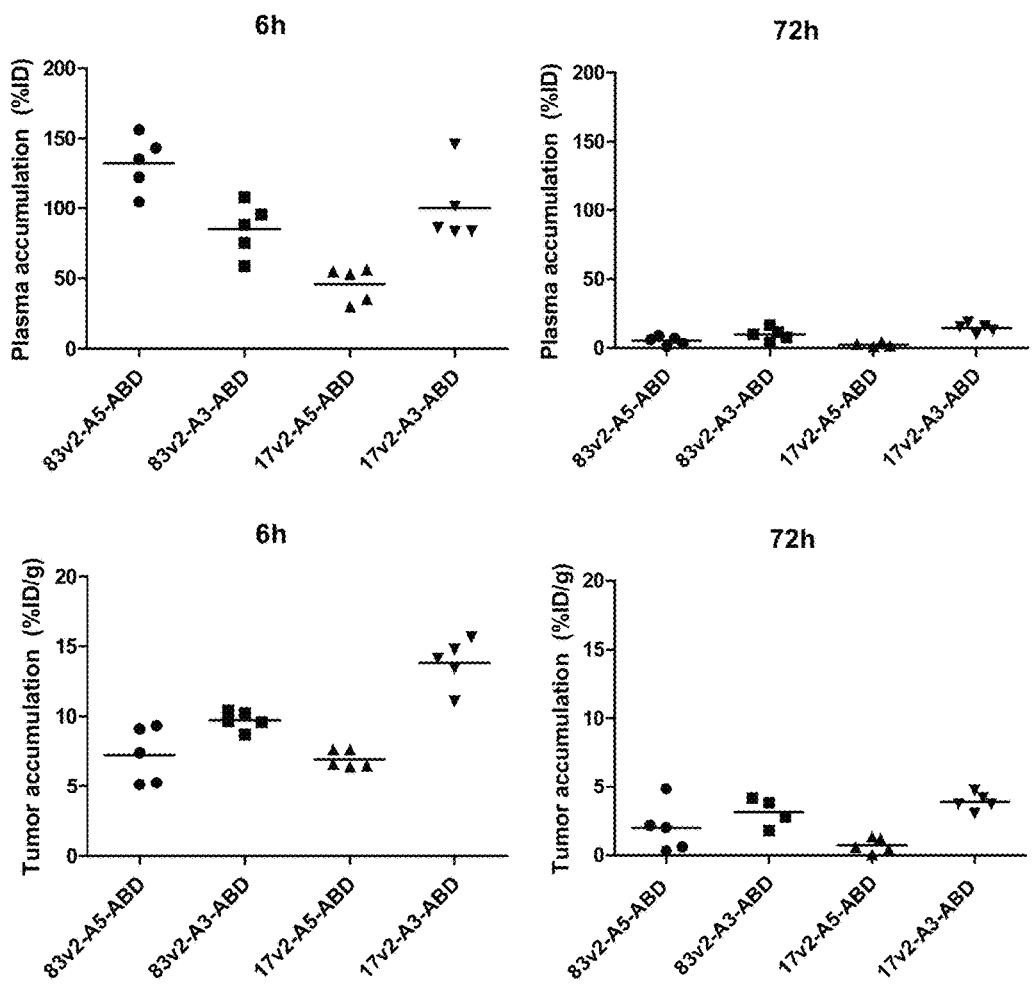
FIG. 7: Plasma (top) and tumor (bottom) accumulation of bispecific EGFR/cMet molecules of variable affinities linked to an albumin binding domain (ABD) are shown 6 h (left) and 72 h (right) after IP dosing. Six hours after dosing, tumor accumulation is maximal in mice dosed with a bispecific molecule harboring a medium affinity EGFR-binding FN3 domain (17v2) or high affinity EGFR binding domain (83v2). The bispecific molecules incorporated high or medium affinity EGFR or c-Met binding FN3 domains as follows: 83v2-A5-ABD (ECB18; high/medium for EGFR/cMet) 83v2-A3-ABD (ECB38; high/high) 17v2-A5 (ECB28; medium/medium) 17v2-A3-ABD (ECB39; medium/high). In the figure, 83v2 refers to p54AR4-83v2; 17v2 refers to p53A1R5-17v2; A3 refers to p114AR7P94-A3 and A5 refers to p114AR5P74-A5.

The concentration of each bispecific EGFR/c-Met molecule was measured at 6 and 72 hours after dosing in the blood and in the tumor (FIG. 7). Interestingly, the bispecific molecule with the medium affinity EGFR-binding domain (P53A1R5-17v2; $K_D$=1.9 nM) but high affinity c-Met-binding FN3 domain (P114AR7P94-A3; $K_D$=0.4 nM) had significantly more tumor accumulation at 6 hours relative to the other molecules, while the difference is diminished by 72 hours. It can be hypothesized that cells outside the tumor have lower levels of both EGFR and c-Met surface expression and therefore the medium affinity EGFR molecule doesn't bind to normal tissue as tightly compared to the higher affinity EGFR-binding FN3 domain. Therefore there is more free medium affinity EGFR-binding FN3 domain available to bind in the tumor. Therefore, identifying the appropriate affinities to each receptor may allow for identification of a therapeutic with decreased systemic toxicities and increased tumor accumulation.

Tumor Efficacy Studies with Bispecific EGFR/c-Met Molecules

Figure 8:
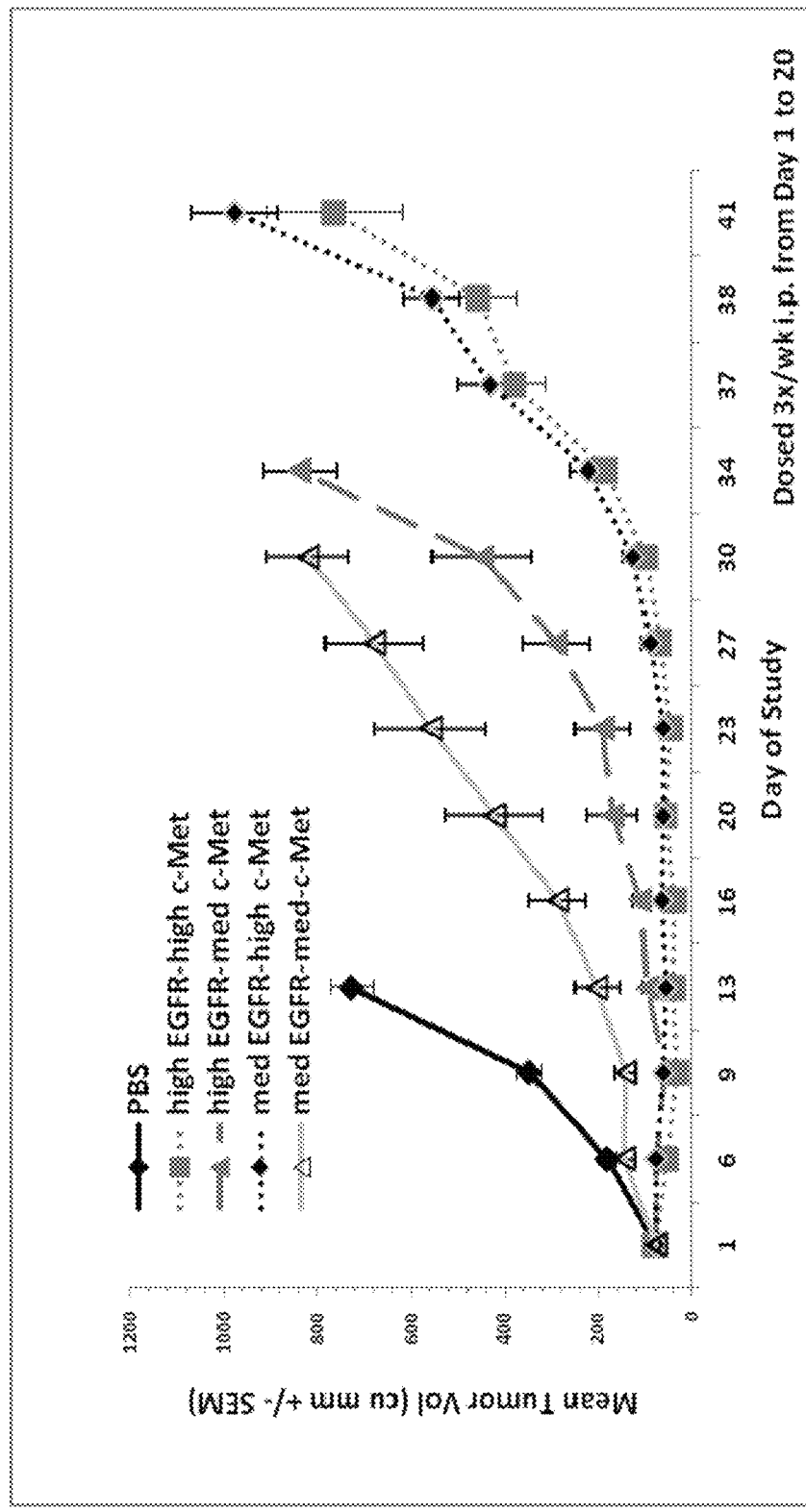
FIG. 8. H292-HGF tumor xenografts were implanted into SCID beige mice. When tumors reached an average volume of approximately 80 mm$^3$, mice were dosed three times per week with bispecific EGFR/c-Met molecules (25 mg/kg) or PBS vehicle. All bispecific molecules reduced tumor growth, the tumor growth inhibition (TGI) being dependent on the affinities of the molecules for c-Met and EGFR. (high EGFR-high cMet refers to p54AR4-83v2-p114AR7P94-A3 (ECB38); high EGFR-med cMet refers to p54AR4-83v2-p114AR5P74-A5 (ECB18); med EGFR-high cMet refers to p53A1R5-17v2-p114AR7P94-A3 (ECB39); med EGFR-med-cMet refers to p53A1R5-17-p114AR5P74-A 5 (ECB28)).

SCID Beige mice were subcutaneously inoculated with NCI-H292 cells expressing human HGF ($2.0 \times 10^6$ cells in Cultrex (Trevigen) in 200 μL) in the dorsal flank of each animal. One week after implantation, mice were stratified into groups with equivalent tumor volumes (mean tumor volume=77.9+/−1.7 mm$^3$). Mice were dosed three times per week with the bispecific molecules and tumor volumes were recorded twice weekly. Tumor growth inhibition (TGI) was observed with four different bispecific molecules, with variable affinities for c-Met and EGFR. FIG. 8 shows the benefit of inhibiting both c-Met and EGFR as a delay in tumor growth was observed in the mice treated with molecules containing the high affinity EGFR-binding FN3 domain compared to the medium affinity EGFR-binding FN3 domain when the c-Met-binding FN3 domain was medium affinity (open vs. closed triangles, P54AR4-83v2-P114AR5P74-A5 compared to P53A1R5-17-P114AR5P74-A5). In addition, the data shows the importance of having a high affinity c-Met-binding FN3 domain as bispecific molecules containing either the high or medium affinity EGFR-binding FN3 domain but high affinity c-Met-binding FN3 domain showed the most efficacy (dotted gray and black lines, P54AR4-83v2-P114AR7P94-A3 and P53A1R5-17v2-P114AR7P94-A3).

Efficacy of Bispecfic Molecule and Other Inhibitors of EGFR and c-Met

The in vivo therapeutic efficacies of a bispecific EGFR/c-Met molecule (ECB38) and the small molecule inhibitors crizotinib (c-Met inhibitor) and erlotinib (EGFR inhibitor), cetuximab (anti-EGFR antibody), each as a single agent, and the combination of crizotnib and erlontinib, were evaluated in the treatment of subcutaneous H292-HGF human lung cancer xenograft model in SCID/Beige mice.

The H292-HGF cells were maintained in vitro in RPMI1640 medium supplemented with fetal bovine serum (10% v/v), and L-glutamine (2 mM) at 37° C. in an atmosphere of 5% CO2 in air. The cells were routinely subcultured twice weekly by trypsin-EDTA treatment. The cells growing in an exponential growth phase were harvested and counted for tumor inoculation.

TABLE 14

| Group | N | Treatment | Dose (mg/kg) | Dosing Route | Planned Schedule | Actual Schedule |
|---|---|---|---|---|---|---|
| 1 | 10 | Vehicle Control | 0 | i.p. | QD × 3 weeks | QD × 3 weeks |
| 2 | 10 | bispecific EGFR/c-Met molecule | 25 | i.p. | 3 times/ week × 3 weeks | 3 times/ week × 3 weeks |
| 3 | 10 | Crizotinib | 50 | p.o. | QD × 3 weeks | QD × 17 days |
| 4 | 10 | Erlotinib | 50 | p.o. | QD × 2 weeks | QD × 3 weeks |
| 5 | 10 | Crizotinib | 50 | p.o. | QD × 3 weeks | QD × 3 weeks |
| 6 | 10 | Cetuximab | 1 mg/mouse | i.p. | Q4d*6 | Q4d*6 |

N: animal number;
p.o.: oral administration;
i.p.: intraperitoneal injection 3 times/week: doses were given on days 1, 3 and 5 of the week.
QD: once daily
Q4d: once every four days; the interval of the combination of crizotinib and erlotinib was 0.5 hrs; dosing volume was adjusted based on body weight (10 1/g);
a: dosing was not given on day 14 post grouping.

Each mouse was inoculated subcutaneously at the right flank region with H292-HGF tumor cells (2×10$^6$) in 0.1 ml of PBS with cultrex (1:1) for tumor development. The treatments were started when the mean tumor size reached 139 mm$^3$. The test article administration and the animal numbers in each study group were shown in the following experimental design table. The date of tumor cell inoculation was denoted as day 0. Table 14 shows the treatment groups.

Before commencement of treatment, all animals were weighed and the tumor volumes were measured. Since the tumor volume can affect the effectiveness of any given treatment, mice were assigned into groups using randomized block design based upon their tumor volumes. This ensures that all the groups are comparable at the baseline. The randomized block design was used to assign experimental animals to groups. First, the experimental animals were divided into homogeneous blocks according to their initial tumor volume. Secondly, within each block, randomization of experimental animals to treatments was conducted. Using randomized block design to assign experimental animals ensured that each animal had the same probability of being assigned to a given treatment and therefore systematic error was reduced.

At the time of routine monitoring, the animals were checked for any effects of tumor growth and treatments on normal behavior, such as mobility, visual estimation of food and water consumption, body weight gain/loss (body weights were measured twice weekly), eye/hair matting and any other abnormal effect.

The endpoint was whether tumor growth can be delayed or tumor bearing mice can be cured. Tumor size was measured twice weekly in two dimensions using a caliper, and the volume was expressed in mm$^3$ using the formula: $V = 0.5\ a \times b^2$ where a and b are the long and short diameters of the tumor, respectively. The tumor size was then used for calculations of both T-C and T/C values. T-C was calculated with T as the time (in days) required for the mean tumor size of the treatment group to reach 1000 mm$^3$, and C was the time (in days) for the mean tumor size of the control group to reach the same size. The T/C value (in percent) was an indication of antitumor efficacy; T and C were the mean tumor volume of the treated and control groups, respectively, on a given day. Complete tumor regression (CR) is defined as tumors that are reduced to below the limit of palpation (62.5 mm$^3$) Partial tumor regression (PR) is defined as tumors that are reduced from initial tumor volume. A minimum duration of CR or PR in 3 or more successive tumor measurements is required for a CP or PR to be considered durable.

Animals for which the body weight loss exceeded 20%, or for which the mean tumor size of the group exceeds 2000 mm$^3$ were euthanized. The study was terminated after two weeks of observation after the final dose.

Summary statistics, including mean and the standard error of the mean (SEM), are provided for the tumor volume of each group at each time point are shown in Table 15. Statistical analyses of difference in tumor volume among the groups were evaluated using a one-way ANOVA followed by individual comparisons using Games-Howell (equal variance not assumed). All data were analyzed using SPSS 18.0. p<0.05 was considered to be statistically significant.

TABLE 15

| | Tumor volume (mm$^3$)a | | | | | |
|---|---|---|---|---|---|---|
| Days | Vehicle | bispecific EGFR/c-Met molecule at 25 mg/kg | Crizotinib at 50 mg/kg | Erlotinib at 50 mg/kg | Crizotinib; Erlotinib at 50 mg/kg; 50 mg/kg | Cetuximab at 1 mg/mouse |
| 7 | 137 ± 7 | 137 ± 7 | 140 ± 9 | 141 ± 8 | 139 ± 8 | 139 ± 10 |
| 9 | 230 ± 20 | 142 ± 7 | 217 ± 20 | 201 ± 19 | 134 ± 9 | 168 ± 13 |
| 13 | 516 ± 45 | 83 ± 6 | 547 ± 43 | 392 ± 46 | 109 ± 10 | 212 ± 20 |
| 16 | 808 ± 104 | 44 ± 7 | 914 ± 92 | 560 ± 70 | 127 ± 15 | 252 ± 28 |
| 20 | 1280 ± 209 | 30 ± 6 | 1438 ± 239 | 872 ± 136 | 214 ± 30 | 371 ± 48 |
| 23 | 1758 ± 259 | 23 ± 7 | 2102 ± 298 | 1122 ± 202 | 265 ± 40 | 485 ± 61 |
| 27 | 2264 ± 318 | 21 ± 5 | — | 1419 ± 577 | 266 ± 42 | 640 ± 82 |
| 30 | — | 23 ± 6 | — | 1516 ± 623 | 482 ± 61 | 869 ± 100 |

The mean tumor size of the vehicle treated group (Group 1) reached 1,758 mm$^3$ at day 23 after tumor inoculation. Treatment with the bispecific EGFR/c-Met molecule at 25 mg/kg dose level (Group 2) led to complete tumor regression (CR) in all mice which were durable in >3 successive tumor measurements (average TV=23 mm$^3$, T/C value=1%, p=0.004 compared with the vehicle group at day 23).

Treatment with crizotinib as a single agent at 50 mg/kg dose level (Group 3) showed no antitumor activity; the mean tumor size was 2,102 mm$^3$ at day 23 (T/C value=120%, p=0.944 compared with the vehicle group).

Treatment with erlotinib as a single agent at 50 mg/kg dosing level (Group 4) showed minor antitumor activity, but no significant difference was found compared with the vehicle group; the mean tumor size was 1,122 mm$^3$ at day 23 (T/C value=64%, p=0.429 compared with the vehicle group), with 4 days of tumor growth delay at tumor size of 1,000 mm$^3$ compared with the vehicle group.

The combination of crizotinib (50 mg/kg, Group 5) and erlotinib (50 mg/kg, Group 5) showed significant antitumor activity; the mean tumor size was 265 mm³ at day 23 (T/C=15%; p=0.008), with 17 days of tumor growth delay at tumor size of 1,000 mm³ compared with the vehicle group.

Figure 9:
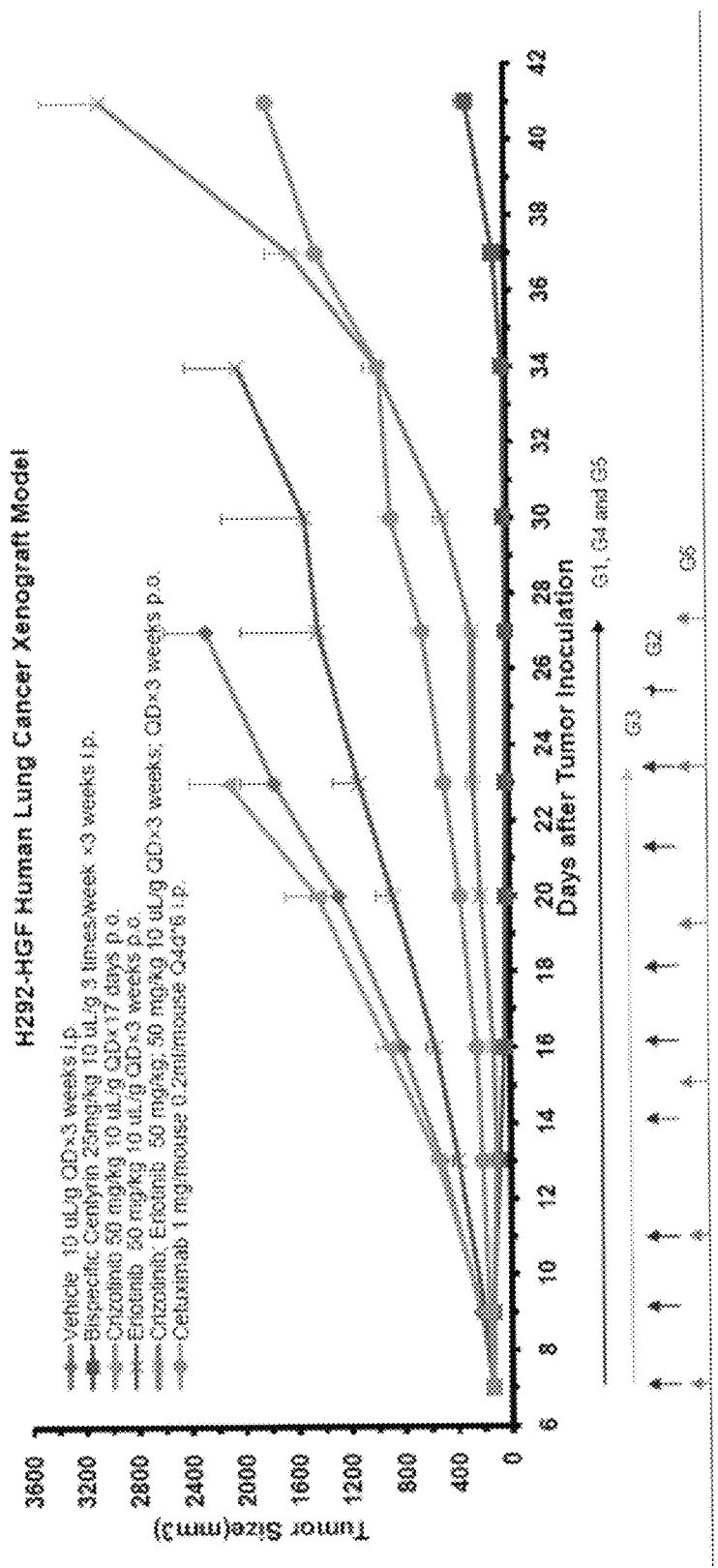
FIG. 9. H292-HGF tumor xenografts were implanted into SCID beige mice and they were treated with different therapies. The anti-tumor activity of the therapies is shown. (bispecific EGFR/c-Met molecule refers to p54AR4-83v2-p114AR7P94-A3-ABD (ECB38); the other therapies are crizotinib, erlotinib, cetuximab, and the combination of crizotinib and erlotinib).

Cetuximab at 1 mg/mouse dosing level as a single agent (Group 6) showed significant antitumor activities; the mean tumor size was 485 mm³ at day 23 (T/C=28%; p=0.018), with 17 days of tumor growth delay at tumor size of 1,000 mm³ compared with the vehicle group. FIG. 9 and Table 16 show the anti-tumor activities of the various therapies.

TABLE 16

| Treatment | Tumor Size (mm³) at day 23 | T/C (%) | T-C (days) at 1000 mm³ | P value |
|---|---|---|---|---|
| Vehicle | 1758 ± 0259 | — | — | — |
| bispecific EGFR/c-Met molecule (25 mg/kg) | 23 ± 7 | 1 | — | 0.004 |
| Crizotinib (50 mg/kg) | 2102 ± 298 | 120 | −1 | 0.944 |
| Erlotinib (50 mg/kg) | 1122 ± 202 | 64 | 4 | 0.429 |
| Crizotinib + Erlotinib (50 mg/kg + 50 mg/kg) | 265 ± 40 | 15 | 17 | 0.008 |
| Cetuximab (1 mg/mouse) | 485 ± 61 | 28 | 17 | 0.018 |

Medium to severe body weight loss was observed in the vehicle group which might be due to the increasing tumor burden; 3 mice died and 1 mouse were euthanized when BWL>20% by day 23. Slight toxicity of the bispecific EGFR/c-Met molecule was observed in Group 2; 3 mice were euthanized when BWL>20% during the treatment period; the body weight was gradually recovered when the treatment was withdrawn during the 2 weeks of observation period. More severe body weight loss was observed in the crizotinib or erlotinib monotherapy group compared to the vehicle group, suggesting the treatment related toxicity. The combination of crizotinib and erlotinib was generally tolerated during the dosing phase, but severe body weight loss was observed at the end of the study, which might be due to the resumption of the fast tumor growth during the non-treatment period. The monotherapy of cetuximab was well tolerated in the study; body weight loss was only observed at the end of the study due to the resume of the tumor growth.

In summary, the bispecific EGFR/c-Met molecule at 25 mg/kg (3 times/week×3 weeks) produced a complete response in H292-HGF human lung cancer xenograft model in SCID/Beige mice. The treatment was tolerated in 7 out of 10 mice, and resulted in severe body weight loss in 3 out of 10 mice. FIG. 9 shows the impact of the various therapies on tumor size during the time points after treatment.

EXAMPLE 8

Half-Life Extension of the Bispecific EGFR/c-Met Molecules

Numerous methods have been described to reduce kidney filtration and thus extend the serum half-life of proteins including modification with polyethylene glycol (PEG) or other polymers, binding to albumin, fusion to protein domains which bind to albumin or other serum proteins, genetic fusion to albumin, fusion to IgG Fc domains, and fusion to long, unstructured amino acid sequences.

Bispecific EGFR/c-Met molecules were modified with PEG in order to increase the hydrodynamic radius by incorporating a free cysteine at the C-terminus of the molecule. Most commonly, the free thiol group of the cysteine residue is used to attach PEG molecules that are functionalized with maleimide or iodoacetemide groups using standard methods. Various forms of PEG can be used to modify the protein including linear PEG of 1000, 2000, 5000, 10,000, 20,000, or 40,000 kDa. Branched PEG molecules of these molecular weights can also be used for modification. PEG groups may also be attached through primary amines in the bispecific EGFR/c-Met molecules in some instances.

In addition to PEGylation, the half-life of bispecific EGFR/c-Met molecules was extended by producing these proteins as fusion molecules with a naturally occurring 3-helix bundle serum albumin binding domain (ABD) or a consensus albumin binding domain (ABDCon). These protein domains were linked to the C-terminus of the c-Met-binding FN3 domain via any of the linkers described in Table 12. The ABD or ABDCon domain may also be placed between the EGFR-binding FN3 domain and the c-Met binding FN3 domain in the primary sequence. In some cases, albumin or albumin variant (SEQ ID NO: 189) was linked to the bispecific EGFR/c-Met molecules to the C-terminus of the c-Met binding FN3 domain.

EXAMPLE 9

Characterization of Select Bispecific EGFR/c-Met Molecules

Select bispecific EGFR/c-Met molecules were characterized for their affinity to both EGFR and c-Met, their ability to inhibit EGFR and c-Met autophosphorylation, and their effect on proliferation of HGF cells. Binding affinity of the bispecific EGFR/c-Met molecules to recombinant EGFR and/or c-Met extracellular domain was further analyzed by surface Plasmon resonance methods using a Proteon Instrument (BioRad) according to protocol described in Example 3. Results of the characterization are shown in Table 17.

TABLE 17

| Molecule | $K_D$ (EGFR, nM) | $K_D$ (c-Met, nM) | pMet inhibition in H441 cells ($IC_{50}$, nM) | pEGFR inhibition in H292 cells ($IC_{50}$, nM) | H292-HGF Proliferation induced H292 cells ($IC_{50}$, nM) |
|---|---|---|---|---|---|
| ECB15 | 0.2 | 2.6 | n/a | 4.2 | 23 |
| ECB94 | 1 | 4.3 | 53.8 | 5.1 | 29.6 |
| ECB95 | 1.1 | 6.2 | 178.8 | 13.6 | 383.4 |
| ECB96 | 1.6 | 22.1 | 835.4 | 24.7 | 9480 |
| ECB97 | 1.3 | 1.7 | 24.2 | 16.6 | 31.0 |
| ECB106 | 16.7 | 5.1 | 53.3 | 367.4 | 484.5 |
| ECB107 | 16.9 | 9 | 29.9 | 812.3 | 2637 |
| ECB108 | 15.3 | 25.5 | 126.2 | 814.4 | 11372 |
| ECB109 | 17.3 | 2.1 | 26 | 432 | 573.6 |
| ECB168 | 0.4 | 0.32 | | | 3.1 |
| ECB158* | 0.9 | 0.58 | | | 10.8 |

*ECB158 is ECB168 conjugated to human serum albumin variant C34S via a (GGGGS)₂ linker of SEQ ID NO: 224

EXAMPLE 10

Paratopes of EGFR and c-Met Binding FN3 Domains

A series of mutations were made to molecule P54AR4-83v2 (SEQ Id NO: 27) in order to define residues critical for binding to the EGFR extracellular domain. For this analysis, every amino acid position in the BC and FG loops were mutated to alanine one at a time to produce 18 new molecules. The affinity that these mutants bind to EGFR was determined by SPR analysis using a Proteon instrument. The results are shown in Table 18. 10 positions resulted in a loss of binding affinity greater than 10-fold indicating that these positions contribute to binding to EGFR. Fold change indicates fold change of the $K_D$ value of a variant when compared to the parent P54AR4-83v2. A combination of residues from the BC and FG loops makes up the binding surface. 10 positions were shown to weaken binding to EGFR by greater than 10-fold, and 5 positions were shown to weaken binding to EGFR by greater than 100-fold (D23, F27, Y28, V77, G85). In addition to P54AR4-83v2, EGFR-binding molecules P54AR4-48, P54AR4-81, P53A1R5-17v2, P54AR4-83v22 and P54AR4-83v23 (SEQ ID NOs: 21, 25, 107, 108 and 109, respectively) have identical residues at paratope positions that weaken EGFR binding by greater than 100-fold when mutated. Several bispecific EGFR/c-Met molecules generated comprise the P54AR4-83v2, P54AR4-48, P54AR4-81, P53A1R5-17v2, P54AR4-83v22 or P54AR4-83v2 as their EGFR-binding FN3 domain as shown in Table 10.

TABLE 18

| Molecule | SEQ ID NO: | $k_a$ (1/Ms) | $k_d$ (1/s) | $K_D$ (nM) | Fold Change |
|---|---|---|---|---|---|
| P54AR4-83v2 | 27 | 3.54E+05 | 4.98E−05 | 0.14 | 1 |
| 83v2 D22A | 194 | 2.15E+05 | 3.01E−05 | 0.14 | 1 |
| 83v2 D23A | 195 | 1.32E+05 | 4.20E−03 | 31.8 | 227 |
| 83v2 P24A | 196 | 7.81E+04 | 2.19E−04 | 2.8 | 20 |
| 83v2 W25A | 197 | 1.10E+05 | 1.69E−04 | 1.5 | 11 |
| 83v2 F27A | 198 | 2.32E+04 | 5.56E−04 | 24 | 171 |
| 83v2 Y28A | 199 | 4.36E+04 | 3.86E−03 | 88.5 | 632 |
| 83v2 H75A | 200 | 1.67E+05 | 6.55E−04 | 3.9 | 28 |
| 83v2 N76A | 201 | 2.08E+05 | 7.43E−05 | 0.36 | 3 |
| 83v2 V77A | 202 | 7.88E+04 | 8.55E−03 | 108 | 771 |
| 83v2 Y78A | 203 | 1.82E+05 | 5.14E−04 | 2.8 | 20 |
| 83v2 K79A | 204 | 6.81E+05 | 2.83E−05 | 0.04 | 0 |
| 83v2 D80A | 205 | 1.23E+05 | 5.46E−05 | 0.45 | 3 |
| 83v2 M83A | 206 | 1.77E+05 | 2.74E−04 | 1.5 | 11 |
| 83v2 R84A | 207 | 2.34E+05 | 1.37E−04 | 0.59 | 4 |
| 83v2 G85A | 208 | 7.30E+04 | 2.20E−03 | 30.1 | 215 |
| 83v2 L86A | 209 | 3.09E+05 | 1.17E−04 | 0.38 | 3 |
| 83v2 T81A | 210 | 2.28E+05 | 8.38E−05 | 0.37 | 3 |
| 83v2 N82A | 211 | 1.94E+05 | 9.67E−05 | 0.5 | 4 |

Likewise, a series of mutations were made to the presumed c-Met interaction surface of molecule P114AR7P95-A3 (SEQ ID NO: 41) in order to define positions critical for target binding. This analysis was done in the context of bispecific molecule ECB15 (SEQ ID NO: 145) and serine was used as a replacement instead of alanine as described above. Serine was chosen to decrease the hydrophobicity of the resulting mutants. Table 19 describes the SPR results with the numbering of each mutation position relative to that of molecule A3 (SEQ ID NO: 41). 7 positions were shown to weaken binding to c-Met by greater than 10-fold. No binding was measurable for mutants M72S, R34S, and I79S. F38S mutation reduced binding to c-Met by greater than 100-fold. This data demonstrates that the positions contributing for c-Met binding are distributed among the C-strand, F-strand, CD loop, and FG loop. Fold change indicates fold change of the $K_D$ value of a variant when compared to the parent P114AR7P95-A3. In addition to P114AR7P94-A3, c-Met-binding molecules P114AR7P92-F3, P114AR7P95-D3, P114AR7P95-F10 and P114AR7P95-H8 (SEQ ID NOs: 34, 44, 47 and 49, respectively) have identical residues at paratope positions that weaken c-Met binding by greater than 100-fold when mutated.

TABLE 19

| Sample | SEQ ID NO: | ka (1/Ms) | kd (1/s) | KD (nM) | Fold Change |
|---|---|---|---|---|---|
| ECB15 | 145 | 3.51E+05 | 1.33E−04 | 0.4 | 1 |
| A3 K78S | 212 | 4.40E+05 | 1.50E−04 | 0.3 | 0.75 |
| A3 G405 | 213 | 1.85E+05 | 3.20E−04 | 1.7 | 4.25 |
| A3 L39S | 214 | 4.75E+05 | 1.27E−03 | 2.7 | 6.75 |
| A3 V68S | 215 | 3.29E+05 | 1.20E−03 | 3.6 | 9 |
| A3 N705 | 216 | 4.25E+05 | 2.49E−03 | 5.9 | 14.75 |
| A3 P81S | 217 | 3.21E+05 | 5.36E−04 | 1.7 | 4.25 |
| A3 F36S | 218 | 1.88E+05 | 5.12E−03 | 27.2 | 68 |
| A3 W32S | 219 | 2.89E+05 | 8.60E−03 | 29.8 | 74.5 |
| A3 M72S | 220 | — | — | — | |
| A3 R34S | 221 | — | — | — | |
| A3 F38S | 222 | 4.51E+04 | 3.23E−02 | 717 | 1792.5 |
| A3 1795 | 223 | — | — | — | |

EXAMPLE 11

Inhibition of Human Tumor Cell Growth by Bispecific EGFR/c-Met Molecules

Inhibition of human tumor cell growth was assessed in standard attachment culture as described in Examples 3 or 6, or in low attachment conditions. To assess survival in low attachment conditions, cells were plated in Ultra Low Attachment 96-well plates (Corning Costar) in 50 μL/well of RPMI medium (Invitrogen) containing GlutaMAX and 25 mM Hepes, supplemented with 1 mM sodium pyruvate (Gibco), 0.1 mM NEAA (Gibco), and 10% heat inactivated fetal bovine serum (Gibco), and allowed to attach overnight at 37° C., 5% $CO_2$. Cells were treated with varying concentrations of antibodies (0.035-700 nM final), along with HGF (7.5 ng/mL, R&D Systems cat#294-HGN), then incubated at 37° C., 5% $CO_2$ for 72 hours. Some wells were left untreated with either HGF or antibodies as controls. Viable cells were detected using CellTiter-Glo® reagent (Promega), and data were analyzed as described above in "Inhibition of Human Tumor Cell Growth (NCI-H292 growth and NCI-H322 growth assay)" in Example 3, except that lysates were transferred to opaque white 96-well tissue culture-treated plates (PerkinElmer) prior to reading luminescence.

Cell line was classified as a strong responder to EGFR/c-Met bispecific molecule in those instances when maximum inhibition of cell growth was >40% and relative $IC_{50}$<5 mM.

Inhibitory activity of ECB15 was assessed in multiple cell lines having wild type, amplified or mutant EGFR and wild type or amplified c-Met. ECB15 inhibited tumor cell growth of cell lines shown in Table 20. ECB15 also inhibited growth of NCI-H1975 cell line having mutation T790M which has been show to result in resistance to TKIs such as erlotinib.

TABLE 20

| Cell line | Histology | EGFR | c-Met |
|---|---|---|---|
| NCI-H1650 | Broncho-alveolar-adenocarcinoma | Del(E746, A750) | WT |
| SKMES-1 | Squamous | WT | WT |
| NCI-H1563 | Adenocarcinoma | | |
| GLC-82 | Adenocarcinoma | | |
| Calu-3 | Adenocarcinoma | | |
| NCI-H1573 | Adenocarcinoma | AMP | AMP |

TABLE 20-continued

| Cell line | Histology | EGFR | c-Met |
|---|---|---|---|
| NCI-H1435 | NSCLC | | |
| NCI-H1975 | NSCLC | L858R; T790M | WT |
| NCI-H1666 | Broncho-alveolar-adenocarcinoma | | |
| HCC2935 | NSCLC | del (E746 - T751), S752I | |
| HCC4006 | Adenocarcinoma | del (L747 - E749), A750P | |
| H292 | Mucoepidermoid | WT | WT |
| H322 | Adenocarcinoma | WT | WT |
| HCC827 | Adenocarcinoma | del (E746, A750); AMP | WT |
| H596 | Adeno-squamous mixed | WT | Exon 14 deletion |
| H1869 | Squamous | WT | WT |

WT: wild type
AMP: amplified
Del: deletion

What is claimed:

1. An isolated bispecific FN3 domain containing molecule comprising a first fibronectin type III (FN3) domain and a second FN3 domain, wherein the first FN3 domain specifically binds epidermal growth factor receptor (EGFR) and blocks binding of epidermal growth factor (EGF) to EGFR, and the second FN3 domain specifically binds hepatocyte growth factor receptor (c-Met), and blocks binding of hepatocyte growth factor (HGF) to c-Met, wherein the first FN3 domain comprises an amino acid sequence of SEQ ID NO: 27, and the second FN3 domain comprises an amino acid sequence of SEQ ID NO: 41.

2. The bispecific molecule of claim 1, wherein
   a) the first FN3 domain inhibits EGF-induced EGFR phosphorylation at EGFR residue Tyrosine 1173 with an $IC_{50}$ value of less than about $2.5 \times 10^{-6}$ M when measured in A431 cells using 50 ng/mL human EGF, and the second FN3 domain inhibits HGF-induced c-Met phosphorylation at c-Met residue Tyrosine 1349 with an $IC_{50}$ value of less than about $1.5 \times 10^{-6}$ M when measured in NCI-H441 cells using 100 ng/mL human HGF;
   b) the first FN3 domain inhibits EGF-induced EGFR phosphorylation at EGFR residue Tyrosine 1173 with an $IC_{50}$ value between about $1.8 \times 10^{-8}$ M and about $2.5 \times 10^{-6}$ M when measured in A431 cells using 50 ng/mL human EGF, and the second FN3 domain inhibits HGF-induced c-Met phosphorylation at c-Met residue Tyrosine 1349 with an $IC_{50}$ value between about $4 \times 10^{-9}$ M and about $1.5 \times 10^{-6}$ M when measured in NCI-H441 cells using 100 ng/mL human HGF;
   c) the first FN3 domain binds human EGFR with a dissociation constant ($K_D$) of less than about $1 \times 10^{-8}$ M, and the second FN3 domain binds human c-Met with a $K_D$ of less than about $5 \times 10^{-8}$ M, wherein the $K_D$ is measured using surface plasmon resonance; or
   d) the first FN3 domain binds human EGFR with a $K_D$ of between about $2 \times 10^{-10}$ to about $1 \times 10^{-8}$ M, and the second FN3 domain binds human c-Met with a $K_D$ of between about $3 \times 10^{-10}$ to about $5 \times 10^{-8}$ M, wherein the $K_D$ is measured using surface plasmon resonance.

3. The bispecific molecule of claim 1, wherein the bispecific molecule inhibits NCI-H292 cell proliferation with an $IC_{50}$ value that is at least 30-fold less when compared to the $IC_{50}$ value of inhibition of NCI-H292 cell growth with a mixture of the first FN3 domain and the second FN3 domain, wherein the cell proliferation is induced with 10% FBS containing 7.5 ng/mL HGF.

4. The bispecific molecule of claim 1, wherein the bispecific molecule
   a) inhibits EGF-induced EGFR phosphorylation at EGFR residue Tyrosine 1173 with an $IC_{50}$ value of less than about $8 \times 10^{-7}$ M when measured in NCI-H292 cells using 50 ng/mL human EGF;
   b) inhibits HGF-induced c-Met phosphorylation at c-Met residue Tyrosine 1349 with an $IC_{50}$ value of less than about $8.4 \times 10^{-7}$ M when measured in NCI-H441 cells using 100 ng/mL human HGF;
   c) inhibits HGF-induced NCI-H292 cell proliferation with an $IC_{50}$ value of less than about $9.5 \times 10^{-6}$ M, wherein the cell proliferation is induced with 10% FBS containing 7.5 ng HGF;
   d) binds EGFR with a $K_D$ of less than about $2.0 \times 10^{-8}$ M; or
   e) binds c-Met with a $K_D$ of less than about $2.0 \times 10^{-8}$ M, wherein the $K_D$ is measured using surface plasmon resonance.

5. The bispecific molecule of claim 1, wherein the first FN3 domain and/or the second FN3 domain comprises substitutions at one or more residue positions corresponding to positions 11, 14, 17, 37, 46, 73 and 86 in Tencon (SEQ ID NO: 1).

6. The bispecific molecule of claim 1, wherein the first FN3 domain and/or the second FN3 domain comprises one, two or three substitutions corresponding to substitutions L17A, N46V and E86I in Tencon (SEQ ID NO: 1).

7. The bispecific molecule of claim 6, wherein the first FN3 domain and/or the second FN3 domain is isolated from a library designed based on a Tencon sequence of SEQ ID NO: 1.

8. The bispecific molecule of claim 1, wherein the first FN3 domain and the second FN3 domain are coupled by a linker.

9. The bispecific molecule of claim 8, wherein the linker comprises the amino acid sequence shown in one of SEQ ID NOs: 78-84.

10. The bispecific molecule of claim 1, further comprising a cysteine linked to the C-terminus of the molecule.

11. The bispecific molecule of claim 1 coupled to a half-life extending moiety.

12. The bispecific molecule of claim 11, wherein the half-life extending moiety is an albumin binding molecule, a polyethylene glygol (PEG), albumin, or at least a portion of an Fc region of an immunoglobulin.

13. A pharmaceutical composition comprising the bispecific molecule of claim 1 and a pharmaceutically acceptable carrier.

* * * * *

```
                    SEQUENCE LISTING

<160> NUMBER OF SEQ ID NOS: 224

<210> SEQ ID NO 1
<211> LENGTH: 89
<212> TYPE: PRT
<213> ORGANISM: Artificial Sequence
<220> FEATURE:
<223> OTHER INFORMATION: Tencon FN3 scaffold

<400> SEQUENCE: 1

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85

<210> SEQ ID NO 2
<211> LENGTH: 58
<212> TYPE: DNA
<213> ORGANISM: Artificial Sequence
<220> FEATURE:
<223> OTHER INFORMATION: primer

<400> SEQUENCE: 2
ggaaacagga tctaccatgc tgccggcgcc gaaaaacctg gttgtttctg aagttacc      58

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
aacaccgtag atagaaacgg t                                              21

<210> SEQ ID NO 4
<211> LENGTH: 131
<212> TYPE: DNA
<213> ORGANISM: Artificial Sequence
<220> FEATURE:
<223> OTHER INFORMATION: primer

<400> SEQUENCE: 4
```

```
cggcggttag aacgcggcta caattaatac ataaccccat cccccctgttg acaattaatc    60 atcggctcgt ataatgtgtg gaattgtgag cggataacaa tttcacacag gaaacaggat   120
ctaccatgct g                                                        131
```

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5

```
cggcggttag aacgcggcta c                                              21
```

<210> SEQ ID NO 6
<211> LENGTH: 66
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t

<400> SEQUENCE: 6

```
ggtggtgaat tccgcagaca gcggsnnsnn snnsnnsnns nnsnnaacac cgtagataga    60
aacggt                                                               66
```

<210> SEQ ID NO 7
<211> LENGTH: 69
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t

<400> SEQUENCE: 7
ggtggtgaat tccgcagaca gcggsnnsnn snnsnnsnns nnsnnsnnaa caccgtagat    60
agaaacggt                                                            69

<210> SEQ ID NO 8
<211> LENGTH: 72
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t

<400> SEQUENCE: 8
ggtggtgaat tccgcagaca gcggsnnsnn snnsnnsnns nnsnnsnnsn naacaccgta    60
gatagaaacg gt                                                        72

<210> SEQ ID NO 9

```
<211> LENGTH: 75
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t

<400> SEQUENCE: 9
ggtggtgaat tccgcagaca gcggsnnsnn snnsnnsnns nnsnnsnnsn nsnnaacacc      60
gtagatagaa acggt                                                      75

<210> SEQ ID NO 10
<211> LENGTH: 80
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
```

```
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 10
rmggtggtga attccgcaga cagcggsnns nnsnnsnnsn nsnnsnnsnn snnsnnsnna      60
acaccgtaga tagaaacggt                                                 80

<210> SEQ ID NO 11
<211> LENGTH: 81
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
```

<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t

<400> SEQUENCE: 11
ggtggtgaat tccgcagaca gcggsnnsnn snnsnnsnns nnsnnsnnsn nsnnsnnsnn    60
aacaccgtag atagaaacgg t                                              81

<210> SEQ ID NO 12
<211> LENGTH: 81
<212> TYPE: DNA
<213> ORGANISM: Artificial Sequence
<220> FEATURE:
<223> OTHER INFORMATION: primer

<400> SEQUENCE: 12
aagatcagtt gcggccgcta gactagaacc gctgccatgg tgatggtgat ggtgaccgcc    60
ggtggtgaat tccgcagaca g                                              81

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
cggcggttag aacgcggcta caattaatac                                     30

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
catgattacg ccaagctcag aa                                             22

<210> SEQ ID NO 15
<211> LENGTH: 65
<212> TYPE: DNA
<213> ORGANISM: Artificial Sequence
<220> FEATURE:
<223> OTHER INFORMATION: primer

<400> SEQUENCE: 15
gagccgccgc caccggttta atggtgatgg tgatggtgac caccggtggt gaattccgca    60
gacag                                                                65

<210> SEQ ID NO 16
<211> LENGTH: 37
<212> TYPE: DNA
<213> ORGANISM: Artificial Sequence
<220> FEATURE:
<223> OTHER INFORMATION: primer

<400> SEQUENCE: 16
aagaaggaga accggtatgc tgccggcgcc gaaaaac                             37

<210> SEQ ID NO 17
<211> LENGTH: 89
<212> TYPE: DNA
<213> ORGANISM: Artificial Sequence
<220> FEATURE:
<223> OTHER INFORMATION: primer

<400> SEQUENCE: 17
tttgggaagc ttctaggtct cggcggtcac catcaccatc accatggcag cggttctagt    60
ctagcggccc caactgatct tcaccaaac                                      89

<210> SEQ ID NO 18
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 18

Leu Pro Ala Pro Lys Asn Leu Val Val Ser Glu Val Thr Glu Asp Ser
1               5                   10                  15

Leu Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 19
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 19

Leu Pro Ala Pro Lys Asn Leu Val Val Ser Glu Val Thr Glu Asp Ser
1               5                   10                  15

Leu Arg Leu Ser Trp Thr Tyr Asp Arg Asp Gly Tyr Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 20
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 20

```
Leu Pro Ala Pro Lys Asn Leu Val Val Ser Glu Val Thr Glu Asp Ser
1               5                   10                  15

Leu Arg Leu Ser Trp Gly Tyr Asn Gly Asp His Phe Asp Ser Phe Leu
            20                  25                  30

Ile Gln Tyr Gln Glu Ser Glu Lys Val Gly Glu Ala Ile Asn Leu Thr
                35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90
```

<210> SEQ ID NO 21
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 21

```
Leu Pro Ala Pro Lys Asn Leu Val Val Ser Glu Val Thr Glu Asp Ser
1               5                   10                  15

Leu Arg Leu Ser Trp Asp Asp Pro Arg Gly Phe Tyr Glu Ser Phe Leu
            20                  25                  30

Ile Gln Tyr Gln Glu Ser Glu Lys Val Gly Glu Ala Ile Asn Leu Thr
                35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90
```

<210> SEQ ID NO 22
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 22

```
Leu Pro Ala Pro Lys Asn Leu Val Val Ser Glu Val Thr Glu Asp Ser
1               5                   10                  15

Leu Arg Leu Ser Trp Thr Trp Pro Tyr Ala Asp Leu Asp Ser Phe Leu
            20                  25                  30

Ile Gln Tyr Gln Glu Ser Glu Lys Val Gly Glu Ala Ile Asn Leu Thr
                35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90
```

<210> SEQ ID NO 23
<211> LENGTH: 94
<212> TYPE: PRT
<213> ORGANISM: Artificial Sequence

```
<220> FEATURE:
<223> OTHER INFORMATION: EGFR binding FN3 domain

<400> SEQUENCE: 23

Leu Pro Ala Pro Lys Asn Leu Val Val Ser Glu Val Thr Glu Asp Ser
1               5                   10                  15

Leu Arg Leu Ser Trp Gly Tyr Asn Gly Asp His Phe Asp Ser Phe Leu
                20                  25                  30

Ile Gln Tyr Gln Glu Ser Glu Lys Val Gly Glu Ala Ile Asn Leu Thr
                35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 24
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 24

Leu Pro Ala Pro Lys Asn Leu Val Val Ser Glu Val Thr Glu Asp Ser
1               5                   10                  15

Leu Arg Leu Ser Trp Asp Tyr Asp Leu Gly Val Tyr Phe Asp Ser Phe
                20                  25                  30

Leu Ile Gln Tyr Gln Glu Ser Glu Lys Val Gly Glu Ala Ile Asn Leu
                35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 25
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 25

Leu Pro Ala Pro Lys Asn Leu Val Val Ser Glu Val Thr Glu Asp Ser
1               5                   10                  15

Leu Arg Leu Ser Trp Asp Asp Pro Trp Ala Phe Tyr Glu Ser Phe Leu
                20                  25                  30

Ile Gln Tyr Gln Glu Ser Glu Lys Val Gly Glu Ala Ile Asn Leu Thr
                35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90
```

```
<210> SEQ ID NO 26
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 26

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
                20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Leu Gly Ser Tyr Val Phe
65                  70                  75                  80

Glu His Asp Val Met Leu Pro Leu Ser Ala Glu Phe Thr Thr
                85                  90

<210> SEQ ID NO 27
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 27

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 28
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 28

Leu Pro Ala Pro Lys Asn Leu Val Val Ser Glu Val Thr Glu Asp Ser
1               5                   10                  15

Ala Arg Leu Ser Trp Thr Ala Pro Asp Ala Ala Phe Asp Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Leu Gly Ser Tyr Val Phe
```

```
            65                  70                  75                  80
Glu His Asp Val Met Leu Pro Leu Ser Ala Ile Phe Thr Thr
                        85                  90

<210> SEQ ID NO 29
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 29

Leu Pro Ala Pro Lys Asn Leu Val Val Ser Glu Val Thr Glu Asp Ser
1               5                   10                  15

Leu Arg Leu Ser Trp Thr Trp Pro Tyr Ala Asp Leu Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 30
<211> LENGTH: 37
<212> TYPE: PRT
<213> ORGANISM: Artificial Sequence
<220> FEATURE:
<223> OTHER INFORMATION: primer

<400> SEQUENCE: 30

Ala Ala Gly Ala Ala Gly Gly Ala Gly Ala Ala Cys Cys Gly Gly Thr
1               5                   10                  15

Ala Thr Gly Cys Thr Gly Cys Cys Gly Gly Cys Gly Cys Cys Gly Ala
            20                  25                  30

Ala Ala Ala Ala Cys
            35

<210> SEQ ID NO 31
<211> LENGTH: 65
<212> TYPE: PRT
<213> ORGANISM: Artificial Sequence
<220> FEATURE:
<223> OTHER INFORMATION: primer

<400> SEQUENCE: 31

Gly Ala Gly Cys Cys Gly Cys Cys Gly Cys Ala Cys Cys Gly Gly
1               5                   10                  15

Thr Thr Thr Ala Ala Thr Gly Gly Thr Gly Ala Thr Gly Gly Thr Gly
            20                  25                  30

Ala Thr Gly Gly Thr Gly Ala Cys Cys Ala Cys Cys Gly Gly Thr Gly
        35                  40                  45

Gly Thr Gly Ala Ala Gly Ala Thr Cys Gly Cys Ala Gly Ala Cys Ala
    50                  55                  60

Gly
65

<210> SEQ ID NO 32
```

```
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 32

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Asp Glu Val Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Tyr Val Asn Ile Leu Gly Val Lys Gly Ser Ile Ser
65                  70                  75                  80

Val Pro Leu Ser Ala Ile Phe Thr Thr
                85

<210> SEQ ID NO 33
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 33

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Phe
            20                  25                  30

Ile Arg Tyr Asp Glu Phe Leu Arg Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Thr Ile Leu Gly Val Lys Gly Leu Val Ser
65                  70                  75                  80

Thr Pro Leu Ser Ala Ile Phe Thr Thr
                85

<210> SEQ ID NO 34
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 34

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ile Val Asn Ile Met Gly Val Lys Gly Gly Ser Ile Ser
65                  70                  75                  80
```

His Pro Leu Ser Ala Ile Phe Thr Thr
                85

<210> SEQ ID NO 35
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 35

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Leu Gly Val Lys Gly Gly Leu Ser
65                  70                  75                  80

Val Pro Leu Ser Ala Ile Phe Thr Thr
                85

<210> SEQ ID NO 36
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 36

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Val
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Gln Ile Leu Gly Val Lys Gly Gly Tyr Ile Ser
65                  70                  75                  80

Ile Pro Leu Ser Ala Ile Phe Thr Thr
                85

<210> SEQ ID NO 37
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 37

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Leu Glu Phe Leu Leu Gly Gly Glu Ala Ile Val Leu Thr
        35                  40                  45

Val Pro Gly Ser Glu Arg Ser Tyr Asp Leu Thr Gly Leu Lys Pro Gly

```
              50                  55                  60
Thr Glu Tyr Val Val Gln Ile Met Gly Val Lys Gly Gly Thr Val Ser
 65                  70                  75                  80

Pro Pro Leu Ser Ala Ile Phe Thr Thr
                 85

<210> SEQ ID NO 38
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 38

Leu Pro Ala Pro Lys Asn Leu Val Val Ser Arg Val Thr Glu Asp Ser
 1                5                  10                  15

Ala Arg Leu Ser Trp Thr Ala Pro Asp Ala Ala Phe Asp Ser Phe Trp
                 20                  25                  30

Ile Arg Tyr Phe Glu Phe Leu Gly Ser Gly Glu Ala Ile Val Leu Thr
             35                  40                  45

Val Pro Gly Ser Glu Arg Ser Tyr Asp Leu Thr Gly Leu Lys Pro Gly
         50                  55                  60

Thr Glu Tyr Val Val Gly Ile Asn Gly Val Lys Gly Gly Tyr Ile Ser
 65                  70                  75                  80

Tyr Pro Leu Ser Ala Ile Phe Thr Thr
                 85

<210> SEQ ID NO 39
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 39

Leu Pro Ala Pro Lys Asn Leu Val Val Ser Arg Val Thr Glu Asp Ser
 1                5                  10                  15

Ala Arg Leu Ser Trp Thr Ala Pro Asp Ala Ala Phe Asp Ser Phe Trp
                 20                  25                  30

Ile Arg Tyr Phe Glu Phe Leu Gly Ser Gly Glu Ala Ile Val Leu Thr
             35                  40                  45

Val Pro Gly Ser Glu Arg Ser Tyr Asp Leu Thr Asp Leu Lys Pro Gly
         50                  55                  60

Thr Glu Tyr Gly Val Thr Ile Asn Gly Val Lys Gly Gly Arg Val Ser
 65                  70                  75                  80

Thr Pro Leu Ser Ala Ile Phe Thr Thr
                 85

<210> SEQ ID NO 40
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 40

Leu Pro Ala Pro Lys Asn Leu Val Val Ser Arg Val Thr Glu Asp Ser
 1                5                  10                  15

Ala Arg Leu Ser Trp Thr Ala Pro Asp Ala Ala Phe Asp Ser Phe Trp
                 20                  25                  30
```

```
Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Gln Ile Ile Gly Val Lys Gly His Ile Ser
65                  70                  75                  80

Leu Pro Leu Ser Ala Ile Phe Thr Thr
                85

<210> SEQ ID NO 41
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 41

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Asn Ile Met Gly Val Lys Gly Lys Ile Ser
65                  70                  75                  80

Pro Pro Leu Ser Ala Ile Phe Thr Thr
                85

<210> SEQ ID NO 42
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 42

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Ala Val Asn Ile Met Gly Val Lys Gly Gly Arg Val Ser
65                  70                  75                  80

Val Pro Leu Ser Ala Ile Phe Thr Thr
                85

<210> SEQ ID NO 43
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 43
```

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Val Val Gln Ile Leu Gly Val Lys Gly Gly Ser Ile Ser
65                  70                  75                  80

Val Pro Leu Ser Ala Ile Phe Thr Thr
                85
```

<210> SEQ ID NO 44
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 44

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Ser Ile Ser
65                  70                  75                  80

Tyr Pro Leu Ser Ala Ile Phe Thr Thr
                85
```

<210> SEQ ID NO 45
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 45

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Val Val Gln Ile Leu Gly Val Lys Gly Gly Tyr Ile Ser
65                  70                  75                  80

Ile Pro Leu Ser Ala Ile Phe Thr Thr
                85
```

<210> SEQ ID NO 46
<211> LENGTH: 89
<212> TYPE: PRT
<213> ORGANISM: Artificial Sequence

```
<220> FEATURE:
<223> OTHER INFORMATION: c-Met binding FN3 domain

<400> SEQUENCE: 46

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Gln Ile Met Gly Val Lys Gly Thr Val Ser
65                  70                  75                  80

Pro Pro Leu Ser Ala Ile Phe Thr Thr
                85

<210> SEQ ID NO 47
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 47

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Thr Thr Ala Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Ser Ile Ser
65                  70                  75                  80

Pro Pro Leu Ser Ala Ile Phe Thr Thr
                85

<210> SEQ ID NO 48
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 48

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Leu Leu Ser Thr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Ser Ile Ser
65                  70                  75                  80

Pro Pro Leu Ser Ala Ile Phe Thr Thr
                85
```

```
<210> SEQ ID NO 49
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 49

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Val Ser Lys Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Ser Ile Ser
65                  70                  75                  80

Pro Pro Leu Ser Ala Ile Phe Thr Thr
                85

<210> SEQ ID NO 50
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 50

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Gly
                85                  90                  95

Gly Gly Gly Ser Gly Gly Gly Ser Gly Gly Gly Gly Ser Gly Gly
            100                 105                 110

Gly Gly Ser Met Leu Pro Ala Pro Lys Asn Leu Val Val Ser Arg Val
            115                 120                 125

Thr Glu Asp Ser Ala Arg Leu Ser Trp Thr Ala Pro Asp Ala Ala Phe
            130                 135                 140

Asp Ser Phe Trp Ile Arg Tyr Asp Glu Val Val Val Gly Gly Glu Ala
145                 150                 155                 160

Ile Val Leu Thr Val Pro Gly Ser Glu Arg Ser Tyr Asp Leu Thr Gly
                165                 170                 175

Leu Lys Pro Gly Thr Glu Tyr Tyr Val Asn Ile Leu Gly Val Lys Gly
            180                 185                 190

Gly Ser Ile Ser Val Pro Leu Ser Ala Ile Phe Thr Thr
            195                 200                 205

<210> SEQ ID NO 51
```

<211> LENGTH: 204
<212> TYPE: PRT
<213> ORGANISM: Artificial Sequence
<220> FEATURE:
<223> OTHER INFORMATION: bispecific EGFR/cMet binding molecule

<400> SEQUENCE: 51

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Gly
                85                  90                  95

Gly Gly Gly Ser Gly Gly Gly Ser Gly Gly Gly Ser Gly Gly
            100                 105                 110

Gly Gly Ser Leu Pro Ala Pro Lys Asn Leu Val Val Ser Arg Val Thr
            115                 120                 125

Glu Asp Ser Ala Arg Leu Ser Trp Thr Ala Pro Asp Ala Ala Phe Asp
    130                 135                 140

Ser Phe Trp Ile Arg Tyr Phe Glu Phe Leu Gly Ser Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Val Val Asn Ile Met Gly Val Lys Gly Gly
                180                 185                 190

Lys Ile Ser Pro Pro Leu Ser Ala Ile Phe Thr Thr
            195                 200

<210> SEQ ID NO 52
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 52

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Gly
                85                  90                  95

Gly Gly Gly Ser Gly Gly Gly Ser Gly Gly Gly Ser Gly Gly
            100                 105                 110

Gly Gly Ser Met Leu Pro Ala Pro Lys Asn Leu Val Val Ser Arg Val

```
                 115                 120                 125
Thr Glu Asp Ser Ala Arg Leu Ser Trp Thr Ala Pro Asp Ala Ala Phe
        130                 135                 140

Asp Ser Phe Trp Ile Arg Tyr Phe Glu Phe Leu Gly Ser Gly Glu Ala
145                 150                 155                 160

Ile Val Leu Thr Val Pro Gly Ser Glu Arg Ser Tyr Asp Leu Thr Gly
                165                 170                 175

Leu Lys Pro Gly Thr Glu Tyr Val Val Gln Ile Ile Gly Val Lys Gly
            180                 185                 190

Gly His Ile Ser Leu Pro Leu Ser Ala Ile Phe Thr Thr
                195                 200                 205

<210> SEQ ID NO 53
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 53

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60
Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Gly
                85                  90                  95

Gly Gly Gly Ser Gly Gly Gly Gly Ser Gly Gly Gly Gly Ser Gly Gly
            100                 105                 110

Gly Gly Ser Met Leu Pro Ala Pro Lys Asn Leu Val Val Ser Arg Val
        115                 120                 125

Thr Glu Asp Ser Ala Arg Leu Ser Trp Thr Ala Pro Asp Ala Ala Phe
    130                 135                 140
Asp Ser Phe Phe Ile Arg Tyr Asp Glu Phe Leu Arg Ser Gly Glu Ala
145                 150                 155                 160

Ile Val Leu Thr Val Pro Gly Ser Glu Arg Ser Tyr Asp Leu Thr Gly
                165                 170                 175

Leu Lys Pro Gly Thr Glu Tyr Trp Val Thr Ile Leu Gly Val Lys Gly
            180                 185                 190

Gly Leu Val Ser Thr Pro Leu Ser Ala Ile Phe Thr Thr
        195                 200                 205

<210> SEQ ID NO 54
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 54

Met Leu Pro Ala Pro Lys Asn Leu Val Val Ser Glu Val Thr Glu Asp
1               5                   10                  15
```

```
Ser Ala Arg Leu Ser Trp Ala Asp Pro His Gly Phe Tyr Asp Ser Phe
             20                  25                  30

Leu Ile Gln Tyr Gln Glu Ser Glu Lys Val Gly Glu Ala Ile Val Leu
         35                  40                  45

Thr Val Pro Gly Ser Glu Arg Ser Tyr Asp Leu Thr Gly Leu Lys Pro
     50                  55                  60

Gly Thr Glu Tyr Thr Val Ser Ile Tyr Gly Val His Asn Val Tyr Lys
65                   70                  75                  80

Asp Thr Asn Met Arg Gly Leu Pro Leu Ser Ala Ile Phe Thr Thr Gly
                 85                  90                  95

Gly Gly Gly Ser Gly Gly Gly Ser Gly Gly Gly Gly Ser Gly Gly
            100                 105                 110

Gly Gly Ser Met Leu Pro Ala Pro Lys Asn Leu Val Val Ser Arg Val
            115                 120                 125

Thr Glu Asp Ser Ala Arg Leu Ser Trp Thr Ala Pro Asp Ala Ala Phe
    130                 135                 140

Asp Ser Phe Trp Ile Arg Tyr Phe Glu Phe Leu Gly Ser Gly Glu Ala
145                 150                 155                 160

Ile Val Leu Thr Val Pro Gly Ser Glu Arg Ser Tyr Asp Leu Thr Gly
                165                 170                 175

Leu Lys Pro Gly Thr Glu Tyr Val Val Asn Ile Met Gly Val Lys Gly
            180                 185                 190

Gly Lys Ile Ser Pro Pro Leu Ser Ala Ile Phe Thr Thr
            195                 200                 205

<210> SEQ ID NO 55
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 55

Met Leu Pro Ala Pro Lys Asn Leu Val Val Ser Glu Val Thr Glu Asp
1                5                  10                  15

Ser Ala Arg Leu Ser Trp Ala Asp Pro His Gly Phe Tyr Asp Ser Phe
             20                  25                  30

Leu Ile Gln Tyr Gln Glu Ser Glu Lys Val Gly Glu Ala Ile Val Leu
         35                  40                  45

Thr Val Pro Gly Ser Glu Arg Ser Tyr Asp Leu Thr Gly Leu Lys Pro
     50                  55                  60

Gly Thr Glu Tyr Thr Val Ser Ile Tyr Gly Val His Asn Val Tyr Lys
65                   70                  75                  80

Asp Thr Asn Met Arg Gly Leu Pro Leu Ser Ala Ile Phe Thr Thr Gly
                 85                  90                  95

Gly Gly Gly Ser Gly Gly Gly Ser Gly Gly Gly Gly Ser Gly Gly
            100                 105                 110

Gly Gly Ser Met Leu Pro Ala Pro Lys Asn Leu Val Val Ser Arg Val
            115                 120                 125

Thr Glu Asp Ser Ala Arg Leu Ser Trp Thr Ala Pro Asp Ala Ala Phe
    130                 135                 140

Asp Ser Phe Trp Ile Arg Tyr Phe Glu Phe Leu Gly Ser Gly Glu Ala
145                 150                 155                 160

Ile Val Leu Thr Val Pro Gly Ser Glu Arg Ser Tyr Asp Leu Thr Gly
                165                 170                 175
```

```
Leu Lys Pro Gly Thr Glu Tyr Val Val Gln Ile Ile Gly Val Lys Gly
            180                 185                 190

Gly His Ile Ser Leu Pro Leu Ser Ala Ile Phe Thr Thr
        195                 200                 205

<210> SEQ ID NO 56
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 56

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Gly
                85                  90                  95

Gly Gly Gly Ser Gly Gly Gly Ser Gly Gly Gly Ser Gly Gly
            100                 105                 110

Gly Gly Ser Met Leu Pro Ala Pro Lys Asn Leu Val Val Ser Arg Val
        115                 120                 125

Thr Glu Asp Ser Ala Arg Leu Ser Trp Thr Ala Pro Asp Ala Ala Phe
    130                 135                 140

Asp Ser Phe Trp Ile Arg Tyr Phe Glu Phe Leu Gly Ser Gly Glu Ala
145                 150                 155                 160

Ile Val Leu Thr Val Pro Gly Ser Glu Arg Ser Tyr Asp Leu Thr Gly
                165                 170                 175

Leu Lys Pro Gly Thr Glu Tyr Val Val Gln Ile Ile Gly Val Lys Gly
            180                 185                 190

Gly His Ile Ser Leu Pro Leu Ser Ala Ile Phe Thr Thr
        195                 200                 205

<210> SEQ ID NO 57
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 57

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80
```

-continued

Asp Thr Asn Met Arg Gly Leu Pro Leu Ser Ala Ile Phe Thr Thr Ala
                85                  90                  95

Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Gly Val Lys Gly Gly Lys Ile Ser Pro Pro Leu Ser Ala Ile Phe
            180                 185                 190

Thr Thr

<210> SEQ ID NO 58
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 58

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Asp Glu Val Val
    130                 135                 140

Val Gly Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Tyr Val Asn Ile
                165                 170                 175

Leu Gly Val Lys Gly Gly Ser Ile Ser Val Pro Leu Ser Ala Ile Phe
            180                 185                 190

Thr Thr

<210> SEQ ID NO 59
<211> LENGTH: 195
<212> TYPE: PRT
<213> ORGANISM: Artificial Sequence
<220> FEATURE:
<223> OTHER INFORMATION: bispecific EGFR/cMet binding molecule

<400> SEQUENCE: 59

```
Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Met Leu Pro Ala Pro Lys Asn
            100                 105                 110

Leu Val Val Ser Arg Val Thr Glu Asp Ser Ala Arg Leu Ser Trp Thr
        115                 120                 125

Ala Pro Asp Ala Ala Phe Asp Ser Phe Trp Ile Arg Tyr Phe Glu Phe
130                 135                 140

Leu Gly Ser Gly Glu Ala Ile Val Leu Thr Val Pro Gly Ser Glu Arg
145                 150                 155                 160

Ser Tyr Asp Leu Thr Gly Leu Lys Pro Gly Thr Glu Tyr Val Val Asn
                165                 170                 175

Ile Met Gly Val Lys Gly Gly Lys Ile Ser Pro Pro Leu Ser Ala Ile
            180                 185                 190

Phe Thr Thr
        195
```

<210> SEQ ID NO 60
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 60

```
Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Asp Glu Val Val
130                 135                 140
```

-continued

Val Gly Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Tyr Val Asn Ile
            165                 170                 175

Leu Gly Val Lys Gly Gly Ser Ile Ser Val Pro Leu Ser Ala Ile Phe
            180                 185                 190

Thr Thr

<210> SEQ ID NO 61
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 61

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
            85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
            130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Asn Ile
            165                 170                 175

Leu Gly Val Lys Gly Gly Lys Ile Ser Pro Pro Leu Ser Ala Ile Phe
            180                 185                 190

Thr Thr

<210> SEQ ID NO 62
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 62

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Val
        130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
            180                 185                 190

Thr Thr

<210> SEQ ID NO 63
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 63

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Val
        130                 135                 140

Ser Lys Gly Asp Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
            180                 185                 190

Thr Thr

<210> SEQ ID NO 64
<211> LENGTH: 194

```
<212> TYPE: PRT
<213> ORGANISM: Artificial Sequence
<220> FEATURE:
<223> OTHER INFORMATION: bispecific EGFR/cMet binding molecule

<400> SEQUENCE: 64

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
            130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
                180                 185                 190

Thr Thr

<210> SEQ ID NO 65
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 65

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125
```

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Lys Ile Ser Pro Pro Leu Ser Ala Ile Phe
                180                 185                 190

Thr Thr

<210> SEQ ID NO 66
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 66

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Val
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
                180                 185                 190

Thr Thr

<210> SEQ ID NO 67
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 67

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
                20                  25                  30

Leu Ile Gln Tyr Gln Glu Ser Glu Lys Val Gly Glu Ala Ile Val Leu

```
                35                  40                  45
Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr Ala
                 85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
                115                 120                 125

Pro Asp Ala Ala Phe Asp Ser Phe Trp Ile Arg Tyr Phe Glu Phe Val
                130                 135                 140

Ser Lys Gly Asp Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
                180                 185                 190

Thr Thr
```

<210> SEQ ID NO 68
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 68

```
Met Leu Pro Ala Pro Lys Asn Leu Val Val Ser Glu Val Thr Glu Asp
 1               5                  10                  15

Ser Ala Arg Leu Ser Trp Asp Asp Pro His Ala Phe Tyr Glu Ser Phe
                 20                  25                  30

Leu Ile Gln Tyr Gln Glu Ser Glu Lys Val Gly Glu Ala Ile Val Leu
                 35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr Ala
                 85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
                115                 120                 125

Pro Asp Ala Ala Phe Asp Ser Phe Trp Ile Arg Tyr Phe Glu Phe Leu
                130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
                180                 185                 190

Thr Thr
```

```
<210> SEQ ID NO 69
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 69

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Lys Ile Ser Pro Pro Leu Ser Ala Ile Phe
            180                 185                 190

Thr Thr

<210> SEQ ID NO 70
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 70

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110
```

```
Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Val
        130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
            180                 185                 190

Thr Thr

<210> SEQ ID NO 71
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 71

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Val
        130                 135                 140

Ser Lys Gly Asp Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
            180                 185                 190

Thr Thr

<210> SEQ ID NO 72
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 72

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
```

```
                 20                  25                  30
Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
                180                 185                 190

Thr Thr

<210> SEQ ID NO 73
<211> LENGTH: 1210
<212> TYPE: PRT
<213> ORGANISM: HOMO SAPIENS

<400> SEQUENCE: 73

Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
                180                 185                 190

Ser Cys Pro Asn Gly Ser Cys Trp Gly Ala Gly Glu Glu Asn Cys Gln
```

-continued

```
            195                 200                 205
Lys Leu Thr Lys Ile Ile Cys Ala Gln Gln Cys Ser Gly Arg Cys Arg
210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
                260                 265                 270
Thr Thr Tyr Gln Met Asp Val Asn Pro Glu Gly Lys Tyr Ser Phe Gly
                275                 280                 285
Ala Thr Cys Val Lys Lys Cys Pro Arg Asn Tyr Val Val Thr Asp His
290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
                340                 345                 350
Ala Thr Asn Ile Lys His Phe Lys Asn Cys Thr Ser Ile Ser Gly Asp
                355                 360                 365
Leu His Ile Leu Pro Val Ala Phe Arg Gly Asp Ser Phe Thr His Thr
                370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
                420                 425                 430
His Gly Gln Phe Ser Leu Ala Val Val Ser Leu Asn Ile Thr Ser Leu
                435                 440                 445
Gly Leu Arg Ser Leu Lys Glu Ile Ser Asp Gly Asp Val Ile Ile Ser
450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
                500                 505                 510
Glu Gly Cys Trp Gly Pro Glu Pro Arg Asp Cys Val Ser Cys Arg Asn
                515                 520                 525
Val Ser Arg Gly Arg Glu Cys Val Asp Lys Cys Asn Leu Leu Glu Gly
530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
                580                 585                 590
Lys Thr Cys Pro Ala Gly Val Met Gly Glu Asn Asn Thr Leu Val Trp
                595                 600                 605
Lys Tyr Ala Asp Ala Gly His Val Cys His Leu Cys His Pro Asn Cys
                610                 615                 620
```

```
Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
            645                 650                 655

Leu Leu Val Val Ala Leu Gly Ile Gly Leu Phe Met Arg Arg Arg His
                660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
            930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu  Asp Met Asp
            995                 1000                1005

Asp Val  Val Asp Ala Asp  Glu Tyr Leu Ile Pro Gln  Gln Gly Phe
     1010                1015                1020

Phe Ser  Ser Pro Ser Thr Ser  Arg Thr Pro Leu Leu  Ser Ser Leu
     1025                1030                1035
```

```
Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 74
<211> LENGTH: 53
<212> TYPE: PRT
<213> ORGANISM: HOMO SAPIENS

<400> SEQUENCE: 74

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 75
<211> LENGTH: 2201
<212> TYPE: PRT
<213> ORGANISM: Homo sapiens

<400> SEQUENCE: 75

Met Gly Ala Met Thr Gln Leu Leu Ala Gly Val Phe Leu Ala Phe Leu
1               5                   10                  15

Ala Leu Ala Thr Glu Gly Gly Val Leu Lys Lys Val Ile Arg His Lys
            20                  25                  30

Arg Gln Ser Gly Val Asn Ala Thr Leu Pro Glu Glu Asn Gln Pro Val
        35                  40                  45

Val Phe Asn His Val Tyr Asn Ile Lys Leu Pro Val Gly Ser Gln Cys
    50                  55                  60

Ser Val Asp Leu Glu Ser Ala Ser Gly Glu Lys Asp Leu Ala Pro Pro
65                  70                  75                  80
```

```
Ser Glu Pro Ser Glu Ser Phe Gln Glu His Thr Val Asp Gly Glu Asn
            85                  90                  95
Gln Ile Val Phe Thr His Arg Ile Asn Ile Pro Arg Arg Ala Cys Gly
        100                 105                 110
Cys Ala Ala Ala Pro Asp Val Lys Glu Leu Leu Ser Arg Leu Glu Glu
            115                 120                 125
Leu Glu Asn Leu Val Ser Ser Leu Arg Glu Gln Cys Thr Ala Gly Ala
130                 135                 140
Gly Cys Cys Leu Gln Pro Ala Thr Gly Arg Leu Asp Thr Arg Pro Phe
145                 150                 155                 160
Cys Ser Gly Arg Gly Asn Phe Ser Thr Glu Gly Cys Gly Cys Val Cys
                165                 170                 175
Glu Pro Gly Trp Lys Gly Pro Asn Cys Ser Glu Pro Glu Cys Pro Gly
            180                 185                 190
Asn Cys His Leu Arg Gly Arg Cys Ile Asp Gly Gln Cys Ile Cys Asp
        195                 200                 205
Asp Gly Phe Thr Gly Glu Asp Cys Ser Gln Leu Ala Cys Pro Ser Asp
    210                 215                 220
Cys Asn Asp Gln Gly Lys Cys Val Asn Gly Val Cys Ile Cys Phe Glu
225                 230                 235                 240
Gly Tyr Ala Gly Ala Asp Cys Ser Arg Glu Ile Cys Pro Val Pro Cys
                245                 250                 255
Ser Glu Glu His Gly Thr Cys Val Asp Gly Leu Cys Val Cys His Asp
            260                 265                 270
Gly Phe Ala Gly Asp Asp Cys Asn Lys Pro Leu Cys Leu Asn Asn Cys
        275                 280                 285
Tyr Asn Arg Gly Arg Cys Val Glu Asn Glu Cys Val Cys Asp Glu Gly
    290                 295                 300
Phe Thr Gly Glu Asp Cys Ser Glu Leu Ile Cys Pro Asn Asp Cys Phe
305                 310                 315                 320
Asp Arg Gly Arg Cys Ile Asn Gly Thr Cys Tyr Cys Glu Glu Gly Phe
                325                 330                 335
Thr Gly Glu Asp Cys Gly Lys Pro Thr Cys Pro His Ala Cys His Thr
            340                 345                 350
Gln Gly Arg Cys Glu Glu Gly Gln Cys Val Cys Asp Glu Gly Phe Ala
        355                 360                 365
Gly Val Asp Cys Ser Glu Lys Arg Cys Pro Ala Asp Cys His Asn Arg
    370                 375                 380
Gly Arg Cys Val Asp Gly Arg Cys Glu Cys Asp Asp Gly Phe Thr Gly
385                 390                 395                 400
Ala Asp Cys Gly Glu Leu Lys Cys Pro Asn Gly Cys Ser Gly His Gly
                405                 410                 415
Arg Cys Val Asn Gly Gln Cys Val Cys Asp Glu Gly Tyr Thr Gly Glu
            420                 425                 430
Asp Cys Ser Gln Leu Arg Cys Pro Asn Asp Cys His Ser Arg Gly Arg
        435                 440                 445
Cys Val Glu Gly Lys Cys Val Cys Glu Gln Gly Phe Lys Gly Tyr Asp
    450                 455                 460
Cys Ser Asp Met Ser Cys Pro Asn Asp Cys His Gln His Gly Arg Cys
465                 470                 475                 480
Val Asn Gly Met Cys Val Cys Asp Asp Gly Tyr Thr Gly Glu Asp Cys
                485                 490                 495
Arg Asp Arg Gln Cys Pro Arg Asp Cys Ser Asn Arg Gly Leu Cys Val
```

-continued

```
                500                 505                 510
Asp Gly Gln Cys Val Cys Glu Asp Gly Phe Thr Gly Pro Asp Cys Ala
            515                 520                 525

Glu Leu Ser Cys Pro Asn Asp Cys His Gly Gln Gly Arg Cys Val Asn
            530                 535                 540

Gly Gln Cys Val Cys His Glu Gly Phe Met Gly Lys Asp Cys Lys Glu
545                 550                 555                 560

Gln Arg Cys Pro Ser Asp Cys His Gly Gln Gly Arg Cys Val Asp Gly
            565                 570                 575

Gln Cys Ile Cys His Glu Gly Phe Thr Gly Leu Asp Cys Gly Gln His
            580                 585                 590

Ser Cys Pro Ser Asp Cys Asn Asn Leu Gly Gln Cys Val Ser Gly Arg
            595                 600                 605

Cys Ile Cys Asn Glu Gly Tyr Ser Gly Glu Asp Cys Ser Glu Val Ser
610                 615                 620

Pro Pro Lys Asp Leu Val Val Thr Glu Val Thr Glu Thr Val Asn
625                 630                 635                 640

Leu Ala Trp Asp Asn Glu Met Arg Val Thr Glu Tyr Leu Val Val Tyr
            645                 650                 655

Thr Pro Thr His Glu Gly Gly Leu Glu Met Gln Phe Arg Val Pro Gly
            660                 665                 670

Asp Gln Thr Ser Thr Ile Ile Gln Glu Leu Glu Pro Gly Val Glu Tyr
            675                 680                 685

Phe Ile Arg Val Phe Ala Ile Leu Glu Asn Lys Lys Ser Ile Pro Val
            690                 695                 700

Ser Ala Arg Val Ala Thr Tyr Leu Pro Ala Pro Glu Gly Leu Lys Phe
705                 710                 715                 720

Lys Ser Ile Lys Glu Thr Ser Val Glu Val Glu Trp Asp Pro Leu Asp
            725                 730                 735

Ile Ala Phe Glu Thr Trp Glu Ile Ile Phe Arg Asn Met Asn Lys Glu
            740                 745                 750

Asp Glu Gly Glu Ile Thr Lys Ser Leu Arg Arg Pro Glu Thr Ser Tyr
            755                 760                 765

Arg Gln Thr Gly Leu Ala Pro Gly Gln Glu Tyr Glu Ile Ser Leu His
            770                 775                 780

Ile Val Lys Asn Asn Thr Arg Gly Pro Gly Leu Lys Arg Val Thr Thr
785                 790                 795                 800

Thr Arg Leu Asp Ala Pro Ser Gln Ile Glu Val Lys Asp Val Thr Asp
            805                 810                 815

Thr Thr Ala Leu Ile Thr Trp Phe Lys Pro Leu Ala Glu Ile Asp Gly
            820                 825                 830

Ile Glu Leu Thr Tyr Gly Ile Lys Asp Val Pro Gly Asp Arg Thr Thr
            835                 840                 845

Ile Asp Leu Thr Glu Asp Glu Asn Gln Tyr Ser Ile Gly Asn Leu Lys
            850                 855                 860

Pro Asp Thr Glu Tyr Glu Val Ser Leu Ile Ser Arg Arg Gly Asp Met
865                 870                 875                 880

Ser Ser Asn Pro Ala Lys Glu Thr Phe Thr Thr Gly Leu Asp Ala Pro
            885                 890                 895

Arg Asn Leu Arg Arg Val Ser Gln Thr Asp Asn Ser Ile Thr Leu Glu
            900                 905                 910

Trp Arg Asn Gly Lys Ala Ala Ile Asp Ser Tyr Arg Ile Lys Tyr Ala
            915                 920                 925
```

-continued

```
Pro Ile Ser Gly Gly Asp His Ala Glu Val Asp Val Pro Lys Ser Gln
    930                 935                 940

Gln Ala Thr Thr Lys Thr Thr Leu Thr Gly Leu Arg Pro Gly Thr Glu
945                 950                 955                 960

Tyr Gly Ile Gly Val Ser Ala Val Lys Glu Asp Lys Glu Ser Asn Pro
                965                 970                 975

Ala Thr Ile Asn Ala Ala Thr Glu Leu Asp Thr Pro Lys Asp Leu Gln
            980                 985                 990

Val Ser Glu Thr Ala Glu Thr Ser Leu Thr Leu Leu Trp Lys Thr Pro
        995                 1000                1005

Leu Ala Lys Phe Asp Arg Tyr Arg Leu Asn Tyr Ser Leu Pro Thr
    1010                1015                1020

Gly Gln Trp Val Gly Val Gln Leu Pro Arg Asn Thr Thr Ser Tyr
    1025                1030                1035

Val Leu Arg Gly Leu Glu Pro Gly Gln Glu Tyr Asn Val Leu Leu
    1040                1045                1050

Thr Ala Glu Lys Gly Arg His Lys Ser Lys Pro Ala Arg Val Lys
    1055                1060                1065

Ala Ser Thr Glu Gln Ala Pro Glu Leu Glu Asn Leu Thr Val Thr
    1070                1075                1080

Glu Val Gly Trp Asp Gly Leu Arg Leu Asn Trp Thr Ala Ala Asp
    1085                1090                1095

Gln Ala Tyr Glu His Phe Ile Ile Gln Val Gln Glu Ala Asn Lys
    1100                1105                1110

Val Glu Ala Ala Arg Asn Leu Thr Val Pro Gly Ser Leu Arg Ala
    1115                1120                1125

Val Asp Ile Pro Gly Leu Lys Ala Ala Thr Pro Tyr Thr Val Ser
    1130                1135                1140

Ile Tyr Gly Val Ile Gln Gly Tyr Arg Thr Pro Val Leu Ser Ala
    1145                1150                1155

Glu Ala Ser Thr Gly Glu Thr Pro Asn Leu Gly Glu Val Val Val
    1160                1165                1170

Ala Glu Val Gly Trp Asp Ala Leu Lys Leu Asn Trp Thr Ala Pro
    1175                1180                1185

Glu Gly Ala Tyr Glu Tyr Phe Phe Ile Gln Val Gln Glu Ala Asp
    1190                1195                1200

Thr Val Glu Ala Ala Gln Asn Leu Thr Val Pro Gly Gly Leu Arg
    1205                1210                1215

Ser Thr Asp Leu Pro Gly Leu Lys Ala Ala Thr His Tyr Thr Ile
    1220                1225                1230

Thr Ile Arg Gly Val Thr Gln Asp Phe Ser Thr Thr Pro Leu Ser
    1235                1240                1245

Val Glu Val Leu Thr Glu Val Pro Asp Met Gly Asn Leu Thr
    1250                1255                1260

Val Thr Glu Val Ser Trp Asp Ala Leu Arg Leu Asn Trp Thr Thr
    1265                1270                1275

Pro Asp Gly Thr Tyr Asp Gln Phe Thr Ile Gln Val Gln Glu Ala
    1280                1285                1290

Asp Gln Val Glu Glu Ala His Asn Leu Thr Val Pro Gly Ser Leu
    1295                1300                1305

Arg Ser Met Glu Ile Pro Gly Leu Arg Ala Gly Thr Pro Tyr Thr
    1310                1315                1320
```

-continued

| | | | | | | | | | | | |
|---|---|---|---|---|---|---|---|---|---|---|---|
| Val | Thr | Leu | His | Gly | Glu | Val | Arg | Gly | His | Ser | Thr | Arg | Pro | Leu |
| 1325 | | | | | 1330 | | | | | 1335 | | | | |

Val Thr Leu His Gly Glu Val Arg Gly His Ser Thr Arg Pro Leu
1325                1330               1335

Ala Val Glu Val Val Thr Glu Asp Leu Pro Gln Leu Gly Asp Leu
1340                1345               1350

Ala Val Ser Glu Val Gly Trp Asp Gly Leu Arg Leu Asn Trp Thr
1355                1360               1365

Ala Ala Asp Asn Ala Tyr Glu His Phe Val Ile Gln Val Gln Glu
1370                1375               1380

Val Asn Lys Val Glu Ala Ala Gln Asn Leu Thr Leu Pro Gly Ser
1385                1390               1395

Leu Arg Ala Val Asp Ile Pro Gly Leu Glu Ala Ala Thr Pro Tyr
1400                1405               1410

Arg Val Ser Ile Tyr Gly Val Ile Arg Gly Tyr Arg Thr Pro Val
1415                1420               1425

Leu Ser Ala Glu Ala Ser Thr Ala Lys Glu Pro Glu Ile Gly Asn
1430                1435               1440

Leu Asn Val Ser Asp Ile Thr Pro Glu Ser Phe Asn Leu Ser Trp
1445                1450               1455

Met Ala Thr Asp Gly Ile Phe Glu Thr Phe Thr Ile Glu Ile Ile
1460                1465               1470

Asp Ser Asn Arg Leu Leu Glu Thr Val Glu Tyr Asn Ile Ser Gly
1475                1480               1485

Ala Glu Arg Thr Ala His Ile Ser Gly Leu Pro Pro Ser Thr Asp
1490                1495               1500

Phe Ile Val Tyr Leu Ser Gly Leu Ala Pro Ser Ile Arg Thr Lys
1505                1510               1515

Thr Ile Ser Ala Thr Ala Thr Thr Glu Ala Leu Pro Leu Leu Glu
1520                1525               1530

Asn Leu Thr Ile Ser Asp Ile Asn Pro Tyr Gly Phe Thr Val Ser
1535                1540               1545

Trp Met Ala Ser Glu Asn Ala Phe Asp Ser Phe Leu Val Thr Val
1550                1555               1560

Val Asp Ser Gly Lys Leu Leu Asp Pro Gln Glu Phe Thr Leu Ser
1565                1570               1575

Gly Thr Gln Arg Lys Leu Glu Leu Arg Gly Leu Ile Thr Gly Ile
1580                1585               1590

Gly Tyr Glu Val Met Val Ser Gly Phe Thr Gln Gly His Gln Thr
1595                1600               1605

Lys Pro Leu Arg Ala Glu Ile Val Thr Glu Ala Glu Pro Glu Val
1610                1615               1620

Asp Asn Leu Leu Val Ser Asp Ala Thr Pro Asp Gly Phe Arg Leu
1625                1630               1635

Ser Trp Thr Ala Asp Glu Gly Val Phe Asp Asn Phe Val Leu Lys
1640                1645               1650

Ile Arg Asp Thr Lys Lys Gln Ser Glu Pro Leu Glu Ile Thr Leu
1655                1660               1665

Leu Ala Pro Glu Arg Thr Arg Asp Ile Thr Gly Leu Arg Glu Ala
1670                1675               1680

Thr Glu Tyr Glu Ile Glu Leu Tyr Gly Ile Ser Lys Gly Arg Arg
1685                1690               1695

Ser Gln Thr Val Ser Ala Ile Ala Thr Thr Ala Met Gly Ser Pro
1700                1705               1710

Lys Glu Val Ile Phe Ser Asp Ile Thr Glu Asn Ser Ala Thr Val

```
                    1715                1720                1725

Ser Trp Arg Ala Pro Thr Ala Gln Val Glu Ser Phe Arg Ile Thr
    1730                1735                1740

Tyr Val Pro Ile Thr Gly Gly Thr Pro Ser Met Val Thr Val Asp
    1745                1750                1755

Gly Thr Lys Thr Gln Thr Arg Leu Val Lys Leu Ile Pro Gly Val
    1760                1765                1770

Glu Tyr Leu Val Ser Ile Ile Ala Met Lys Gly Phe Glu Glu Ser
    1775                1780                1785

Glu Pro Val Ser Gly Ser Phe Thr Thr Ala Leu Asp Gly Pro Ser
    1790                1795                1800

Gly Leu Val Thr Ala Asn Ile Thr Asp Ser Glu Ala Leu Ala Arg
    1805                1810                1815

Trp Gln Pro Ala Ile Ala Thr Val Asp Ser Tyr Val Ile Ser Tyr
    1820                1825                1830

Thr Gly Glu Lys Val Pro Glu Ile Thr Arg Thr Val Ser Gly Asn
    1835                1840                1845

Thr Val Glu Tyr Ala Leu Thr Asp Leu Glu Pro Ala Thr Glu Tyr
    1850                1855                1860

Thr Leu Arg Ile Phe Ala Glu Lys Gly Pro Gln Lys Ser Ser Thr
    1865                1870                1875

Ile Thr Ala Lys Phe Thr Thr Asp Leu Asp Ser Pro Arg Asp Leu
    1880                1885                1890

Thr Ala Thr Glu Val Gln Ser Glu Thr Ala Leu Leu Thr Trp Arg
    1895                1900                1905

Pro Pro Arg Ala Ser Val Thr Gly Tyr Leu Leu Val Tyr Glu Ser
    1910                1915                1920

Val Asp Gly Thr Val Lys Glu Val Ile Val Gly Pro Asp Thr Thr
    1925                1930                1935

Ser Tyr Ser Leu Ala Asp Leu Ser Pro Ser Thr His Tyr Thr Ala
    1940                1945                1950

Lys Ile Gln Ala Leu Asn Gly Pro Leu Arg Ser Asn Met Ile Gln
    1955                1960                1965

Thr Ile Phe Thr Thr Ile Gly Leu Leu Tyr Pro Phe Pro Lys Asp
    1970                1975                1980

Cys Ser Gln Ala Met Leu Asn Gly Asp Thr Thr Ser Gly Leu Tyr
    1985                1990                1995

Thr Ile Tyr Leu Asn Gly Asp Lys Ala Glu Ala Leu Glu Val Phe
    2000                2005                2010

Cys Asp Met Thr Ser Asp Gly Gly Gly Trp Ile Val Phe Leu Arg
    2015                2020                2025

Arg Lys Asn Gly Arg Glu Asn Phe Tyr Gln Asn Trp Lys Ala Tyr
    2030                2035                2040

Ala Ala Gly Phe Gly Asp Arg Arg Glu Glu Phe Trp Leu Gly Leu
    2045                2050                2055

Asp Asn Leu Asn Lys Ile Thr Ala Gln Gly Gln Tyr Glu Leu Arg
    2060                2065                2070

Val Asp Leu Arg Asp His Gly Glu Thr Ala Phe Ala Val Tyr Asp
    2075                2080                2085

Lys Phe Ser Val Gly Asp Ala Lys Thr Arg Tyr Lys Leu Lys Val
    2090                2095                2100

Glu Gly Tyr Ser Gly Thr Ala Gly Asp Ser Met Ala Tyr His Asn
    2105                2110                2115
```

```
Gly Arg Ser Phe Ser Thr Phe Asp Lys Asp Thr Asp Ser Ala Ile
    2120            2125            2130

Thr Asn Cys Ala Leu Ser Tyr Lys Gly Ala Phe Trp Tyr Arg Asn
    2135            2140            2145

Cys His Arg Val Asn Leu Met Gly Arg Tyr Gly Asp Asn Asn His
    2150            2155            2160

Ser Gln Gly Val Asn Trp Phe His Trp Lys Gly His Glu His Ser
    2165            2170            2175

Ile Gln Phe Ala Glu Met Lys Leu Arg Pro Ser Asn Phe Arg Asn
    2180            2185            2190

Leu Glu Gly Arg Arg Lys Arg Ala
    2195            2200

<210> SEQ ID NO 76
<211> LENGTH: 89
<212> TYPE: PRT
<213> ORGANISM: Artificial Sequence
<220> FEATURE:
<223> OTHER INFORMATION: Fibcon FN3 domain

<400> SEQUENCE: 76

Leu Asp Ala Pro Thr Asp Leu Gln Val Thr Asn Val Thr Asp Thr Ser
1               5                   10                  15

Ile Thr Val Ser Trp Thr Pro Pro Ser Ala Thr Ile Thr Gly Tyr Arg
            20                  25                  30

Ile Thr Tyr Thr Pro Ser Asn Gly Pro Gly Glu Pro Lys Glu Leu Thr
        35                  40                  45

Val Pro Pro Ser Ser Thr Ser Val Thr Ile Thr Gly Leu Thr Pro Gly
    50                  55                  60

Val Glu Tyr Val Val Ser Leu Tyr Ala Leu Lys Asp Asn Gln Glu Ser
65                  70                  75                  80

Pro Pro Leu Val Gly Thr Gln Thr Thr
                85

<210> SEQ ID NO 77
<211> LENGTH: 94
<212> TYPE: PRT
<213> ORGANISM: Homo sapiens

<400> SEQUENCE: 77

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 78
<211> LENGTH: 4
<212> TYPE: PRT
<213> ORGANISM: Artificial Sequence
<220> FEATURE:
```

```
<223> OTHER INFORMATION: linker

<400> SEQUENCE: 78

Gly Ser Gly Ser
1

<210> SEQ ID NO 79
<211> LENGTH: 25
<212> TYPE: PRT
<213> ORGANISM: Artificial Sequence
<220> FEATURE:
<223> OTHER INFORMATION: linker

<400> SEQUENCE: 79

Gly Gly Gly Gly Ser Gly Gly Gly Ser Gly Gly Gly Ser Gly
1               5                   10                  15

Gly Gly Gly Ser Gly Gly Gly Gly Ser
            20                  25

<210> SEQ ID NO 80
<211> LENGTH: 4
<212> TYPE: PRT
<213> ORGANISM: Artificial Sequence
<220> FEATURE:
<223> OTHER INFORMATION: linker

<400> SEQUENCE: 80

Ala Pro Ala Pro
1

<210> SEQ ID NO 81
<211> LENGTH: 10
<212> TYPE: PRT
<213> ORGANISM: Artificial Sequence
<220> FEATURE:
<223> OTHER INFORMATION: linker

<400> SEQUENCE: 81

Ala Pro Ala Pro Ala Pro Ala Pro Ala Pro
1               5                   10

<210> SEQ ID NO 82
<211> LENGTH: 20
<212> TYPE: PRT
<213> ORGANISM: Artificial Sequence
<220> FEATURE:
<223> OTHER INFORMATION: linker

<400> SEQUENCE: 82

Ala Pro Ala Pro Ala Pro Ala Pro Ala Pro Ala Pro Ala Pro Ala Pro
1               5                   10                  15

Ala Pro Ala Pro
            20

<210> SEQ ID NO 83
<211> LENGTH: 40
<212> TYPE: PRT
<213> ORGANISM: Artificial Sequence
<220> FEATURE:
<223> OTHER INFORMATION: linker

<400> SEQUENCE: 83

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
```

-continued

```
                 20                  25                  30

Ala Pro Ala Pro Ala Pro Ala Pro
            35                  40

<210> SEQ ID NO 84
<211> LENGTH: 29
<212> TYPE: PRT
<213> ORGANISM: Artificial Sequence
<220> FEATURE:
<223> OTHER INFORMATION: linker

<400> SEQUENCE: 84

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala Ala Ala
            20                  25

<210> SEQ ID NO 85
<211> LENGTH: 8
<212> TYPE: PRT
<213> ORGANISM: Artificial Sequence
<220> FEATURE:
<223> OTHER INFORMATION: tencon BC loop

<400> SEQUENCE: 85

Thr Ala Pro Asp Ala Ala Phe Asp
1               5

<210> SEQ ID NO 86
<211> LENGTH: 7
<212> TYPE: PRT
<213> ORGANISM: Artificial Sequence
<220> FEATURE:
<223> OTHER INFORMATION: tencon FG loop

<400> SEQUENCE: 86

Lys Gly Gly His Arg Ser Asn
1               5

<210> SEQ ID NO 87
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 87

Ala Asp Pro His Gly Phe Tyr Asp
1               5

<210> SEQ ID NO 88
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 88

Thr Tyr Asp Arg Asp Gly Tyr Asp
1               5

<210> SEQ ID NO 89
<211> LENGTH: 8
<212> TYPE: PRT
<213> ORGANISM: Artificial Sequence
<220> FEATURE:
```

<223> OTHER INFORMATION: EGFR binding FN3 domain BC loop

<400> SEQUENCE: 89

Trp Asp Pro Phe Ser Phe Tyr Asp
1               5

<210> SEQ ID NO 90
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 90

Asp Asp Pro Arg Gly Phe Tyr Glu
1               5

<210> SEQ ID NO 91
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 91

Thr Trp Pro Tyr Ala Asp Leu Asp
1               5

<210> SEQ ID NO 92
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 92

Gly Tyr Asn Gly Asp His Phe Asp
1               5

<210> SEQ ID NO 93
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 93

Asp Tyr Asp Leu Gly Val Tyr Asp
1               5

<210> SEQ ID NO 94
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 94

Asp Asp Pro Trp Asp Phe Tyr Glu
1               5

<210> SEQ ID NO 95
<211> LENGTH: 12
<212> TYPE: PRT
<213> ORGANISM: Artificial Sequence
<220> FEATURE:
<223> OTHER INFORMATION: EGFR binding FN3 domain FG loop

<400> SEQUENCE: 95

His Asn Val Tyr Lys Asp Thr Asn Met Arg Gly Leu
1               5                   10

<210> SEQ ID NO 96
<211> LENGTH: 11
<212> TYPE: PRT
<213> ORGANISM: Artificial Sequence
<220> FEATURE:
<223> OTHER INFORMATION: EGFR binding FN3 domain FG loop

<400> SEQUENCE: 96

Leu Gly Ser Tyr Val Phe Glu His Asp Val Met
1               5                   10

<210> SEQ ID NO 97
<211> LENGTH: 285
<212> TYPE: DNA
<213> ORGANISM: Artificial Sequence
<220> FEATURE:
<223> OTHER INFORMATION: EGFR binding FN3 domain from ECB97; P54AR4-
      83V22

<400> SEQUENCE: 97
atgttgccag cgccgaagaa cctggtagtt agcgaggtta ctgaggacag cgcgcgtctg        60
agctgggacg atccgtgggc gttctacgag agctttctga tccagtatca agagagcgag      120
aaagtcggtg aagcgattgt gctgaccgtc ccgggctccg agcgttccta cgacctgacc      180
ggtttgaagc cgggtaccga gtatacggtg agcatctacg tgttcacaaa tgtctataag      240
gacactaata tccgcggtct gcctctgagc gccattttca ccacc                       285

<210> SEQ ID NO 98
<211> LENGTH: 285
<212> TYPE: DNA
<213> ORGANISM: Artificial Sequence
<220> FEATURE:
<223> OTHER INFORMATION: EGFR binding FN3 domain from ECB15; P54AR4-
      83V2

<400> SEQUENCE: 98
atgctgccag cccctaagaa tctggtcgtg agcgaagtaa ccgaggacag cgcccgcctg        60
agctgggacg acccgtgggc gttctatgag tctttcctga ttcagtatca agaaagcgaa      120
aaagttggcg aagcgatcgt cctgaccgtc ccgggtagcg agcgctccta cgatctgacc      180
ggcctgaaac cgggtacgga gtacacggtg tccatttacg tgttcacaaa tgtgtataaa      240
gacaccaaca tgcgtggcct gccgctgtcg gcgattttca ccacc                       285

<210> SEQ ID NO 99
<211> LENGTH: 89
<212> TYPE: PRT
<213> ORGANISM: Artificial Sequence
<220> FEATURE:
<223> OTHER INFORMATION: tencon27 FN3 domain

<400> SEQUENCE: 99

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

-continued

```
Val Pro Gly Ser Glu Arg Ser Tyr Asp Leu Thr Gly Leu Lys Pro Gly
         50                  55                  60

Thr Glu Tyr Thr Val Ser Ile Tyr Gly Val Lys Gly Gly His Arg Ser
 65                  70                  75                  80

Asn Pro Leu Ser Ala Ile Phe Thr Thr
                 85

<210> SEQ ID NO 100
<211> LENGTH: 89
<212> TYPE: PRT
<213> ORGANISM: Artificial Sequence
<220> FEATURE:
<223> OTHER INFORMATION: TCL14 library
<220> FEATURE:
<221> NAME/KEY: MISC_FEATURE
<222> LOCATION: (32)..(32)
<223> OTHER INFORMATION: Xaa is any amino acid
<220> FEATURE:
<221> NAME/KEY: MISC_FEATURE
<222> LOCATION: (34)..(34)
<223> OTHER INFORMATION: Xaa is any amino acid
<220> FEATURE:
<221> NAME/KEY: MISC_FEATURE
<222> LOCATION: (36)..(36)
<223> OTHER INFORMATION: Xaa is any amino acid
<220> FEATURE:
<221> NAME/KEY: MISC_FEATURE
<222> LOCATION: (38)..(38)
<223> OTHER INFORMATION: Xaa is any amino acid
<220> FEATURE:
<221> NAME/KEY: MISC_FEATURE
<222> LOCATION: (39)..(39)
<223> OTHER INFORMATION: Xaa is any amino acid
<220> FEATURE:
<221> NAME/KEY: MISC_FEATURE
<222> LOCATION: (40)..(40)
<223> OTHER INFORMATION: Xaa is any amino acid
<220> FEATURE:
<221> NAME/KEY: MISC_FEATURE
<222> LOCATION: (41)..(41)
<223> OTHER INFORMATION: Xaa is any amino acid
<220> FEATURE:
<221> NAME/KEY: MISC_FEATURE
<222> LOCATION: (68)..(68)
<223> OTHER INFORMATION: Xaa is any amino acid
<220> FEATURE:
<221> NAME/KEY: MISC_FEATURE
<222> LOCATION: (70)..(70)
<223> OTHER INFORMATION: Xaa is any amino acid
<220> FEATURE:
<221> NAME/KEY: MISC_FEATURE
<222> LOCATION: (72)..(72)
<223> OTHER INFORMATION: Xaa is any amino acid
<220> FEATURE:
<221> NAME/KEY: MISC_FEATURE
<222> LOCATION: (78)..(78)
<223> OTHER INFORMATION: Xaa is any amino acid
<220> FEATURE:
<221> NAME/KEY: MISC_FEATURE
<222> LOCATION: (79)..(79)
<223> OTHER INFORMATION: Xaa is any amino acid
<220> FEATURE:
<221> NAME/KEY: MISC_FEATURE
<222> LOCATION: (81)..(81)
<223> OTHER INFORMATION: Xaa is any amino acid

<400> SEQUENCE: 100

Leu Pro Ala Pro Lys Asn Leu Val Val Ser Arg Val Thr Glu Asp Ser
  1               5                  10                  15

Ala Arg Leu Ser Trp Thr Ala Pro Asp Ala Ala Phe Asp Ser Phe Xaa
                 20                  25                  30

Ile Xaa Tyr Xaa Glu Xaa Xaa Xaa Xaa Gly Glu Ala Ile Val Leu Thr
```

```
                35                  40                  45
Val Pro Gly Ser Glu Arg Ser Tyr Asp Leu Thr Gly Leu Lys Pro Gly
     50                  55                  60

Thr Glu Tyr Xaa Val Xaa Ile Xaa Gly Val Lys Gly Gly Xaa Xaa Ser
65                  70                  75                  80

Xaa Pro Leu Ser Ala Ile Phe Thr Thr
                 85

<210> SEQ ID NO 101
<211> LENGTH: 1408
<212> TYPE: PRT
<213> ORGANISM: HOMO SAPIENS

<400> SEQUENCE: 101

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
             35                  40                  45

Glu Thr Pro Ile Gln Asn Val Ile Leu His Glu His His Ile Phe Leu
     50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                 85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320
```

```
Tyr Val Ser Lys Pro Gly Ala Gln Leu Ala Arg Gln Ile Gly Ala Ser
            325                 330                 335

Leu Asn Asp Asp Ile Leu Phe Gly Val Phe Ala Gln Ser Lys Pro Asp
        340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
```

-continued

```
                740                 745                 750
Phe Ile Ser Thr Trp Trp Lys Glu Pro Leu Asn Ile Val Ser Phe Leu
            755                 760                 765
Phe Cys Phe Ala Ser Gly Gly Ser Thr Ile Thr Gly Val Gly Lys Asn
            770                 775                 780
Leu Asn Ser Val Ser Val Pro Arg Met Val Ile Asn Val His Glu Ala
785                 790                 795                 800
Gly Arg Asn Phe Thr Val Ala Cys Gln His Arg Ser Asn Ser Glu Ile
            805                 810                 815
Ile Cys Cys Thr Thr Pro Ser Leu Gln Gln Leu Asn Leu Gln Leu Pro
            820                 825                 830
Leu Lys Thr Lys Ala Phe Phe Met Leu Asp Gly Ile Leu Ser Lys Tyr
            835                 840                 845
Phe Asp Leu Ile Tyr Val His Asn Pro Val Phe Lys Pro Phe Glu Lys
            850                 855                 860
Pro Val Met Ile Ser Met Gly Asn Glu Asn Val Leu Glu Ile Lys Gly
865                 870                 875                 880
Asn Asp Ile Asp Pro Glu Ala Val Lys Gly Glu Val Leu Lys Val Gly
            885                 890                 895
Asn Lys Ser Cys Glu Asn Ile His Leu His Ser Glu Ala Val Leu Cys
            900                 905                 910
Thr Val Pro Asn Asp Leu Leu Lys Leu Asn Ser Glu Leu Asn Ile Glu
            915                 920                 925
Trp Lys Gln Ala Ile Ser Ser Thr Val Leu Gly Lys Val Ile Val Gln
            930                 935                 940
Pro Asp Gln Asn Phe Thr Gly Leu Ile Ala Gly Val Val Ser Ile Ser
945                 950                 955                 960
Thr Ala Leu Leu Leu Leu Leu Gly Phe Phe Leu Trp Leu Lys Lys Arg
            965                 970                 975
Lys Gln Ile Lys Asp Leu Gly Ser Glu Leu Val Arg Tyr Asp Ala Arg
            980                 985                 990
Val His Thr Pro His Leu Asp Arg Leu Val Ser Ala Arg Ser Val Ser
            995                1000                1005
Pro Thr Thr Glu Met Val Ser Asn Glu Ser Val Asp Tyr Arg Ala
            1010                1015                1020
Thr Phe Pro Glu Asp Gln Phe Pro Asn Ser Ser Gln Asn Gly Ser
            1025                1030                1035
Cys Arg Gln Val Gln Tyr Pro Leu Thr Asp Met Ser Pro Ile Leu
            1040                1045                1050
Thr Ser Gly Asp Ser Asp Ile Ser Ser Pro Leu Leu Gln Asn Thr
            1055                1060                1065
Val His Ile Asp Leu Ser Ala Leu Asn Pro Glu Leu Val Gln Ala
            1070                1075                1080
Val Gln His Val Val Ile Gly Pro Ser Ser Leu Ile Val His Phe
            1085                1090                1095
Asn Glu Val Ile Gly Arg Gly His Phe Gly Cys Val Tyr His Gly
            1100                1105                1110
Thr Leu Leu Asp Asn Asp Gly Lys Lys Ile His Cys Ala Val Lys
            1115                1120                1125
Ser Leu Asn Arg Ile Thr Asp Ile Gly Glu Val Ser Gln Phe Leu
            1130                1135                1140
Thr Glu Gly Ile Ile Met Lys Asp Phe Ser His Pro Asn Val Leu
            1145                1150                1155
```

```
Ser Leu Leu Gly Ile Cys Leu Arg Ser Glu Gly Ser Pro Leu Val
    1160            1165            1170

Val Leu Pro Tyr Met Lys His Gly Asp Leu Arg Asn Phe Ile Arg
    1175            1180            1185

Asn Glu Thr His Asn Pro Thr Val Lys Asp Leu Ile Gly Phe Gly
    1190            1195            1200

Leu Gln Val Ala Lys Gly Met Lys Tyr Leu Ala Ser Lys Lys Phe
    1205            1210            1215

Val His Arg Asp Leu Ala Ala Arg Asn Cys Met Leu Asp Glu Lys
    1220            1225            1230

Phe Thr Val Lys Val Ala Asp Phe Gly Leu Ala Arg Asp Met Tyr
    1235            1240            1245

Asp Lys Glu Tyr Tyr Ser Val His Asn Lys Thr Gly Ala Lys Leu
    1250            1255            1260

Pro Val Lys Trp Met Ala Leu Glu Ser Leu Gln Thr Gln Lys Phe
    1265            1270            1275

Thr Thr Lys Ser Asp Val Trp Ser Phe Gly Val Leu Leu Trp Glu
    1280            1285            1290

Leu Met Thr Arg Gly Ala Pro Pro Tyr Pro Asp Val Asn Thr Phe
    1295            1300            1305

Asp Ile Thr Val Tyr Leu Leu Gln Gly Arg Arg Leu Leu Gln Pro
    1310            1315            1320

Glu Tyr Cys Pro Asp Pro Leu Tyr Glu Val Met Leu Lys Cys Trp
    1325            1330            1335

His Pro Lys Ala Glu Met Arg Pro Ser Phe Ser Glu Leu Val Ser
    1340            1345            1350

Arg Ile Ser Ala Ile Phe Ser Thr Phe Ile Gly Glu His Tyr Val
    1355            1360            1365

His Val Asn Ala Thr Tyr Val Asn Val Lys Cys Val Ala Pro Tyr
    1370            1375            1380

Pro Ser Leu Leu Ser Ser Glu Asp Asn Ala Asp Asp Glu Val Asp
    1385            1390            1395

Thr Arg Pro Ala Ser Phe Trp Glu Thr Ser
    1400            1405

<210> SEQ ID NO 102
<211> LENGTH: 697
<212> TYPE: PRT
<213> ORGANISM: HOMO SAPIENS

<400> SEQUENCE: 102

Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
                20                  25                  30

Val Asn Thr Ala Asp Gln Cys Ala Asn Arg Cys Thr Arg Asn Lys Gly
            35                  40                  45

Leu Pro Phe Thr Cys Lys Ala Phe Val Phe Asp Lys Ala Arg Lys Gln
        50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
```

```
            100                 105                 110
Lys Ser Gly Ile Lys Cys Gln Pro Trp Ser Ser Met Ile Pro His Glu
        115                 120                 125
His Ser Phe Leu Pro Ser Ser Tyr Arg Gly Lys Asp Leu Gln Glu Asn
        130                 135                 140
Tyr Cys Arg Asn Pro Arg Gly Glu Glu Gly Gly Pro Trp Cys Phe Thr
145                 150                 155                 160
Ser Asn Pro Glu Val Arg Tyr Glu Val Cys Asp Ile Pro Gln Cys Ser
                165                 170                 175
Glu Val Glu Cys Met Thr Cys Asn Gly Glu Ser Tyr Arg Gly Leu Met
                180                 185                 190
Asp His Thr Glu Ser Gly Lys Ile Cys Gln Arg Trp Asp His Gln Thr
            195                 200                 205
Pro His Arg His Lys Phe Leu Pro Glu Arg Tyr Pro Asp Lys Gly Phe
        210                 215                 220
Asp Asp Asn Tyr Cys Arg Asn Pro Asp Gly Gln Pro Arg Pro Trp Cys
225                 230                 235                 240
Tyr Thr Leu Asp Pro His Thr Arg Trp Glu Tyr Cys Ala Ile Lys Thr
                245                 250                 255
Cys Ala Asp Asn Thr Met Asn Asp Thr Asp Val Pro Leu Glu Thr Thr
                260                 265                 270
Glu Cys Ile Gln Gly Gln Gly Glu Gly Tyr Arg Gly Thr Val Asn Thr
            275                 280                 285
Ile Trp Asn Gly Ile Pro Cys Gln Arg Trp Asp Ser Gln Tyr Pro His
        290                 295                 300
Glu His Asp Met Thr Pro Glu Asn Phe Lys Cys Lys Asp Leu Arg Glu
305                 310                 315                 320
Asn Tyr Cys Arg Asn Pro Asp Gly Ser Glu Ser Pro Trp Cys Phe Thr
                325                 330                 335
Thr Asp Pro Asn Ile Arg Val Gly Tyr Cys Ser Gln Ile Pro Asn Cys
                340                 345                 350
Asp Met Ser His Gly Gln Asp Cys Tyr Arg Gly Asn Gly Lys Asn Tyr
            355                 360                 365
Met Gly Asn Leu Ser Gln Thr Arg Ser Gly Leu Thr Cys Ser Met Trp
        370                 375                 380
Asp Lys Asn Met Glu Asp Leu His Arg His Ile Phe Trp Glu Pro Asp
385                 390                 395                 400
Ala Ser Lys Leu Asn Glu Asn Tyr Cys Arg Asn Pro Asp Asp Asp Ala
                405                 410                 415
His Gly Pro Trp Cys Tyr Thr Gly Asn Pro Leu Ile Pro Trp Asp Tyr
                420                 425                 430
Cys Pro Ile Ser Arg Cys Glu Gly Asp Thr Thr Pro Thr Ile Val Asn
            435                 440                 445
Leu Asp His Pro Val Ile Ser Cys Ala Lys Thr Lys Gln Leu Arg Val
        450                 455                 460
Val Asn Gly Ile Pro Thr Arg Thr Asn Ile Gly Trp Met Val Ser Leu
465                 470                 475                 480
Arg Tyr Arg Asn Lys His Ile Cys Gly Gly Ser Leu Ile Lys Glu Ser
                485                 490                 495
Trp Val Leu Thr Ala Arg Gln Cys Phe Pro Ser Arg Asp Leu Lys Asp
                500                 505                 510
Tyr Glu Ala Trp Leu Gly Ile His Asp Val His Gly Arg Gly Asp Glu
            515                 520                 525
```

Lys Cys Lys Gln Val Leu Asn Val Ser Gln Leu Val Tyr Gly Pro Glu
    530                 535                 540

Gly Ser Asp Leu Val Leu Met Lys Leu Ala Arg Pro Ala Val Leu Asp
545                 550                 555                 560

Asp Phe Val Ser Thr Ile Asp Leu Pro Asn Tyr Gly Cys Thr Ile Pro
                565                 570                 575

Glu Lys Thr Ser Cys Ser Val Tyr Gly Trp Gly Tyr Thr Gly Leu Ile
            580                 585                 590

Asn Tyr Asp Gly Leu Leu Arg Val Ala His Leu Tyr Ile Met Gly Asn
        595                 600                 605

Glu Lys Cys Ser Gln His His Arg Gly Lys Val Thr Leu Asn Glu Ser
    610                 615                 620

Glu Ile Cys Ala Gly Ala Glu Lys Ile Gly Ser Gly Pro Cys Glu Gly
625                 630                 635                 640

Asp Tyr Gly Gly Pro Leu Val Cys Glu Gln His Lys Met Arg Met Val
                645                 650                 655

Leu Gly Val Ile Val Pro Gly Arg Gly Cys Ala Ile Pro Asn Arg Pro
            660                 665                 670

Gly Ile Phe Val Arg Val Ala Tyr Tyr Ala Lys Trp Ile His Lys Ile
        675                 680                 685

Ile Leu Thr Tyr Lys Val Pro Gln Ser
    690                 695

<210> SEQ ID NO 103
<211> LENGTH: 276
<212> TYPE: DNA
<213> ORGANISM: Artificial Sequence
<220> FEATURE:
<223> OTHER INFORMATION: c-Met binding FN3 domain

<400> SEQUENCE: 103
ctgccggctc cgaagaactt ggtggtgagc cgtgttaccg aagatagcgc acgcctgagc      60
tggacggcac cggatgcggc gttcgatagc ttctggattc gctattttga gtttctgggt     120
agcggtgagg caattgttct gacggtgccg ggctctgaac gctcctacga tttgaccggt     180
ctgaaaccgg gcaccgagta tgtggtgaac attctgagcg ttaagggcgg tagcatcagc     240
ccaccgctga gcgcgatctt cacgactggt ggttgc                              276

<210> SEQ ID NO 104
<211> LENGTH: 267
<212> TYPE: DNA
<213> ORGANISM: Artificial Sequence
<220> FEATURE:
<223> OTHER INFORMATION: c-Met binding FN3 domain

<400> SEQUENCE: 104
ctgccggcac cgaagaacct ggttgtcagc cgtgtgaccg aggatagcgc acgtttgagc      60
tggaccgctc cggatgcagc ctttgacagc ttctggattc gttactttga atttctgggt     120
agcggtgagg cgatcgttct gacggtgccg ggctctgaac gcagctatga tttgacgggc     180
ctgaagccgg gtactgagta cgtggttaac atcatgggcg ttaagggtgg taaaatcagc     240
ccgccattgt ccgcgatctt taccacg                                         267

<210> SEQ ID NO 105
<211> LENGTH: 5
<212> TYPE: PRT
<213> ORGANISM: Artificial Sequence
<220> FEATURE:
<223> OTHER INFORMATION: linker

<400> SEQUENCE: 105

Gly Gly Gly Gly Ser
1               5

<210> SEQ ID NO 106
<211> LENGTH: 194
<212> TYPE: PRT
<213> ORGANISM: Artificial Sequence
<220> FEATURE:
<223> OTHER INFORMATION: Bispecific EGFR/c-Met binding molecule

<400> SEQUENCE: 106

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
            180                 185                 190

Thr Thr

<210> SEQ ID NO 107
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 107

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp 65                  70                  75                  80

Thr Asn Met Arg Gly Leu Pro Leu Ser Ala Ile Phe Thr Thr
                85                  90

<210> SEQ ID NO 108
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 108

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr
                85                  90

<210> SEQ ID NO 109
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 109

Leu Pro Ala Pro Lys Asn Leu Val Val Ser Glu Val Thr Glu Asp Ser
1               5                   10                  15

Ala Arg Leu Ser Trp Asp Asp Pro His Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr
                85                  90

<210> SEQ ID NO 110
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 110

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
 65                  70                  75                  80

Thr Asn Ile Arg Gly Leu Pro Leu Ser Ala Ile Phe Thr Thr
                85                  90

<210> SEQ ID NO 111
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 111

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
                20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Asn Ile Leu Gly Val Lys Gly Lys Ile Ser
 65                  70                  75                  80

Pro Pro Leu Ser Ala Ile Phe Thr Thr
                85

<210> SEQ ID NO 112
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 112

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
                20                  25                  30

Ile Arg Tyr Phe Glu Phe Val Gly Ser Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Asn Ile Leu Gly Val Lys Gly Ser Ile Ser
 65                  70                  75                  80

Pro Pro Leu Ser Ala Ile Phe Thr Thr
                85

<210> SEQ ID NO 113
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 113

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
            20                  25                  30

Ile Arg Tyr Phe Glu Phe Val Ser Lys Gly Asp Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Leu Gly Val Lys Gly Gly Ser Ile Ser
65                  70                  75                  80

Pro Pro Leu Ser Ala Ile Phe Thr Thr
                85

<210> SEQ ID NO 114
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 114

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Leu Ser Val Lys Gly Gly Ser Ile Ser
65                  70                  75                  80

Pro Pro Leu Ser Ala Ile Phe Thr Thr
                85

<210> SEQ ID NO 115
<211> LENGTH: 591
<212> TYPE: DNA
<213> ORGANISM: Artificial Sequence
<220> FEATURE:
<223> OTHER INFORMATION: Bispecific EGFR/c-Met binding molecule

<400> SEQUENCE: 115
atgttgccag cgccgaagaa cctggtagtt agcgaggtta ctgaggacag cgcgcgtctg      60
agctgggacg atccgtgggc gttctacgag agctttctga tccagtatca agagagcgag     120
aaagtcggtg aagcgattgt gctgaccgtc ccgggctccg agcgttccta cgacctgacc     180
ggtttgaagc cgggtaccga gtatacggtg agcatctacg gtgttcacaa tgtctataag     240
gacactaata tccgcggtct gcctctgagc gccattttca ccaccgcacc ggcaccggct     300
ccggctcctg ccccgctgcc ggctccgaag aacttggtgg tgagccgtgt taccgaagat     360
agcgcacgcc tgagctggac ggcaccggat gcggcgttcg atagcttctg gattcgctat     420
tttgagtttc tgggtagcgg tgaggcaatt gttctgacgg tgccgggctc tgaacgctcc     480
tacgatttga ccggtctgaa accgggcacc gagtatgtgg tgaacattct gagcgttaag     540
ggcggtagca tcagcccacc gctgagcgcg atcttcacga ctggtggttg c              591

<210> SEQ ID NO 116
<211> LENGTH: 582
<212> TYPE: DNA
<213> ORGANISM: Artificial Sequence
<220> FEATURE:

-continued

<223> OTHER INFORMATION: Bispecific EGFR/c-Met binding molecule

<400> SEQUENCE: 116

```
atgctgccag cccctaagaa tctggtcgtg agcgaagtaa ccgaggacag cgcccgcctg      60
agctgggacg acccgtgggc gttctatgag tctttcctga ttcagtatca agaaagcgaa     120
aaagttggcg aagcgatcgt cctgaccgtc ccgggtagcg agcgctccta cgatctgacc     180
ggcctgaaac cgggtacgga gtacacggtg tccatttacg gtgttcacaa tgtgtataaa     240
gacaccaaca tgcgtggcct gccgctgtcg gcgattttca ccaccgcgcc tgcgccagcg     300
cctgcaccgg ctccgctgcc ggcaccgaag aacctggttg tcagccgtgt gaccgaggat     360
agcgcacgtt tgagctggac cgctccggat gcagcctttg acagcttctg gattcgttac     420
tttgaatttc tgggtagcgg tgaggcgatc gttctgacgg tgccgggctc tgaacgcagc     480
tatgatttga cgggcctgaa gccgggtact gagtacgtgg ttaacatcat gggcgttaag     540
ggtggtaaaa tcagcccgcc attgtccgcg atctttacca cg                        582
```

<210> SEQ ID NO 117
<211> LENGTH: 51
<212> TYPE: PRT
<213> ORGANISM: Artificial Sequence
<220> FEATURE:
<223> OTHER INFORMATION: albumin binding domain

<400> SEQUENCE: 117

```
Thr Ile Asp Glu Trp Leu Leu Lys Glu Ala Lys Glu Lys Ala Ile Glu
1               5                   10                  15
Glu Leu Lys Lys Ala Gly Ile Thr Ser Asp Tyr Tyr Phe Asp Leu Ile
            20                  25                  30
Asn Lys Ala Lys Thr Val Glu Gly Val Asn Ala Leu Lys Asp Glu Ile
        35                  40                  45
Leu Lys Ala
    50
```

<210> SEQ ID NO 118
<211> LENGTH: 250
<212> TYPE: PRT
<213> ORGANISM: Artificial Sequence
<220> FEATURE:
<223> OTHER INFORMATION: Bispecific EGFR/c-Met binding molecule

<400> SEQUENCE: 118

```
Met Leu Pro Ala Pro Lys Asn Leu Val Val Ser Glu Val Thr Glu Asp
1               5                   10                  15
Ser Ala Arg Leu Ser Trp Asp Asp Pro Trp Ala Phe Tyr Glu Ser Phe
            20                  25                  30
Leu Ile Gln Tyr Gln Glu Ser Glu Lys Val Gly Glu Ala Ile Val Leu
        35                  40                  45
Thr Val Pro Gly Ser Glu Arg Ser Tyr Asp Leu Thr Gly Leu Lys Pro
    50                  55                  60
Gly Thr Glu Tyr Thr Val Ser Ile Tyr Gly Val His Asn Val Tyr Lys
65                  70                  75                  80
Asp Thr Asn Met Arg Gly Leu Pro Leu Ser Ala Ile Phe Thr Thr Ala
                85                  90                  95
Pro Ala Pro Ala Pro Ala Pro Ala Pro Leu Pro Ala Pro Lys Asn Leu
            100                 105                 110
Val Val Ser Arg Val Thr Glu Asp Ser Ala Arg Leu Ser Trp Thr Ala
        115                 120                 125
```

```
Pro Asp Ala Ala Phe Asp Ser Phe Trp Ile Arg Tyr Asp Glu Val Val
        130                 135                 140

Val Gly Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Tyr Val Asn Ile
                165                 170                 175

Leu Gly Val Lys Gly Ser Ile Ser Val Pro Leu Ser Ala Ile Phe
            180                 185                 190

Thr Thr Ala Pro Ala Pro Ala Pro Ala Pro Leu Ala Glu Ala
            195                 200                 205

Lys Val Leu Ala Asn Arg Glu Leu Asp Lys Tyr Gly Val Ser Asp Tyr
        210                 215                 220

Tyr Lys Asn Leu Ile Asn Asn Ala Lys Thr Val Glu Gly Val Lys Ala
225                 230                 235                 240

Leu Leu Asp Glu Ile Leu Ala Ala Leu Pro
                245                 250

<210> SEQ ID NO 119
<211> LENGTH: 250
<212> TYPE: PRT
<213> ORGANISM: Artificial Sequence
<220> FEATURE:
<223> OTHER INFORMATION: Bispecific EGFR/c-Met binding molecule

<400> SEQUENCE: 119

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Asp Glu Val Val
        130                 135                 140

Val Gly Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Tyr Val Asn Ile
                165                 170                 175

Leu Gly Val Lys Gly Ser Ile Ser Val Pro Leu Ser Ala Ile Phe
            180                 185                 190

Thr Thr Ala Pro Ala Pro Ala Pro Ala Pro Leu Ala Glu Ala
            195                 200                 205

Lys Val Leu Ala Asn Arg Glu Leu Asp Lys Tyr Gly Val Ser Asp Tyr
        210                 215                 220

Tyr Lys Asn Leu Ile Asn Asn Ala Lys Thr Val Glu Gly Val Lys Ala
225                 230                 235                 240
```

```
Leu Leu Asp Glu Ile Leu Ala Ala Leu Pro
            245                 250

<210> SEQ ID NO 120
<211> LENGTH: 250
<212> TYPE: PRT
<213> ORGANISM: Artificial Sequence
<220> FEATURE:
<223> OTHER INFORMATION: Bispecific EGFR/c-Met binding molecule

<400> SEQUENCE: 120

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
        130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Gly Val Lys Gly Gly Lys Ile Ser Pro Pro Leu Ser Ala Ile Phe
            180                 185                 190

Thr Thr Ala Pro Ala Pro Ala Pro Ala Pro Leu Ala Glu Ala
        195                 200                 205

Lys Val Leu Ala Asn Arg Glu Leu Asp Lys Tyr Gly Val Ser Asp Tyr
    210                 215                 220

Tyr Lys Asn Leu Ile Asn Asn Ala Lys Thr Val Glu Gly Val Lys Ala
225                 230                 235                 240

Leu Leu Asp Glu Ile Leu Ala Ala Leu Pro
            245                 250

<210> SEQ ID NO 121
<211> LENGTH: 250
<212> TYPE: PRT
<213> ORGANISM: Artificial Sequence
<220> FEATURE:
<223> OTHER INFORMATION: Bispecific EGFR/c-Met binding molecule

<400> SEQUENCE: 121

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
```

```
            35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Ile Phe Thr Thr Ala
                 85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
       130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Gly Val Lys Gly Gly Lys Ile Ser Pro Pro Leu Ser Ala Ile Phe
            180                 185                 190

Thr Thr Ala Pro Ala Pro Ala Pro Ala Pro Ala Pro Leu Ala Glu Ala
        195                 200                 205

Lys Val Leu Ala Asn Arg Glu Leu Asp Lys Tyr Gly Val Ser Asp Tyr
210                 215                 220

Tyr Lys Asn Leu Ile Asn Asn Ala Lys Thr Val Glu Gly Val Lys Ala
225                 230                 235                 240

Leu Leu Asp Glu Ile Leu Ala Ala Leu Pro
                245                 250

<210> SEQ ID NO 122
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 122

Met Leu Pro Ala Pro Lys Asn Leu Val Val Ser Glu Val Thr Glu Asp
 1               5                  10                  15

Ser Leu Arg Leu Ser Trp Ala Asp Pro His Gly Phe Tyr Asp Ser Phe
                 20                  25                  30

Leu Ile Gln Tyr Gln Glu Ser Glu Lys Val Gly Glu Ala Ile Asn Leu
            35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Glu Phe Thr Thr
                 85                  90                  95

<210> SEQ ID NO 123
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 123
```

Met Leu Pro Ala Pro Lys Asn Leu Val Val Ser Glu Val Thr Glu Asp
1               5                   10                  15

Ser Leu Arg Leu Ser Trp Thr Tyr Asp Arg Asp Gly Tyr Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 124
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 124

Met Leu Pro Ala Pro Lys Asn Leu Val Val Ser Glu Val Thr Glu Asp
1               5                   10                  15

Ser Leu Arg Leu Ser Trp Gly Tyr Asn Gly Asp His Phe Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 125
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 125

Met Leu Pro Ala Pro Lys Asn Leu Val Val Ser Glu Val Thr Glu Asp
1               5                   10                  15

Ser Leu Arg Leu Ser Trp Asp Asp Pro Arg Gly Phe Tyr Glu Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 126
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 126

Met Leu Pro Ala Pro Lys Asn Leu Val Val Ser Glu Val Thr Glu Asp
1               5                   10                  15

Ser Leu Arg Leu Ser Trp Thr Trp Pro Tyr Ala Asp Leu Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 127
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 127

Met Leu Pro Ala Pro Lys Asn Leu Val Val Ser Glu Val Thr Glu Asp
1               5                   10                  15

Ser Leu Arg Leu Ser Trp Gly Tyr Asn Gly Asp His Phe Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 128
<211> LENGTH: 96
<212> TYPE: PRT
<213> ORGANISM: Artificial Sequence
<220> FEATURE:
<223> OTHER INFORMATION: EGFR binding FN3 domain

<400> SEQUENCE: 128

Met Leu Pro Ala Pro Lys Asn Leu Val Val Ser Glu Val Thr Glu Asp
1               5                   10                  15

Ser Leu Arg Leu Ser Trp Asp Tyr Asp Leu Gly Val Tyr Phe Asp Ser
            20                  25                  30

Phe Leu Ile Gln Tyr Gln Glu Ser Glu Lys Val Gly Glu Ala Ile Asn
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val His Asn Val Tyr
65                  70                  75                  80

Lys Asp Thr Asn Met Arg Gly Leu Pro Leu Ser Ala Glu Phe Thr Thr
                85                  90                  95

<210> SEQ ID NO 129
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 129

```
Met Leu Pro Ala Pro Lys Asn Leu Val Val Ser Glu Val Thr Glu Asp
1               5                   10                  15

Ser Leu Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95
```

<210> SEQ ID NO 130
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 130

```
Met Leu Pro Ala Pro Lys Asn Leu Val Val Ser Glu Val Thr Glu Asp
1               5                   10                  15

Ser Leu Arg Leu Ser Trp Thr Ala Pro Asp Ala Ala Phe Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Leu Gly Ser Tyr Val
65                  70                  75                  80

Phe Glu His Asp Val Met Leu Pro Leu Ser Ala Glu Phe Thr Thr
                85                  90                  95
```

<210> SEQ ID NO 131
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 131

```
Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
```

65                  70                  75                  80

Asp Thr Asn Met Arg Gly Leu Pro Leu Ser Ala Ile Phe Thr Thr
                85                  90                  95

<210> SEQ ID NO 132
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 132

Met Leu Pro Ala Pro Lys Asn Leu Val Val Ser Glu Val Thr Glu Asp
1               5                   10                  15

Ser Ala Arg Leu Ser Trp Thr Ala Pro Asp Ala Ala Phe Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val Leu Gly Ser Tyr Val
65                  70                  75                  80

Phe Glu His Asp Val Met Leu Pro Leu Ser Ala Ile Phe Thr Thr
                85                  90                  95

<210> SEQ ID NO 133
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 133

Met Leu Pro Ala Pro Lys Asn Leu Val Val Ser Glu Val Thr Glu Asp
1               5                   10                  15

Ser Leu Arg Leu Ser Trp Thr Trp Pro Tyr Ala Asp Leu Asp Ser Phe
                20                  25                  30

Leu Ile Gln Tyr Gln Glu Ser Glu Lys Val Gly Glu Ala Ile Asn Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 134
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 134

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
                20                  25                  30

Leu Ile Gln Tyr Gln Glu Ser Glu Lys Val Gly Glu Ala Ile Val Leu
            35                  40                  45

```
Thr Val Pro Gly Ser Glu Arg Ser Tyr Asp Leu Thr Gly Leu Lys Pro
            50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Ile Phe Thr Thr
                85                  90                  95

<210> SEQ ID NO 135
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 135

Met Leu Pro Ala Pro Lys Asn Leu Val Val Ser Glu Val Thr Glu Asp
  1               5                  10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
            50                  55                  60

Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr
                85                  90                  95

<210> SEQ ID NO 136
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 136

Met Leu Pro Ala Pro Lys Asn Leu Val Val Ser Glu Val Thr Glu Asp
  1               5                  10                  15

Ser Ala Arg Leu Ser Trp Asp Asp Pro His Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
            50                  55                  60

Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr
                85                  90                  95

<210> SEQ ID NO 137
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 137

Met Leu Pro Ala Pro Lys Asn Leu Val Val Ser Glu Val Thr Glu Asp
  1               5                  10                  15
```

```
Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr
                85                  90                  95

<210> SEQ ID NO 138
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 138

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
                85                  90                  95

Gly Gly Ser Gly Gly Gly Gly Ser Gly Gly Gly Gly Ser Gly Gly Gly
            100                 105                 110

Gly Ser Met Leu Pro Ala Pro Lys Asn Leu Val Val Ser Arg Val Thr
            115                 120                 125

Glu Asp Ser Ala Arg Leu Ser Trp Thr Ala Pro Asp Ala Ala Phe Asp
        130                 135                 140

Ser Phe Trp Ile Arg Tyr Asp Glu Val Val Gly Gly Glu Ala Ile Val
145                 150                 155                 160

Val Leu Thr Val Pro Gly Ser Glu Arg Ser Tyr Asp Leu Thr Gly Leu
                165                 170                 175

Lys Pro Gly Thr Glu Tyr Tyr Val Asn Ile Leu Gly Val Lys Gly Gly
            180                 185                 190

Ser Ile Ser Val Pro Leu Ser Ala Ile Phe Thr Thr
        195                 200

<210> SEQ ID NO 139
<211> LENGTH: 203
<212> TYPE: PRT
<213> ORGANISM: Artificial Sequence
<220> FEATURE:
<223> OTHER INFORMATION: Bispecific EGFR/c-Met binding domain

<400> SEQUENCE: 139

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30
```

```
Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
                85                  90                  95

Gly Gly Ser Gly Gly Gly Ser Gly Gly Gly Ser Gly Gly
                100                 105                 110

Gly Ser Leu Pro Ala Pro Lys Asn Leu Val Val Ser Arg Val Thr Glu
            115                 120                 125

Asp Ser Ala Arg Leu Ser Trp Thr Ala Pro Asp Ala Ala Phe Asp Ser
        130                 135                 140

Phe Trp Ile Arg Tyr Phe Glu Phe Leu Gly Ser Gly Glu Ala Ile Val
145                 150                 155                 160

Leu Thr Val Pro Gly Ser Glu Arg Ser Tyr Asp Leu Thr Gly Leu Lys
                165                 170                 175

Pro Gly Thr Glu Tyr Val Val Asn Ile Met Gly Val Lys Gly Gly Lys
            180                 185                 190

Ile Ser Pro Pro Leu Ser Ala Ile Phe Thr Thr
        195                 200

<210> SEQ ID NO 140
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 140

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
                85                  90                  95

Gly Gly Ser Gly Gly Gly Ser Gly Gly Gly Ser Gly Gly
                100                 105                 110

Gly Ser Met Leu Pro Ala Pro Lys Asn Leu Val Val Ser Arg Val Thr
            115                 120                 125

Glu Asp Ser Ala Arg Leu Ser Trp Thr Ala Pro Asp Ala Ala Phe Asp
        130                 135                 140

Ser Phe Trp Ile Arg Tyr Phe Glu Phe Leu Gly Ser Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Val Val Gln Ile Ile Gly Val Lys Gly Gly
            180                 185                 190
```

His Ile Ser Leu Pro Leu Ser Ala Ile Phe Thr Thr
        195                 200

<210> SEQ ID NO 141
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 141

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
            85                  90                  95

Gly Gly Ser Gly Gly Gly Gly Ser Gly Gly Gly Gly Ser Gly Gly Gly
            100                 105                 110

Gly Ser Met Leu Pro Ala Pro Lys Asn Leu Val Val Ser Arg Val Thr
            115                 120                 125

Glu Asp Ser Ala Arg Leu Ser Trp Thr Ala Pro Asp Ala Ala Phe Asp
        130                 135                 140

Ser Phe Phe Ile Arg Tyr Asp Glu Phe Leu Arg Ser Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Trp Val Thr Ile Leu Gly Val Lys Gly Gly
            180                 185                 190

Leu Val Ser Thr Pro Leu Ser Ala Ile Phe Thr Thr
        195                 200

<210> SEQ ID NO 142
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 142

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly

```
                    85                  90                  95

Gly Gly Ser Gly Gly Gly Gly Ser Gly Gly Gly Ser Gly Gly
                100                 105                 110

Gly Ser Met Leu Pro Ala Pro Lys Asn Leu Val Val Ser Arg Val Thr
            115                 120                 125

Glu Asp Ser Ala Arg Leu Ser Trp Thr Ala Pro Asp Ala Ala Phe Asp
        130                 135                 140

Ser Phe Trp Ile Arg Tyr Phe Glu Phe Leu Gly Ser Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Val Val Asn Ile Met Gly Val Lys Gly Gly
                180                 185                 190

Lys Ile Ser Pro Pro Leu Ser Ala Ile Phe Thr Thr
                195                 200

<210> SEQ ID NO 143
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 143

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
                85                  90                  95

Gly Gly Ser Gly Gly Gly Gly Ser Gly Gly Gly Ser Gly Gly
                100                 105                 110

Gly Ser Met Leu Pro Ala Pro Lys Asn Leu Val Val Ser Arg Val Thr
            115                 120                 125

Glu Asp Ser Ala Arg Leu Ser Trp Thr Ala Pro Asp Ala Ala Phe Asp
        130                 135                 140

Ser Phe Trp Ile Arg Tyr Phe Glu Phe Leu Gly Ser Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Val Val Gln Ile Gly Val Lys Gly Gly
                180                 185                 190

His Ile Ser Leu Pro Leu Ser Ala Ile Phe Thr Thr
                195                 200

<210> SEQ ID NO 144
<211> LENGTH: 204
<212> TYPE: PRT
<213> ORGANISM: Artificial Sequence
<220> FEATURE:
<223> OTHER INFORMATION: Bispecific EGFR/c-Met binding domain
```

<400> SEQUENCE: 144

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
                85                  90                  95

Gly Gly Ser Gly Gly Gly Gly Ser Gly Gly Gly Gly Ser Gly Gly Gly
            100                 105                 110

Gly Ser Met Leu Pro Ala Pro Lys Asn Leu Val Val Ser Arg Val Thr
        115                 120                 125

Glu Asp Ser Ala Arg Leu Ser Trp Thr Ala Pro Asp Ala Ala Phe Asp
130                 135                 140

Ser Phe Trp Ile Arg Tyr Phe Glu Phe Leu Gly Ser Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Val Val Gln Ile Ile Gly Val Lys Gly Gly
            180                 185                 190

His Ile Ser Leu Pro Leu Ser Ala Ile Phe Thr Thr
            195                 200

<210> SEQ ID NO 145
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 145

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Leu Gly
    130                 135                 140

```
Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Met
                165                 170                 175

Gly Val Lys Gly Gly Lys Ile Ser Pro Pro Leu Ser Ala Ile Phe Thr
            180                 185                 190

Thr
```

```
<210> SEQ ID NO 146
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 146

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Asp Glu Val Val Val
        130                 135                 140

Gly Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Tyr Val Asn Ile Leu
                165                 170                 175

Gly Val Lys Gly Gly Ser Ile Ser Val Pro Leu Ser Ala Ile Phe Thr
            180                 185                 190

Thr
```

```
<210> SEQ ID NO 147
<211> LENGTH: 194
<212> TYPE: PRT
<213> ORGANISM: Artificial Sequence
<220> FEATURE:
<223> OTHER INFORMATION: Bispecific EGFR/c-Met binding domain

<400> SEQUENCE: 147

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
```

```
                  50                  55                  60
Thr Glu Tyr Thr Val Ser Ile Tyr Gly Val His Asn Val Tyr Lys Asp
 65                  70                  75                  80

Thr Asn Met Arg Gly Leu Pro Leu Ser Ala Ile Phe Thr Thr Ala Pro
                 85                  90                  95

Ala Pro Ala Pro Ala Pro Ala Pro Met Leu Pro Ala Pro Lys Asn Leu
                100                 105                 110

Val Val Ser Arg Val Thr Glu Asp Ser Ala Arg Leu Ser Trp Thr Ala
                115                 120                 125

Pro Asp Ala Ala Phe Asp Ser Phe Trp Ile Arg Tyr Phe Glu Phe Leu
130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Gly Val Lys Gly Lys Ile Ser Pro Pro Leu Ser Ala Ile Phe
                180                 185                 190

Thr Thr
```

<210> SEQ ID NO 148
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 148

```
Leu Pro Ala Pro Lys Asn Leu Val Val Ser Glu Val Thr Glu Asp Ser
 1               5                  10                  15

Ala Arg Leu Ser Trp Ala Asp Pro His Gly Phe Tyr Asp Ser Phe Leu
                20                  25                  30

Ile Gln Tyr Gln Glu Ser Glu Lys Val Gly Glu Ala Ile Val Leu Thr
                35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val His Asn Val Tyr Lys Asp
 65                  70                  75                  80

Thr Asn Met Arg Gly Leu Pro Leu Ser Ala Ile Phe Thr Thr Ala Pro
                 85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
                115                 120                 125

Asp Ala Ala Phe Asp Ser Phe Trp Ile Arg Tyr Asp Glu Val Val Val
130                 135                 140

Gly Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Tyr Val Asn Ile Leu
                165                 170                 175

Gly Val Lys Gly Gly Ser Ile Ser Val Pro Leu Ser Ala Ile Phe Thr
                180                 185                 190

Thr
```

<210> SEQ ID NO 149
<211> LENGTH: 193

```
<212> TYPE: PRT
<213> ORGANISM: Artificial Sequence
<220> FEATURE:
<223> OTHER INFORMATION: Bispecific EGFR/c-Met binding domain

<400> SEQUENCE: 149

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Lys Ile Ser Pro Pro Leu Ser Ala Ile Phe Thr
                180                 185                 190

Thr

<210> SEQ ID NO 150
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 150

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125
```

```
Asp Ala Ala Phe Asp Ser Phe Trp Ile Arg Tyr Phe Glu Phe Val Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
            180                 185                 190

Thr
```

<210> SEQ ID NO 151
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 151

```
Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Val Ser
    130                 135                 140

Lys Gly Asp Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
            180                 185                 190

Thr
```

<210> SEQ ID NO 152
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 152

```
Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
```

```
            35                  40                  45
Val Pro Gly Ser Glu Arg Ser Tyr Asp Leu Thr Gly Leu Lys Pro Gly
    50                  55                  60
Thr Glu Tyr Thr Val Ser Ile Tyr Gly Val His Asn Val Tyr Lys Asp
65                  70                  75                  80
Thr Asn Ile Arg Gly Leu Pro Leu Ser Ala Ile Phe Thr Thr Ala Pro
                85                  90                  95
Ala Pro Ala Pro Ala Pro Ala Pro Leu Pro Ala Pro Lys Asn Leu Val
            100                 105                 110
Val Ser Arg Val Thr Glu Asp Ser Ala Arg Leu Ser Trp Thr Ala Pro
            115                 120                 125
Asp Ala Ala Phe Asp Ser Phe Trp Ile Arg Tyr Phe Glu Phe Leu Gly
        130                 135                 140
Ser Gly Glu Ala Ile Val Leu Thr Val Pro Gly Ser Glu Arg Ser Tyr
145                 150                 155                 160
Asp Leu Thr Gly Leu Lys Pro Gly Thr Glu Tyr Val Val Asn Ile Leu
                165                 170                 175
Ser Val Lys Gly Gly Ser Ile Ser Pro Pro Leu Ser Ala Ile Phe Thr
            180                 185                 190
Thr
```

```
<210> SEQ ID NO 153
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 153

Leu Pro Ala Pro Lys Asn Leu Val Val Ser Glu Val Thr Glu Asp Ser
1               5                   10                  15
Ala Arg Leu Ser Trp Asp Asp Pro His Ala Phe Tyr Glu Ser Phe Leu
            20                  25                  30
Ile Gln Tyr Gln Glu Ser Glu Lys Val Gly Glu Ala Ile Val Leu Thr
        35                  40                  45
Val Pro Gly Ser Glu Arg Ser Tyr Asp Leu Thr Gly Leu Lys Pro Gly
    50                  55                  60
Thr Glu Tyr Thr Val Ser Ile Tyr Gly Val His Asn Val Tyr Lys Asp
65                  70                  75                  80
Thr Asn Ile Arg Gly Leu Pro Leu Ser Ala Ile Phe Thr Thr Ala Pro
                85                  90                  95
Ala Pro Ala Pro Ala Pro Ala Pro Leu Pro Ala Pro Lys Asn Leu Val
            100                 105                 110
Val Ser Arg Val Thr Glu Asp Ser Ala Arg Leu Ser Trp Thr Ala Pro
            115                 120                 125
Asp Ala Ala Phe Asp Ser Phe Trp Ile Arg Tyr Phe Glu Phe Leu Gly
        130                 135                 140
Ser Gly Glu Ala Ile Val Leu Thr Val Pro Gly Ser Glu Arg Ser Tyr
145                 150                 155                 160
Asp Leu Thr Gly Leu Lys Pro Gly Thr Glu Tyr Val Val Asn Ile Leu
                165                 170                 175
Gly Val Lys Gly Gly Lys Ile Ser Pro Pro Leu Ser Ala Ile Phe Thr
            180                 185                 190
Thr
```

<210> SEQ ID NO 154
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 154

```
Leu Pro Ala Pro Lys Asn Leu Val Val Ser Glu Val Thr Glu Asp Ser
1               5                   10                  15

Ala Arg Leu Ser Trp Asp Asp Pro His Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Val Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
                180                 185                 190

Thr
```

<210> SEQ ID NO 155
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 155

```
Leu Pro Ala Pro Lys Asn Leu Val Val Ser Glu Val Thr Glu Asp Ser
1               5                   10                  15

Ala Arg Leu Ser Trp Asp Asp Pro His Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110
```

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Val Ser
        130                 135                 140

Lys Gly Asp Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
            165                 170                 175

Gly Val Lys Gly Gly Ser Ile Ser Pro Pro Leu Ser Ala Ile Phe Thr
            180                 185                 190

Thr

<210> SEQ ID NO 156
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 156

Leu Pro Ala Pro Lys Asn Leu Val Val Ser Glu Val Thr Glu Asp Ser
1               5                   10                  15

Ala Arg Leu Ser Trp Asp Asp Pro His Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
        130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
            165                 170                 175

Ser Val Lys Gly Gly Ser Ile Ser Pro Pro Leu Ser Ala Ile Phe Thr
            180                 185                 190

Thr

<210> SEQ ID NO 157
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 157

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu

```
                    20                  25                  30
Ile Gln Tyr Gln Glu Ser Glu Lys Val Gly Glu Ala Ile Val Leu Thr
                35                  40                  45

Val Pro Gly Ser Glu Arg Ser Tyr Asp Leu Thr Gly Leu Lys Pro Gly
            50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
                115                 120                 125

Asp Ala Ala Phe Asp Ser Phe Trp Ile Arg Tyr Phe Glu Phe Leu Gly
                130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Lys Ile Ser Pro Pro Leu Ser Ala Ile Phe Thr
                180                 185                 190

Thr
```

<210> SEQ ID NO 158
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 158

```
Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
                20                  25                  30

Ile Gln Tyr Gln Glu Ser Glu Lys Val Gly Glu Ala Ile Val Leu Thr
                35                  40                  45

Val Pro Gly Ser Glu Arg Ser Tyr Asp Leu Thr Gly Leu Lys Pro Gly
            50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
                115                 120                 125

Asp Ala Ala Phe Asp Ser Phe Trp Ile Arg Tyr Phe Glu Phe Val Gly
                130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
                180                 185                 190
```

Thr

<210> SEQ ID NO 159
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 159

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Val Ser
    130                 135                 140

Lys Gly Asp Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
            180                 185                 190

Thr

<210> SEQ ID NO 160
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 160

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

```
Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
            130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Ser Val Lys Gly Gly Ser Ile Ser Pro Pro Leu Ser Ala Ile Phe Thr
            180                 185                 190

Thr

<210> SEQ ID NO 161
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 161

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
            130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Ser Val Lys Gly Gly Ser Ile Ser Pro Pro Leu Ser Ala Ile Phe Thr
            180                 185                 190

Thr

<210> SEQ ID NO 162
<211> LENGTH: 249
<212> TYPE: PRT
<213> ORGANISM: Artificial Sequence
<220> FEATURE:
<223> OTHER INFORMATION: Bispecific EGFR/c-Met binding domain

<400> SEQUENCE: 162

Leu Pro Ala Pro Lys Asn Leu Val Val Ser Glu Val Thr Glu Asp Ser
```

```
   1               5                   10                  15
Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Asp Glu Val Val Val
        130                 135                 140

Gly Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Tyr Val Asn Ile Leu
                165                 170                 175

Gly Val Lys Gly Gly Ser Ile Ser Val Pro Leu Ser Ala Ile Phe Thr
            180                 185                 190

Thr Ala Pro Ala Pro Ala Pro Ala Pro Ala Pro Leu Ala Glu Ala Lys
            195                 200                 205

Val Leu Ala Asn Arg Glu Leu Asp Lys Tyr Gly Val Ser Asp Tyr Tyr
        210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245

<210> SEQ ID NO 163
<211> LENGTH: 249
<212> TYPE: PRT
<213> ORGANISM: Artificial Sequence
<220> FEATURE:
<223> OTHER INFORMATION: Bispecific EGFR/c-Met binding domain

<400> SEQUENCE: 163

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
```

```
                 115                 120                 125
Asp Ala Ala Phe Asp Ser Phe Trp Ile Arg Tyr Asp Glu Val Val Val
            130                 135                 140

Gly Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Tyr Val Asn Ile Leu
                165                 170                 175

Gly Val Lys Gly Gly Ser Ile Ser Val Pro Leu Ser Ala Ile Phe Thr
            180                 185                 190

Thr Ala Pro Ala Pro Ala Pro Ala Pro Ala Pro Leu Ala Glu Ala Lys
                195                 200                 205

Val Leu Ala Asn Arg Glu Leu Asp Lys Tyr Gly Val Ser Asp Tyr Tyr
            210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245

<210> SEQ ID NO 164
<211> LENGTH: 249
<212> TYPE: PRT
<213> ORGANISM: Artificial Sequence
<220> FEATURE:
<223> OTHER INFORMATION: Bispecific EGFR/c-Met binding domain

<400> SEQUENCE: 164

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Leu Gly
            130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Met
                165                 170                 175

Gly Val Lys Gly Gly Lys Ile Ser Pro Pro Leu Ser Ala Ile Phe Thr
            180                 185                 190

Thr Ala Pro Ala Pro Ala Pro Ala Pro Ala Pro Leu Ala Glu Ala Lys
                195                 200                 205

Val Leu Ala Asn Arg Glu Leu Asp Lys Tyr Gly Val Ser Asp Tyr Tyr
            210                 215                 220

Lys Asn Leu Ile Asn Asn Ala Lys Thr Val Glu Gly Val Lys Ala Leu
```

Leu Asp Glu Ile Leu Ala Ala Leu Pro
                245

<210> SEQ ID NO 165
<211> LENGTH: 249
<212> TYPE: PRT
<213> ORGANISM: Artificial Sequence
<220> FEATURE:
<223> OTHER INFORMATION: Bispecific EGFR/c-Met binding domain

<400> SEQUENCE: 165

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Met
                165                 170                 175

Gly Val Lys Gly Gly Lys Ile Ser Pro Pro Leu Ser Ala Ile Phe Thr
            180                 185                 190

Thr Ala Pro Ala Pro Ala Pro Ala Pro Leu Ala Glu Ala Lys
        195                 200                 205

Val Leu Ala Asn Arg Glu Leu Asp Lys Tyr Gly Val Ser Asp Tyr Tyr
    210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245

<210> SEQ ID NO 166
<211> LENGTH: 588
<212> TYPE: DNA
<213> ORGANISM: Artificial Sequence
<220> FEATURE:
<223> OTHER INFORMATION: Bispecific EGFR/c-Met binding domain

<400> SEQUENCE: 166
ttgccagcgc cgaagaacct ggtagttagc gaggttactg aggacagcgc gcgtctgagc      60
tgggacgatc cgtgggcgtt ctacgagagc tttctgatcc agtatcaaga gagcgagaaa    120
gtcggtgaag cgattgtgct gaccgtcccg ggctccgagc gttcctacga cctgaccggt    180

```
ttgaagccgg gtaccgagta tacggtgagc atctacggtg ttcacaatgt ctataaggac      240
actaatatcc gcggtctgcc tctgagcgcc attttcacca ccgcaccggc accggctccg      300
gctcctgccc cgctgccggc tccgaagaac ttggtggtga ccgtgttac cgaagatagc       360 gcacgcctga gctggacggc accggatgcg gcgttcgata gcttctggat tcgctatttt      420
gagtttctgg gtagcggtga ggcaattgtt ctgacggtgc cgggctctga acgctcctac      480
gatttgaccg gtctgaaacc gggcaccgag tatgtggtga acattctgag cgttaagggc      540
ggtagcatca gcccaccgct gagcgcgatc ttcacgactg gtggttgc                   588

<210> SEQ ID NO 167
<211> LENGTH: 579
<212> TYPE: DNA
<213> ORGANISM: Artificial Sequence
<220> FEATURE:
<223> OTHER INFORMATION: Bispecific EGFR/c-Met binding domain

<400> SEQUENCE: 167
ctgccagccc ctaagaatct ggtcgtgagc gaagtaaccg aggacagcgc ccgcctgagc      60
tgggacgacc cgtgggcgtt ctatgagtct ttcctgattc agtatcaaga aagcgaaaaa     120
gttggcgaag cgatcgtcct gaccgtcccg ggtagcgagc gctcctacga tctgaccggc     180
ctgaaaccgg gtacggagta cacggtgtcc atttacggtg ttcacaatgt gtataaagac     240
accaacatgc gtgtgcctgcc gctgtcgcg attttcacca ccgcgcctgc gccagcgcct    300
gcaccggctc cgctgccggc accgaagaac ctggttgtca ccgtgtgac cgaggatagc      360 gcacgtttga gctggaccgc tccggatgca gcctttgaca gcttctggat tcgttacttt     420
gaatttctgg gtagcggtga ggcgatcgtt ctgacggtgc cgggctctga acgcagctat     480
gatttgacgg gcctgaagcc gggtactgag tacgtggtta acatcatggg cgttaagggt     540
ggtaaaatca gcccgccatt gtccgcgatc tttaccacg                            579

<210> SEQ ID NO 168
<211> LENGTH: 282
<212> TYPE: DNA
<213> ORGANISM: Artificial Sequence
<220> FEATURE:
<223> OTHER INFORMATION: EGFR binding FN3 domain from ECB97

<400> SEQUENCE: 168
ttgccagcgc cgaagaacct ggtagttagc gaggttactg aggacagcgc gcgtctgagc      60
tgggacgatc cgtgggcgtt ctacgagagc tttctgatcc agtatcaaga gagcgagaaa     120
gtcggtgaag cgattgtgct gaccgtcccg ggctccgagc gttcctacga cctgaccggt     180
ttgaagccgg gtaccgagta tacggtgagc atctacggtg ttcacaatgt ctataaggac     240
actaatatcc gcggtctgcc tctgagcgcc attttcacca cc                        282

<210> SEQ ID NO 169
<211> LENGTH: 282
<212> TYPE: DNA
<213> ORGANISM: Artificial Sequence
<220> FEATURE:
<223> OTHER INFORMATION: EGFR binding FN3 domain from ECB15

<400> SEQUENCE: 169
ctgccagccc ctaagaatct ggtcgtgagc gaagtaaccg aggacagcgc ccgcctgagc      60
tgggacgacc cgtgggcgtt ctatgagtct ttcctgattc agtatcaaga aagcgaaaaa     120
gttggcgaag cgatcgtcct gaccgtcccg ggtagcgagc gctcctacga tctgaccggc     180
```

-continued ctgaaaccgg gtacggagta cacggtgtcc atttacggtg ttcacaatgt gtataaagac     240
accaacatgc gtggcctgcc gctgtcggcg attttcacca cc                        282

<210> SEQ ID NO 170
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 170

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Lys Ile Ser Pro Pro Leu Ser Ala Ile Phe
            180                 185                 190

Thr Thr Cys
        195

<210> SEQ ID NO 171
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 171

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95
Pro Ala Pro Ala Pro Ala Pro Ala Pro Leu Pro Ala Pro Lys Asn Leu
            100                 105                 110
Val Val Ser Arg Val Thr Glu Asp Ser Ala Arg Leu Ser Trp Thr Ala
            115                 120                 125
Pro Asp Ala Ala Phe Asp Ser Phe Trp Ile Arg Tyr Phe Glu Phe Val
            130                 135                 140
Gly Ser Gly Glu Ala Ile Val Leu Thr Val Pro Gly Ser Glu Arg Ser
145                 150                 155                 160
Tyr Asp Leu Thr Gly Leu Lys Pro Gly Thr Glu Tyr Val Val Asn Ile
            165                 170                 175
Leu Gly Val Lys Gly Gly Ser Ile Ser Pro Pro Leu Ser Ala Ile Phe
            180                 185                 190
Thr Thr Cys
        195

<210> SEQ ID NO 172
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 172

Met Leu Pro Ala Pro Lys Asn Leu Val Val Ser Glu Val Thr Glu Asp
1               5                   10                  15
Ser Ala Arg Leu Ser Trp Asp Asp Pro Trp Ala Phe Tyr Glu Ser Phe
            20                  25                  30
Leu Ile Gln Tyr Gln Glu Ser Glu Lys Val Gly Glu Ala Ile Val Leu
            35                  40                  45
Thr Val Pro Gly Ser Glu Arg Ser Tyr Asp Leu Thr Gly Leu Lys Pro
        50                  55                  60
Gly Thr Glu Tyr Thr Val Ser Ile Tyr Gly Val His Asn Val Tyr Lys
65                  70                  75                  80
Asp Thr Asn Ile Arg Gly Leu Pro Leu Ser Ala Ile Phe Thr Thr Ala
                85                  90                  95
Pro Ala Pro Ala Pro Ala Pro Ala Pro Leu Pro Ala Pro Lys Asn Leu
            100                 105                 110
Val Val Ser Arg Val Thr Glu Asp Ser Ala Arg Leu Ser Trp Thr Ala
            115                 120                 125
Pro Asp Ala Ala Phe Asp Ser Phe Trp Ile Arg Tyr Phe Glu Phe Val
            130                 135                 140
Ser Lys Gly Asp Ala Ile Val Leu Thr Val Pro Gly Ser Glu Arg Ser
145                 150                 155                 160
Tyr Asp Leu Thr Gly Leu Lys Pro Gly Thr Glu Tyr Val Val Asn Ile
            165                 170                 175
Leu Gly Val Lys Gly Gly Ser Ile Ser Pro Pro Leu Ser Ala Ile Phe
            180                 185                 190
Thr Thr Cys
        195

<210> SEQ ID NO 173
<211> LENGTH: 195
<212> TYPE: PRT
<213> ORGANISM: Artificial Sequence
<220> FEATURE:

<223> OTHER INFORMATION: Bispecific EGFR/c-Met binding molecule

<400> SEQUENCE: 173

```
Met Leu Pro Ala Pro Lys Asn Leu Val Val Ser Glu Val Thr Glu Asp
1               5                   10                  15
Ser Ala Arg Leu Ser Trp Asp Asp Pro Trp Ala Phe Tyr Glu Ser Phe
                20                  25                  30
Leu Ile Gln Tyr Gln Glu Ser Glu Lys Val Gly Glu Ala Ile Val Leu
            35                  40                  45
Thr Val Pro Gly Ser Glu Arg Ser Tyr Asp Leu Thr Gly Leu Lys Pro
        50                  55                  60
Gly Thr Glu Tyr Thr Val Ser Ile Tyr Gly Val His Asn Val Tyr Lys
65                  70                  75                  80
Asp Thr Asn Ile Arg Gly Leu Pro Leu Ser Ala Ile Phe Thr Thr Ala
                85                  90                  95
Pro Ala Pro Ala Pro Ala Pro Ala Pro Leu Pro Ala Pro Lys Asn Leu
            100                 105                 110
Val Val Ser Arg Val Thr Glu Asp Ser Ala Arg Leu Ser Trp Thr Ala
        115                 120                 125
Pro Asp Ala Ala Phe Asp Ser Phe Trp Ile Arg Tyr Phe Glu Phe Leu
    130                 135                 140
Gly Ser Gly Glu Ala Ile Val Leu Thr Val Pro Gly Ser Glu Arg Ser
145                 150                 155                 160
Tyr Asp Leu Thr Gly Leu Lys Pro Gly Thr Glu Tyr Val Val Asn Ile
                165                 170                 175
Leu Ser Val Lys Gly Gly Ser Ile Ser Pro Pro Leu Ser Ala Ile Phe
            180                 185                 190
Thr Thr Cys
        195
```

<210> SEQ ID NO 174
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 174

```
Met Leu Pro Ala Pro Lys Asn Leu Val Val Ser Glu Val Thr Glu Asp
1               5                   10                  15
Ser Ala Arg Leu Ser Trp Asp Asp Pro His Ala Phe Tyr Glu Ser Phe
                20                  25                  30
Leu Ile Gln Tyr Gln Glu Ser Glu Lys Val Gly Glu Ala Ile Val Leu
            35                  40                  45
Thr Val Pro Gly Ser Glu Arg Ser Tyr Asp Leu Thr Gly Leu Lys Pro
        50                  55                  60
Gly Thr Glu Tyr Thr Val Ser Ile Tyr Gly Val His Asn Val Tyr Lys
65                  70                  75                  80
Asp Thr Asn Ile Arg Gly Leu Pro Leu Ser Ala Ile Phe Thr Thr Ala
                85                  90                  95
Pro Ala Pro Ala Pro Ala Pro Ala Pro Leu Pro Ala Pro Lys Asn Leu
            100                 105                 110
Val Val Ser Arg Val Thr Glu Asp Ser Ala Arg Leu Ser Trp Thr Ala
        115                 120                 125
Pro Asp Ala Ala Phe Asp Ser Phe Trp Ile Arg Tyr Phe Glu Phe Leu
    130                 135                 140
```

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Lys Ile Ser Pro Pro Leu Ser Ala Ile Phe
            180                 185                 190

Thr Thr Cys
        195

<210> SEQ ID NO 175
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 175

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Val
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
            180                 185                 190

Thr Thr Cys
        195

<210> SEQ ID NO 176
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 176

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
            20                  25                  30

Leu Ile Gln Tyr Gln Glu Ser Glu Lys Val Gly Glu Ala Ile Val Leu

```
                35                  40                  45
Thr Val Pro Gly Ser Glu Arg Ser Tyr Asp Leu Thr Gly Leu Lys Pro
 50                  55                  60
Gly Thr Glu Tyr Thr Val Ser Ile Tyr Gly Val His Asn Val Tyr Lys
 65                  70                  75                  80
Asp Thr Asn Ile Arg Gly Leu Pro Leu Ser Ala Ile Phe Thr Thr Ala
                 85                  90                  95
Pro Ala Pro Ala Pro Ala Pro Ala Pro Leu Pro Ala Pro Lys Asn Leu
                100                 105                 110
Val Val Ser Arg Val Thr Glu Asp Ser Ala Arg Leu Ser Trp Thr Ala
                115                 120                 125
Pro Asp Ala Ala Phe Asp Ser Phe Trp Ile Arg Tyr Phe Glu Phe Val
            130                 135                 140
Ser Lys Gly Asp Ala Ile Val Leu Thr Val Pro Gly Ser Glu Arg Ser
145                 150                 155                 160
Tyr Asp Leu Thr Gly Leu Lys Pro Gly Thr Glu Tyr Val Val Asn Ile
                165                 170                 175
Leu Gly Val Lys Gly Gly Ser Ile Ser Pro Pro Leu Ser Ala Ile Phe
                180                 185                 190
Thr Thr Cys
        195

<210> SEQ ID NO 177
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 177

Met Leu Pro Ala Pro Lys Asn Leu Val Val Ser Glu Val Thr Glu Asp
 1               5                  10                  15
Ser Ala Arg Leu Ser Trp Asp Asp Pro His Ala Phe Tyr Glu Ser Phe
                20                  25                  30
Leu Ile Gln Tyr Gln Glu Ser Glu Lys Val Gly Glu Ala Ile Val Leu
                35                  40                  45
Thr Val Pro Gly Ser Glu Arg Ser Tyr Asp Leu Thr Gly Leu Lys Pro
 50                  55                  60
Gly Thr Glu Tyr Thr Val Ser Ile Tyr Gly Val His Asn Val Tyr Lys
 65                  70                  75                  80
Asp Thr Asn Ile Arg Gly Leu Pro Leu Ser Ala Ile Phe Thr Thr Ala
                 85                  90                  95
Pro Ala Pro Ala Pro Ala Pro Ala Pro Leu Pro Ala Pro Lys Asn Leu
                100                 105                 110
Val Val Ser Arg Val Thr Glu Asp Ser Ala Arg Leu Ser Trp Thr Ala
                115                 120                 125
Pro Asp Ala Ala Phe Asp Ser Phe Trp Ile Arg Tyr Phe Glu Phe Leu
            130                 135                 140
Gly Ser Gly Glu Ala Ile Val Leu Thr Val Pro Gly Ser Glu Arg Ser
145                 150                 155                 160
Tyr Asp Leu Thr Gly Leu Lys Pro Gly Thr Glu Tyr Val Val Asn Ile
                165                 170                 175
Leu Ser Val Lys Gly Gly Ser Ile Ser Pro Pro Leu Ser Ala Ile Phe
                180                 185                 190
Thr Thr Cys
```

-continued

<210> SEQ ID NO 178
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 178

Met Leu Pro Ala Pro Lys Asn Leu Val Val Ser Glu Val Thr Glu Asp
1               5                   10                  15
Ser Ala Arg Leu Ser Trp Asp Asp Pro Trp Ala Phe Tyr Glu Ser Phe
            20                  25                  30
Leu Ile Gln Tyr Gln Glu Ser Glu Lys Val Gly Glu Ala Ile Val Leu
        35                  40                  45
Thr Val Pro Gly Ser Glu Arg Ser Tyr Asp Leu Thr Gly Leu Lys Pro
    50                  55                  60
Gly Thr Glu Tyr Thr Val Ser Ile Tyr Gly Val His Asn Val Tyr Lys
65                  70                  75                  80
Asp Thr Asn Ile Arg Gly Leu Pro Leu Ser Ala Ile Phe Thr Thr Ala
                85                  90                  95
Pro Ala Pro Ala Pro Ala Pro Ala Pro Leu Pro Ala Pro Lys Asn Leu
            100                 105                 110
Val Val Ser Arg Val Thr Glu Asp Ser Ala Arg Leu Ser Trp Thr Ala
        115                 120                 125
Pro Asp Ala Ala Phe Asp Ser Phe Trp Ile Arg Tyr Phe Glu Phe Leu
    130                 135                 140
Gly Ser Gly Glu Ala Ile Val Leu Thr Val Pro Gly Ser Glu Arg Ser
145                 150                 155                 160
Tyr Asp Leu Thr Gly Leu Lys Pro Gly Thr Glu Tyr Val Val Asn Ile
                165                 170                 175
Leu Ser Val Lys Gly Gly Ser Ile Ser Pro Pro Leu Ser Ala Ile Phe
            180                 185                 190
Thr Thr Cys
        195

<210> SEQ ID NO 179
<211> LENGTH: 12
<212> TYPE: PRT
<213> ORGANISM: Artificial Sequence
<220> FEATURE:
<223> OTHER INFORMATION: Consensus FG loop of EGFR bindiing FN3 domain
<220> FEATURE:
<221> NAME/KEY: VARIANT
<222> LOCATION: (9)..(9)
<223> OTHER INFORMATION: Xaa may be Met or Ile

<400> SEQUENCE: 179

His Asn Val Tyr Lys Asp Thr Asn Xaa Arg Gly Leu
1               5                   10

<210> SEQ ID NO 180
<211> LENGTH: 12
<212> TYPE: PRT
<213> ORGANISM: Artificial Sequence
<220> FEATURE:
<223> OTHER INFORMATION: GF loop of EGFR binding FN3 domain

<400> SEQUENCE: 180

Leu Gly Ser Tyr Val Phe Glu His Asp Val Met Leu

```
                        1               5                   10

<210> SEQ ID NO 181
<211> LENGTH: 8
<212> TYPE: PRT
<213> ORGANISM: Artificial Sequence
<220> FEATURE:
<223> OTHER INFORMATION: Consensus BC loop of EGFR binding FN3 domain
<220> FEATURE:
<221> NAME/KEY: VARIANT
<222> LOCATION: (1)..(1)
<223> OTHER INFORMATION: Xaa may be Ala, Thr, Gly or Asp
<220> FEATURE:
<221> NAME/KEY: VARIANT
<222> LOCATION: (2)..(2)
<223> OTHER INFORMATION: Xaa may be Ala, Asp, Tyr or Trp
<220> FEATURE:
<221> NAME/KEY: VARIANT
<222> LOCATION: (3)..(3)
<223> OTHER INFORMATION: Xaa may be Pro, Asp or Asn
<220> FEATURE:
<221> NAME/KEY: VARIANT
<222> LOCATION: (4)..(4)
<223> OTHER INFORMATION: Xaa may be Leu or absent
<220> FEATURE:
<221> NAME/KEY: VARIANT
<222> LOCATION: (5)..(5)
<223> OTHER INFORMATION: Xaa may be Asp, His, Arg, Gly, Tyr or Trp
<220> FEATURE:
<221> NAME/KEY: VARIANT
<222> LOCATION: (6)..(6)
<223> OTHER INFORMATION: Xaa may be Glu, Asp or Ala
<220> FEATURE:
<221> NAME/KEY: VARIANT
<222> LOCATION: (7)..(7)
<223> OTHER INFORMATION: Xaa may be Ala, Phe, Gly, His or Asp
<220> FEATURE:
<221> NAME/KEY: VARIANT
<222> LOCATION: (8)..(8)
<223> OTHER INFORMATION: Xaa may be Tyr, Phe or Leu

<400> SEQUENCE: 181

Xaa Xaa Xaa Xaa Xaa Xaa Xaa Xaa
1               5

<210> SEQ ID NO 182
<211> LENGTH: 95
<212> TYPE: PRT
<213> ORGANISM: Artificial Sequence
<220> FEATURE:
<223> OTHER INFORMATION: EGFR binding FN3 domain consensus sequence
<220> FEATURE:
<221> NAME/KEY: VARIANT
<222> LOCATION: (22)..(22)
<223> OTHER INFORMATION: Xaa may be Ala, Thr, Gly or Asp
<220> FEATURE:
<221> NAME/KEY: VARIANT
<222> LOCATION: (23)..(23)
<223> OTHER INFORMATION: Xaa may be Ala, Asp, Tyr or Trp
<220> FEATURE:
<221> NAME/KEY: VARIANT
<222> LOCATION: (24)..(24)
<223> OTHER INFORMATION: Xaa may be Pro, Asp or Asn
<220> FEATURE:
<221> NAME/KEY: VARIANT
<222> LOCATION: (25)..(25)
<223> OTHER INFORMATION: Xaa may be Leu or absent
<220> FEATURE:
<221> NAME/KEY: VARIANT
<222> LOCATION: (26)..(26)
<223> OTHER INFORMATION: Xaa may be Asp, His, Arg, Gly, Tyr or Trp
<220> FEATURE:
<221> NAME/KEY: VARIANT
<222> LOCATION: (27)..(27)
<223> OTHER INFORMATION: Xaa may be Gly, Asp or Ala
<220> FEATURE:
```

```
<221> NAME/KEY: VARIANT
<222> LOCATION: (28)..(28)
<223> OTHER INFORMATION: Xaa may be Ala, Phe, Gly, His or Asp
<220> FEATURE:
<221> NAME/KEY: VARIANT
<222> LOCATION: (29)..(29)
<223> OTHER INFORMATION: Xaa may be Tyr, Phe or Leu
<220> FEATURE:
<221> NAME/KEY: VARIANT
<222> LOCATION: (84)..(84)
<223> OTHER INFORMATION: Xaa may be Met or Ile

<400> SEQUENCE: 182

Leu Pro Ala Pro Lys Asn Leu Val Val Ser Glu Val Thr Glu Asp Ser
1               5                   10                  15

Leu Arg Leu Ser Trp Xaa Xaa Xaa Xaa Xaa Xaa Xaa Asp Ser Phe
            20                  25                  30

Leu Ile Gln Tyr Gln Glu Ser Glu Lys Val Gly Glu Ala Ile Asn Leu
                35                  40                  45

Thr Val Pro Gly Ser Glu Arg Ser Tyr Asp Leu Thr Gly Leu Lys Pro
            50                  55                  60

Gly Thr Glu Tyr Thr Val Ser Ile Tyr Gly Val His Asn Val Tyr Lys
65              70                  75                  80

Asp Thr Asn Xaa Arg Gly Leu Pro Leu Ser Ala Glu Phe Thr Thr
                85                  90                  95

<210> SEQ ID NO 183
<211> LENGTH: 95
<212> TYPE: PRT
<213> ORGANISM: Artificial Sequence
<220> FEATURE:
<223> OTHER INFORMATION: EGFR binding FN3 domain consensus sequence
<220> FEATURE:
<221> NAME/KEY: VARIANT
<222> LOCATION: (22)..(22)
<223> OTHER INFORMATION: Xaa may be Ala, Thr, Gly or Asp
<220> FEATURE:
<221> NAME/KEY: VARIANT
<222> LOCATION: (23)..(23)
<223> OTHER INFORMATION: Xaa may be Ala, Asp, Tyr or Trp
<220> FEATURE:
<221> NAME/KEY: VARIANT
<222> LOCATION: (24)..(24)
<223> OTHER INFORMATION: Xaa may be Pro, Asp or Asn
<220> FEATURE:
<221> NAME/KEY: VARIANT
<222> LOCATION: (25)..(25)
<223> OTHER INFORMATION: Xaa may be Leu or absent
<220> FEATURE:
<221> NAME/KEY: VARIANT
<222> LOCATION: (26)..(26)
<223> OTHER INFORMATION: Xaa may be Asp, His, Arg, Gly, Tyr or Trp
<220> FEATURE:
<221> NAME/KEY: VARIANT
<222> LOCATION: (27)..(27)
<223> OTHER INFORMATION: Xaa may be Gly, Asp or Ala
<220> FEATURE:
<221> NAME/KEY: VARIANT
<222> LOCATION: (28)..(28)
<223> OTHER INFORMATION: Xaa may be Ala, Phe, Gly, His or Asp
<220> FEATURE:
<221> NAME/KEY: VARIANT
<222> LOCATION: (29)..(29)
<223> OTHER INFORMATION: Xaa may be Tyr, Phe or Leu

<400> SEQUENCE: 183

Leu Pro Ala Pro Lys Asn Leu Val Val Ser Glu Val Thr Glu Asp Ser
1               5                   10                  15

Leu Arg Leu Ser Trp Xaa Xaa Xaa Xaa Xaa Xaa Xaa Asp Ser Phe
            20                  25                  30
```

```
Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val Leu Gly Ser Tyr Val
 65                  70                  75                  80

Phe Glu His Asp Val Met Leu Pro Leu Ser Ala Glu Phe Thr Thr
                 85                  90                  95

<210> SEQ ID NO 184
<211> LENGTH: 15
<212> TYPE: PRT
<213> ORGANISM: Artificial Sequence
<220> FEATURE:
<223> OTHER INFORMATION: c-Met binding FN3 domain C strand and CD loop
      consensus sequence
<220> FEATURE:
<221> NAME/KEY: VARIANT
<222> LOCATION: (4)..(4)
<223> OTHER INFORMATION: Xaa is Trp, Phe or Val
<220> FEATURE:
<221> NAME/KEY: VARIANT
<222> LOCATION: (8)..(8)
<223> OTHER INFORMATION: Xaa is Asp, Phe or Leu
<220> FEATURE:
<221> NAME/KEY: VARIANT
<222> LOCATION: (10)..(10)
<223> OTHER INFORMATION: Xaa is Val, Phe or Leu
<220> FEATURE:
<221> NAME/KEY: VARIANT
<222> LOCATION: (11)..(11)
<223> OTHER INFORMATION: Xaa is Val, Leu or Thr
<220> FEATURE:
<221> NAME/KEY: VARIANT
<222> LOCATION: (12)..(12)
<223> OTHER INFORMATION: Xaa is Val, Arg, Gly, Leu, Thr or Ser
<220> FEATURE:
<221> NAME/KEY: VARIANT
<222> LOCATION: (13)..(13)
<223> OTHER INFORMATION: Xaa is Gly, Ser, Ala, Thr or Lys
<220> FEATURE:
<221> NAME/KEY: VARIANT
<222> LOCATION: (15)..(15)
<223> OTHER INFORMATION: Xaa is Glu or Asp

<400> SEQUENCE: 184

Asp Ser Phe Xaa Ile Arg Tyr Xaa Glu Xaa Xaa Xaa Xaa Gly Xaa
 1               5                  10                  15

<210> SEQ ID NO 185
<211> LENGTH: 17
<212> TYPE: PRT
<213> ORGANISM: Artificial Sequence
<220> FEATURE:
<223> OTHER INFORMATION: c-Met binding FN3 domain F strand and FG loop
      consensus sequence
<220> FEATURE:
<221> NAME/KEY: VARIANT
<222> LOCATION: (4)..(4)
<223> OTHER INFORMATION: Xaa is Tyr, Trp, Ile, Val, Gly or Ala
<220> FEATURE:
<221> NAME/KEY: VARIANT
<222> LOCATION: (6)..(6)
<223> OTHER INFORMATION: Xaa is Asn, Thr, Qln or Gly
<220> FEATURE:
<221> NAME/KEY: VARIANT
<222> LOCATION: (8)..(8)
<223> OTHER INFORMATION: Xaa is Leu, Met, Asn or Ile
<220> FEATURE:
<221> NAME/KEY: VARIANT
<222> LOCATION: (9)..(9)
<223> OTHER INFORMATION: Xaa is Gly or Ser
```

```
<220> FEATURE:
<221> NAME/KEY: VARIANT
<222> LOCATION: (14)..(14)
<223> OTHER INFORMATION: Xaa is Ser, Leu, Gly, Tyr, Thr, Arg, His or Lys
<220> FEATURE:
<221> NAME/KEY: VARIANT
<222> LOCATION: (15)..(15)
<223> OTHER INFORMATION: Xaa is Ile, Val or Leu
<220> FEATURE:
<221> NAME/KEY: VARIANT
<222> LOCATION: (17)..(17)
<223> OTHER INFORMATION: Xaa is Val, Thr, His, Ile, Pro, Tyr or Leu

<400> SEQUENCE: 185

Thr Glu Tyr Xaa Val Xaa Ile Xaa Xaa Val Lys Gly Gly Xaa Xaa Ser
1               5                   10                  15

Xaa

<210> SEQ ID NO 186
<211> LENGTH: 89
<212> TYPE: PRT
<213> ORGANISM: Artificial Sequence
<220> FEATURE:
<223> OTHER INFORMATION: c-Met binding FN3 domain consensus sequence
<220> FEATURE:
<221> NAME/KEY: VARIANT
<222> LOCATION: (32)..(32)
<223> OTHER INFORMATION: Xaa is Trp, Phe or Val
<220> FEATURE:
<221> NAME/KEY: VARIANT
<222> LOCATION: (36)..(36)
<223> OTHER INFORMATION: Xaa is Asp, Phe or Leu
<220> FEATURE:
<221> NAME/KEY: VARIANT
<222> LOCATION: (38)..(38)
<223> OTHER INFORMATION: Xaa is Val, Phe or Leu
<220> FEATURE:
<221> NAME/KEY: VARIANT
<222> LOCATION: (39)..(39)
<223> OTHER INFORMATION: Xaa is Val, Leu or Thr
<220> FEATURE:
<221> NAME/KEY: VARIANT
<222> LOCATION: (40)..(40)
<223> OTHER INFORMATION: Xaa is Val, Arg, Gly, Leu, Thr or Ser
<220> FEATURE:
<221> NAME/KEY: VARIANT
<222> LOCATION: (41)..(41)
<223> OTHER INFORMATION: Xaa is Gly, Ser, Ala, Thr or Lys
<220> FEATURE:
<221> NAME/KEY: VARIANT
<222> LOCATION: (43)..(43)
<223> OTHER INFORMATION: Xaa is Glu or Asp
<220> FEATURE:
<221> NAME/KEY: VARIANT
<222> LOCATION: (68)..(68)
<223> OTHER INFORMATION: Xaa is Tyr, Trp, Ile, Val, Gly or Ala
<220> FEATURE:
<221> NAME/KEY: VARIANT
<222> LOCATION: (70)..(70)
<223> OTHER INFORMATION: Xaa is Asn, Thr, Qln or Gly
<220> FEATURE:
<221> NAME/KEY: VARIANT
<222> LOCATION: (72)..(72)
<223> OTHER INFORMATION: Xaa is Leu, Met, Asn or Ile
<220> FEATURE:
<221> NAME/KEY: VARIANT
<222> LOCATION: (73)..(73)
<223> OTHER INFORMATION: Xaa is Gly or Ser
<220> FEATURE:
<221> NAME/KEY: VARIANT
<222> LOCATION: (78)..(78)
<223> OTHER INFORMATION: Xaa is Ser, Leu, Gly, Tyr, Thr, Arg, His or Lys
<220> FEATURE:
<221> NAME/KEY: VARIANT
<222> LOCATION: (79)..(79)
<223> OTHER INFORMATION: Xaa is Ile, Val or Leu
```

```
<220> FEATURE:
<221> NAME/KEY: VARIANT
<222> LOCATION: (81)..(81)
<223> OTHER INFORMATION: Xaa is Val, Thr, His, Ile, Pro, Tyr or Leu

<400> SEQUENCE: 186

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
                20                  25                  30

Ile Arg Tyr Xaa Glu Xaa Xaa Xaa Xaa Gly Xaa Ala Ile Val Leu Thr
            35                  40                  45

Val Pro Gly Ser Glu Arg Ser Tyr Asp Leu Thr Gly Leu Lys Pro Gly
50                  55                  60

Thr Glu Tyr Xaa Val Xaa Ile Xaa Xaa Val Lys Gly Gly Xaa Xaa Ser
65                  70                  75                  80

Xaa Pro Leu Ser Ala Glu Phe Thr Thr
                85

<210> SEQ ID NO 187
<211> LENGTH: 94
<212> TYPE: PRT
<213> ORGANISM: Artificial Sequence
<220> FEATURE:
<223> OTHER INFORMATION: EGFR consensus FN3 domain of bispecific
      EGFR/c-Met molecule
<220> FEATURE:
<221> NAME/KEY: VARIANT
<222> LOCATION: (11)..(11)
<223> OTHER INFORMATION: Xaa is Glu, Asn or Arg
<220> FEATURE:
<221> NAME/KEY: VARIANT
<222> LOCATION: (14)..(14)
<223> OTHER INFORMATION: Xaa is Glu or Pro
<220> FEATURE:
<221> NAME/KEY: VARIANT
<222> LOCATION: (17)..(17)
<223> OTHER INFORMATION: Xaa is Leu or Ala
<220> FEATURE:
<221> NAME/KEY: VARIANT
<222> LOCATION: (25)..(25)
<223> OTHER INFORMATION: Xaa is His or Trp
<220> FEATURE:
<221> NAME/KEY: VARIANT
<222> LOCATION: (29)..(29)
<223> OTHER INFORMATION: Xaa is Glu or Asp
<220> FEATURE:
<221> NAME/KEY: VARIANT
<222> LOCATION: (37)..(37)
<223> OTHER INFORMATION: Xaa is Glu or Pro
<220> FEATURE:
<221> NAME/KEY: VARIANT
<222> LOCATION: (46)..(46)
<223> OTHER INFORMATION: Xaa is Asn or Val
<220> FEATURE:
<221> NAME/KEY: VARIANT
<222> LOCATION: (73)..(73)
<223> OTHER INFORMATION: Xaa is Gly or Tyr
<220> FEATURE:
<221> NAME/KEY: VARIANT
<222> LOCATION: (83)..(83)
<223> OTHER INFORMATION: Xaa is Met or Ile
<220> FEATURE:
<221> NAME/KEY: VARIANT
<222> LOCATION: (91)..(91)
<223> OTHER INFORMATION: Xaa is Glu or Ile

<400> SEQUENCE: 187

Leu Pro Ala Pro Lys Asn Leu Val Val Ser Xaa Val Thr Xaa Asp Ser
1               5                   10                  15
```

-continued

```
Xaa Arg Leu Ser Trp Asp Asp Pro Xaa Ala Phe Tyr Xaa Ser Phe Leu
            20                  25                  30

Ile Gln Tyr Gln Xaa Ser Glu Lys Val Gly Glu Ala Ile Xaa Leu Thr
        35                  40                      45

Val Pro Gly Ser Glu Arg Ser Tyr Asp Leu Thr Gly Leu Lys Pro Gly
    50                  55                  60

Thr Glu Tyr Thr Val Ser Ile Tyr Xaa Val His Asn Val Tyr Lys Asp
65                  70                  75                  80

Thr Asn Xaa Arg Gly Leu Pro Leu Ser Ala Xaa Phe Thr Thr
                85                  90

<210> SEQ ID NO 188
<211> LENGTH: 89
<212> TYPE: PRT
<213> ORGANISM: Artificial Sequence
<220> FEATURE:
<223> OTHER INFORMATION: c-Met consensus FN3 domain of bispecific
      EGFR/c-Met molecule
<220> FEATURE:
<221> NAME/KEY: VARIANT
<222> LOCATION: (11)..(11)
<223> OTHER INFORMATION: Xaa is Glu, Asn or Arg
<220> FEATURE:
<221> NAME/KEY: VARIANT
<222> LOCATION: (14)..(14)
<223> OTHER INFORMATION: Xaa is Glu or Pro
<220> FEATURE:
<221> NAME/KEY: VARIANT
<222> LOCATION: (17)..(17)
<223> OTHER INFORMATION: Xaa is Leu or Ala
<220> FEATURE:
<221> NAME/KEY: VARIANT
<222> LOCATION: (37)..(37)
<223> OTHER INFORMATION: Xaa is Glu or Pro
<220> FEATURE:
<221> NAME/KEY: VARIANT
<222> LOCATION: (39)..(39)
<223> OTHER INFORMATION: Xaa is Val or Leu
<220> FEATURE:
<221> NAME/KEY: VARIANT
<222> LOCATION: (40)..(40)
<223> OTHER INFORMATION: Xaa is Gly or Ser
<220> FEATURE:
<221> NAME/KEY: VARIANT
<222> LOCATION: (41)..(41)
<223> OTHER INFORMATION: Xaa is Ser or Lys
<220> FEATURE:
<221> NAME/KEY: VARIANT
<222> LOCATION: (43)..(43)
<223> OTHER INFORMATION: Xaa is Glu or Asp
<220> FEATURE:
<221> NAME/KEY: VARIANT
<222> LOCATION: (46)..(46)
<223> OTHER INFORMATION: Xaa is Asn or Val
<220> FEATURE:
<221> NAME/KEY: VARIANT
<222> LOCATION: (72)..(72)
<223> OTHER INFORMATION: Xaa is Leu or Met
<220> FEATURE:
<221> NAME/KEY: VARIANT
<222> LOCATION: (73)..(73)
<223> OTHER INFORMATION: Xaa is Gly or Ser
<220> FEATURE:
<221> NAME/KEY: VARIANT
<222> LOCATION: (78)..(78)
<223> OTHER INFORMATION: Xaa is Ser or Lys
<220> FEATURE:
<221> NAME/KEY: VARIANT
<222> LOCATION: (86)..(86)
<223> OTHER INFORMATION: Xaa is Glu or Ile

<400> SEQUENCE: 188

Leu Pro Ala Pro Lys Asn Leu Val Val Ser Xaa Val Thr Xaa Asp Ser
```

```
1               5                   10                  15
Xaa Arg Leu Ser Trp Thr Ala Pro Asp Ala Ala Phe Asp Ser Phe Trp
                20                  25                  30

Ile Arg Tyr Phe Xaa Phe Xaa Xaa Gly Xaa Ala Ile Xaa Leu Thr
                35                  40                  45

Val Pro Gly Ser Glu Arg Ser Tyr Asp Leu Thr Gly Leu Lys Pro Gly
            50                  55                  60

Thr Glu Tyr Val Val Asn Ile Xaa Xaa Val Lys Gly Gly Xaa Ile Ser
65                  70                  75                  80

Pro Pro Leu Ser Ala Xaa Phe Thr Thr
                    85

<210> SEQ ID NO 189
<211> LENGTH: 585
<212> TYPE: PRT
<213> ORGANISM: Homo sapiens
<220> FEATURE:
<221> NAME/KEY: VARIANT
<222> LOCATION: (34)..(34)
<223> OTHER INFORMATION: C34S

<400> SEQUENCE: 189

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ser Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270
```

```
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585

<210> SEQ ID NO 190
<211> LENGTH: 194
<212> TYPE: PRT
<213> ORGANISM: Artificial Sequence
<220> FEATURE:
<223> OTHER INFORMATION: Bispecific EGFR/c-Met molecule

<400> SEQUENCE: 190

Met Leu Pro Ala Pro Lys Asn Leu Val Val Ser Glu Val Thr Glu Asp
1               5                   10                  15
Ser Ala Arg Leu Ser Trp Asp Asp Pro Trp Ala Phe Tyr Glu Ser Phe
                20                  25                  30
Leu Ile Gln Tyr Gln Glu Ser Glu Lys Val Gly Glu Ala Ile Val Leu
        35                  40                  45
```

```
Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr Ala
                 85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
                115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
                180                 185                 190

Thr Thr

<210> SEQ ID NO 191
<211> LENGTH: 193
<212> TYPE: PRT
<213> ORGANISM: Artificial Sequence
<220> FEATURE:
<223> OTHER INFORMATION: Bispecific EGFR/c-Met molecule

<400> SEQUENCE: 191

Leu Pro Ala Pro Lys Asn Leu Val Val Ser Glu Val Thr Glu Asp Ser
  1               5                  10                  15

Ala Arg Leu Ser Trp Asp Asp Pro Trp Ala Phe Tyr Glu Ser Phe Leu
                 20                  25                  30

Ile Gln Tyr Gln Glu Ser Glu Lys Val Gly Glu Ala Ile Val Leu Thr
                 35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val His Asn Val Tyr Lys Asp
 65                  70                  75                  80

Thr Asn Ile Arg Gly Leu Pro Leu Ser Ala Ile Phe Thr Thr Ala Pro
                 85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
                115                 120                 125

Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Ser Val Lys Gly Gly Ser Ile Ser Pro Pro Leu Ser Ala Ile Phe Thr
                180                 185                 190

Thr
```

```
<210> SEQ ID NO 192
<211> LENGTH: 194
<212> TYPE: PRT
<213> ORGANISM: Artificial Sequence
<220> FEATURE:
<223> OTHER INFORMATION: Bispecific EGFR/c-Met molecule

<400> SEQUENCE: 192

Met Leu Pro Ala Pro Lys Asn Leu Val Val Ser Glu Val Thr Glu Asp
1               5                  10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
            180                 185                 190

Thr Thr

<210> SEQ ID NO 193
<211> LENGTH: 193
<212> TYPE: PRT
<213> ORGANISM: Artificial Sequence
<220> FEATURE:
<223> OTHER INFORMATION: Bispecific EGFR/c-Met molecule

<400> SEQUENCE: 193

Leu Pro Ala Pro Lys Asn Leu Val Val Ser Glu Val Thr Glu Asp Ser
1               5                  10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
```

-continued

```
              115                 120                 125
Asp Ala Ala Phe Asp Ser Phe Trp Ile Arg Tyr Phe Glu Phe Leu Gly
        130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Ser Val Lys Gly Gly Ser Ile Ser Pro Pro Leu Ser Ala Ile Phe Thr
            180                 185                 190

Thr

<210> SEQ ID NO 194
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 194

Leu Pro Ala Pro Lys Asn Leu Val Val Ser Glu Val Thr Glu Asp Ser
1               5                   10                  15

Ala Arg Leu Ser Trp Ala Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 195
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 195

Leu Pro Ala Pro Lys Asn Leu Val Val Ser Glu Val Thr Glu Asp Ser
1               5                   10                  15

Ala Arg Leu Ser Trp Asp Ala Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 196
<211> LENGTH: 94
<212> TYPE: PRT
<213> ORGANISM: Artificial Sequence
<220> FEATURE:
<223> OTHER INFORMATION: EGFR binding FN3 domain
```

<400> SEQUENCE: 196

```
Leu Pro Ala Pro Lys Asn Leu Val Val Ser Glu Val Thr Glu Asp Ser
1               5                   10                  15

Ala Arg Leu Ser Trp Asp Ala Trp Ala Phe Tyr Glu Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90
```

<210> SEQ ID NO 197
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 197

```
Leu Pro Ala Pro Lys Asn Leu Val Val Ser Glu Val Thr Glu Asp Ser
1               5                   10                  15

Ala Arg Leu Ser Trp Asp Pro Ala Ala Phe Tyr Glu Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90
```

<210> SEQ ID NO 198
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 198

```
Leu Pro Ala Pro Lys Asn Leu Val Val Ser Glu Val Thr Glu Asp Ser
1               5                   10                  15

Ala Arg Leu Ser Trp Asp Pro Trp Ala Ala Tyr Glu Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90
```

<210> SEQ ID NO 199

```
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 199

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Ala Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 200
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 200

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Ala Asn Val Tyr Lys Asp
65                  70                  75                  80

Thr Asn Met Arg Gly Leu Pro Leu Ser Ala Ile Phe Thr Thr
                85                  90

<210> SEQ ID NO 201
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 201

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Ala Val Tyr Lys Asp
65                  70                  75                  80
```

Thr Asn Met Arg Gly Leu Pro Leu Ser Ala Ile Phe Thr Thr
                85                  90

<210> SEQ ID NO 202
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 202

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Ala Tyr Lys Asp
65                  70                  75                  80

Thr Asn Met Arg Gly Leu Pro Leu Ser Ala Ile Phe Thr Thr
                85                  90

<210> SEQ ID NO 203
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 203

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Ala Lys Asp
65                  70                  75                  80

Thr Asn Met Arg Gly Leu Pro Leu Ser Ala Ile Phe Thr Thr
                85                  90

<210> SEQ ID NO 204
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 204

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly

```
                50                  55                  60
Thr Glu Tyr Thr Val Ser Ile Tyr Gly Val His Asn Val Tyr Ala Asp
 65                  70                  75                  80
Thr Asn Met Arg Gly Leu Pro Leu Ser Ala Ile Phe Thr Thr
                 85                  90

<210> SEQ ID NO 205
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 205

Leu Pro Ala Pro Lys Asn Leu Val Val Ser Glu Val Thr Glu Asp Ser
  1               5                  10                  15

Ala Arg Leu Ser Trp Asp Asp Pro Trp Ala Phe Tyr Glu Ser Phe Leu
                 20                  25                  30

Ile Gln Tyr Gln Glu Ser Glu Lys Val Gly Glu Ala Ile Val Leu Thr
             35                  40                  45

Val Pro Gly Ser Glu Arg Ser Tyr Asp Leu Thr Gly Leu Lys Pro Gly
         50                  55                  60

Thr Glu Tyr Thr Val Ser Ile Tyr Gly Val His Asn Val Tyr Lys Ala
 65                  70                  75                  80

Thr Asn Met Arg Gly Leu Pro Leu Ser Ala Ile Phe Thr Thr
                 85                  90

<210> SEQ ID NO 206
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 206

Leu Pro Ala Pro Lys Asn Leu Val Val Ser Glu Val Thr Glu Asp Ser
  1               5                  10                  15

Ala Arg Leu Ser Trp Asp Asp Pro Trp Ala Phe Tyr Glu Ser Phe Leu
                 20                  25                  30

Ile Gln Tyr Gln Glu Ser Glu Lys Val Gly Glu Ala Ile Val Leu Thr
             35                  40                  45

Val Pro Gly Ser Glu Arg Ser Tyr Asp Leu Thr Gly Leu Lys Pro Gly
         50                  55                  60

Thr Glu Tyr Thr Val Ser Ile Tyr Gly Val His Asn Val Tyr Lys Asp
 65                  70                  75                  80

Thr Asn Ala Arg Gly Leu Pro Leu Ser Ala Ile Phe Thr Thr
                 85                  90

<210> SEQ ID NO 207
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 207

Leu Pro Ala Pro Lys Asn Leu Val Val Ser Glu Val Thr Glu Asp Ser
  1               5                  10                  15

Ala Arg Leu Ser Trp Asp Asp Pro Trp Ala Phe Tyr Glu Ser Phe Leu
                 20                  25                  30
```

Ile Gln Tyr Gln Glu Ser Glu Lys Val Gly Glu Ala Ile Val Leu Thr
              35                  40                  45

Val Pro Gly Ser Glu Arg Ser Tyr Asp Leu Thr Gly Leu Lys Pro Gly
         50                  55                  60

Thr Glu Tyr Thr Val Ser Ile Tyr Gly Val His Asn Val Tyr Lys Asp
 65                  70                  75                  80

Thr Asn Met Ala Gly Leu Pro Leu Ser Ala Ile Phe Thr Thr
                 85                  90

<210> SEQ ID NO 208
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 208

Leu Pro Ala Pro Lys Asn Leu Val Val Ser Glu Val Thr Glu Asp Ser
 1               5                  10                  15

Ala Arg Leu Ser Trp Asp Asp Pro Trp Ala Phe Tyr Glu Ser Phe Leu
             20                  25                  30

Ile Gln Tyr Gln Glu Ser Glu Lys Val Gly Glu Ala Ile Val Leu Thr
              35                  40                  45

Val Pro Gly Ser Glu Arg Ser Tyr Asp Leu Thr Gly Leu Lys Pro Gly
         50                  55                  60

Thr Glu Tyr Thr Val Ser Ile Tyr Gly Val His Asn Val Tyr Lys Asp
 65                  70                  75                  80

Thr Asn Met Arg Ala Leu Pro Leu Ser Ala Ile Phe Thr Thr
                 85                  90

<210> SEQ ID NO 209
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 209

Leu Pro Ala Pro Lys Asn Leu Val Val Ser Glu Val Thr Glu Asp Ser
 1               5                  10                  15

Ala Arg Leu Ser Trp Asp Asp Pro Trp Ala Phe Tyr Glu Ser Phe Leu
             20                  25                  30

Ile Gln Tyr Gln Glu Ser Glu Lys Val Gly Glu Ala Ile Val Leu Thr
              35                  40                  45

Val Pro Gly Ser Glu Arg Ser Tyr Asp Leu Thr Gly Leu Lys Pro Gly
         50                  55                  60

Thr Glu Tyr Thr Val Ser Ile Tyr Gly Val His Asn Val Tyr Lys Asp
 65                  70                  75                  80

Thr Asn Met Arg Gly Ala Pro Leu Ser Ala Ile Phe Thr Thr
                 85                  90

<210> SEQ ID NO 210
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 210

-continued

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Ala Asn Met Arg Gly Leu Pro Leu Ser Ala Ile Phe Thr Thr
                85                  90

<210> SEQ ID NO 211
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 211

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Ala Met Arg Gly Leu Pro Leu Ser Ala Ile Phe Thr Thr
                85                  90

<210> SEQ ID NO 212
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 212

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Ser Ile Ser
65                  70                  75                  80

Pro Pro Leu Ser Ala Ile Phe Thr Thr
                85

<210> SEQ ID NO 213
<211> LENGTH: 89
<212> TYPE: PRT
<213> ORGANISM: Artificial Sequence

```
<220> FEATURE:
<223> OTHER INFORMATION: c-Met binding FN3 domain

<400> SEQUENCE: 213

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Ser Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Lys Ile Ser
65                  70                  75                  80

Pro Pro Leu Ser Ala Ile Phe Thr Thr
                85

<210> SEQ ID NO 214
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 214

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Ser Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Lys Ile Ser
65                  70                  75                  80

Pro Pro Leu Ser Ala Ile Phe Thr Thr
                85

<210> SEQ ID NO 215
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 215

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ser Val Asn Ile Met Gly Val Lys Gly Gly Lys Ile Ser
65                  70                  75                  80

Pro Pro Leu Ser Ala Ile Phe Thr Thr
                85
```

```
<210> SEQ ID NO 216
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 216

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Ser Ile Met Gly Val Lys Gly Gly Lys Ile Ser
65                  70                  75                  80

Pro Pro Leu Ser Ala Ile Phe Thr Thr
                85

<210> SEQ ID NO 217
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 217

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Lys Ile Ser
65                  70                  75                  80

Ser Pro Leu Ser Ala Ile Phe Thr Thr
                85

<210> SEQ ID NO 218
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 218

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Ser Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Lys Ile Ser
```

-continued

```
                65                  70                  75                  80
Pro Pro Leu Ser Ala Ile Phe Thr Thr
                85

<210> SEQ ID NO 219
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 219

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Lys Ile Ser
65                  70                  75                  80

Pro Pro Leu Ser Ala Ile Phe Thr Thr
                85

<210> SEQ ID NO 220
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 220

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Ser Gly Val Lys Gly Lys Ile Ser
65                  70                  75                  80

Pro Pro Leu Ser Ala Ile Phe Thr Thr
                85

<210> SEQ ID NO 221
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 221

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Ser Tyr Phe Glu Phe Leu Gly Ser Gly Glu Ala Ile Val Leu Thr
        35                  40                  45
```

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Lys Ile Ser
65                  70                  75                  80

Pro Pro Leu Ser Ala Ile Phe Thr Thr
                85

<210> SEQ ID NO 222
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 222

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Ser Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Lys Ile Ser
65                  70                  75                  80

Pro Pro Leu Ser Ala Ile Phe Thr Thr
                85

<210> SEQ ID NO 223
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 223

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Lys Ser Ser
65                  70                  75                  80

Pro Pro Leu Ser Ala Ile Phe Thr Thr
                85

<210> SEQ ID NO 224
<211> LENGTH: 10
<212> TYPE: PRT
<213> ORGANISM: Artificial Sequence
<220> FEATURE:
<223> OTHER INFORMATION: linker

<400> SEQUENCE: 224

Gly Gly Gly Gly Ser Gly Gly Gly Gly Ser
1               5                   10